(12) United States Patent
Behnke et al.

(10) Patent No.: US 8,927,551 B2
(45) Date of Patent: Jan. 6, 2015

(54) ISOXAZOLINES AS INHIBITORS OF FATTY ACID AMIDE HYDROLASE

(75) Inventors: Mark L. Behnke, Somerville, MA (US); Alfredo C. Castro, Winchester, MA (US); Lawrence K. Chan, Brookline, MA (US); Catherine A. Evans, Somerville, MA (US); Louis Grenier, Newton, MA (US); Michael J. Grogan, Winchester, MA (US); Yves Leblanc, Kirkland (CA); Tao Liu, Ashland, MA (US); Stephane Peluso, Brookline, MA (US); Daniel A. Snyder, Somerville, MA (US); Thomas T. Tibbitts, Westford, MA (US)

(73) Assignee: Infinity Pharmaceuticals, Inc., Cambridge, MA (US)

( * ) Notice: Subject to any disclaimer, the term of this patent is extended or adjusted under 35 U.S.C. 154(b) by 707 days.

(21) Appl. No.: 12/782,655

(22) Filed: May 18, 2010

(65) Prior Publication Data

US 2011/0028482 A1    Feb. 3, 2011

Related U.S. Application Data

(60) Provisional application No. 61/179,283, filed on May 18, 2009.

(51) Int. Cl.
| | | |
|---|---|---|
| *A61K 31/498* | (2006.01) | |
| *C07D 413/04* | (2006.01) | |
| *A61K 31/4439* | (2006.01) | |
| *C07D 401/14* | (2006.01) | |
| *A61K 31/506* | (2006.01) | |
| *A61K 31/424* | (2006.01) | |
| *C07D 401/04* | (2006.01) | |
| *A61K 31/454* | (2006.01) | |
| *C07D 413/06* | (2006.01) | |
| *A61K 31/496* | (2006.01) | |
| *C07D 403/10* | (2006.01) | |
| *C07D 401/10* | (2006.01) | |
| *C07D 417/04* | (2006.01) | |
| *C07D 417/14* | (2006.01) | |
| *C07D 413/14* | (2006.01) | |
| *C07D 261/04* | (2006.01) | |

(52) U.S. Cl.
CPC .......... *C07D 413/04* (2013.01); *C07D 417/04* (2013.01); *C07D 417/14* (2013.01); *C07D 413/14* (2013.01); *C07D 261/04* (2013.01)
USPC .......... 514/249; 514/380; 514/342; 514/269; 514/365; 514/326; 514/254.04; 514/367; 514/314; 546/269.7; 546/209; 546/167; 548/246; 548/202; 548/163

(58) Field of Classification Search
USPC ............. 514/249, 380, 342, 269, 365, 326, 514/254.04, 367, 314; 546/269.7, 209, 167; 548/246, 202, 163
See application file for complete search history.

(56) References Cited

U.S. PATENT DOCUMENTS

| | | |
|---|---|---|
| 4,270,537 A | 6/1981 | Romaine |
| 4,596,556 A | 6/1986 | Morrow et al. |
| 4,790,824 A | 12/1988 | Morrow et al. |
| 4,886,499 A | 12/1989 | Cirelli et al. |
| 4,933,345 A | 6/1990 | Huth et al. |
| 4,940,460 A | 7/1990 | Casey et al. |
| 4,941,880 A | 7/1990 | Burns |
| 5,015,235 A | 5/1991 | Crossman |
| 5,064,413 A | 11/1991 | McKinnon et al. |
| 5,141,496 A | 8/1992 | Dalto et al. |
| 5,190,521 A | 3/1993 | Hubbard et al. |
| 5,273,989 A | 12/1993 | Schwab et al. |
| 5,312,335 A | 5/1994 | McKinnon et al. |
| 5,328,483 A | 7/1994 | Jacoby |
| 5,334,144 A | 8/1994 | Alchas et al. |
| 5,339,163 A | 8/1994 | Homma et al. |
| 5,348,958 A | 9/1994 | Krueger et al. |

(Continued)

FOREIGN PATENT DOCUMENTS

| | | |
|---|---|---|
| EP | 0237082 B1 | 5/1991 |
| EP | 0440082 A2 | 8/1991 |

(Continued)

OTHER PUBLICATIONS

Badoiu et al., "Asymmetric Lewis acid-catalyzed 1,3-dipolar cycloadditions," *Pure Appl. Chem.* 80(5):1013-1018 (2008).

(Continued)

*Primary Examiner* — San-Ming Hui
*Assistant Examiner* — Kathrien Cruz
(74) *Attorney, Agent, or Firm* — Jones Day

(57) ABSTRACT

The present invention provides isoxazoline FAAH inhibitors of the formula (I):

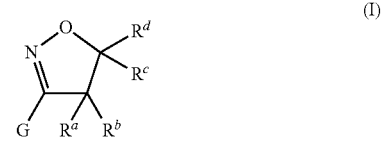

(I)

or pharmaceutically acceptable forms thereof, wherein each of G, $R^a$, $R^b$, $R^c$, and $R^d$ are as defined herein.
The present invention also provides pharmaceutical compositions comprising a compound of formula (I), or a pharmaceutically acceptable form thereof, and a pharmaceutically acceptable excipient.
The present invention also provides methods for treating an FAAH-mediated condition comprising administering a therapeutically effective amount of a compound of formula (I), or pharmaceutically acceptable form thereof, to a subject in need thereof.

45 Claims, No Drawings

(56) References Cited

U.S. PATENT DOCUMENTS

| | | |
|---|---|---|
| 5,383,851 A | 1/1995 | McKinnon et al. |
| 5,417,662 A | 5/1995 | Hjertman et al. |
| 5,466,220 A | 11/1995 | Brenneman |
| 5,480,381 A | 1/1996 | Weston |
| 5,503,627 A | 4/1996 | McKinnon et al. |
| 5,514,505 A | 5/1996 | Limburg et al. |
| 5,520,639 A | 5/1996 | Peterson et al. |
| 5,527,288 A | 6/1996 | Gross et al. |
| 5,541,061 A | 7/1996 | Fodor et al. |
| 5,569,189 A | 10/1996 | Parsons |
| 5,576,220 A | 11/1996 | Hudson et al. |
| 5,599,302 A | 2/1997 | Lilley et al. |
| 5,649,912 A | 7/1997 | Peterson |
| 5,704,911 A | 1/1998 | Parsons |
| 5,849,736 A | 12/1998 | Wityak et al. |
| 5,880,121 A | 3/1999 | Hrib |
| 5,893,397 A | 4/1999 | Peterson et al. |
| 5,993,412 A | 11/1999 | Deily et al. |
| 6,096,784 A | 8/2000 | Lerner et al. |
| 6,271,015 B1 | 8/2001 | Gilula et al. |
| 6,309,406 B1 | 10/2001 | Jones et al. |
| 6,326,156 B1 | 12/2001 | Civelli et al. |
| 6,344,474 B1 | 2/2002 | Maruani et al. |
| 6,479,437 B1 | 11/2002 | Bratz et al. |
| 6,514,910 B1 | 2/2003 | Bratz et al. |
| 6,534,444 B1 | 3/2003 | Sievernich et al. |
| 6,599,926 B2 | 7/2003 | Pinto et al. |
| 6,645,984 B2 | 11/2003 | Braun et al. |
| 6,841,519 B1 | 1/2005 | Nakatani et al. |
| 7,501,418 B2 | 3/2009 | Andres-Gil et al. |
| 7,553,496 B2 | 6/2009 | Ambati |
| 2002/0164769 A1 | 11/2002 | Curtis et al. |
| 2004/0235925 A1 | 11/2004 | Arneric |
| 2005/0113283 A1 | 5/2005 | Solow-Cordero et al. |
| 2011/0028478 A1 | 2/2011 | Behnke et al. |
| 2011/0034437 A1 | 2/2011 | Behnke et al. |

FOREIGN PATENT DOCUMENTS

| | | | |
|---|---|---|---|
| EP | 1 813 606 A1 | | 8/2007 |
| JP | 5-339250 | | 12/1993 |
| JP | 3282045 | | 5/2002 |
| JP | 2005-035924 | | 2/2005 |
| JP | 2005-272452 | | 2/2005 |
| JP | 2005-272443 | | 10/2005 |
| JP | 2005-272452 | | 10/2005 |
| WO | WO 96/29301 | | 9/1996 |
| WO | WO 96/38426 | | 12/1996 |
| WO | WO 97/13537 | | 4/1997 |
| WO | WO 97/34881 | | 9/1997 |
| WO | WO 97/33705 | | 10/1997 |
| WO | WO 98/15541 | | 4/1998 |
| WO | WO 98/24396 | | 6/1998 |
| WO | WO 99/21852 | | 5/1999 |
| WO | WO 99/34850 | | 7/1999 |
| WO | WO 00/50397 | | 8/2000 |
| WO | WO 01/46182 | | 6/2001 |
| WO | WO 01/56979 | | 8/2001 |
| WO | WO 01/56994 | | 8/2001 |
| WO | WO 02/00647 | | 1/2002 |
| WO | WO 02/00651 | | 1/2002 |
| WO | WO 02/06211 | | 1/2002 |
| WO | WO 02/15694 | | 2/2002 |
| WO | WO 02/059155 | | 8/2002 |
| WO | WO 03/024221 | | 3/2003 |
| WO | WO 03/062392 | | 7/2003 |
| WO | WO 2004/004463 | | 1/2004 |
| WO | WO 2004/008849 | | 1/2004 |
| WO | WO 2004/008861 | | 1/2004 |
| WO | WO 2004/010779 | | 2/2004 |
| WO | WO 2004/018410 | | 3/2004 |
| WO | WO 2004/029066 | | 4/2004 |
| WO | WO 2004/044169 | | 5/2004 |
| WO | WO 2004/078770 | | 9/2004 |
| WO | WO 2005/094329 | | 10/2005 |
| WO | WO 2006/090234 | | 8/2006 |
| WO | WO 2007/147828 | | 12/2007 |
| WO | WO 2008/012027 | | 1/2008 |
| WO | WO 2008/013622 | | 1/2008 |
| WO | WO 2008/013925 | | 1/2008 |
| WO | WO2008000469 | * | 1/2008 |
| WO | WO 2008/047229 | | 4/2008 |
| WO | WO 2008/063300 | | 5/2008 |
| WO | WO 2008/138551 | | 11/2008 |
| WO | WO 2009/011904 | | 1/2009 |
| WO | WO 2009/049844 | | 4/2009 |
| WO | WO 2009/054984 | | 4/2009 |
| WO | WO 2009/055514 | | 4/2009 |
| WO | WO 2009/094407 | | 7/2009 |
| WO | WO 2009/094445 | | 7/2009 |
| WO | WO 2009/126691 | | 10/2009 |
| WO | WO 2010/135360 | | 11/2010 |

OTHER PUBLICATIONS

Baldwin et al. "Total Synthesis of Antitumor Agent AT-125, (α-S,5S)-α-Amino-3-Chloro-4,5-Dihydro-5-Isoxazoleacetic Acid," *Tetrahedron* 41(22): 5241-5260 (1985).

Berge et al., "Pharmaceutical Salts," *J. Pharm. Sci.* 66(1):1-19 (1977).

Bianchi and Grünanger, "Conversion of 2-isoxazolines to isoxazoles," *Tetrahedron* 21:817-822 (1965).

Bickerdike et al., "The Influence of 5-Hydroxytryptamine Re-uptake Blockade on CCK Receptor Antagonist Effects in the Rat Elevated Zero-Maze," *Eur. J. Pharm.* 271:403-411 (1994).

Bondarenko et al., "2-Isoxazolines from Arylcyclopropanes: I. Monoarylcyclopropanes in a Reaction with Nitrosyl Chloride Activation by Sulfur(IV) Oxide," *Russ. J. Org. Chem.* 42(2):249-255 (2006) (Abstract Only).

Bondarenko et al., "4,5-Dihydroisoxazoles from arylcyclopropanes by reactions with nitrosyl chloride activated with sulfur trioxide," *Russ. Chem. Bull. Int. Ed.* 52(3):778 (2003).

Bondarenko et al., "4,5-Dihydroisoxazoles from Arylcyclopropanes: II. Reaction of Arycyclopropanes with Nitrosyl Chloride Activated by Sulfur(VI) Oxide," *Russ. J. Org. Chem.* 43(4):564-570 (2007) (Abstract Only).

Bondarenko et al., "Synthesis of 4,5-Dihydroisoxazoles from Arylcyclopropanes and Nitrosyl Chloride," *Russ. J. Org. Chem.* 39(7) 1021-1024 (2003) (Abstract Only).

Bondarenko et al., "$\Delta^2$-isoxazolines from arylcyclopropanes: III. Phenylcyclopropanes substituted in three-membered ring in reaction with nitrosyl chloride activated with oxides of sulfur(IV, VI)," *Russ. J. Org. Chem.* 45(2):218-225 (2009).

Bracey et al., "Structural Adaptations in Membrane Enzyme That Terminates Endocannabinoid Signaling," *Science* 298:1793-1796 (2002).

Caetano et al., "Preparation of β-hydroxyesters from isoxazolines. A selective Ni⁰bpy-catalyzed electrochemical method," *Tetrahedron Lett.* 44:8217-8220 (2003).

Caldirola et al., "Conversion of Isoxazolines to β-Hydroxy Esters. Synthesis of 2-Deoxy-D-Ribose," *Tetrahedron Lett.* 27(38):4647-4650 (1986).

Castelhano et al., "Synthesis, Chemistry, and Absolute Configuration of Novel Transglutaminase Inhibitors Containing a 3-Halo-4,5-dihydroisoxazole," *Bioorg. Chem.* 16:335-340 (1988).

Castro et al., "The Addition of Diallylzinc to 5-Substituted 4,5-Dihydroisoxazoles," *Synlett* 6:798-800 (1999).

Chiacchio et al., "Enantioselective synthesis of homocarbocyclic-2'-oxo-3'-azanucleosides," *Tetrahedron* 62:1171-1181 (2006).

Choi et al., "Chemistry and Biology of Dihydroisoxazole Derivatives: Selectives Inhibitors of Human Transglutaminase 2," *Chem. & Biol.* 12:469-475 (2005).

Conti et al., "Synthesis and biological evaluation of new amino acids structurally related to the antitumor agent acivicin," *Farmaco* 58:683-690 (2003).

Conti et al., "Synthesis and pharmacological characterization at glutamate receptors of erythro- and threo-tricholomic acid and homologues thereof," *Tetrahedron* 63:2249-2256 (2007).

(56) References Cited

OTHER PUBLICATIONS

Conti et al., "Synthesis of New Bicyclic Analogues of Glutamic Acid," *Tetrahedron* 55:5623-5634 (1999).
Coutouli-Argyropoulou and Pilanidou, "An entry to new isoxazoline analogues of dideoxynucleosides by bromonitrile oxide 1,3-dipolar cycloaddition," *Tetrahedron Lett.* 44:3755-3758 (2003).
Cravatt et al., "Functional disassociation of the central and peripheral fatty acid amide signaling systems," *Proc. Natl. Acad. Sci. U.S.A.* 101(29):10821-10826 (2004).
Cravatt et al., "Supersensitivity to Anandamide and Enhanced Endogenous Cannabinoid Signaling in Mice Lacking Fatty Acid Amide Hydrolase," *Proc. Natl. Acad. Sci. U.S.A.* 98:9371-9376 (2001).
Cremonesi et al., "Enzymatic resolution of (±)-5-phenyl-4,5-dihydroisoxazole-3-carboxylic acid ethyl ester and its transformations into polyfunctionalised amino acids and dipeptides," *Tetrahedron: Assymetry* 20:1940-1947 (2009).
Dallanoce et al., "Synthesis and Functional Characterization of Novel Derivatives Related to Oxotremorine and Oxotremorine-M," *Bioorg. Med. Chem.* 7:1539-1547 (1999).
Davies et al., "Chiral Vinyl Dioxazaborocines in Synthesis: Asymmetric Synthesis of 5-Substituted $\Delta^2$-Isoxazolines via Nitrile Oxide Cycloaddition," *Tetrahedron Lett.* 39:8513-8516 (1998).
Davies et al., "Enhanced asymmetric induction in cycloadditions to bridgehead-chiral vinyl dioxazaborocines," *Tetrahedron Lett.* 41:4229-4233 (2000).
De Amici et al., "Analogues of the low-efficacy partial $GABA_A$ agonist 4-PIOL. Syntheses and in vitro pharmacological studies," *Eur. J. Med. Chem.* 26:625-631 (1991).
De Amici et al., "Nitrile Oxides in Medicinal Chemistry-2. Synthesis of the Two Enantiomers of Dihydromuscimol," *Tetrahedron* 46(6):1975-1986 (1990).
De Sarlo et al., "Simple in situ preparation of fulminic acid," *Tetrahedron Lett.* 24(17):1815-1816 (1983).
Desai et al., , A Convenient, Rapid and Eco-Friendly Synthesis of Isoxazoline Heterocyclic Moiety Containing Bridge at 2°-Amine as Potential Pharmacological Agent, *J. Iran. Chem. Soc.* 5(1):67-73 (2008).
DeShong et al., "Stereoselection in Acyclic Systems. The Synthesis of Amino Sugars via Nitrone Cycloadditions," *J. Am. Chem. Soc.* 106:5598-5602 (1984).
Deutsch, "Design of On-Target FAAH Inhibitors," *Chem. Biol.* 12(11):1157-1158 (2005).
Drake et al., "Characterizing high-affinity antigen/antibody complexes by kinetic- and equilibrium-based methods," *Anal. Biochem.* 328(1):35-43 (2004).
El-Seedi et al., "Cycloadditions with Alkoxynitrile Oxides, RO—C=N$^+$—O$^-$, (Alkyl Cyanate N-Oxides)," *Acta Chem. Scand.* 37:1004-1011 (1993).
Fisera, "1,3-Dipolar Cycloadditions of Sugar-Derived Nitrones and their Utilization in Synthesis," *Top. Heterocycl. Chem.* 7:287-323 (2007).
Gavezzotti, "Are Crystal Structures Predictable?" *Acc. Chem. Res.* 27:309-314 (1994).
Gazzaeva et al., "Substituted Phenylcyclopropanes in the Synthesis of 2-Isoxazolines," *Chem. Heterocycl. Compd.* 20(3):246-250 (1984).
Giang and Cravatt, "Molecular characterization of human and mouse fatty acid amide hydrolases," *Proc. Natl. Acad. Sci. U.S.A.* 94(6):2238-2242 (1997).
Girardin et al., "Synthesis of 3-Aminoisoxazoles via the Addition-Elimination of Amines on 3-Bromoisoxazolines," *Org Lett.* 11(5):1159-1162 (2009).
Griesbeck et al., "Synthesis of α-Amino-3-chloro-4,5-dihydro-5-methyl-5-isoxazoleacetic Acid, a Ring-Methylated Analogue of the Antitumor Agent Acivicin," *Liebigs Ann.* (AT-125), 619-623 (1995).
Halling et al., "Synthesis of 3-Hydroxy-4-amino Acids and Butyrolactones via the Isoxazoline Route," *Liebigs Ann. Chem.* 985-990 (1989).

Hausch et al., "Design, Synthesis, and Evaluation of Gluten Peptide Analogs as Selective Inhibitors of Human Tissue Transglutaminase," *Chem. & Biol.* 10:225-231 (2003).
Hillard et al., "Characterization of the kinetics and distribution of N-arachidonylethanolamine (anandamide) hydrolysis by rat brain," *Biochim. Biophys. Acta.* 1257(3):249-256 (1995).
Huang et al., "Identification of a new class of molecules, the arachidonyl amino acids, and characterization of one member that inhibits pain," *J. Biol. Chem.* 276(46):42639-42644 (2001).
Huisgen and Christ, "1,3-Dipolar Cycloadditions of Fulminic Acid," *Angew. Chem., Int. Ed.* 6(5):456-156 (1967).
Iida et al., "Enantioselective Total Synthesis of (+)-Negamycin and (−)-Epinegamycin by an Asymmetric 1,3-Dipolar Cycloaddition," *J. Am. Chem. Soc.* 108(15):4647-4648 (1986).
Insel et al., "Rat Pup Ultrasonic Calls: Possible Mediation by the Benzodiazepine Receptor Complex," *Pharmacol., Biochem. Behav.* 24:1263-1267 (1986).
Ivanavicius et al., "Structural pathology in a rodent model of osteoarthritis is associated with neuropathic pain: increased expression of ATF-3 and pharmacological characterisation," *Pain* 128(3):272-282 (2007).
Karbarz et al., "Biochemical and biological properties of 4-(3-phenyl-[1,2,4] thiadiazol-5-yl)-piperazine-1-carboxylic acid phenylamide, a mechanism-based inhibitor of fatty acid amide hydrolase," *Anesth. Analg.* 108(1):316-329 (2009).
Kasahara et al., "Asymetric Total Synthesis of (+)-Negamycin and (−)-3-Epinegamycin via Enantioselective 1,3-Dipolar Cycloaddition," *J. Org. Chem.* 54:2225-2233 (1989).
Kathuria et al., "Modulation of anxiety through blockade of anandamide hydrolysis," *Nat. Med.* 9(1):76-81 (2003).
Khasabova et al., "decrease in anandamide signaling contributes to the maintenance of cutaneous mechanical hyperalgesia in a model of bone cancer pain," *J. Neurosci.* 28(44):11141-11152 (2008).
Kim and Chung, "An experimental model for peripheral neuropathy produced by segmental spinal nerve ligation in the rat," *Pain* 50(3):355-363 (1992).
Knight et al., "New Regiospecific Catalytic Approaches to 4,5-Dihydroisoxazoles and 2,5-Dihydroisoxazoles from O-Propargylic Hydroxylamines," *Synlett* (4):628-632 (2010).
Kociolek and Kalbarczyk, "Ring Opening of 3-Bromo-2-Isoxazolines to β-Hydroxy Nitriles," *Synth. Comm.* 34(23):4387-4394 (2004).
Kurkowska et al., "Chemoenzymatic synthesis of primary alcohols with a 2-isoxazoline moiety," *J. Chem. Research* (S) 480-482 (2003).
Labar et al., "Fatty Acid Amide Hydrolase: From Characterization to Therapeutics," *Chem. Biodivers.* 4(8):1882-1902 (2007).
Lambert and Fowler, "The Endocannabinoid system: Drug Targets, Lead Compounds, and Potential Therapeutic Applications," *J. Med. Chem.* 48(16):5059-5087 (2005).
Liu et al., "Sodium Percarbonate: A Multifunctional Reagent for the Preparation of Optically Active 4-Hydroxy $\Delta^2$-Isoxazolines," *Tetrahedron Lett.* 38(39):6795-6798 (1997).
Lynch et al., "Effects of Neuropeptide Y on Ingestion of Flavored Solutions in Nondeprived Rats," *Physiol. Behav.* 54:877-880 (1993).
Malamas and Palka, "New Synthesis of Isoxazolidines," *J. Heterocyclic Chem.* 33:475-478 (1996).
Maurelli et al, "Two novel classes of neuroactive fatty acid amides are substrates for mouse neuroblastoma 'anandamide amidohydrolase'," *FEBS Lett.* 377(1):82-86 (1995).
McGovren et al., "Pharmacokinetic and Biochemical Studies on Acivicin in Phase I Clinical Trials," *Cancer Res.* 45:4460-4463 (1985).
McKinney et al., "Structure and Function of Fatty Acid Amide Hydrolase," *Ann. Rev. Biochem.* 74:411-432 (2005).
McPartland et al., "A shifted repertoire of endocannabinoid genes in the zebrafish (*Danio rerio*)," *Mol. Genet. Genomics* 277(5):555-570 (2007).
Mendelson and Basile, "The Hypnotic Actions of the Fatty Acid Amide, Oleamide," *Neuropsychopharmacology* 25(5 Suppl):S36-S39 (2001).
Merino et al., An efficient approach to enantiometric isoxazolidinyl analogues of tiazofurin based on nitrone cycloadditions, *Tetrahedron: Assymmetry* 16:3865-3876, 2005.

(56) References Cited

OTHER PUBLICATIONS

Miczek, et al., "Aggression, Anxiety and Vocalizations in Animals: GABAa and 5-HT Anxiolytics," *Psychopharmacology* 121:38-56 (1995).

Minkkila et al., "Discovery of Boronic Acids as Novel and Potent Inhibitors of Fatty Acid Amide Hydrolase," *J. Med. Chem.* 51:7057-7060 (2008).

Mochalov et al., "Reaction of Substituted 7-Cyclopropyl-1,4-Benzodioxanes with Dinitrogen Tetraoxide," *Chem. Heterocycl. Compd.* 35(3):281-285 (1999).

Mochalov et al., "Transformations of Arylcyclopropanes under the Action of Ninitrogen Tetroxide," *Russian J. Org. Chem.* 34(9):1322-1330 (1998).

Mzengeza and Whitney, "A Total Synthesis of Acivicin," *J. Am. Chem. Soc.* 109(1):276-277 (1987).

Mzengeza and Whitney, "Asymmetric Induction in Nitrone Cycloadditions: A Total Synthesis of Acivicin by Double Asymmetric Induction," *J. Org. Chem.* 53(17):4074-4081 (1988).

Mzengeza and Whitney, "Dipolar Cycloaddition Reaction of N-Tetrahydropyranylnitrone," *J. Chem. Soc., Chem. Commun.* 606-607 (1984).

Nouvet et al., "Synthesis of New Perhydro-(1,4)-diazepin-2-ones as Constrained Peptidomimetics," *Tetrahedron Lett.* 39:2099-2102 (1998).

Nozaki-Taguchi et al., "Vincristine-induced allodynia in the rat," *Pain* 93(1):69-76 (2001).

Pacher et al., "The Endocannabinoid System as an Emerging Target of Pharmacotherapy," *Pharmacol. Rev.* 58(3):389-462 (2006).

Patricelli et al., "Comparative characterization of a wild type and transmembrane domain-deleted fatty acid amide hydrolase: identification of the transmembrane domain as a site for oligomerization," *Biochemistry* 37(43):15177-15187 (1998).

Pennicott and Lindell, "The Preparation of 2-Isoxazolines from O-Propargylic Hydroxylamines via a Tandem Rearrangement—Cyclisation Reaction," *Synlett* 3:463-465 (2006).

Pillarisetti et al., "Pain and beyond: fatty acid amides and fatty acid amide hydrolase inhibitors in cardiovascular and metabolic diseases," *Drug Discov.* 1-14 (2009).

Pinto et al., "Synthesis and Pharmacological Characterization at Glutamate Receptors of the Four Enantiopure Isomers of Tricholomic Acid," *J. Med. Chem.* 51:2311-2315 (2008).

Piomelli et al., "Pharmacological Profile of the Selective FAAH Inhibitor KDS-4103 (URB597)," *CNS Drug Rev.* 12(1):21-38 (2006).

Piperno et al., "First Example of Direct $RuO_4$-Catalyzed Oxidation of Isoxazolidines to 3-Isoxazolidones," *J. Org. Chem.* 72:3958-3960 (2007).

Pohjakallio and Pihko, "A Versatile Entry to 3-Unsubstituted 2-Isoxazolines," *Synlett* 6:827-830 (2008).

Pohjakallio and Pihko, "Enantioselective Synthesis of 2-Isoxazolines by a One-Flask Conjugate Addition/Oxime-Transfer Process," *Chem. Eur. J.* 15:3960-3964 (2009).

Porsolt et al., "Depression: A New Animal Model Sensitive to Antidepressant Treatments," *Nature* 266:730-732 (1977).

Quistad et al., "Fatty Acid Amide Hydrolase Inhibition by Neurotoxic Organophosphous Pesticides," *Toxicol. Appl. Pharmacol.* 173(1):48-55 (2001).

Ramarao et al., "A Fluorescence-Based Assay for Fatty Acid Amide Hydrolase Compatible with High-Throughput Screening," *Anal. Biochem.* 343:143-151 (2005).

Rani et al., "Isoxazolinyl derivatives of anthranilic acid as antiinflammatory agents," *Indian J. Chem.* 42B:1729-1733 (2003).

Rohloff et al., "Bromonitrile Oxide [3+2] Cycloadditions in Water," *Tetrahedron Lett.* 33(22):3113-3116 (1992).

Ros et al., "A Practical Synthesis of Enantiopure 4,5-Dihydroisoxazole-5-carboxylic Acids," *Synlett* (19):2899-2904 (2005).

Saghetelian et al., "A FAAH-regulated class of N-acyl taurines that activates TRP ion channels," *Biochemistry* 45(30):9007-9015 (2006).

Schlosburg et al., "Targeting Fatty Acid Amide Hydrolase (FAAH) to Treat Pain and Inflammation," *The AAOS J.* 11(1):39-44 (2009).

Seo et al., "2-5,Diarylisoxazolidin-3-ones," *J. Korean Chem. Soc.* 36(3):(1992).

Seo et al., "A New Method for the Preparation of β-Hydroxy Nitriles; Transformation of 3-Bromo-2-Isoxazolines to β-Hydroxy Nitriles by Treatment of Alkanethiolates," *Synth. Commun.* 24(10):1433-1439 (1994).

Shabarov et al., "Isoxazolines from arylcyclopropanes," *Zhurnal Organicheskoi Khimii* 18:2627-2628 (1982) (Includes English translation of Abstract).

Shepherd et al., "Behavioural and pharmacological characterisation of the elevated "zero-maze" as an animal model of anxiety," *Psychopharmacology* (Berl).;116(1):56-64 (1994).

Smirnova et al., "Reaction of (p-alkylphenyl)cyclopropanes with dinitrogen tetroxide," *Zhurnal Oraganicheskoi Khimii* 24:1189-1195 (1988) (Includes English translation of Abstract).

Smith et al. "Different sites of acivicin binding and inactivation of γ-glutamyl transpeptidases," *Proc. Natl. Acad. Sci. U.S.A..* 92:2360-2364 (1995).

Steru et al., "The Tail Suspension Test: A New Method for Screening Antidepressants in Mice," *Psychopharmacology* 85:367-370 (1985).

Stevens and Polniaszek, "Synthesis of Analogues of the Antitumor Antibiotic AT-125 (Acivicin)," *Tetrahedron* 9(1):743-747 (1983).

Thorsteinsson et al., "Cycloserine Fatty Acid Derivatives as Prodrugs: Synthesis, Degradation and in Vitro Skin Permeability," *Chem. Pharm. Bull* 50(4):554-557 (2002).

Tokizane et al., "Asymmetric reduction of racemic 2-isoxazolines," *Tetrahedron: Assymetry* 19:2519-2528 (2008).

Torssell and Zeuthen, "Reactions of t-Butyl Nitrones and Trimethylsilyl Nitronates. Synthesis and Reactions of Isoxazolidines and 2-Isoxazolines," *Acta Chem. Scand.* B 32:118-124 (1978).

Vandervoorde, "Overview of the Chemical Families of Fatty Acid Amide Hydrolase and Monoacylglycerol Lipase Inhibitors," *Curr. Top. Med. Chem.* 8(3):247-267 (2008).

Vaughan and Spencer, "5-Phenyl-2-isoxazoline-3-carboxylic Acid," *J. Org. Chem.* 25:1160-1164 (1960).

Vippagunta et al., "Crystalline Solids," *Adv. Drug Deliv. Rev.* 48(1):3-26 (2001).

Volkova et al., "The first synthesis of nitro-substituted cyclopropanes and spiropentanes via oxidation of the corresponding amino derivative," *Tetrahedron Lett.* 50:2793-2796 (2009).

Vyas et al., "A Short, Efficient Total Synthesis of (±) Acivicin and (±) Bromo-Acivicin," *Tetrahedron Lett* .25(5):487-490 (1984).

Wada et al., "Crystal Structures of *Escherichia coli* γ-Glutamyltranspeptidase in Complex with Azaserine and Acivicin: Novel Mechanistic Implication for Inhibition by Glutamine Antagonists," *J. Mol. Biol.* 380: 361-372 (2008).

Wade and Hinney, "Benzenesulfonylnitrile Oxide A 1.3-Dipole Exhibiting Modified Reactivity in Cycloaddition Reactions," *Tetrahedron Lett.* (2):139-142 (1979).

Wade et al., "Benzenesulfonylncarbonitrile Oxide.4 Substitution Reactions of 3-(Phenylsulfonyl) isoxazolines," *J. Org. Chem.* 48:1796-1800 (1983).

Walker et al., (not Walter) "Pain modulation by release of the endogenous cannabinoid anandamide," *Proc. Natl. Acad. Sci. U. S. A..* 96(21):12198-203 (1999).

Wang et al., "High-Throughput Screening for the Discovery of Inhibitors of Fatty Acid Amide Hydrolase Using a Microsome-Based Fluorescent Assay," *J. Biomol. Screen.* 11:519-527(2006).

Wei et al., "A second fatty acid amide hydrolase with variable distribution among placental mammals," *J. Biol. Chem.* 281(48):36569-36578 (2006).

Wilen et al., "Strategies in Optical Resolution," *Tetrahedron* 33:2725-2736 (1977).

Willner, "Validity, Reliability and Utility of the Chronic Mild Stress Model of Depression: a 10-year Review and Evaluation," *Psychopharmacology* 134:319-329 (1997).

Wilson et al., "An animal model of chronic inflammatory pain: pharmacological and temporal differentiation from acute models," *Eur. J. Pain* 10(6):537-549 (2006).

(56) References Cited

OTHER PUBLICATIONS

Winslow et al., "Infant Rat Separation is a Sensitive Test for Novel Anxiolyitics," *Prog. Neuro-Psychopharmacol. & Biol. Psychiat.* 15:745-757 (1991).
Wolfe et al., "Cyclic hydroxamates, especially multiply substituted [1,2]oxazinan-3-ones," *Can. J. Chem.* 81:937-960 (2003).
Yeom et al., "Gold(I)-Catalyzed Hydroaminative Cyclization Leading to 2,5-Dihydro-isoxazole," *Synlett* (14): 2292-2294 (2007).
Zielinska-Blajet et al., "Ring-closure reactions through intramolecular substitution of thiophenoxide by oxygen and nitrogen nucleophiles: simple stereospecific synthesis of 4,5-dihydroisoxazoles and 4,5-dihydropyrazoles," *Tetrahedron* 61:5235-5240 (2005).
Non-Final Office Action dated Jun. 19, 2012 for U.S. Appl. No. 12/782,650.
Non-Final Office Action dated Aug. 1, 2012 for U.S. Appl. No. 12/782,658.
Kozikowaki et al., "Methods for Stereoselective Cis Cyanohydroxylation and Carboxyhydroxylation of Olefins," *J. Org. Chem.* 48:366-372 (1983).
Rover et al., "Synthesis and Biochemical Evaluation of N-(4-Phenylthiazol-2-yl)benzenesulfonamides as High-Affinity Inhibitors of Kynurenine 3-Hydroxylase," *J. Med. Chem.* 40(26):4378-4385 (1997).
Cecchi et al., "1,4-Diazabicyclo[2.2.2]octane (DABCO) as an Efficient Reagent for the Synthesis of Isoxazole Derivatives from Primary Nitro Compounds and Dipolarophiles: The Role of the Base," *Eur. J. Org. Chem.* 4852-4860 (2006).
Conti et al., "Synthesis of New $\Delta^2$-Isoxazoline Derivatives and their Pharmacological Characterization as $\beta$-Adrenergic Receptor Antagonists," *Bioorg. Med. Chem.* 6:401-408 (1998).
Dallanoce et al., "Synthesis of enantiopure $\Delta^2$-isoxazoline derivatives and evaluation of their affinity and efficacy profiles at human $\beta$-adrenergic receptor subtypes," *Bioorg. Med. Chem.* 14(13):4393-4401 (2006).
Conti et al., "Stereoselective Synthesis of 4-Amino-3-hydroxy-4,5,6,6a-tetrahydro-3aH-cyclopenta[d]isoxazole-4carboxylic Acid, a Conformationally Constrained Analogue of Aspartic Acid," *Synthesis* 14:2145-2148 (2007).
Ivanova et al., "Application of a Thermal $\beta$-Elimination Reaction to N-Alkoxy-3,3-dinitro-isoxazolidines: Synthesis of 3-Nitroisoxazolines," *Synthesis* 4:706-710 (2006).
Wade et al., "Diastereofacial Selectivity Studies on 3-Alkenyl-4,5-diphenyl-4,5-dihydroisoxazoles," *J. Org. Chem.* 55:3045-3051 (1990).
Boyd et al., "Stereoselective Cycloaddition of Nitrile Oxides to 4-Vinyl-Oxazolines and -Oxazolidines," *Tetrahedron Lett.* 34(19):3169-3172 (1993).
Non-final Office Action dated May 21, 2013 for U.S. Appl. No. 12/782,650.
RN 1071120-8-4 registry, Nov. 6, 2008.
Moriarty et al., "Oxidation of Phenolic Compounds with Organohypervalent Iodine Reagents," *Organic Reactions* 57:327-415 (2001).
Non-final Office Action dated Jul. 18, 2013 for U.S. Appl. No. 12/782,658.
Final Office Action dated Dec. 19, 2012 for U.S. Appl. No. 12/782,650.
Final Office Action dated Feb. 27, 2013 for U.S. Appl. No. 12/782,658.

* cited by examiner

SEQUENCE LISTING

<160> NUMBER OF SEQ ID NOS: 1

<210> SEQ ID NO 1
<211> LENGTH: 579
<212> TYPE: PRT
<213> ORGANISM: Homo sapiens

<400> SEQUENCE: 1

```
Met Val Gln Tyr Glu Leu Trp Ala Ala Leu Pro Gly Ala Ser Gly Val
1               5                   10                  15

Ala Leu Ala Cys Cys Phe Val Ala Ala Ala Val Ala Leu Arg Trp Ser
                20                  25                  30

Gly Arg Arg Thr Ala Arg Gly Ala Val Val Arg Ala Arg Gln Arg Gln
            35                  40                  45

Arg Ala Gly Leu Glu Asn Met Asp Arg Ala Ala Gln Arg Phe Arg Leu
        50                  55                  60

Gln Asn Pro Asp Leu Asp Ser Glu Ala Leu Leu Ala Leu Pro Leu Pro
65                  70                  75                  80

Gln Leu Val Gln Lys Leu His Ser Arg Glu Leu Ala Pro Glu Ala Val
                85                  90                  95

Leu Phe Thr Tyr Val Gly Lys Ala Trp Glu Val Asn Lys Gly Thr Asn
                100                 105                 110

Cys Val Thr Ser Tyr Leu Ala Asp Cys Glu Thr Gln Leu Ser Gln Ala
            115                 120                 125

Pro Arg Gln Gly Leu Leu Tyr Gly Val Pro Val Ser Leu Lys Glu Cys
        130                 135                 140

Phe Thr Tyr Lys Gly Gln Asp Ser Thr Leu Gly Leu Ser Leu Asn Glu
145                 150                 155                 160

Gly Val Pro Ala Glu Cys Asp Ser Val Val His Val Leu Lys Leu
                165                 170                 175

Gln Gly Ala Val Pro Phe Val His Thr Asn Val Pro Gln Ser Met Phe
            180                 185                 190

Ser Tyr Asp Cys Ser Asn Pro Leu Phe Gly Gln Thr Val Asn Pro Trp
        195                 200                 205

Lys Ser Ser Lys Ser Pro Gly Gly Ser Ser Gly Gly Glu Gly Ala Leu
        210                 215                 220

Ile Gly Ser Gly Gly Ser Pro Leu Gly Leu Gly Thr Asp Ile Gly Gly
225                 230                 235                 240

Ser Ile Arg Phe Pro Ser Ser Phe Cys Gly Ile Cys Gly Leu Lys Pro
                245                 250                 255

Thr Gly Asn Arg Leu Ser Lys Ser Gly Leu Lys Gly Cys Val Tyr Gly
                260                 265                 270

Gln Glu Ala Val Arg Leu Ser Val Gly Pro Met Ala Arg Asp Val Glu
            275                 280                 285

Ser Leu Ala Leu Cys Leu Arg Ala Leu Leu Cys Glu Asp Met Phe Arg
```

```
            290                 295                 300
Leu Asp Pro Thr Val Pro Pro Leu Pro Phe Arg Glu Glu Val Tyr Thr
305                 310                 315                 320

Ser Ser Gln Pro Leu Arg Val Gly Tyr Tyr Glu Thr Asp Asn Tyr Thr
                325                 330                 335

Met Pro Ser Pro Ala Met Arg Arg Ala Val Leu Glu Thr Lys Gln Ser
                340                 345                 350

Leu Glu Ala Ala Gly His Thr Leu Val Pro Phe Leu Pro Ser Asn Ile
                355                 360                 365

Pro His Ala Leu Glu Thr Leu Ser Thr Gly Gly Leu Phe Ser Asp Gly
                370                 375                 380

Gly His Thr Phe Leu Gln Asn Phe Lys Gly Asp Phe Val Asp Pro Cys
385                 390                 395                 400

Leu Gly Asp Leu Val Ser Ile Leu Lys Leu Pro Gln Trp Leu Lys Gly
                405                 410                 415

Leu Leu Ala Phe Leu Val Lys Pro Leu Leu Pro Arg Leu Ser Ala Phe
                420                 425                 430

Leu Ser Asn Met Lys Ser Arg Ser Ala Gly Lys Leu Trp Glu Leu Gln
                435                 440                 445

His Glu Ile Glu Val Tyr Arg Lys Thr Val Ile Ala Gln Trp Arg Ala
                450                 455                 460

Leu Asp Leu Asp Val Val Leu Thr Pro Met Leu Ala Pro Ala Leu Asp
465                 470                 475                 480

Leu Asn Ala Pro Gly Arg Ala Thr Gly Ala Val Ser Tyr Thr Met Leu
                485                 490                 495

Tyr Asn Cys Leu Asp Phe Pro Ala Gly Val Val Pro Val Thr Thr Val
                500                 505                 510

Thr Ala Glu Asp Glu Ala Gln Met Glu His Tyr Arg Gly Tyr Phe Gly
                515                 520                 525

Asp Ile Trp Asp Lys Met Leu Gln Lys Gly Met Lys Lys Ser Val Gly
                530                 535                 540

Leu Pro Val Ala Val Gln Cys Val Ala Leu Pro Trp Gln Glu Glu Leu
545                 550                 555                 560

Cys Leu Arg Phe Met Arg Glu Val Glu Arg Leu Met Thr Pro Glu Lys
                565                 570                 575

Gln Ser Ser
```

ISOXAZOLINES AS INHIBITORS OF FATTY ACID AMIDE HYDROLASE

CROSS REFERENCE TO RELATED APPLICATIONS

The present application claims priority to U.S. provisional patent application Ser. No. 61/179,283 filed May 18, 2009, the entirety of which is hereby incorporated herein by reference.

SEQUENCE LISTING

In accordance with 37 CFR 1.52(e)(5), a Sequence Listing in the form of a text file (entitled "SequenceListing.txt," created on Jul. 27, 2010, and 6 kilobytes) is incorporated herein by reference in its entirety.

BACKGROUND

Fatty acid amide hydrolase (FAAH), also referred to as oleamide hydrolase and anandamide amidohydrolase, is an integral membrane protein responsible for the hydrolysis of several important endogenous neuromodulating fatty acid amides (FAAs), including anadamide, oleoylethanolamide and palmitoylethanolamide, and is intimately involved in their regulation. Because these FAAs interact with cannabinoid and vanilliod receptors, they are often referred to as "endocannabinoids" or "endovanilliods". Initial interest in this area focused on developing FAAH inhibitors to augment the actions of FAAs and reduce pain. Further investigation found FAAH inhibitors, through interactions of the FAAs with unique extracellular and intracellular receptors, can be used to treat a variety of conditions that include, but are not limited to, inflammation, metabolic disorders (e.g., obesity-related conditions and wasting conditions such as cachexias and anorexia), disorders of the central nervous system (e.g., disorders associated with neurotoxicity and/or neurotrauma, stroke, multiple sclerosis, spinal cord injury, movement disorders such as basal ganglia disorders, amylotrophic lateral sclerosis, Alzheimer's disease, epilepsy, mental disorders such as anxiety, depression, learning disorders and Schizophrenia, sleep disorders such as insomnia, nausea and/or emesis, and drug addiction), cardiac disorders (e.g., hypertention, circulatory shock, myocardial reperfusion injury and atherosclerosis) and glaucoma (Pacher et al., "The Endocannabinoid System as an Emerging Target of Pharmacotherapy" *Pharmacological Reviews* (2006) 58:389-462; Pillarisetti et al., "Pain and Beyond: Fatty Acid Amides and Fatty Acid Amide Hydrolase Inhibitors in Cardiovascular and Metabolic Diseases" *Drug Discovery Today* (2009) 597:1-14).

SUMMARY

The present invention provides isoxazoline FAAH inhibitor compounds of the formula (I):

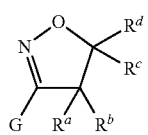

(I)

or pharmaceutically acceptable forms thereof, wherein:
each of $R^a$, $R^b$, and $R^c$ independently is selected from —H, $C_{1\text{-}10}$ alkyl and $C_{1\text{-}10}$ perhaloalkyl, $R^d$ is the group -L-Z, and Z is selected from 3-14 membered heterocyclyl and 5-14 membered heteroaryl;

L is a covalent bond or a divalent $C_1$ hydrocarbon group, wherein one, two or three methylene units of L are optionally and independently replaced with one or more oxygen, sulfur or nitrogen atoms;

G is selected from —CN, —NO$_2$, —S(=O)R$^e$, —SO$_2$R$^e$, —SO$_2$NR$^f$R$^e$, —PO$_2$R$^e$, —PO$_2$OR$^e$, —PO$_2$NR$^f$R$^e$, —(C=O)R$^e$, —(C=O)OR$^e$, —(C=O)NR$^f$R$^e$, —Br, —I, —F, —Cl, —OR$^e$, —ONR$^f$R$^e$, —ONR$^f$(C=O)R$^e$, —ONR$^f$SO$_2$R$^e$, —ONR$^f$PO$_2$R$^e$, —ONR$^f$PO$_2$OR$^e$, —SR$^e$, —OSO$_2$R$^e$, —NR$^f$SO$_2$R$^e$, —OPO$_2$R$^e$, —OPO$_2$OR$^e$, —NR$^f$PO$_2$R$^e$, —NR$^f$PO$_2$OR$^e$, —OPO$_2$NR$^f$R$^e$, —O(C=O)R$^e$, —O(C=O)OR$^e$, —NR$^f$R$^e$, —NR$^f$(C=O)R$^e$, —NR$^f$(C=O)OR$^e$, —O(C=O)NR$^f$R$^e$, —NR$^f$(C=NR$^f$)NR$^f$R$^e$, —O(C=NR$^f$)NR$^f$R$^e$, —NR$^f$(C=NR$^f$)OR$^e$, —[N(R$^f$)$_2$R$^e$]$^+$ X$^-$ wherein X$^-$ is a counterion;

each $R^e$ is selected from $C_{1\text{-}10}$ alkyl, $C_{2\text{-}10}$ alkenyl, $C_{2\text{-}10}$ alkynyl, $C_{3\text{-}10}$ carbocyclyl, $C_{6\text{-}14}$ aryl, 3-14 membered heterocyclyl and 5-14 membered heteroaryl; each $R^f$ attached to a nitrogen atom is, independently, selected from —H, $C_{1\text{-}10}$ alkyl, or an amino protecting group; or $R^e$ and $R^f$ are joined to form an 3-14 membered heterocyclyl ring or an 5-14 membered heteroaryl ring.

The present invention also provides pharmaceutical compositions comprising a compound of formula (I), or a pharmaceutically acceptable form thereof, and a pharmaceutically acceptable excipient.

The present invention also provides methods for treating an FAAH-mediated condition in a subject comprising administering a therapeutically effective amount of a compound of formula (I), or a pharmaceutically acceptable form thereof, to a subject in need thereof.

The details of additional embodiments of the invention are set forth in the accompanying Detailed Description and Exemplification as described below. Other features, objects, and advantages of the invention will be apparent from this description and from the claims.

DEFINITIONS

Definitions of specific functional groups ad chemical terms are described in more detail below. The chemical elements are identified in accordance with the Periodic Table of the Elements, CAS version, Handbook of Chemistry and Physics, 75th Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5th Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3rd Edition, Cambridge University Press, Cambridge, 1987.

Certain compounds of the present invention can comprise one or more asymmetric centers, and thus can exist in various isomeric forms, e.g., enantiomers and/or diastereomers. The compounds provided herein can be in the form of an individual enantiomer, diastereomer or geometric isomer, or can be in the form of a mixture of stereoisomers, including racemic mixtures and mixtures enriched in one or more stereoisomer. In certain embodiments, the compounds of the invention are enantiopure compounds. In certain other embodiments, mixtures of stereoisomers are provided.

Furthermore, certain compounds, as described herein may have one or more double bonds that can exist as either the cis or trans, or the E or Z isomer, unless otherwise indicated. The invention additionally encompasses the compounds as individual isomers substantially free of other isomers, and alternatively, as mixtures of various isomers, e.g., racemic mixtures of E/Z isomers or mixtures enriched in one E/Z isomer.

The terms "enantiomerically enriched," "enantiomerically pure" and "non-racemic," as used interchangeably herein, refer to compositions in which the percent by weight of one enantiomer is greater than the amount of that one enantiomer in a control mixture of the racemic composition (e.g., greater than 1:1 by weight). For example, an enantiomerically enriched preparation of the (S)-enantiomer, means a preparation of the compound having greater than 50% by weight of the (S)-enantiomer relative to the (R)-enantiomer, more preferably at least 75% by weight, and even more preferably at least 80% by weight. In some embodiments, the enrichment can be much greater than 80% by weight, providing a "substantially enantiomerically enriched," "substantially enantiomerically pure" or a "substantially non-racemic" preparation, which refers to preparations of compositions which have at least 85% by weight of one enantiomer relative to other enantiomer, more preferably at least 90% by weight, and even more preferably at least 95% by weight. In preferred embodiments, the enantiomerically enriched composition has a higher potency with respect to therapeutic utility per unit mass than does the racemic mixture of that composition. Enantiomers can be isolated from mixtures by methods known to those skilled in the art, including chiral high pressure liquid chromatography (HPLC) and the formation and crystallization of chiral salts; or preferred enantiomers can be prepared by asymmetric syntheses. See, for example, Jacques, et al., *Enantiomers, Racemates and Resolutions* (Wiley Interscience, New York, 1981); Wilen, S. H., et al., *Tetrahedron* 33:2725 (1977); Eliel, E. L. *Stereochemistry of Carbon Compounds* (McGraw-Hill, NY, 1962); and Wilen, S. H. *Tables of Resolving Agents and Optical Resolutions* p. 268 (E. L. Eliel, Ed., Univ. of Notre Dame Press, Notre Dame, Ind. 1972).

When a range of values is listed, it is intended to encompass each value and sub-range within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

As used herein a "direct bond" or "covalent bond" refers to a single bond joining two groups.

As used herein, alone or as part of another group, "halo" and "halogen" refer to fluorine (fluoro, —F), chlorine (chloro, —Cl), bromine (bromo, —Br), or iodine (iodo, —I).

As used herein, alone or as part of another group, "alkyl" refers to a monoradical of a straight-chain or branched saturated hydrocarbon group having from 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), n-propyl ($C_3$), isopropyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Additional examples of alkyl groups include n-heptyl ($C_7$), n-octyl ($C_8$) and the like. Unless otherwise specified, each instance of an alkyl group is independently unsubstituted (an "unsubstituted alkyl") or substituted (a "substituted alkyl") are substituted with 1, 2, 3, 4, or 5 substituents as described herein. In certain embodiments, the alkyl group is an unsubstituted $C_{1-10}$ alkyl (e.g., —$CH_3$). In certain embodiments, the alkyl group is a substituted $C_{1-10}$ alkyl.

"Perhaloalkyl" as defined herein refers to an alkyl group having from 1 to 10 carbon atoms wherein all of the hydrogen atoms are each independently replaced halogen, e.g., selected from fluoro, bromo, chloro or iodo ("$C_{1-10}$ perhaloalkyl"). In some embodiments, the alkyl moiety has 1 to 8 carbon atoms ("$C_{1-8}$ perhaloalkyl"). In some embodiments, the alkyl moiety has 1 to 6 carbon atoms ("$C_{1-6}$ perhaloalkyl"). In some embodiments, the alkyl moiety has 1 to 4 carbon atoms ("$C_{1-4}$ perhaloalkyl"). In some embodiments, the alkyl moiety has 1 to 3 carbon atoms ("$C_{1-3}$ perhaloalkyl"). In some embodiments, the alkyl moiety has 1 to 2 carbon atoms ("$C_{1-2}$ perhaloalkyl"). In some embodiments, all of the hydrogen atoms are each replaced with fluoro. In some embodiments, all of the hydrogen atoms are each replaced with chloro. Examples of perhaloalkyl groups include —$CF_3$, —$CF_2CF_3$, —$CF_2CF_2CF_3$, —$CCl_3$, —$CFCl_2$, —$CF_2Cl$ and the like.

As used herein, alone or as part of another group, "alkenyl" refers to a monoradical of a straight-chain or branched hydrocarbon group having from 2 to 10 carbon atoms and one or more carbon-carbon double bonds ("$C_{2-10}$ alkenyl"). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$) and the like. Examples of $C_{2-6}$ alkenyl groups include the aforementioned $C_{2-4}$ alkenyl groups as well as pentenyl ($C_5$), pentadienyl ($C_5$), hexenyl ($C_6$) and the like. Additional examples of alkenyl include heptenyl ($C_7$), octenyl ($C_8$), octatrienyl ($C_8$) and the like. Unless otherwise specified, each instance of an alkenyl group is independently unsubstituted (an "unsubstituted alkenyl") or substituted (a "substituted alkenyl") with 1, 2, 3, 4, or 5 substituents as described herein. In certain embodiments, the alkenyl group is an unsubstituted $C_{2-10}$ alkenyl. In certain embodiments, the alkenyl group is a substituted $C_2$-10 alkenyl.

As used herein, alone or as part of another group, "alkynyl" refers to a monoradical of a straight-chain or branched hydrocarbon group having from 2 to 10 carbon atoms and one or more carbon-carbon triple bonds ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-8}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atom ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$) and the like. Examples of $C_{2-6}$ alkenyl groups include the aforementioned $C_{2-4}$ alkynyl groups as well as pentynyl ($C_5$), hexynyl ($C_6$) and the like. Additional examples of alkynyl include heptynyl ($C_7$), octynyl ($C_8$) and the like. Unless otherwise specified, each instance of an alkynyl group is independently unsubstituted (an "unsubstituted alkynyl") or substituted (a "substituted alkynyl") with 1, 2, 3, 4, or 5 substituents as described herein. In certain embodiments, the alkynyl group is an unsubstituted $C_{2-10}$ alkynyl. In certain embodiments, the alkynyl group is a substituted $C_{2-10}$ alkynyl.

A "divalent $C_{1-6}$ hydrocarbon group" is a divalent $C_{1-6}$ alkyl group, divalent $C_{1-6}$ alkenyl group or divalent $C_1$ alkynyl group wherein one, two or three methylene units (—$CH_2$—) of the hydrocarbon chain are optionally and independently replaced with one or more oxygen, sulfur or nitrogen atoms. In certain embodiments, the divalent $C_{1-6}$ hydrocarbon group is a divalent $C_{is}$ alkyl group. In certain embodiments, the divalent $C_{1-6}$ hydrocarbon group is an unsubstituted divalent $C_{1-6}$ hydrocarbon group (e.g., an unsubstituted divalent $C_1$ alkyl group).

As used herein, alone or as part of another group, "alkoxy" refers to an alkyl group, as defined herein, substituted with an oxygen atom, wherein the point of attachment is the oxygen atom. In certain embodiments, the alkyl group has 1 to 10 carbon atoms ("$C_{1-10}$ alkoxy"). In some embodiments, the alkyl group has 1 to 8 carbon atoms ("$C_{1-8}$ alkoxy"). In some embodiments, the alkyl group has 1 to 6 carbon atoms ("$C_{1-6}$ alkoxy"). In some embodiments, the alkyl group has 1 to 4 carbon atoms ("$C_{1-4}$ alkoxy"). Examples of $C_{1-4}$ alkoxy groups include methoxy ($C_1$), ethoxy ($C_2$), propoxy ($C_3$), isopropoxy ($C_3$), butoxy ($C_4$), tert-butoxy ($C_5$) and the like. Examples of $C_{1-6}$ alkoxy groups include the aforementioned $C_{1-4}$ alkoxy groups as well as pentyloxy ($C_5$), isopentyloxy ($C_5$), neopentyloxy ($C_5$), hexyloxy ($C_6$) and the like. Additional examples of alkoxy groups include heptyloxy ($C_7$), octyloxy ($C_8$) and the like. Unless otherwise specified, each instance of the alkyl moiety of the alkoxy group is independently unsubstituted (an "unsubstituted alkoxy") or substituted (a "substituted alkoxy") are substituted with 1, 2, 3, 4, or 5 substituents as described herein. In certain embodiments, the alkoxy group is an unsubstituted $C_{2-10}$ alkoxy (e.g., —$OCH_3$). In certain embodiments, the alkoxy group is a substituted $C_{2-10}$ alkoxy (e.g., perhaloalkoxy as defined herein).

"Perhaloalkoxy" refers to an alkoxy group wherein the all the hydrogen atoms of the alkyl moiety are each independently replaced with halogen atoms selected from fluoro, chloro, bromo and iodo. In certain embodiments, the alkyl moiety has 1 to 10 carbon atoms ("$C_{1-10}$ perhaloalkoxy"). In some embodiments, the alkyl moiety has 1 to 8 carbon atoms ("$C_{1-8}$ perhaloalkoxy"). In some embodiments, the alkyl moiety has 1 to 6 carbon atoms ("$C_{1-6}$ perhaloalkoxy"). In some embodiments, the alkyl moiety has 1 to 4 carbon atoms ("$C_{1-4}$ perhaloalkoxy"). In some embodiments, the alkyl moiety has 1 to 3 carbon atoms ("$C_{1-3}$ perhaloalkoxy"). In some embodiments, the alkyl moiety has 1 to 2 carbon atoms ("$C_{1-2}$ perhaloalkoxy"). In some embodiments, all of the hydrogen atoms are each replaced with fluoro. In some embodiments, all of the hydrogen atoms are each replaced with chloro. Examples of perhaloalkoxy groups include, but are not limited to, —$OCF_3$, —$OCF_2CF_3$, —$OCF_2CF_2CF_3$, —$OCCl_3$, —$OCFCl_2$, —$OCF_2Cl$ and the like.

As used herein, alone or as part of another group, "carbocyclyl" refers to a radical of a non-aromatic cyclic hydrocarbon group having from 3 to 10 ring carbon atoms ("$C_{3-10}$ carbocyclyl") and zero heteroatoms in the non-aromatic ring system. In some embodiments, a carbocyclyl group has 3 to 8 ring carbon atoms ("$C_{3-8}$ carbocyclyl"). In some embodiments, a carbocyclyl group has 3 to 6 ring carbon atoms ("$C_{3-6}$ carbocyclyl"). In some embodiments, a carbocyclyl group has 3 to 6 ring carbon atoms ("$C_{3-6}$ carbocyclyl"). In some embodiments, a carbocyclyl group has 5 to 10 ring carbon atoms ("$C_{5-10}$ carbocyclyl"). Examples of $C_{3-6}$ carbocyclyl groups include, without limitation, cyclopropyl ($C_3$), cyclobutyl ($C_4$), cyclopentyl ($C_5$), cyclopentenyl ($C_5$), cyclohexyl ($C_6$), cyclohexenyl ($C_6$), cyclohexadienyl ($C_6$) and the like. Examples of $C_{3-8}$ carbocyclyl groups include the aforementioned $C_{3-6}$ carbocyclyl groups as well as cycloheptyl ($C_7$), cycloheptadienyl ($C_7$), cycloheptatrienyl ($C_7$), cyclooctyl ($C_8$), bicyclo[2.2.1]heptanyl, bicyclo[2.2.2]octanyl, and the like. Examples of $C_{3-10}$ carbocyclyl groups include the aforementioned $C_{3-8}$ carbocyclyl groups as well as octahydro-1H-indenyl, decahydronaphthalenyl, spiro[4.5]decanyl and the like. As the foregoing examples illustrate, in certain embodiments, the carbocyclyl group is either monocyclic ("monocyclic carbocyclyl") or polycyclic (e.g., containing a fused, bridged or spiraling system such as a bicyclic system ("bicyclic carbocyclyl") or tricyclic system ("tricyclic carbocyclyl")) and can be saturated or can contain one or more carbon-carbon double or triple bonds. "Carbocyclyl" also includes ring systems wherein the carbocyclyl ring, as defined above, is fused with one or more aryl or heteroaryl groups wherein the point of attachment is on the carbocyclyl ring. Unless otherwise specified, each instance of a carbocyclyl group is independently unsubstituted (an "unsubstituted carbocyclyl") or substituted (a "substituted carbocyclyl") with 1, 2, 3, 4, or 5 substituents as described herein. In certain embodiments, the carbocyclyl group is an unsubstituted $C_{3-10}$ carbocyclyl. In certain embodiments, the carbocyclyl group is a substituted $C_{3-10}$ carbocyclyl.

In some embodiments, "carbocyclyl" is a monocyclic, saturated carbocyclyl group having from 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_{5-6}$ cycloalkyl groups include cyclopentyl ($C_5$) and cyclohexyl ($C_5$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with 1, 2, 3, 4, or 5 substituents as described herein. In certain embodiments, the cycloalkyl group is an unsubstituted $C_{3-10}$ cycloalkyl. In certain embodiments, the cycloalkyl group is a substituted $C_{3-10}$ cycloalkyl.

As used herein, alone or as part of another group, "heterocyclyl" refers to a radical of a 3- to 14-membered non-aromatic ring system having ring carbon atoms and 1 to 4 ring heteroatoms, wherein each heteroatom is independently selected from nitrogen, oxygen and sulfur ("3-14 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or polycyclic (e.g., a fused, bridged or spiraling system such as a bicyclic system ("bicyclic heterocyclyl") or tricyclic system ("tricyclic heterocyclyl")), and can be saturated or can contain one or more carbon-carbon double or triple bonds. Heterocyclyl polycyclic ring systems can include one or more heteroatoms in one or both rings. "Heterocyclyl" also includes ring systems wherein the heterocycyl ring, as defined above, is fused with one or more carbocycyl groups wherein the point of attachment is either on the carbocycyl or heterocyclyl ring, or ring systems wherein the heterocyclyl ring, as defined above, is fused with one or more aryl or heteroaryl groups, wherein the point of attachment is on the heterocyclyl ring. In some embodiments, a heterocyclyl group is a 5-10 membered non-aromatic ring system having ring carbon atoms and 1-4 ring heteroatoms, wherein each heteroatom is independently selected from nitrogen, oxygen and sulfur ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen and sulfur ("5-6 membered heterocyclyl"). In some embodiments, the 5-6 membered heterocyclyl has 1-3 ring heteroatoms selected from nitrogen, oxygen and sulfur. In some embodiments, the 5-6 membered heterocyclyl has 1-2 ring heteroatoms selected from nitrogen, oxygen and sulfur. In some embodiments, the 5-6 membered heterocyclyl has 1 ring heteroatom selected from nitrogen, oxygen and sulfur. Exemplary 3-membered heterocyclyls containing 1 heteroatom include, without limitation, azirdinyl, oxiranyl, thiorenyl. Exemplary 4-membered heterocyclyls containing 1 heteroatom include, without limitation, azetidinyl, oxetanyl and thietanyl. Exemplary 5-membered heterocyclyls containing 1 heteroatom include, without limitation, tetrahydrofuranyl, dihydrofuranyl, tetrahydrothiophenyl, dihydrothiophenyl, pyrrolidinyl, dihydropyrrolyl and pyrrolyl-2,5-dione. Exemplary 5-membered heterocyclyls containing 2 heteroatoms include, without limitation, dioxolanyl, oxathiolanyl and dithiolanyl. Exemplary 5-membered heterocyclyls containing 3 heteroatoms include, without limitation, triazolinyl, oxadiazolinyl, and thiadiazolinyl. Exemplary 6-membered heterocyclyl groups containing 1 heteroatom include, without limitation, piperidinyl, tetrahydropyranyl, dihydropyridinyl, and thianyl. Exemplary 6-membered heterocyclyl groups containing 2 heteroatoms include, without limitation, piperazinyl, morpholinyl, dithianyl, dioxanyl. Exemplary 6-membered heterocyclyl groups containing 2 heteroatoms include, without limitation, triazinanyl. Exemplary 7-membered heterocyclyl groups containing 1 heteroatom include, without limitation, azepanyl, oxepanyl and thiepanyl. Exemplary 8-membered heterocyclyl groups containing 1 heteroatom include, without limitation, azocanyl, oxecanyl and thiocanyl. Exemplary bicyclic heterocyclyl groups include, without limitation, indolinyl, isoindolinyl, dihydrobenzofuranyl, dihydrobenzothienyl, tetrahydrobenzothienyl, tetrahydrobenzofuranyl, tetrahydroindolyl, tetrahydroquinolinyl, tetrahydroisoquinolinyl, decahydroquinolinyl, decahydroisoquinolinyl, octahydrochromenyl, octahydroisochromenyl, decahydronaphthyridinyl, dec ahydro-1,8-naphthyridinyl, octahydropyrrolo[3,2-b]pyrrole, indolinyl, phthalimidyl, naphthalimidyl, chromanyl, chromenyl, 1H-benzo[e][1,4]diazepinyl, 1,4,5,7-tetrahydropyrano[3,4-b]pyrrolyl, 5,6-dihydro-4H-furo[3,2-b]pyrrolyl, 6,7-dihydro-5H-furo[3,2-b]pyranyl, 5,7-dihydro-4H-thieno[2,3-c]pyranyl, 2,3-dihydro-1H-pyrrolo[2,3-b]pyridinyl, 2,3-dihydrofuro[2,3-b]pyridinyl, 4,5,6,7-tetrahydro-1H-pyrrolo[2,3-b]pyridinyl, 4,5,6,7-tetrahydrofuro[3,2-c]pyridinyl, 4,5,6,7-tetrahydrothieno[3,2-b]pyridinyl, 1,2,3,4-tetrahydro-1,6-naphthyridinyl, and the like. Unless otherwise specified, each instance of heterocyclyl is independently unsubstituted (an "unsubstituted heterocyclyl") or substituted (a "substituted heterocyclyl") with 1, 2, 3, 4, or 5 substituents as described herein. In certain embodiments, the heterocyclyl group is an unsubstituted 3-14 membered heterocyclyl. In certain embodiments, the heterocyclyl group is a substituted 3-14 membered heterocyclyl.

As used herein, alone or as part of another group, "aryl" refers to a radical of a monocyclic or polycyclic (e.g., bicyclic or tricyclic) aromatic ring system (e.g., having 6, 10 or 14 π electrons shared in a cyclic array) having 6-14 ring carbon atoms and zero heteroatoms provided in the aromatic ring system ("$C_{6-14}$ aryl"). In some embodiments, an aryl group has 6 ring carbon atoms ("$C_6$ aryl"; e.g., phenyl). In some embodiments, an aryl group has 10 ring carbon atoms ("$C_{10}$ aryl"; e.g., naphthyl such as 1-naphthyl and 2-naphthyl). In some embodiments, an aryl group has 14 ring carbon atoms ("$C_{1-4}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring. Unless otherwise specified, each instance of an aryl group is independently unsubstituted (an "unsubstituted aryl") or substituted (a "substituted aryl") with 1, 2, 3, 4, or 5 substituents as described herein. In certain embodiments, the aryl group is an unsubstituted $C_{6-14}$ aryl. In certain embodiments, the aryl group is a substituted $C_{6-14}$ aryl.

"Aralkyl" is a subset of "alkyl" and refers to an alkyl group, as defined herein, substituted by an aryl group, as defined herein, wherein the point of attachment is on the alkyl moiety.

As used herein, alone or as part of another group, "heteroaryl" refers to a radical of a 5-14 membered monocyclic or polycyclic (e.g., bicyclic or tricyclic) aromatic ring system (e.g., having 6, 10 or 14 π electrons shared in a cyclic array) having ring carbon atoms and 1-4 ring heteroatoms provided in the aromatic ring system, wherein each heteroatom is independently selected from nitrogen, oxygen and sulfur ("5-14 membered heteroaryl"). In heteroaryl groups that contain one or more nitrogen atoms, the point of attachment can be a carbon or nitrogen atom, as valency permits. Heteroaryl polycyclic ring systems can include one or more heteroatoms in one or both rings. "Heteroaryl" also includes ring systems wherein the heteroaryl ring, as defined above, is fused with one or more aryl groups wherein the point of attachment is either on the aryl or on the heteroaryl ring, or wherein the heteroaryl ring, as defined above, is fused with one or more carbocycyl or heterocycyl groups wherein the point of attachment is on the heteroaryl ring. For polycyclic heteroaryl groups wherein one ring does not contain a heteroatom (e.g., indolyl, quinolinyl, carbazolyl and the like) the point of attachment can be on either ring, i.e., either the ring bearing a heteroatom (e.g., 2-indolyl) or the ring that does not contain a heteroatom (e.g., 5-indolyl). In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen and sulfur ("5-6 membered heteroaryl"). In some embodiments, the 5-6 membered heteroaryl has 1-3 ring heteroatoms selected from nitrogen, oxygen and sulfur. In some embodiments, the 5-6 membered heteroaryl has 1-2 ring heteroatoms selected from nitrogen, oxygen and sulfur. In some embodiments, the 5-6 membered heteroaryl has 1 ring heteroatom selected from nitrogen, oxygen and sulfur. Exemplary 5-membered heteroaryls containing 1 heteroatom include, without limitation, pyrrolyl, furanyl and thiophenyl. Exemplary 5-membered heteroaryls containing 2 heteroatoms include, without limitation, imidazolyl, pyrazolyl, oxazolyl, isoxazolyl, thiazolyl, and isothiazolyl. Exemplary 5-membered heteroaryls containing 3 heteroatoms include, without limitation, triazolyl, oxadiazolyl, thiadiazolyl. Exemplary 5-membered heteroaryls containing 4 heteroatoms include, without limitation, tetrazolyl. Exemplary 6-membered heteroaryls containing 1 heteroatom include, without limitation, pyridinyl. Exemplary 6-membered heteroaryls containing 2 heteroatoms include, without limitation, pyridazinyl, pyrimidinyl and pyrazinyl. Exemplary 6-membered heteroaryls containing 3 or 4 heteroatoms include, without limitation, triazinyl and tetrazinyl, respectively. Exemplary 7 membered heteroaryls containing 1 heteroatom include, without limitation, azepinyl, oxepinyl and thiepinyl. Exemplary 5,6-bicyclic heteroaryls include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryls include, without limitation, naphthyridinyl, pteridinyl, quinolinyl, isoquinolinyl, cinnolinyl, quinoxalinyl, phthalazinyl and quinazolinyl. Exemplary tricyclic heteroaryls include, without limitation, phenanthridinyl, dibenzofuranyl, carbazolyl, acridinyl, phenothiazinyl, phenoxazinyl and phenazinyl. Unless otherwise specified, each instance of a heteroaryl group is independently unsubstituted (an "unsubstituted heteroaryl") or substituted (a "substituted heteroaryl") with 1, 2, 3, 4, or 5 substituents as described herein. In certain embodiments, the heteroaryl group is an unsubstituted 5-14 membered heteroaryl. In certain embodiments, the heteroaryl group is a substituted 5-14 membered heteroaryl.

"Heteroaralkyl" is a subset of "alkyl" and refers to an alkyl group, as defined herein, substituted by a heteroaryl group, as defined herein, wherein the point of attachment is on the alkyl moiety.

As used herein, the term "partially unsaturated" refers to a ring moiety that includes at least one double or triple bond. The term "partially unsaturated" is intended to encompass rings having multiple sites of unsaturation, but is not intended to include aromatic groups (e.g., aryl or heteroaryl moieties) as herein defined.

Alkyl, alkenyl, alkynyl, carbocyclyl, heterocyclyl, aryl and heteroaryl groups, as defined herein, are optionally substituted (e.g., "substituted" or "unsubstituted" alkyl, "substituted" or "unsubstituted" alkenyl, "substituted" or "unsubstituted" alkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted", whether preceded by the term "optionally" or not, means that at least one hydrogen present on a group (e.g., a carbon or nitrogen atom etc.) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position.

Exemplary carbon atom substituents include, but are not limited to, halogen (i.e., fluoro (—F), bromo (—Br), chloro (—Cl), and iodo (—I)), —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$OR$^{aa}$, —OSO$_2$R$^{aa}$, —S(=O)R$^{aa}$, —OS(=O)R$^{aa}$, —OSi(R$^{aa}$)$_3$ —C(=S)N(R$^{bb}$)$_2$, —C(=O)SR$^{aa}$, —C(=S)SR$^{aa}$, —SC(S)SR$^{aa}$, —P(=O)$_2$R$^{aa}$, —OP(=O)$_2$R$^{aa}$, —P(=O)(R$^{aa}$)$_2$, —OP(=O)(R$^{bb}$)$_2$, —OP(=O)(OR$^{cc}$)$_2$, —P(=O)$_2$N(R$^{bb}$)$_2$, —OP(=O)$_2$N(R$^{bb}$)$_2$, —P(=O)(NR$^{bb}$)$_2$, —OP(=O)(NR$^{bb}$)$_2$, —NR$^{bb}$P(=O)(OR$^{cc}$)$_2$, —NR$^{bb}$P(=O)(NR$^{bb}$)$_2$, —P(R$^{cc}$)$_2$, —P(R$^{cc}$)$_3$, —OP(R$^{cc}$)$_2$, —OP(R$^{cc}$)$_3$, —B(OR$^{cc}$)$_2$, —BR$^{aa}$(OR$^{cc}$), C$_{1-10}$ alkyl, C$_{1-10}$ perhaloalkyl, C$_{2-10}$ alkenyl, C$_{2-10}$ alkynyl, C$_{3-14}$ carbocyclyl, 3-14 membered heterocyclyl, C$_{6-14}$ aryl, and 5-14 membered heteroaryl, wherein each alkyl, alkenyl, alkynyl, carbocyclyl, heterocyclyl, aryl, and heteroaryl is independently substituted with 0, 1, 2, 3, 4, or 5 R$^{dd}$ groups;

or two geminal hydrogens on a carbon atom are replaced with the group =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, =NOR$^{cc}$;

each instance of R$^{aa}$ is, independently, selected from C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{bb}$ is, independently, selected from hydrogen, —OH, —N(R$^{cc}$)$_2$, —CN, —C(=O)R$^{aa}$, —C(=O)N(R$^{cc}$)$_2$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups attached to an N atom are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of $R^{cc}$ is, independently, selected from hydrogen, $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two $R^{cc}$ groups attached to an N atom are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups;

each instance of $R^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3$$^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R)$_2$, —OC(=O)N(R)$_2$, —NR$^{ff}$C(=O)R$^{ee}$, —NeCO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)$_2$R$^{ee}$, —P(=O)(R$^{ee}$)$_2$, —OP(=O)(R$^{ee}$)$_2$, —OP(=O)(OR$^{ee}$)$_2$, $C_{1-6}$ alkyl, $C_{1-6}$ perhaloalkyl, $C_{2-6}$ alkenyl, $C_{2-6}$ alkynyl, $C_{3-10}$ carbocyclyl, 3-10 membered heterocyclyl, $C_{6-10}$ aryl, 5-10 membered heteroaryl, wherein each alkyl, alkenyl, alkynyl, carbocyclyl, heterocyclyl, aryl, and heteroaryl is independently substituted with 0, 1, 2, 3, 4, or 5 $R^{gg}$ groups, or two geminal $R^{dd}$ substituents can be joined to form =O or =S;

each instance of $R^{ee}$ is, independently, selected from $C_{1-6}$ alkyl, $C_{1-6}$ perhaloalkyl, $C_{2-6}$ alkenyl, $C_{2-6}$ alkynyl, $C_{3-10}$ carbocyclyl, $C_{6-10}$ aryl, 3-10 membered heterocyclyl, and 3-10 membered heteroaryl, wherein each alkyl, alkenyl, alkynyl, carbocyclyl, heterocyclyl, aryl, and heteroaryl is independently substituted with 0, 1, 2, 3, 4, or 5 $R^{gg}$ groups;

each instance of $R^{ff}$ is, independently, selected from hydrogen, $C_{1-6}$ alkyl, $C_{1-6}$ perhaloalkyl, $C_{2-6}$ alkenyl, $C_{2-6}$ alkynyl, $C_{3-10}$ carbocyclyl, 3-10 membered heterocyclyl, $C_{6-10}$ aryl and 5-10 membered heteroaryl, or two $R^{ff}$ groups attached to an N atom are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{gg}$ groups; and each instance of $R^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3$X, —NH(C$_{1-6}$ alkyl)$_2$X, —NH$_2$(C$_{1-6}$ alkyl)X, —NH$_3$X, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —OC$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$ (C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{is}$ alkyl)$_3$ —C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)$_2$(C$_{1-6}$ alkyl), —P(=O)(C$_{1-6}$ alkyl)$_2$, —OP(=O)(C$_{1-6}$ alkyl)$_2$, —OP(=O)(OC$_{1-6}$ alkyl)$_2$, $C_1$ alkyl, $C_1$ perhaloalkyl, $C_{2-6}$ alkenyl, $C_{2-6}$ alkynyl-$C_{3-10}$ carbocyclyl, $C_{6-10}$ aryl, 3-10 membered heterocyclyl, 5-10 membered heteroaryl; or two geminal $R^{gg}$ substituents can be joined to form =O or =S;

wherein X$^-$ is a counterion.

As used herein, a "counterion" is a negatively charged group associated with a positively charged quarternary amine in order to maintain electronic neutrality. Exemplary counterions include halide ions (e.g., F$^-$, Cl$^-$, Br$^-$, I$^-$), NO$_3^-$, ClO$_4^-$, OH$^-$, H$_2$PO$_4^-$, HSO$_4^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like) and carboxylate ions (e.g., acetate, ethanoate, propanoate, benzoate, glycerate, lactate, tartrate, glycolate, and the like).

Nitrogen atoms can be substituted or unsubstituted as valency permits, and include primary, secondary, tertiary and quarternary nitrogen atoms. Exemplary nitrogen atom substitutents include, but are not limited to, hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{cc}$, —SO$_2$R$^{cc}$, —C(=NR$^{bb}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two $R^{cc}$ groups attached to an N atom are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined above.

In certain embodiments, the substituent present on the nitrogen atom is an amino protecting group. Amino protecting groups include, but are not limited to, —OH, —OR$^{aa}$, —N(R$^{cc}$)$_2$, —C(=O)R$^{aa}$, —C(=O)N(R$^{cc}$)$_2$, —CO$_2$R$^{aa}$, —SO$_2$R$^{aa}$, —C(=NR$^{cc}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{aa}$, —SO$_2$OR$^{cc}$, —SOR$^{aa}$, —C(=S)N(R$^{cc}$)$_2$, —C(=O)SR$^{cc}$, —C(=S)SR$^{cc}$, $C_{1-10}$ alkyl (e.g., aralkyl groups), $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl groups, wherein each alkyl, alkenyl, alkynyl, carbocyclyl, heterocyclyl, aralkyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined above. Amino protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

For example, amino protecting groups such as amide groups (e.g., —C(=O)R$^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxycarbonylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitro cinnamide, N-acetylmethionine derivative, o-nitrobenzamide and o-(benzoyloxymethyl)benzamide.

Amino protecting groups such as carbamate groups (e.g., —C(=O)OR$^{aa}$) include, but are not limited to, methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10, 10-dioxo-10,10,10,10-tetrahydrothioxanthyl)]methyl carbamate (DBD-Tmoc), 4-methoxyphenacyl carbamate (Phenoc), 2,2,2-trichloro ethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 24N,N-dicyclohexylcarboxamido)ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitrobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluene sulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxycarbonylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium)benzyl carbamate, and 2,4,6-trimethylbenzyl carbamate.

Amino protecting groups such as sulfonamide groups (e.g., —S(=O)$_2$R$^{aa}$) include, but are not limited to, p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzene sulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other amino protecting groups include, but are not limited to, phenothiazinyl-(10)-carbonyl derivative, N'-p-toluenesulfonylamino carbonyl derivative, N'-phenylaminothiocarbonyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethylene amine, N-[(2-pyridyl)mesityl]methyleneamine, N—(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl) amine, N-borane derivative, N-diphenylborinic acid derivative, N-[phenyl(pentacarbonylchromium- or tungsten) carbonyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide and 3-nitropyridinesulfenamide (Npys).

As used herein, a "leaving group" is an art-understood term referring to a molecular fragment that departs with a pair of electrons in heterolytic bond cleavage, wherein the molecular fragment is an anion or neutral molecule. See, for example, Smith, March *Advanced Organic Chemistry* 6th ed. (501-502).

These and other exemplary substituents are described in more detail in the Detailed Description, the Exemplification and in the claims. The invention is not intended to be limited in any manner by the above exemplary listing of substituents.

As used herein, a "pharmaceutically acceptable form thereof" includes pharmaceutically acceptable salts, hydrates, solvates, prodrugs, tautomers, isomers, and/or polymorphs of a compound of the present invention, as defined below and herein.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}\text{-alkyl})_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate.

In certain embodiments, the pharmaceutically acceptable form thereof is an isomer. As used herein, the term "isomer" includes any and all geometric isomers and stereoisomers. For example, "isomers" include cis- and trans-isomers, E- and Z-isomers, R- and S-enantiomers, diastereomers, (D)-isomers, (L)-isomers, racemic mixtures thereof, and other mixtures thereof, as falling within the scope of the invention.

In certain embodiments, the pharmaceutically acceptable form thereof is a tautomer. As used herein, the term "tautomer" includes two or more interconvertable compounds resulting from at least one formal migration of a hydrogen atom and at least one change in valency (e.g., a single bond to a double bond, a triple bond to a single bond, or vice versa). The exact ratio of the tautomers depends on several factors, including temperature, solvent, and pH. Tautomerizations (i.e., the reaction providing a tautomeric pair) may catalyzed by acid or base. Exemplary tautomerizations include keto-to-enol; amide-to-imide; lactam-to-lactim; enamine-to-imine; and enamine-to-(a different) enamine tautomerizations.

In certain embodiments, the pharmaceutically acceptable form thereof is a hydrate or solvate. As used herein, the term "hydrate" refers to a compound non-covalently associated with one or more molecules of water. Likewise, "solvate" refers to a compound non-covalently associated with one or more molecules of an organic solvent.

In certain embodiments, the pharmaceutically acceptable form thereof is a prodrug. As used herein, the term "prodrug" refers to a derivative of a parent compound that requires transformation within the body in order to release the parent compound. In certain cases, a prodrug has improved physical and/or delivery properties over the parent compound. Prodrugs are typically designed to enhance pharmaceutically and/or pharmacokinetically based properties associated with the parent compound. The advantage of a prodrug can lie in its physical properties, such as enhanced water solubility for parenteral administration at physiological pH compared to the parent compound, or it enhances absorption from the digestive tract, or it may enhance drug stability for long-term storage.

In certain embodiments, the pharmaceutically acceptable form thereof is a polymorph. As used herein, "polymorph" refers to a compound having more than one crystal structure, e.g., resulting from differences in molecular packing and/or molecular conformation of the compound in the solid state.

SEQUENCE IDENTIFICATION NUMBERS

```
SEQ. ID. NO.: Homo sapiens FAAH amino acid
sequence (SEQ ID NO: 1):
MVQYELWAALPGASGVALACCFVAAAVALRWSGRRTARGAVVRARQRQRA

GLENMDRAAQRFRLQNPDLDSEALLALPLPQLVQKLHSRELAPEAVLFTY

VGKAWEVNKGTNCVTSYLADCETQLSQAPRQGLLYGVPVSLKECFTYKGQ

DSTLGLSLNEGVPAECDSVVVHVLKLQGAVPFVHTNVPQSMFSYDCSNPL

FGQTVNPWKSSKSPGGSSGGEGALIGSGGSPLGLGTDIGGSIRFPSSFCG

ICGLKPTGNRLSKSGLKGCVYGQEAVRLSVGPMARDVESLALCLRALLCE

DMFRLDPTVPPLPFREEVYTSSQPLRVGYYETDNYTMPSPAMRRAVLETK

QSLEAAGHTLVPFLPSNIPHALETLSTGGLFSDGGHTFLQNFKGDFVDPC

LGDLVSILKLPQWLKGLLAFLVKPLLPRLSAFLSNMKSRSAGKLWELQHE

IEVYRKTVIAQWRALDLDVVLTPMLAPALDLNAPGRATGAVSYTMLYNCL

DFPAGVVPVTTVTAEDEAQMEHYRGYFGDIWDKMLQKGMKKSVGLPVAVQ

CVALPWQEELCLRFMREVERLMTPEKQSS
```

DETAILED DESCRIPTION

I. Compounds

The present invention provides isoxazoline FAAH inhibitor compounds of the formula (I):

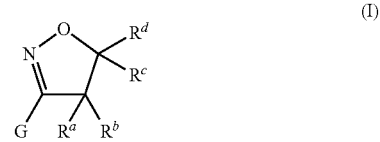

or a pharmaceutically acceptable form thereof,
wherein:
each of $R^a$, $R^b$, and $R^c$ independently is selected from —H, $C_{1-10}$ alkyl and $C_{1-10}$ perhaloalkyl, $R^d$ is the group -L-Z, and Z is selected from 3-14 membered heterocyclyl and 5-14 membered heteroaryl;

L is a covalent bond or a divalent $C_{1-6}$ hydrocarbon group, wherein one, two or three methylene units of L are optionally and independently replaced with one or more oxygen, sulfur or nitrogen atoms;

G is selected from —CN, —NO$_2$, —S(=O)$R^e$, —SO$_2R^e$, —SO$_2$NR$^f$R$^e$, —PO$_2R^e$, —PO$_2$OR$^e$, —PO$_2$NR$^f$R$^e$, —(C=O)R$^e$, —(C=O)OR$^e$, —(C=O)NR$^f$R$^e$, —Br, —I, —F, —Cl, —OR$^e$, —ONR$^f$R$^e$, —ONR$^f$(C=O)R$^e$, —ONR$^f$SO$_2R^e$, —ONR$^f$PO$_2R^e$, —ONR$^f$PO$_2$OR$^e$, —SR$^e$, —OSO$_2R^e$, —NR$^f$SO$_2R^e$, —OPO$_2R^e$, —OPO$_2$OR$^e$, —NR$^f$PO$_2R^e$, —NR$^f$PO$_2$OR$^e$, —OPO$_2$NR$^f$R$^e$, —O(C=O)R$^e$, —O(C=O)OR$^e$, —NR$^f$R$^e$, —NR$^f$(C=O)R$^e$, —NR$^f$ (C=O)OR$^e$, —O(C=O)NR$^f$R$^e$, —NR$^f$(C=NR$^f$)NR$^f$R$^e$, —O(C=NR$^f$)NR$^f$R$^e$, —NR$^f$(C=NR$^f$)OR$^e$, —[N(R$^f$)$_2$R$^e$]$^+$X$^-$ wherein X$^-$ is a counterion; and each R$^e$ is selected from C$_{1-10}$ alkyl, C$_{2-10}$ alkenyl, C$_{2-10}$ alkynyl, C$_{3-10}$ carbocyclyl, C$_{6-14}$ aryl, 3-14 membered heterocyclyl and 5-14 membered heteroaryl; each R$^f$ attached to a nitrogen atom is, independently, selected from —H, C$_{1-10}$ alkyl, or an amino protecting group; or R$^e$ and R$^f$ are joined to form an 3-14 membered heterocyclyl ring or an 5-14 membered heteroaryl ring.

Group G

As defined above, G is selected from —CN, —NO$_2$, —S(=O)R$^e$, —SO$_2$R$^e$, —SO$_2$NR$^f$R$^e$, —PO$_2$R$^e$, —PO$_2$OR$^e$, —PO$_2$NR$^f$R$^e$, —(C=O)R$^e$, —(C=O)OR$^e$, —(C=O)NR$^f$R$^e$, —Br, —I, —F, —Cl, —OR$^e$, —ONR$^f$R$^e$, —ONR$^f$(C=O)R$^e$, —ONR$^f$SO$_2$R$^e$, —ONR$^f$PO$_2$R$^e$, —ONR$^f$PO$_2$OR$^e$, —SR$^e$, —OSO$_2$R$^e$, —NR$^f$SO$_2$R$^e$, —OPO$_2$R$^e$, —OPO$_2$OR$^e$, —NR$^f$PO$_2$R$^e$, —NR$^f$PO$_2$OR$^e$, —OPO$_2$NR$^f$R$^e$, —O(C=O)R$^e$, —O(C=O)OR$^e$, —NR$^f$R$^e$, —NR$^f$(C=O)R$^e$, —NR$^f$(C=O)OR$^e$, —O(C=O)NR$^f$R$^e$, —NR$^f$(C=NR$^f$)NR$^f$R$^e$, —O(C=NR$^f$)NR$^f$R$^e$, —NR$^f$(C=NR$^f$)OR$^e$, —[N(R$^f$)$_2$R$^e$]$^+$X$^-$ wherein X$^-$ is a counterion;

and wherein R$^e$ is selected from C$_{1-10}$ alkyl, C$_{2-10}$ alkenyl, C$_{2-10}$ alkynyl, C$_{3-10}$ carbocyclyl, C$_{6-14}$ aryl, 3-14 membered heterocyclyl and 5-14 membered heteroaryl; each R$^f$ attached to a nitrogen atom is, independently, selected from —H, C$_{1-10}$ alkyl, or an amino protecting group; or R$^e$ and R$^f$ are joined to form an 3-14 membered heterocyclyl ring or an 5-14 membered heteroaryl ring.

In certain embodiments, G is not a leaving group, e.g., for example, G is selected from —F, —CN, —NO$_2$, —S(=O)R$^e$, —SO$_2$R$^e$, —SO$_2$NR$^f$R$^e$, —PO$_2$R$^e$, —PO$_2$OR$^e$, —PO$_2$NR$^f$R$^e$, —(C=O)R$^e$, —(C=O)OR$^e$, and —(C=O)NR$^f$R$^e$.

In certain embodiments, G is selected from —CN and —NO$_2$. In certain embodiments, G is —CN. In certain embodiments, G is —NO$_2$.

In certain embodiments, G is selected from —S(=O)R$^e$, —SO$_2$R$^e$, and —SO$_2$NR$^f$R$^e$. In certain embodiments, G is —S(=O)R$^e$. In certain embodiments, G is —SO$_2$R$^e$. In certain embodiments, G is —SO$_2$NR$^f$R$^e$.

In certain embodiments, G is selected from —PO$_2$R$^e$, —PO$_2$OR$^e$ and —PO$_2$NR$^f$R$^e$. In certain embodiments, G is —PO$_2$R$^e$. In certain embodiments, G is —PO$_2$OR$^e$. In certain embodiments, G is —PO$_2$NR$^f$R$^e$.

In certain embodiments, G is selected from —(C=O)R$^e$, —(C=O)OR$^e$ and —(C=O)NR$^f$R$^e$. In certain embodiments, G is —(C=O)R$^e$. In certain embodiments, G is —(C=O)OR$^e$. In certain embodiments, G is —(C=O)NR$^f$R$^e$.

However, in certain embodiments, G is a leaving group, e.g., for example, G is selected from —Cl, —Br, —I, —OR$^e$, —ONR$^f$R$^e$, —ONR$^f$(C=O)R$^e$, —ONR$^f$SO$_2$R$^e$, —ONR$^f$PO$_2$R$^e$, —ONR$^f$PO$_2$OR$^e$, —SR$^e$, —OSO$_2$R$^e$, —NR$^f$SO$_2$R$^e$, —OPO$_2$R$^e$, —OPO$_2$OR$^e$, —NR$^f$PO$_2$R$^e$, —NR$^f$PO$_2$OR$^e$, —OPO$_2$NR$^f$R$^e$, —O(C=O)R$^e$, —O(C=O)OR$^e$, —NR$^f$R$^e$, —NR$^f$(C=O)R$^e$, —NR$^f$(C=O)OR$^e$, —O(C=O)NR$^f$R$^e$, —NR$^f$(C=NR$^f$)NR$^f$R$^e$, —O(C=NR$^f$)NR$^f$R$^e$, —NR$^f$(C=NR$^f$)OR$^e$, and —[N(R$^f$)$_2$R$^e$] wherein X$^-$ is a counterion.

In certain embodiments, G is a halogen; i.e., selected from —F, —Cl, —Br and —I. In certain embodiments, G is —F. In certain embodiments, G is —Br. In certain embodiments, G is —I. In certain embodiments, G is —Cl. However, in certain embodiments, G is not a halogen. For example, in certain embodiments, G is not —Br. In certain embodiments, G is not —I. In certain embodiments, G is not —F. In certain embodiments, G is not —Cl.

In certain embodiments, G is selected from –OR$^e$, —ONR$^f$R$^e$, —ONR$^f$(C=O)R$^e$, —ONR$^f$SO$_2$R$^e$, —ONR$^f$PO$_2$R$^e$, —ONR$^f$PO$_2$OR$^e$, —OSO$_2$R$^e$, —OPO$_2$R$^e$, —OPO$_2$OR$^e$, —OPO$_2$NR$^f$R$^e$, —O(C=O)R$^e$, —O(C=O)OR$^e$, —O(C=O)NR$^f$R$^e$ and —O(C=NR$^f$)NR$^f$R$^e$. In certain embodiments, G is selected from —OR$^e$, —O(C=O)R$^e$, —O(C=O)OR$^e$, —O(C=O)NR$^f$R$^e$ and —O(C=NR$^f$)NR$^f$R$^e$. In certain embodiments, G is selected from —ONR$^f$R$^e$, —ONR$^f$(C=O)R$^e$, —ONR$^f$SO$_2$R$^e$, —ONR$^f$PO$_2$R$^e$, —ONR$^f$PO$_2$OR$^e$, —OPO$_2$NR$^f$R$^e$, —O(C=O)NR$^f$R$^e$ and —O(C=NR$^f$)NR$^f$R$^e$. In certain embodiments, G is —OR$^e$. In certain embodiments, G is —ONR$^f$R$^e$. In certain embodiments, G is —ONR$^f$(C=O)R$^e$. In certain embodiments, G is —ONR$^f$SO$_2$R$^e$. In certain embodiments, G is —ONR$^f$PO$_2$R$^e$. In certain embodiments, G is —ONR$^f$PO$_2$OR$^e$. In certain embodiments, G is —OSO$_2$R$^e$. In certain embodiments, G is —OPO$_2$R$^e$. In certain embodiments, G is —OPO$_2$OR$^e$. In certain embodiments, G is —OPO$_2$NR$^f$R$^e$. In certain embodiments, G is —O(C=O)R$^e$. In certain embodiments, G is —O(C=O)OR$^e$. In certain embodiments, G is —O(C=O)NR$^f$R$^e$. In certain embodiments, G is —O(C=NR$^f$)NR$^f$R$^e$.

In certain embodiments, G is selected from —OR$^e$ and —SR$^e$. In certain embodiments, G is selected from —OR$^e$. In certain embodiments, G is —SR$^e$.

In certain embodiments, G is selected from —NR$^f$SO$_2$R$^e$, —NR$^f$PO$_2$R$^e$, —NR$^f$PO$_2$OR$^e$, —NR$^f$R$^e$, —NR$^f$(C=O)R$^e$, —NR$^f$(C=O)OR$^e$, —NR$^f$(C=NR$^f$)NR$^f$R$^e$, —NR$^f$(C=NR$^f$)OR$^e$ and —[N(R$^f$)$_2$R$^e$]$^+$X$^-$ wherein X$^-$ is a counterion. In certain embodiments, G is selected from —NR$^f$SO$_2$R$^e$, —NR$^f$PO$_2$R$^e$, —NR$^f$PO$_2$OR$^e$, —NR$^f$R$^e$, —NR$^f$(C=O)R$^e$ and —NR$^f$(C=O)OR$^e$. In certain embodiments, G is selected from —NR$^f$SO$_2$R$^e$, —NR$^f$R$^e$, —NR$^f$(C=O)R$^e$ and —NR$^f$(C=O)OR$^e$. In certain embodiments, G is —NR$^f$SO$_2$R$^e$. In certain embodiments, G is —NR$^f$PO$_2$R$^e$. In certain embodiments, G is —NR$^f$PO$_2$OR$^e$. In certain embodiments, G is —NR$^f$R$^e$. In certain embodiments, G is —NR$^f$(C=O)R$^e$. In certain embodiments, G is —NR$^f$(C=O)OR$^e$. In certain embodiments, G is —NR$^f$(C=NR$^f$)NR$^f$R$^e$. In certain embodiments, G is —NR$^f$(C=NR$^f$)OR$^e$. In certain embodiments, G is —[N(R$^f$)$_2$R$^e$]$^+$X$^-$ wherein X$^-$ is a counterion.

Additional embodiments of G, included in the description of groups R$^e$ and R$^f$, and further exemplified in the Tables and Examples, is provided below and herein.

R$^e$ of Group G

As defined generally above, in certain embodiments, wherein G is selected from —S(=O)R$^e$, —SO$_2$R$^e$, —SO$_2$NR$^f$R$^e$, —PO$_2$R$^e$, —PO$_2$OR$^e$, —PO$_2$NR$^f$R$^e$, —(C=O)R$^e$, —(C=O)OR$^e$, —(C=O)NR$^f$R$^e$, —OR$^e$, —ONR$^f$R$^e$, —ONR$^f$(C=O)R$^e$, —ONR$^f$SO$_2$R$^e$, —ONR$^f$PO$_2$R$^e$, —ONR$^f$PO$_2$OR$^e$, —SR$^e$, —OSO$_2$R$^e$, —NR$^f$SO$_2$R$^e$, —OPO$_2$R$^e$, —OPO$_2$OR$^e$, —NR$^f$PO$_2$R$^e$, —NR$^f$PO$_2$OR$^e$, —OPO$_2$NR$^f$R$^e$, —O(C=O)R$^e$, —O(C=O)OR$^e$, —NR$^f$R$^e$, —NR$^f$(C=O)R$^e$, —NR$^f$(C=O)OR$^e$, —O(C=O)NR$^f$R$^e$, —NR$^f$(C=NR$^f$)NR$^f$R$^e$, —O(C=NR$^f$)NR$^f$R$^e$, —NR$^f$(C=NR$^f$)OR$^e$, and —[N(R$^f$)$_2$R$^e$]$^+$X$^-$ wherein X$^-$ is a counterion, R$^e$ is selected from C$_{1-10}$ alkyl, C$_{2-10}$ alkenyl, C$_{2-10}$ alkynyl, C$_{3-10}$ carbocyclyl, C$_{6-14}$ aryl, 3-14 membered heterocyclyl and 5-14 membered heteroaryl.

In certain embodiments, R$^e$ is selected from C$_{1-10}$ alkyl, C$_{2-10}$ alkenyl, C$_{2-10}$ alkynyl, C$_{3-10}$ carbocyclyl, C$_{6-14}$ aryl, 3-14 membered heterocyclyl and 5-14 membered heteroaryl, wherein the alkyl, alkenyl, alkynyl, carbocycyl, aryl, heterocyclyl, and heteroaryl groups are substituted with 0, 1, 2, 3, 4 or 5 $R^h$ groups, as defined below and herein.

In certain embodiments, $R^e$ is $C_{1-10}$ alkyl. In certain embodiments, $R^e$ is $C_{1-6}$ alkyl. In certain embodiments, $R^e$ is $C_{1-6}$ alkyl substituted with 0, 1, 2, 3, 4 or 5 $R^h$ groups. In certain embodiments, $R^e$ is a $C_{1-5}$ alkyl substituted with 0, 1, 2, 3, 4 or 5 $R^h$ groups. In certain embodiments, $R^e$ is a $C_{1-4}$ alkyl substituted with 0, 1, 2, 3 or 4 $R^h$ groups. In certain embodiments, $R^e$ is a $C_{1-3}$ alkyl substituted with 0, 1, 2 or 3 $R^h$ groups. In certain embodiments, $R^e$ is a $C_{1-2}$ alkyl substituted with 0, 1 or 2 $R^h$ groups. Exemplary alkyl groups include, but are not limited to, methyl, ethyl, propyl, isopropyl, butyl, isobutyl, sec-butyl, tert-butyl, pentyl, isopentyl, neopentyl, and hexyl, wherein such groups are substituted with 0, 1, 2, 3, 4 or 5 $R^h$ groups.

In certain embodiments, $R^e$ is a $C_{1-6}$ perhaloalkyl. In certain embodiments, $R^e$ is a $C_{1-5}$ perhaloalkyl. In certain embodiments, $R^e$ is a $C_{1-2}$ perhaloalkyl. In certain embodiments, $R^e$ is a $C_{1-3}$ perhaloalkyl. In certain embodiments, $R^e$ is a $C_{1-2}$ perhaloalkyl. Exemplary $R^e$ perhaloalkyl groups include, but are not limited to, —$CF_3$, —$CF_2CF_3$, —$CF_2CF_2CF_3$, —$CCl_3$, —$CFCl_2$, and —$CF_2Cl$.

In certain embodiments, $R^e$ is $C_{2-10}$ alkenyl. In certain embodiments, $R^e$ is $C_{2-6}$ alkenyl. In certain embodiments, $R^e$ is a $C_{2-6}$ alkenyl substituted with 0, 1, 2, 3, 4 or 5 $R^h$ groups. In certain embodiments, $R^e$ is a $C_{2-5}$ alkenyl substituted with 0, 1, 2, 3, 4 or 5 $R^h$ groups. In certain embodiments, $R^e$ is a $C_{2-3}$ alkenyl substituted with 0, 1, 2, or 3 $R^h$ groups. Exemplary alkenyl groups include, but are not limited to, ethenyl, 1-propenyl, 2-propenyl, 1-butenyl, 2-butenyl, butadienyl, pentenyl, pentadienyl and hexenyl, wherein such groups are substituted with 0, 1, 2, 3, 4 or 5 $R^h$ groups.

In certain embodiments, $R^e$ is $C_{2-10}$ alkynyl. In certain embodiments, $R^e$ is $C_{2-6}$ alkynyl. In certain embodiments, $R^e$ is $C_{2-6}$ alkynyl substituted with 0, 1, 2, 3, 4 or 5 $R^h$ groups. In certain embodiments, $R^e$ is $C_{2-5}$ alkynyl substituted with 0, 1, 2, 3, 4 or 5 $R^h$ groups. In certain embodiments, $R^e$ is $C_{2-4}$ alkynyl substituted with 0, 1, 2, 3 or 4 $R^h$ groups. In certain embodiments, $R^e$ is $C_{2-3}$ alkynyl substituted with 0, 1, 2 or 3 $R^h$ groups. Exemplary $R^e$ alkynyl groups include, but are not limited to, ethynyl, 1-propynyl, 2-propynyl, 1-butynyl, 2-butynyl, pentynyl and hexynyl, wherein such groups are substituted with 0, 1, 2, 3, 4 or 5 $R^h$ groups.

However, in certain embodiments, wherein G is —$OR^e$, then $R^e$ is not $C_{1-6}$ alkyl (e.g., methyl, ethyl, propyl, isopropyl, aralkyl). In certain embodiments, wherein G is —$OR^e$, then $R^e$ is not $C_{2-6}$ alkenyl (e.g., allyl).

In certain embodiments, wherein G is —$SR^e$, then $R^e$ is not then $R^e$ is not $C_{1-6}$ alkyl (e.g., methyl, ethyl, propyl, isopropyl, aralkyl).

In certain embodiments, wherein G is —$NR^eR^f$ and $R^f$ is —H or $C_{1-3}$ alkyl (e.g., methyl, ethyl, aralkyl) then $R^e$ is not $C_{1-6}$ alkyl.

In certain embodiments, $R^e$ is $C_{6-14}$ aryl. In certain embodiments, $R^e$ is $C_{6-10}$ aryl. In certain embodiments, $R^e$ is $C_{6-10}$ aryl substituted with 0, 1, 2, 3, 4 or 5 $R^h$ groups. In certain embodiments, $R^e$ is $C_6$ aryl (e.g., phenyl) substituted with 0, 1, 2, 3, 4 or 5 $R^h$ groups. In certain embodiments, $R^e$ is a $C_{10}$ aryl (e.g., naphthyl) substituted with 0, 1, 2, 3, 4 or 5 $R^h$ groups.

In certain embodiments, $R^e$ is phenyl. In certain embodiments, $R^e$ is phenyl substituted with 0, 1, 2, 3 or 4 $R^h$ groups. In certain embodiments, $R^e$ is phenyl substituted with 0, 1, 2 or 3 $R^h$ groups. In certain embodiments, $R^e$ is phenyl substituted with 0, 1 or 2 $R^h$ groups. In certain embodiments, $R^e$ is phenyl substituted with 0 or 1 $R^h$ groups. In certain embodiments, $R^e$ is a disubstituted phenyl (i.e., substituted with 2 $R^h$ groups). In certain embodiments, $R^e$ is a monosubstituted phenyl (i.e., substituted with 1 $R^h$ group). In certain embodiments, $R^e$ is an unsubstituted phenyl (i.e., substituted with 0 $R^h$ groups).

In certain embodiments, $R^e$ is phenyl substituted with at least one ortho $R^h$ group. In certain embodiments, $R^e$ is phenyl substituted with at least one meta $R^h$ group. In certain embodiments, $R^e$ is phenyl substituted with at least one para $R^h$ group.

In certain embodiments, $R^e$ is a phenyl group of the formula:

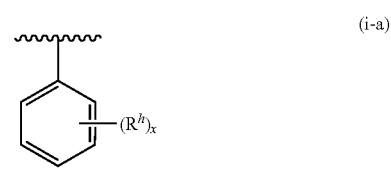

(i-a)

wherein x is 0, 1, 2, 3, 4 or 5, and $R^h$ is as defined below and herein. In certain embodiments, x is 0, 1, 2, 3 or 4. In certain embodiments, x is 0, 1, 2 or 3. In certain embodiments, x is 0, 1 or 2. In certain embodiments, x is 0 or 1. In certain embodiments, x is 3. In certain embodiments, $R^e$ is a disubstituted phenyl group (i.e., wherein x is 2). In certain embodiments, $R^e$ is a monosubstituted phenyl group (i.e., wherein x is 1). In certain embodiments, $R^e$ is an unsubstituted phenyl group (i.e., wherein x is 0).

For example, in certain embodiments, $R^e$ is a substituted or unsubstituted phenyl group of any one of the formulae:

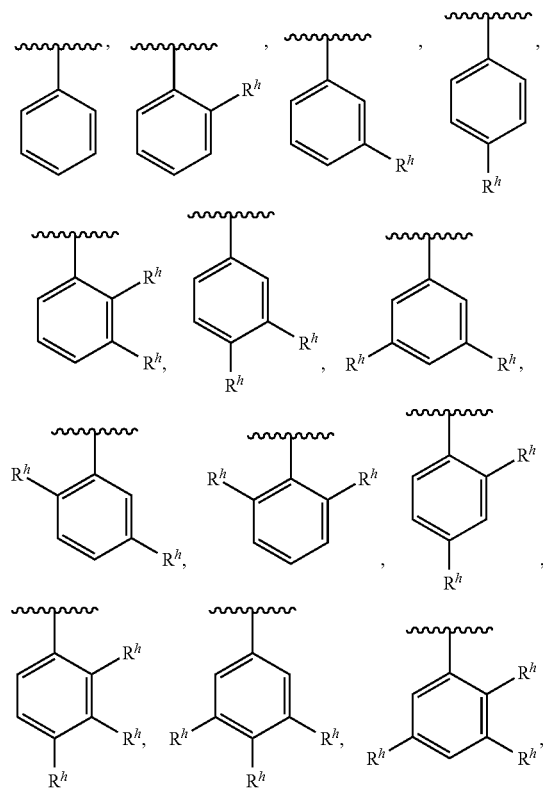

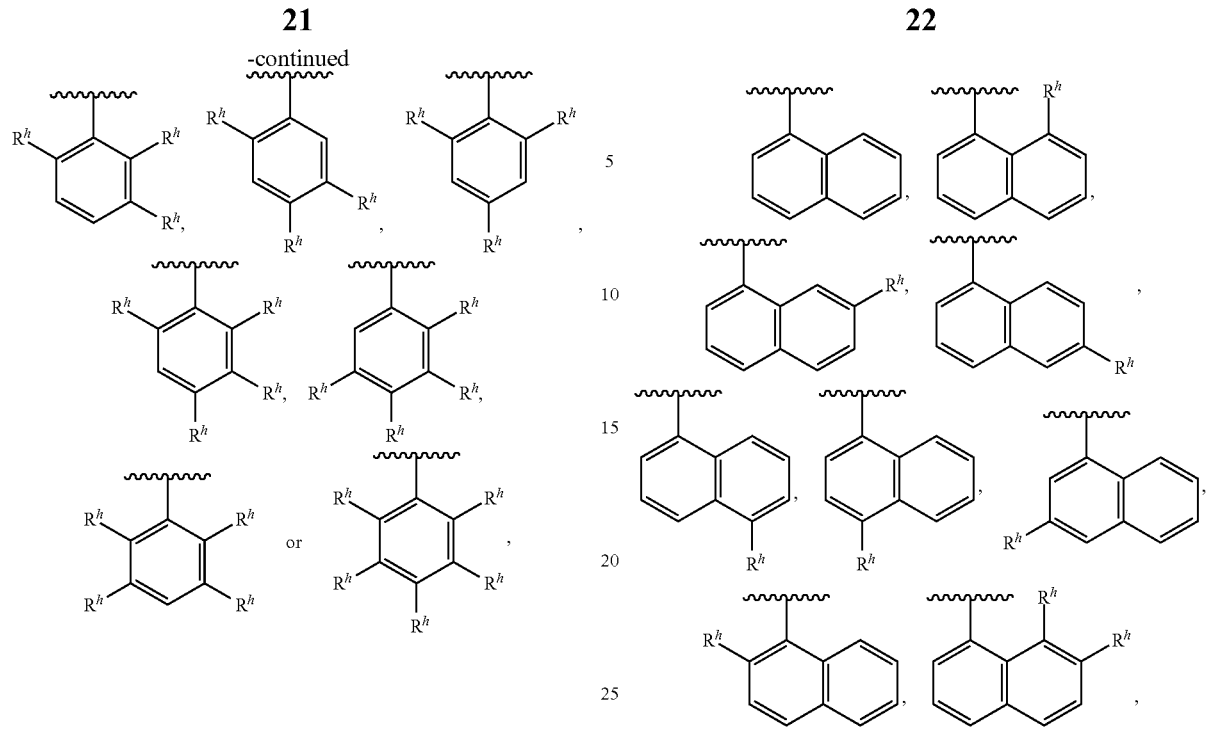

wherein $R^h$ is as defined below and herein.

In certain embodiments, $R^e$ is a naphthyl. In certain embodiments, $R^e$ is a naphthyl group of any one of the formulae:

(i-b)

(i-c)

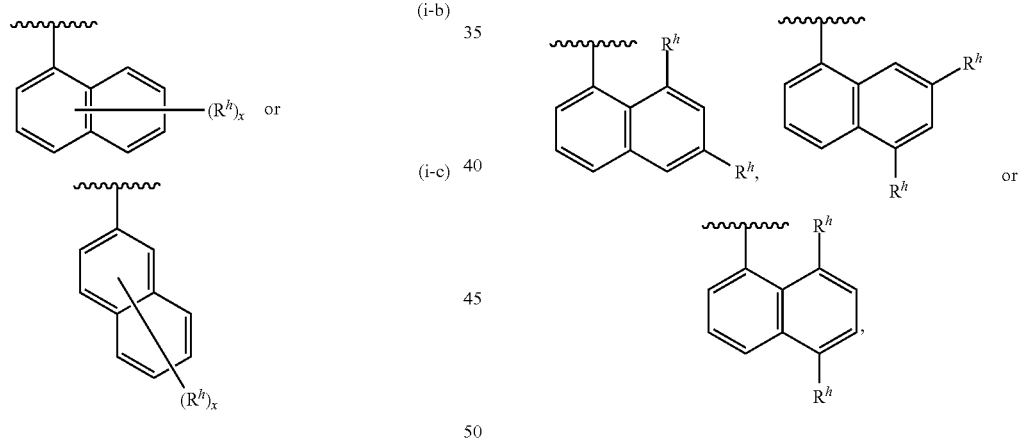

wherein x is 0, 1, 2, 3, 4 or 5, and $R^h$ is as defined below and herein. In certain embodiments, x is 0, 1, 2, 3 or 4. In certain embodiments, x is 0, 1, 2 or 3. In certain embodiments, x is 0, 1 or 2. In certain embodiments, x is 0 or 1. In certain embodiments, $R^e$ is a trisubstituted naphthyl group (i.e., wherein x is 3). In certain embodiments, $R^e$ is a disubstituted naphthyl group (i.e., wherein x is 2). In certain embodiments, $R^e$ is a monosubstituted naphthyl group (i.e., wherein x is 1). In certain embodiments, $R^e$ is an unsubstituted naphthyl group (i.e., wherein x is 0).

For example, in certain embodiments, $R^e$ is a substituted or unsubstituted 1-naphthyl group of any one of the formulae:

wherein $R^h$ is as defined below and herein.

In certain embodiments, $R^e$ is a substituted or unsubstituted 2-naphthyl group of any one of the formulae:

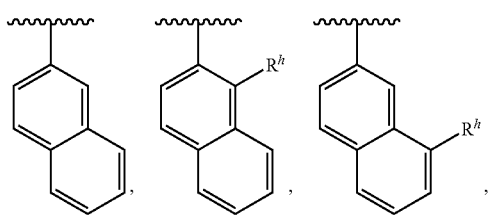

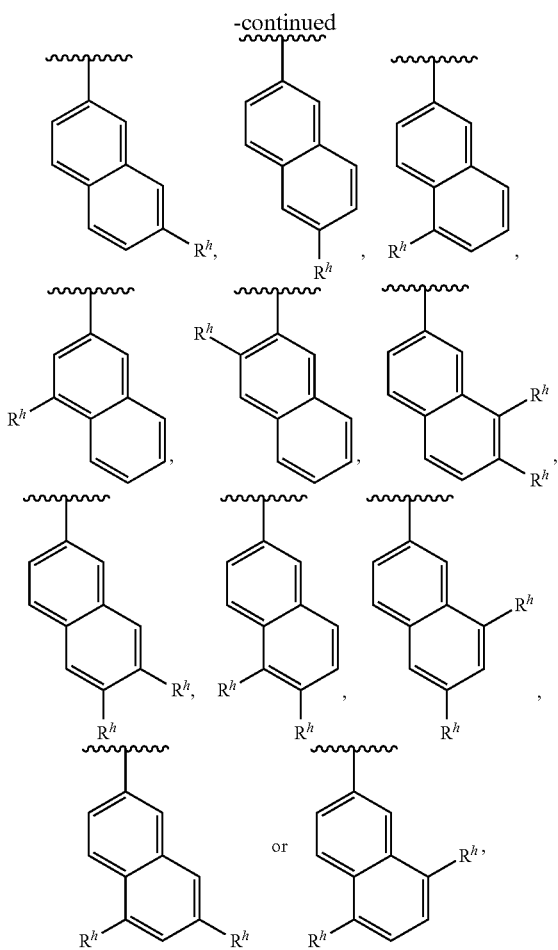

wherein $R^h$ is as defined below and herein.

However, in certain embodiments, wherein G is —$OR^e$, then $R^e$ is not $C_{10}$ aryl (e.g., 1-naphthyl, 2-naphthyl).

In certain embodiments, $R^e$ is 5-14 membered heteroaryl. In certain embodiments, $R^e$ is a 5-10 membered heteroaryl substituted with 0, 1, 2, 3, 4 or 5 $R^h$ groups. In certain embodiments, $R^e$ is a 5-8 membered heteroaryl substituted with 0, 1, 2, 3, 4 or 5 $R^h$ groups. In certain embodiments, $R^e$ is a 5-6 membered heteroaryl substituted with 0, 1, 2, 3 or 4 $R^h$ groups. In certain embodiments, $R^e$ is a 9-10 membered heteroaryl substituted with 0, 1, 2, 3, 4 or 5 $R^h$ groups.

Exemplary $R^e$ heteroaryl groups include, but are not limited to, pyrrolyl, furanyl and thiophenyl, imidazolyl, pyrazolyl, oxazolyl, isoxazolyl, thiazolyl, isothiazolyl, triazolyl, oxadiazolyl, thiadiazolyl, tetrazolyl, pyridinyl (e.g., 2-pyridinyl, 3-pyridinyl, 4-pyridinyl), pyridazinyl (e.g., 3-pyridazinyl, 4-pyridazinyl), pyrimidinyl (e.g. 2-pyrimidinyl, 4-pyrimidinyl, 5-pyrimidinyl), pyrazinyl, triazinyl, tetrazinyl, azepinyl, oxepinyl, thiepinyl, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, purinyl, naphthyridinyl, pteridinyl, quinolinyl, isoquinolinyl, cinnolinyl, quinoxalinyl, phthalazinyl, quinazolinyl, phenanthridinyl, dibenzofuranyl, carbazolyl, acridinyl, phenothiazinyl, phenoxazinyl and phenazinyl, wherein such groups are substituted with 0, 1, 2, 3, 4 or 5 $R^h$ groups.

In certain embodiments, $R^e$ is a 5-membered heteroaryl. In certain embodiments, $R^e$ is a 5-membered heteroaryl substituted with 0, 1, 2 or 3 $R^h$ groups. In certain embodiments, $R^e$ is a 5-membered heteroaryl selected pyrrolyl, furanyl, thiophenyl, imidazolyl, pyrazolyl, oxazolyl, isoxazolyl, thiazolyl, isothiazolyl, triazolyl, oxadiazolyl, thiadiazolyl and tetrazolyl, wherein such groups are substituted with 0, 1, 2 or 3 $R^h$ groups.

For example, in certain embodiments, $R^e$ is a 5-membered heteroaryl of the formula:

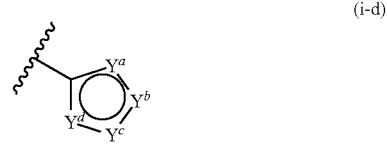

(i-d)

wherein $Y^a, Y^b, Y^c$ and $Y^d$ are, independently, selected from CH, $CR^h$, O, S, N, or $NR^k$, with the proviso that at least one of $Y^a, Y^b, Y^c$ and $Y^d$ is O, S, N or $NR^k$, and wherein $R^h$ and $R^k$ are defined below and herein.

In certain embodiments of the above formula (i-d), $Y^a$ is O, S, N, or $NR^k$ and $Y^b, Y^c$ and $Y^d$ are, independently, selected from CH, $CR^h$, $NR^k$ or N. In certain embodiments of the above formula (i-d), $Y^a$ is O, S, N, or $NR^k$ and $Y^b, Y^c$ and $Y^d$ are, independently, selected from CH or $CR^h$. In certain embodiments of the above formula (i-d), $Y^a$ is O, S, or $NR^k$, $Y^c$ is N and $Y^b$ and $Y^d$ are, independently, selected from CH or $CR^h$.

In certain embodiments of the above formula (i-d), $Y^b$ is O, S, or $NR^k$ and $Y^a, Y^c$ and $Y^d$ are, independently, selected from CH, $CR^h$ or N. In certain embodiments of the above formula (i-d), $Y^b$ is O, S, or $NR^k$ and $Y^a, Y^c$ and $Y^d$ are, independently, selected from CH or $CR^h$. In certain embodiments of the above formula (i-d), $Y^b$ is O, S, or $NR^k$, $Y^d$ is N and $Y^a$ and $Y^c$ are, independently, selected from CH or $CR^h$.

In certain embodiments, $R^e$ is a substituted or unsubstituted 5-membered heteroaryl of any one of the formulae:

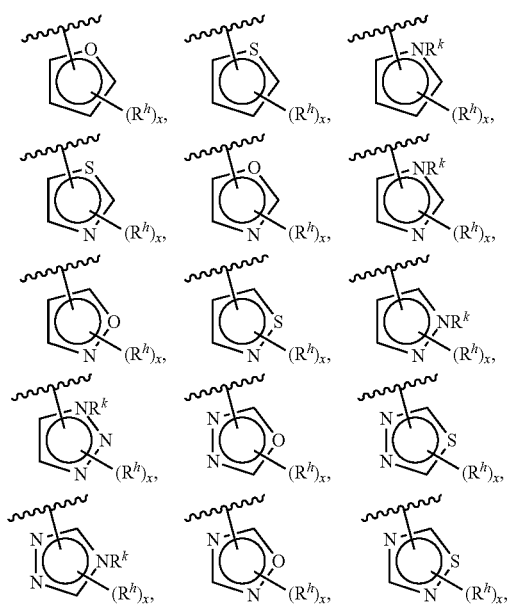

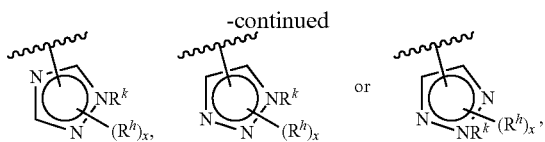

wherein x is 0, 1 or 2, and $R^h$ and $R^k$ are as defined below and herein. In certain embodiments, $R^e$ is an unsubstituted 5-membered heteroaryl (i.e., wherein x is 0). In certain embodiments, $R^e$ is a substituted 5-membered heteroaryl (e.g., wherein x is 1 or 2). In certain embodiments, $R^e$ is a monosubstituted 5-membered heteroaryl (i.e., wherein x is 1). In certain embodiments, $R^e$ is a disubstituted 5-membered heteroaryl (i.e., wherein x is 2). In certain embodiments, x is 0, 1 or 2. In certain embodiments, x is 0 or 1.

However, in certain embodiments, wherein G is —$OR^e$, $R^e$ is not thiazolyl, e.g., of the formula:

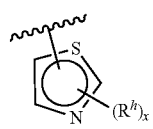

wherein x is 0, 1 or 2, and $R^h$ and $R^k$ are as defined below and herein.

In certain embodiments, $R^e$ is a 6-membered heteroaryl. In certain embodiments, $R^e$ is a 6-membered heteroaryl substituted with 0, 1, 2, 3 or 4 $R^h$ groups. In certain embodiments, $R^e$ is a 6-membered heteroaryl selected from the group consisting of pyridinyl (e.g., 2-pyridinyl, 3-pyridinyl, 4-pyridinyl), pyridazinyl (e.g., 3-pyridazinyl, 4-pyridazinyl), pyrimidinyl (e.g. 2-pyrimidinyl, 4-pyrimidinyl, 5-pyrimidinyl), pyrazinyl, triazinyl and tetrazinyl, wherein such groups are substituted with 0, 1, 2, 3 or 4 $R^h$ groups.

For example, in certain embodiments, $R^e$ is a 6-membered heteroaryl group of the formula:

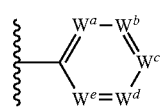
(i-e)

wherein $W^a$, $W^b$, $W^c$, $W^d$ and $W^e$ are, independently, selected from CH, $CR^h$ or N, with the proviso that at least one of $W^a$, $W^b$, $W^c$, $W^d$, and $W^e$ is N, and wherein $R^h$ is as defined below and herein.

In certain embodiments, $R^e$ is a pyrindinyl group. In certain embodiments, $R^e$ is a pyrindinyl group substituted with 0, 1, 2, 3 or 4 $R^h$ groups. For example, in certain embodiments, $R^e$ is a pyrindinyl group of the formula:

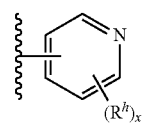

wherein x is 0, 1, 2, 3 or 4, and $R^h$ is as defined below and herein. In certain embodiments, $R^e$ is an unsubstituted pyrindinyl (i.e., wherein x is 0). In certain embodiments, $R^e$ is a substituted pyrindinyl (e.g., wherein x is 1, 2, 3 or 4). In certain embodiments, $R^e$ is a monosubstituted pyrindinyl (i.e., wherein x is 1). In certain embodiments, $R^e$ is a disubstituted pyrindinyl (i.e., wherein x is 2). In certain embodiments, $R^e$ is a trisubstituted pyrindinyl (i.e., wherein x is 3). In certain embodiments, x is 0, 1, 2 or 3. In certain embodiments, x is 0, 1 or 2. In certain embodiments, x is 0 or 1.

In certain embodiments, $R^e$ is a 2-pyrindinyl group, e.g., of the formula (i-e) wherein $W^a$ is N and $W^b$, $W^c$, $W^d$ and $W^e$ are, independently, CH or $CR^h$. In certain embodiments $R^e$ is a 3-pyrindinyl group, e.g., of the formula (i-e) wherein $W^b$ is N and $W^a$, $W^c$, $W^d$ and $W^e$ are, independently, CH or $CR^h$. In certain embodiments $R^e$ is a 4-pyrindinyl group, e.g., of the formula (i-e) wherein $W^c$ is N and $W^a$, $W^b$, $W^d$ and $W^e$ are, independently, CH or $CR^h$.

In certain embodiments, $R^e$ is a substituted or unsubstituted 2-pyridinyl group of any one of the formulae:

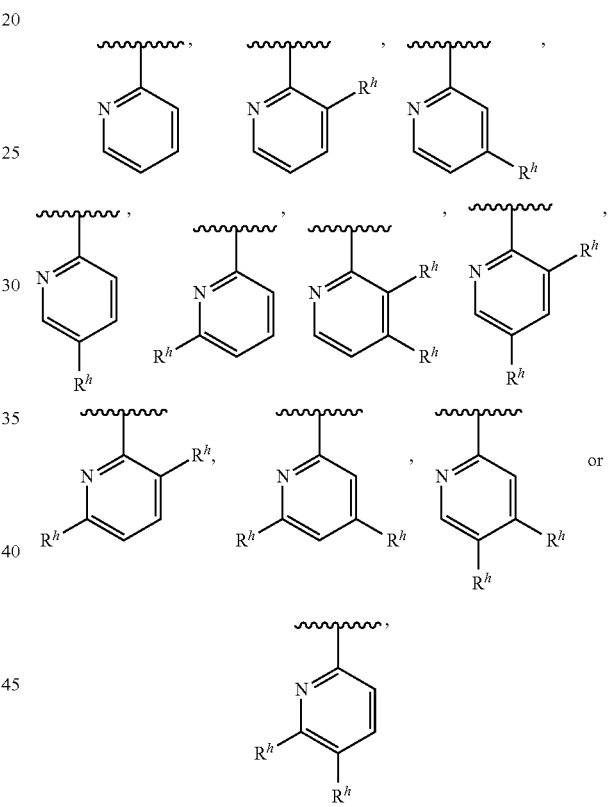

wherein $R^h$ is as defined below and herein.

In certain embodiments, $R^e$ is a substituted or unsubstituted 3-pyridinyl group of any one of the formulae:

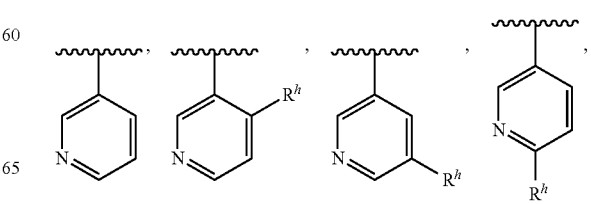

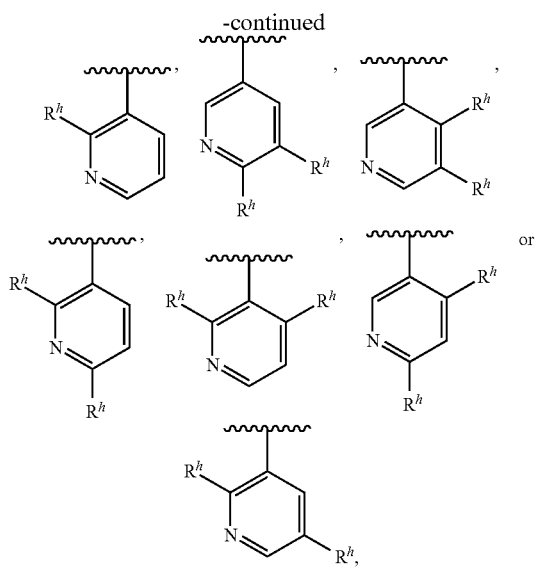

wherein $R^h$ is as defined below and herein.

In certain embodiments, $R^e$ is a substituted or unsubstituted 4-pyridinyl group of any one of the formulae:

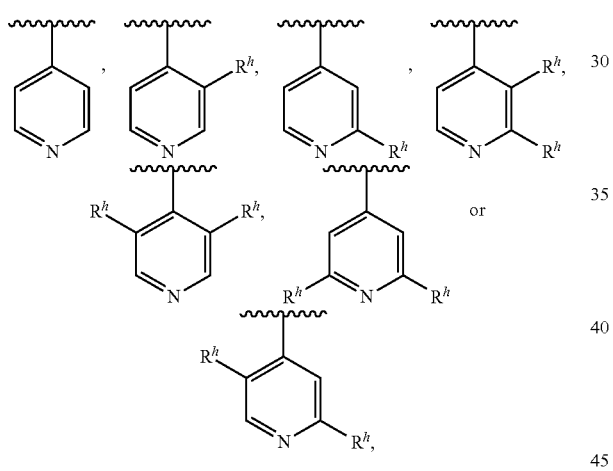

wherein $R^h$ is as defined below and herein.

In certain embodiments, $R^e$ is a pyridazinyl group. In certain embodiments, $R^e$ is a pyridazinyl group substituted with 0, 1, 2 or 3 $R^h$ groups. For example, in certain embodiments, $R^e$ is a pyridazinyl group of the formula:

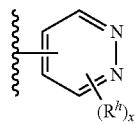

wherein x is 0, 1, 2 or 3, and $R^h$ is as defined below and herein. In certain embodiments, $R^e$ is an unsubstituted pyridazinyl (i.e., wherein x is 0). In certain embodiments, $R^e$ is a substituted pyridazinyl (e.g., wherein x is 1, 2 or 3). In certain embodiments, $R^e$ is a monosubstituted pyridazinyl (i.e., wherein x is 1). In certain embodiments, $R^e$ is a disubstituted pyridazinyl (i.e., wherein x is 2). In certain embodiments, $R^e$ is a trisubstituted pyridazinyl (i.e., wherein x is 3).

In certain embodiments, x is 0, 1, 2 or 3. In certain embodiments, x is 0, 1 or 2. In certain embodiments, x is 0 or 1.

In certain embodiments, $R^e$ is a 3-pyridazinyl group, e.g., of the formula (i-e) wherein $W^a$ and $W^b$ are N and $W^c$, $W^d$ and $W^e$ are, independently, CH or $CR^h$. In certain embodiments $R^e$ is a 4-pyridazinyl group, e.g., of the formula (i-e) wherein $W^b$ and $W^c$ are N and $W^a$, $W^d$ and $W^e$ are, independently, CH or $CR^h$.

In certain embodiments, $R^e$ is a substituted or unsubstituted 3-pyridazinyl group of any one of the formulae:

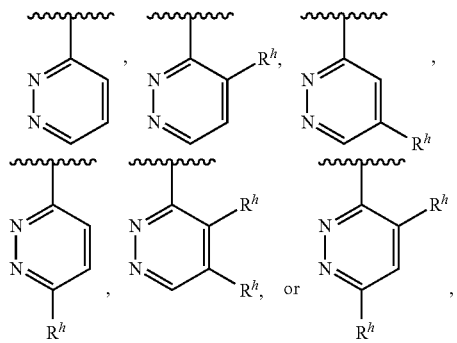

wherein $R^h$ is as defined below and herein.

In certain embodiments, $R^e$ is a substituted or unsubstituted 4-pyridazinyl group of any one of the formulae:

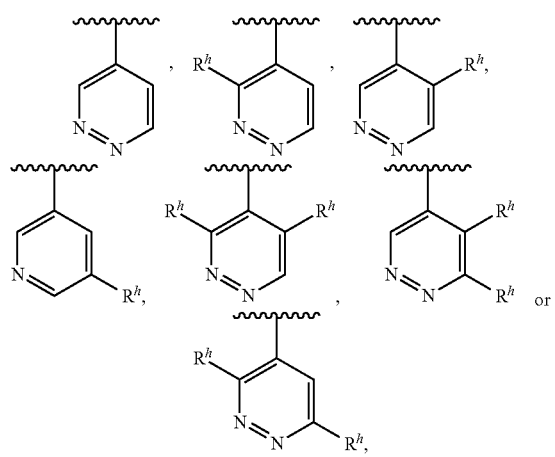

wherein $R^h$ is as defined below and herein.

In certain embodiments, $R^e$ is a pyrimidinyl group. In certain embodiments, $R^e$ is a pyrimidinyl group substituted with 0, 1, 2 or 3 $R^h$ groups. For example, in certain embodiments, $R^e$ is a pyrimidinyl group of the formula:

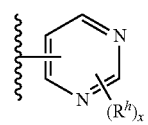

wherein x is 0, 1, 2 or 3, and $R^h$ is as defined below and herein. In certain embodiments, $R^e$ is an unsubstituted pyrimidinyl (i.e., wherein x is 0). In certain embodiments, $R^e$ is a substituted pyrimidinyl (e.g., wherein x is 1, 2 or 3). In certain embodiments, $R^e$ is a monosubstituted pyrimidinyl (i.e., wherein x is 1). In certain embodiments, $R^e$ is a disubstituted pyridazinyl (i.e., wherein x is 2). In certain embodiments, $R^e$ is a trisubstituted pyrimidinyl (i.e., wherein x is 3). In certain embodiments, x is 0, 1, 2 or 3. In certain embodiments, x is 0, 1 or 2. In certain embodiments, x is 0 or 1.

In certain embodiments, $R^e$ is a 2-pyrimidinyl group, e.g., of the formula (i-e) wherein $W^a$ and $W^e$ are N and $W^b$, $W^c$ and $W^d$ are, independently, CH or $CR^h$. In certain embodiments $R^e$ is a 4-pyrimidinyl group, e.g., of the formula (i-e) wherein $W^a$ and $W^c$ are N and $W^b$, $W^d$ and $W^e$ are, independently, CH or $CR^h$. In certain embodiments $R^e$ is a 5-pyrimidinyl group, e.g., of the formula (i-e) wherein $W^b$ and $W^d$ are N and $W^a$, $W^c$ and $W^e$ are, independently, CH or $CR^h$.

In certain embodiments, $R^e$ is a substituted or unsubstituted 2-pyrimidinyl group of any one of the formulae:

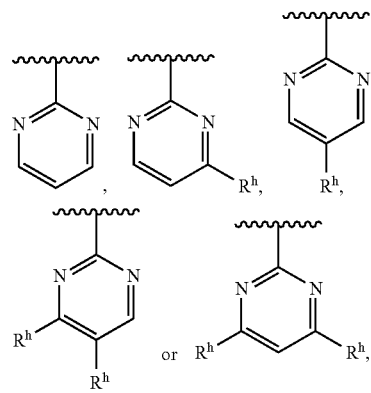

wherein $R^h$ is as defined below and herein.

In certain embodiments, $R^e$ is a substituted or unsubstituted 4-pyrimidinyl group of any one of the formulae:

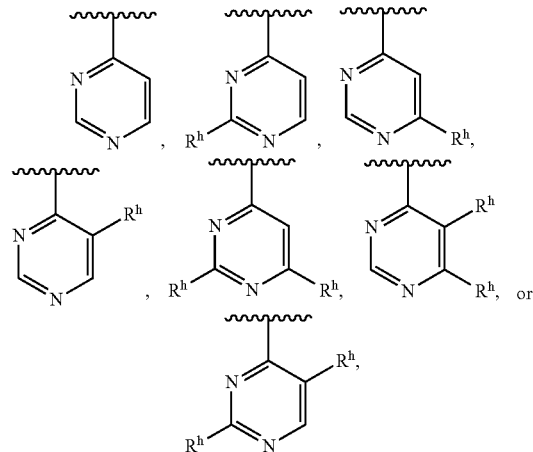

wherein is as defined below and herein.

In certain embodiments, $R^e$ is a substituted or unsubstituted 5-pyrimidinyl group of any one of the formulae:

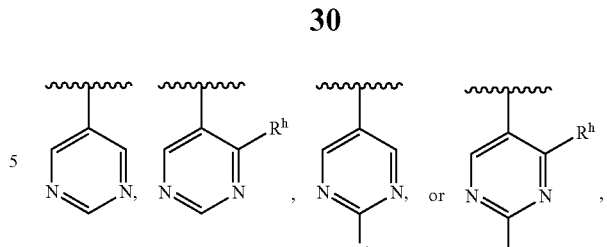

wherein $R^h$ is as defined below and herein.

In certain embodiments, $R^e$ is a pyrazinyl group. In certain embodiments, $R^e$ is a pyrazinyl group substituted with 0, 1, 2 or 3 $R^h$ groups. For example, in certain embodiments, $R^e$ is a pyrazinyl group of the formula:

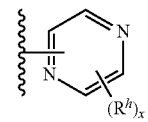

wherein x is 0, 1, 2 or 3, and $R^h$ is as defined below and herein. In certain embodiments, $R^e$ is an unsubstituted pyrazinyl (i.e., wherein x is 0). In certain embodiments, $R^e$ is a substituted pyrazinyl (e.g., wherein x is 1, 2 or 3). In certain embodiments, $R^e$ is a monosubstituted pyrazinyl (i.e., wherein x is 1). In certain embodiments, $R^e$ is a disubstituted pyrazinyl (i.e., wherein x is 2). In certain embodiments, $R^e$ is a trisubstituted pyrazinyl (i.e., wherein x is 3). In certain embodiments, x is 0, 1, 2 or 3. In certain embodiments, x is 0, 1 or 2. In certain embodiments, x is 0 or 1.

In certain embodiments, $R^e$ is a substituted or unsubstituted pyrazinyl group of any one of the formulae:

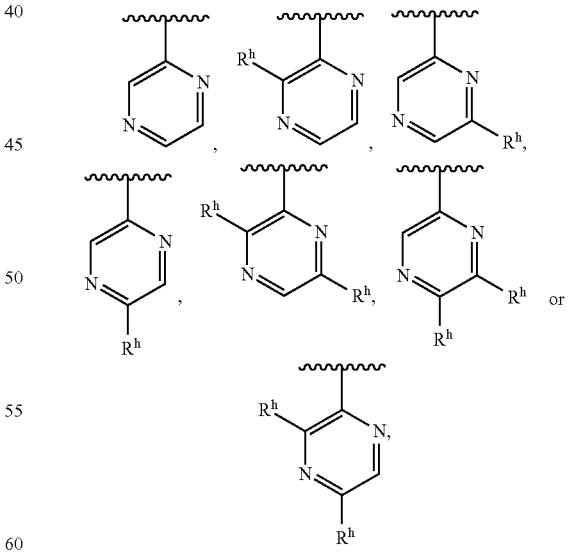

wherein $R^h$ is as defined below and herein.

In certain embodiments $R^e$ is a triazinyl group. In certain embodiments $R^e$ is a triazinyl group substituted with 0, 1 or 2 $R^h$ groups. For example, in certain embodiments, $R^e$ is a triazinyl group of the formula:

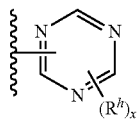

wherein x is 0, 1 or 2, and $R^h$ is as defined below and herein. In certain embodiments, $R^e$ is an unsubstituted pyrazinyl (i.e., wherein x is 0). In certain embodiments, $R^e$ is a substituted pyrazinyl (e.g., wherein x is 1 or 2). In certain embodiments, $R^e$ is a monosubstituted pyrazinyl (i.e., wherein x is 1). In certain embodiments, $R^e$ is a disubstituted pyrazinyl (i.e., wherein x is 2). In certain embodiments, x is 0, 1 or 2. In certain embodiments, x is 0 or 1.

In certain embodiments, $R^e$ is a substituted or unsubstituted triazinyl group of any one of the formulae:

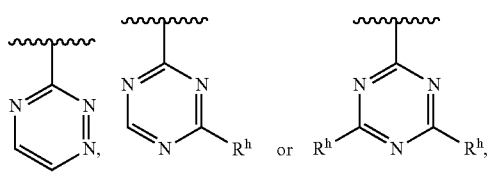

wherein $R^h$ is as defined below and herein.

In certain embodiments $R^e$ is a tetrazinyl group. In certain embodiments $R^e$ is a tetrazinyl group substituted with 0 or 1 $R^h$ groups. For example, in certain embodiments, $R^e$ is a tetrazinyl group of the formula:

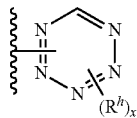

wherein x is 0 or 1, and $R^h$ is as defined below and herein. In certain embodiments, $R^e$ is an unsubstituted pyrazinyl (i.e., wherein x is 0). In certain embodiments, $R^e$ is a substituted pyrazinyl (e.g., wherein x is 1). In certain embodiments, x is 0 or 1.

In certain embodiments, $R^e$ is a substituted or unsubstituted tetrazinyl group of any one of the formulae:

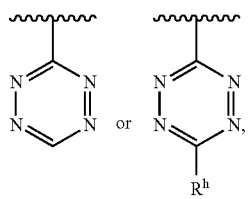

wherein $R^h$ is as defined below and herein.

In certain embodiments, $R^e$ is a 9-membered heteroaryl (e.g., a 5,6-bicyclic heteroaryl). In certain embodiments, $R^e$ is a 5,6-bicyclic heteroaryl substituted with 0, 1, 2, 3, 4 or 5 $R^h$ groups. In certain embodiments, $R^e$ is a 5,6-bicyclic heteroaryl selected from indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl, wherein such groups are substituted with 0, 1, 2, 3, 4 or 5 $R^h$ groups.

For example, in certain embodiments, $R^e$ is a 5,6-bicyclic heteroaryl of the formula:

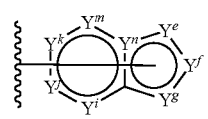

(i-f)

wherein $Y^e, Y^f, Y^g, Y^i, Y^k$ and $Y^m$ are, independently, C, CH, $CR^h$, O, S, N, or $NR^k$ and V is C or N, with the proviso that at least one of $Y^e, Y^f, Y^g$ is selected from O, S, N or $NR^k$ wherein $R^h$ and $R^k$ are as defined below and herein.

In certain embodiments, $R^e$ is a 5,6-bicyclic heteroaryl group of the formula (i-f), wherein $Y^e$ is selected from O, S, or $NR^k$, V is C, and $Y^f, Y^g, Y^i, Y^j, Y^k$ and $Y^m$ are, independently, C, CH, or $CR^h$. For example, in certain embodiments, $R^e$ is a 5,6-bicyclic heteroaryl group of the formulae:

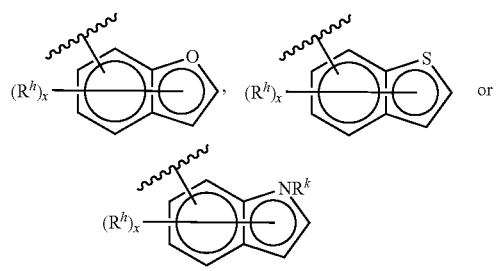

wherein x is 0, 1, 2, 3, 4 or 5 and $R^h$ and $R^k$ are defined below and herein. In certain embodiments, $R^e$ is an unsubstituted 5,6-bicyclic heteroaryl (i.e., wherein x is 0). In certain embodiments, $R^e$ is a substituted 5,6-bicyclic heteroaryl (e.g., wherein x is 1, 2, 3, 4 or 5). In certain embodiments, $R^e$ is a monosubstituted 5,6-bicyclic heteroaryl (i.e., wherein x is 1). In certain embodiments, $R^e$ is a disubstituted 5,6-bicyclic heteroaryl (i.e., wherein x is 2). In certain embodiments, $R^e$ is a trisubstituted 5,6-bicyclic heteroaryl (i.e., wherein x is 3). In certain embodiments, x is 0, 1, 2 or 3. In certain embodiments, x is 0, 1 or 2. In certain embodiments, x is 0 or 1.

In certain embodiments, $R^e$ is a 5,6-bicyclic heteroaryl wherein $Y^e$ is selected from O, S, or $NR^k$; $Y^g$ is N; V is C; $Y^f$ is C, CH, or $CR^h$ or N, and $Y^i, Y^j, Y^k$ and $Y^m$ are, independently, C, CH, or $CR^h$. For example, in certain embodiments, $R^e$ is a 5,6-bicyclic heteroaryl group of the formulae:

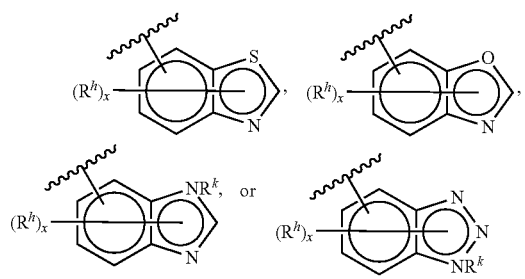

wherein x is 0, 1, 2, 3, 4 or 5 and $R^h$ and $R^k$ are defined below and herein. In certain embodiments, $R^e$ is an unsubstituted 5,6-bicyclic heteroaryl (i.e., wherein x is 0). In certain embodiments, $R^e$ is a substituted 5,6-bicyclic heteroaryl (e.g., wherein x is 1, 2, 3, 4 or 5). In certain embodiments, $R^e$ is a monosubstituted 5,6-bicyclic heteroaryl (i.e., wherein x is 1). In certain embodiments, $R^e$ is a disubstituted 5,6-bicyclic heteroaryl (i.e., wherein x is 2). In certain embodiments, $R^e$ is a trisubstituted 5,6-bicyclic heteroaryl (i.e., wherein x is 3). In certain embodiments, x is 0, 1, 2 or 3. In certain embodiments, x is 0, 1 or 2. In certain embodiments, x is 0 or 1.

In certain embodiments, $R^e$ is a 5,6-bicyclic heteroaryl wherein $Y^e$ is $NR^k$, S or O; $Y^m$ is N; $Y^n$ is C; and $Y^f$, $Y^g$, $Y^i$, $Y^j$, and $Y^k$ are, independently, C, CH, or $CR^h$. For example, in certain embodiments, $R^e$ is a 5,6-bicyclic heteroaryl group of the formulae:

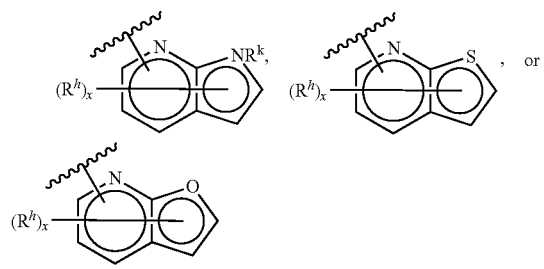

wherein x is 0, 1, 2, 3, 4 or 5 and $R^h$ and $R^k$ are defined below and herein. In certain embodiments, $R^e$ is an unsubstituted 5,6-bicyclic heteroaryl (i.e., wherein x is 0). In certain embodiments, $R^e$ is a substituted 5,6-bicyclic heteroaryl (e.g., wherein x is 1, 2, 3, 4 or 5). In certain embodiments, $R^e$ is a monosubstituted 5,6-bicyclic heteroaryl (i.e., wherein x is 1). In certain embodiments, $R^e$ is a disubstituted 5,6-bicyclic heteroaryl (i.e., wherein x is 2). In certain embodiments, $R^e$ is a trisubstituted 5,6-bicyclic heteroaryl (i.e., wherein x is 3). In certain embodiments, x is 0, 1, 2 or 3. In certain embodiments, x is 0, 1 or 2. In certain embodiments, x is 0 or 1.

In certain embodiments, $R^e$ is a 5,6-bicyclic heteroaryl wherein $Y^g$ is O, S, or $NR^k$; $Y^m$ is N; V is C; and $Y^e$, $Y^f$, $Y^i$, $Y^j$ and $Y^k$ are, independently, C, CH, or $CR^h$. For example, in certain embodiments, $R^e$ is a 5,6-bicyclic heteroaryl group of the formulae:

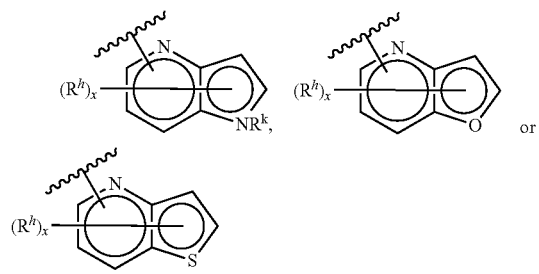

wherein x is 0, 1, 2, 3, 4 or 5 and $R^h$ and $R^k$ are defined below and herein. In certain embodiments, $R^e$ is an unsubstituted 5,6-bicyclic heteroaryl (i.e., wherein x is 0). In certain embodiments, $R^e$ is a substituted 5,6-bicyclic heteroaryl (e.g., wherein x is 1, 2, 3, 4 or 5). In certain embodiments, $R^e$ is a monosubstituted 5,6-bicyclic heteroaryl (i.e., wherein x is 1). In certain embodiments, $R^e$ is a disubstituted 5,6-bicyclic heteroaryl (i.e., wherein x is 2). In certain embodiments, $R^e$ is a trisubstituted 5,6-bicyclic heteroaryl (i.e., wherein x is 3). In certain embodiments, x is 0, 1, 2 or 3. In certain embodiments, x is 0, 1 or 2. In certain embodiments, x is 0 or 1.

In certain embodiments, $R^e$ is a 5,6-bicyclic heteroaryl wherein $Y^e$ is selected from N; $Y^n$ is N; and $Y^f$, $Y^i$, $Y^j$, $Y^k$ and $Y^m$ are, independently, C, CH, or $CR^h$. For example, in certain embodiments, $R^e$ is a 5,6-bicyclic heteroaryl group of the formula:

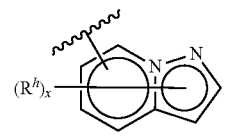

wherein x is 0, 1, 2, 3, 4 or 5 and $R^h$ and $R^k$ are defined below and herein. In certain embodiments, $R^e$ is an unsubstituted 5,6-bicyclic heteroaryl (i.e., wherein x is 0). In certain embodiments, $R^e$ is a substituted 5,6-bicyclic heteroaryl (e.g., wherein x is 1, 2, 3, 4 or 5). In certain embodiments, $R^e$ is a monosubstituted 5,6-bicyclic heteroaryl (i.e., wherein x is 1). In certain embodiments, $R^e$ is a disubstituted 5,6-bicyclic heteroaryl (i.e., wherein x is 2). In certain embodiments, $R^e$ is a trisubstituted 5,6-bicyclic heteroaryl (i.e., wherein x is 3). In certain embodiments, x is 0, 1, 2 or 3. In certain embodiments, x is 0, 1 or 2. In certain embodiments, x is 0 or 1.

In certain embodiments, $R^e$ is a 10-membered heteroaryl (e.g., a 6,6-bicyclic heteroaryl). In certain embodiments, $R^e$ is a 6,6-bicyclic heteroaryl substituted with 0, 1, 2, 3, 4 or 5 $R^h$ groups. In certain embodiments, $R^e$ is a 6,6-bicyclic heteroaryl selected from naphthyridinyl, pteridinyl, quinolinyl, isoquinolinyl, cinnolinyl, quinoxalinyl, phthalazinyl and quinazolinyl, wherein such groups are substituted with 0, 1, 2, 3, 4 or 5 $R^h$ groups.

For example, in certain embodiments, $R^e$ is a 6,6-bicyclic heteroaryl of the formula:

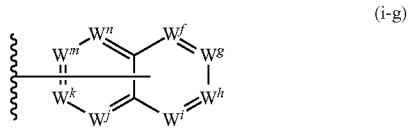

(i-g)

wherein $W^f$, $W^g$, $W^h$, $W^i$, $W^j$, $W^k$, $W^m$ and are, independently, selected from C, CH, $CR^h$ or N, with the proviso that at least one of $W^f$, $W^g$, $W^h$, $W^i$, $W^j$, $W^k$, $W^m$ and $W^n$ is N, and wherein $R^h$ is as defined below and herein.

In certain embodiments, $R^e$ is a quinolinyl group; e.g., of the formula (i-g) wherein $W^i$ is N and $W^g$, $W^h$, $W^f$, $W^j$, $W^k$, $W^m$ and $W^n$ are, independently, C, CH, or $CR^h$. For example, in certain embodiments, $R^e$ is a quinolinyl group of the formulae:

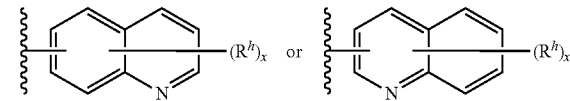

wherein x is 0, 1, 2, 3, 4 or 5, and $R^h$ is as defined below and herein. In certain embodiments, $R^e$ is an unsubstituted quinolinyl (i.e., wherein x is 0). In certain embodiments, $R^e$ is a substituted quinolinyl (e.g., wherein x is 1, 2, 3, 4 or 5). In certain embodiments, $R^e$ is a monosubstituted quinolinyl (i.e., wherein x is 1). In certain embodiments, $R^e$ is a disubstituted quinolinyl (i.e., wherein x is 2). In certain embodiments, $R^e$ is a trisubstituted quinolinyl (i.e., wherein x is 3). In certain embodiments, x is 0, 1, 2 or 3. In certain embodiments, x is 0, 1 or 2. In certain embodiments, x is 0 or 1.

In certain embodiments, $R^e$ is an isoquinolinyl group; e.g., of the formula (i-g) wherein $W^h$ is N and $W^f$, $W^g$, $W^i$, $W^j$, $W^k$, $W^m$ and are, independently, C, CH, or $CR^h$. For example, in certain embodiments, $R^e$ is an isoquinolinyl group of the formulae:

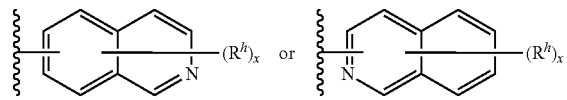

wherein x is 0, 1, 2, 3, 4 or 5, and $R^h$ is as defined below and herein. In certain embodiments, $R^e$ is an unsubstituted isoquinolinyl (i.e., wherein x is 0). In certain embodiments, $R^e$ is a substituted isoquinolinyl (e.g., wherein x is 1, 2, 3, 4 or 5). In certain embodiments, $R^e$ is a monosubstituted isoquinolinyl (i.e., wherein x is 1). In certain embodiments, $R^e$ is a disubstituted isoquinolinyl (i.e., wherein x is 2). In certain embodiments, $R^e$ is a trisubstituted isoquinolinyl (i.e., wherein x is 3). In certain embodiments, x is 0, 1, 2 or 3. In certain embodiments, x is 0, 1 or 2. In certain embodiments, x is 0 or 1.

In certain embodiments, $R^e$ is a quinoxalinyl group; e.g., of the formula (i-g) wherein $W^f$ and $W^i$ are N and $W^g$, $W^h$, $W^j$, $W^k$, $W^m$ and are, independently, C, CH, or $CR^h$. For example, in certain embodiments, $R^e$ is a quinoxalinyl group of the formulae:

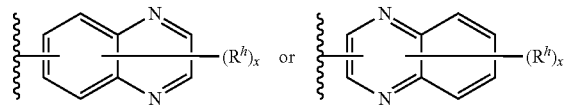

wherein x is 0, 1, 2, 3, 4 or 5, and $R^h$ is as defined below and herein. In certain embodiments, $R^e$ is an unsubstituted quinoxalinyl (i.e., wherein x is 0). In certain embodiments, $R^e$ is a substituted quinoxalinyl (e.g., wherein x is 1, 2, 3, 4 or 5). In certain embodiments, $R^e$ is a monosubstituted quinoxalinyl (i.e., wherein x is 1). In certain embodiments, $R^e$ is a disubstituted quinoxalinyl (i.e., wherein x is 2). In certain embodiments, $R^e$ is a trisubstituted quinoxalinyl (i.e., wherein x is 3). In certain embodiments, x is 0, 1, 2 or 3. In certain embodiments, x is 0, 1 or 2. In certain embodiments, x is 0 or 1.

In certain embodiments, $R^e$ is a 3-14 membered heterocyclyl. In certain embodiments, $R^e$ is a 3-14 membered heterocyclyl substituted with 0, 1, 2, 3, 4 or 5 $R^h$ groups. In certain embodiments, $R^e$ is a 5-10 membered heterocyclyl substituted with 0, 1, 2, 3, 4 or 5 $R^h$ groups. In certain embodiments, $R^e$ is a 5-8 membered heterocyclyl substituted with 0, 1, 2, 3, 4 or 5 $R^h$ groups. In certain embodiments, $R^e$ is a 5-6 membered heterocyclyl substituted with 0, 1, 2, 3, 4 or 5 $R^h$ groups. In certain embodiments, $R^e$ is a 9-10 membered heterocyclyl substituted with 0, 1, 2, 3, 4 or 5 $R^h$ groups.

Exemplary heterocyclyl $R^e$ groups include, but are not limited to, azirdinyl, oxiranyl, thiorenyl, azetidinyl, oxetanyl, thietanyl, tetrahydrofuranyl, dihydrofuranyl, tetrahydrothiophenyl, dihydrothiophenyl, pyrrolidinyl, dihydropyrrolyl, pyrrolyl-2,5-dione, dioxolanyl, oxathiolanyl, dithiolanyl, triazolinyl, oxadiazolinyl, thiadiazolinyl, piperidinyl, tetrahydropyranyl, dihydropyridinyl, thianyl, piperazinyl, morpholinyl, dithianyl, dioxanyl, triazinanyl, azepanyl, oxepanyl, thiepanyl, azocanyl, oxecanyl, thiocanyl, indolinyl, isoindolinyl, dihydrobenzofuranyl, dihydrobenzothienyl, tetrahydrobenzothienyl, tetrahydrobenzofuranyl, tetrahydroindolyl, tetrahydroquinolinyl, tetrahydroisoquinolinyl, decahydroquinolinyl, decahydroisoquinolinyl, octahydrochromenyl, octahydroisochromenyl, decahydronaphthyridinyl, decahydro-1,8-naphthyridinyl, octahydropyrrolo[3,2-b]pyrrole, indolinyl, phthalimidyl, naphthalimidyl, chromanyl, chromenyl, 1H-benzo[e][1,4]diazepinyl, 1,4,5,7-tetrahydro-pyrano[3,4-b]pyrrolyl, 5,6-dihydro-4H-furo[3,2-b]pyrrolyl, 6,7-dihydro-5H-furo[3,2-b]pyranyl, 5,7-dihydro-4H-thieno[2,3-c]pyranyl, 2,3-dihydro-1H-pyrrolo[2,3-b]pyridinyl, 2,3-dihydrofuro[2,3-b]pyridinyl, 4,5,6,7-tetrahydro-1H-pyrrolo[2,3-b]pyridinyl, 4,5,6,7-tetra-hydrofuro[3,2-c]pyridinyl, and 4,5,6,7-tetrahydrothieno[3,2-b]pyridinyl, 1,2,3,4-tetrahydro-1,6-naphthyridinyl, wherein such groups are substituted with 0, 1, 2, 3, 4 or 5 $R^h$ groups.

In certain embodiments, $R^e$ is a 6-membered heterocyclyl substituted with 0, 1, 2, 3, 4 or 5 $R^h$ groups. In certain embodiments, $R^e$ is a 6-membered heterocyclyl selected from piperidinyl, tetrahydropyranyl, dihydropyridinyl, thianyl, piperazinyl, morpholinyl, dithianyl, dioxanyl, and triazinanyl, wherein such groups are substituted with 0, 1, 2, 3, 4 or 5 $R^h$ groups.

For example, in certain embodiments, $R^e$ is a 6-membered heterocyclyl of the formula:

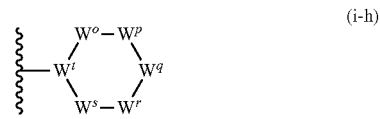

wherein $W^o$, $W^p$, $W^q$, $W^r$, and $W^s$ are, independently, selected from $CH_2$, $CHR^h$, $C(R^h)_2$, $NR^k$, O or S, and $W^t$ is N, CH, $CR^h$, with the proviso that at least one of $W^o$, $W^p$, $W^q$, $W^r$ and $W^s$ is selected from N, $NR^k$, O or S, and wherein $R^h$ and $R^k$ are defined below and herein.

In certain embodiments, $R^e$ is a piperidinyl group. In certain embodiments, $R^e$ is a piperidinyl group substituted with 0, 1, 2, 3, 4 or 5 $R^h$ groups, e.g., of the formulae:

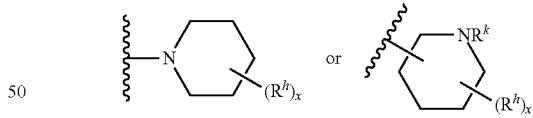

wherein x is 0, 1, 2, 3, 4 or 5, and $R^h$ and $R^k$ are as defined below and herein. In certain embodiments, $R^e$ is an unsubstituted piperidinyl (i.e., wherein x is 0). In certain embodiments, $R^e$ is a substituted piperidinyl (e.g., wherein x is 1, 2, 3, 4 or 5). In certain embodiments, $R^e$ is a monosubstituted piperidinyl (i.e., wherein x is 1). In certain embodiments, $R^e$ is a disubstituted piperidinyl (i.e., wherein x is 2). In certain embodiments, $R^e$ is a trisubstituted piperidinyl (i.e., wherein x is 3). In certain embodiments, x is 0, 1, 2 or 3. In certain embodiments, x is 0, 1 or 2. In certain embodiments, x is 0 or 1.

In certain embodiments, $R^e$ is a 1-piperidinyl group, e.g., of the formula (i-h) wherein $W^t$ is N and $W^o$, $W^p$, $W^q$, $W^r$, and $W^s$ are, independently, selected from $CH_2$, $CHR^h$, $C(R^h)_2$. In certain embodiments, $R^e$ is a 2-piperidinyl group, e.g., of the formula (i-h) wherein $W^o$ is $NR^k$; $W^p$, $W^q$, $W^r$, and $W^s$ are, independently, $CHR^h$, $C(R^h)_2$, or $CH_2$; and $W^t$ is CH or $CR^h$. In certain embodiments, $R^e$ is a 3-piperidinyl group, e.g., of the formula (i-h) wherein $W^p$ is $NR^k$; $W^o$, $W^q$, $Q^f$, and $W^s$ are, independently, $CHR^h$, $C(R^h)_2$, or $CH_2$; and $W^t$ is CH or $CR^h$. In certain embodiments, $R^e$ is a 4-piperidinyl group, e.g., of the formula (i-h) wherein $W^q$ is $NR^k$; $W^o$, $W^p$, $W^r$, and $W^s$ are, independently, $CHR^h$, $C(R^h)_2$, or $CH_2$; and $W^t$ is CH or $CR^h$.

In certain embodiments, $R^e$ is a piperazinyl group. In certain embodiments, $R^e$ is a piperazinyl group substituted with 0, 1, 2, 3 or 4 $R^h$ groups, e.g., of the formulae:

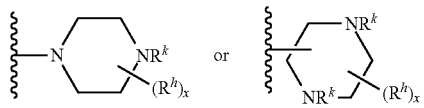

wherein x is 0, 1, 2, 3, 4 or 5, and $R^h$ and $R^k$ are as defined below and herein. In certain embodiments, $R^e$ is an unsubstituted piperazinyl (i.e., wherein x is 0). In certain embodiments, $R^e$ is a substituted piperazinyl (e.g., wherein x is 1, 2, 3, 4 or 5). In certain embodiments, $R^e$ is a monosubstituted piperazinyl (i.e., wherein x is 1). In certain embodiments, $R^e$ is a disubstituted piperazinyl (i.e., wherein x is 2). In certain embodiments, $R^e$ is a trisubstituted piperazinyl (i.e., wherein x is 3). In certain embodiments, x is 0, 1, 2 or 3. In certain embodiments, x is 0, 1 or 2. In certain embodiments, x is 0 or 1.

In certain embodiments, $R^e$ is a 1-piperazinyl group, e.g., of the formula (i-h) wherein $W^t$ is N, $W^q$ is $NR^k$ and $W^o$, $W^p$, $W^r$, and $W^s$ are, independently, selected from $CH_2$, $CHR^h$, $C(R^h)_2$. In certain embodiments, $R^e$ is a 2-piperazinyl group, e.g., of the formula (i-h) wherein $W^o$ and $W^r$ are independently $NR^k$ and $W^p$, $W^q$, $W^r$, and $W^s$ are, independently, $CHR^h$, $C(R^h)_2$, or $CH_2$; and $W^t$ is CH or $CR^h$.

In certain embodiments, $R^e$ is a morpholinyl group. In certain embodiments, $R^e$ is a morpholinyl group substituted with 0, 1, 2, 3 or 4 $R^h$ groups, e.g., of the formulae:

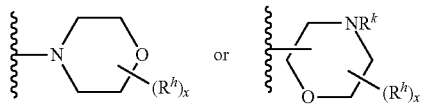

wherein x is 0, 1, 2, 3, 4 or 5, and $R^h$ and $R^k$ are as defined below and herein. In certain embodiments, $R^e$ is an unsubstituted morpholinyl (i.e., wherein x is 0). In certain embodiments, $R^e$ is a substituted morpholinyl (e.g., wherein x is 1, 2, 3, 4 or 5). In certain embodiments, $R^e$ is a monosubstituted morpholinyl (i.e., wherein x is 1). In certain embodiments, $R^e$ is a disubstituted morpholinyl (i.e., wherein x is 2). In certain embodiments, $R^e$ is a trisubstituted morpholinyl (i.e., wherein x is 3). In certain embodiments, x is 0, 1, 2 or 3. In certain embodiments, x is 0, 1 or 2. In certain embodiments, x is 0 or 1.

In certain embodiments, $R^e$ is a morpholinyl group of the formula (i-h) wherein $W^t$ is N, $W^q$ is O and $W^o$, $W^p$, $W^r$, and $W^s$ are, independently, selected from $CH_2$, $CHR^h$, $C(R^h)_2$.

In certain embodiments, $R^e$ is a dioxanyl group. In certain embodiments, $R^e$ is a dioxanyl group substituted with 0, 1, 2, 3 or 4 $R^h$ groups, e.g., of the formulae:

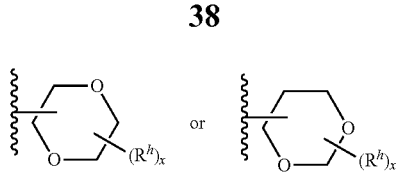

wherein x is 0, 1, 2, 3, 4 or 5, and $R^h$ and $R^k$ are as defined below and herein. In certain embodiments, $R^e$ is an unsubstituted dioxanyl (i.e., wherein x is 0). In certain embodiments, $R^e$ is a substituted dioxanyl (e.g., wherein x is 1, 2, 3, 4 or 5). In certain embodiments, $R^e$ is a monosubstituted dioxanyl (i.e., wherein x is 1). In certain embodiments, $R^e$ is a disubstituted dioxanyl (i.e., wherein x is 2). In certain embodiments, $R^e$ is a trisubstituted dioxanyl (i.e., wherein x is 3). In certain embodiments, x is 0, 1, 2 or 3. In certain embodiments, x is 0, 1 or 2. In certain embodiments, x is 0 or 1.

In certain embodiments, $R^e$ is a dioxanyl group, e.g., of the formula (i-h) wherein $W^o$ and $W^r$ are O and $W^p$, $W^q$, $W^r$, and $W^s$ are, independently, $CHR^h$, $C(R^h)_2$, or $CH_2$; and $W^t$ is CH or $CR^h$.

Other 6-membered heterocycyl $R^e$ groups encompassed by formula (i-h) include monosaccharide sugars, e.g., for example, pyranosides selected from ribose, arabinose, xylose, lyxose, allose, altrose, glucose, mannose, gulose, iodose, galactose and talose.

In certain embodiments, $R^e$ is a $C_{3-10}$ carbocycyl. In certain embodiments, $R^e$ is a C3-10 carbocycyl substituted with 0, 1, 2, 3, 4, or 5 $R^h$ groups. In certain embodiments, $R^e$ is a C5-8 carbocycyl substituted with 0, 1, 2, 3, 4, or 5 $R^h$ groups. In certain embodiments, $R^e$ is a C5-6 carbocycyl substituted with 0, 1, 2, 3 or 4 $R^h$ groups. In certain embodiments, $R^e$ is a C9-10 carbocycyl substituted with 0, 1, 2, 3, 4, or 5 $R^h$ groups.

Exemplary $R^e C_{3-10}$ carbocycyl groups include, but are not limited to, cyclopropyl, cyclobutyl, cyclopentyl, cyclopentenyl, cyclohexyl, cyclohexenyl, cyclohexadienyl, cycloheptyl, and cycloheptadienyl, wherein such groups are substituted with 0, 1, 2, 3, 4, or 5 $R^h$ groups.

$R^f$ of Group G

As defined generally above, in certain embodiments, wherein G is selected from $-SO_2NR^fR^e$, $-PO_2NR^fR^e$, $-(C=O)NR^fR^e$, $-ONR^fR^e$, $-ONR^f(C=O)R^e$, $-ONR^fSO_2R^e$, $-ONR^fPO_2R^e$, $-ONR^fPO_2OR^e$, $-NR^fSO_2R^e$, $-NR^fPO_2R^e$, $-NR^fPO_2OR^e$, $-OPO_2NR^fR^e$, $-NR^fR^e$, $-NR^f(C=O)R^e$, $-NR^f(C=O)OR^e$, $-O(C=O)NR^fR^e$, $-NR^f(C=NR^f)NR^fR^e$, $-O(C=NR^f)NR^fR^e$, $-NR^f(C=NR^f)OR^e$, and $-[N(R^f)_2R^e]^+X^-$ wherein $X^-$ is a counterion, each $R^f$ attached to a nitrogen atom is, independently, selected from $-H$ or $C_{1-10}$ alkyl, or an amino protecting group, or $R^e$ and $R^f$ are joined to form an 3-14 membered heterocyclyl ring or an 5-14 membered heteroaryl ring.

In certain embodiments, $R^f$ is H or a $C_{1-10}$ alkyl group.

In certain embodiments, $R^f$ is H.

In certain embodiments, $R^f$ is a $C_{1-10}$ alkyl group. In certain embodiments, $R^f$ is $C_{1-10}$ alkyl substituted with 0, 1, 2, 3, 4, or 5 $R^h$ groups. Exemplary $R^f$ alkyl groups include, but are not limited to, methyl, ethyl, propyl, allyl, and benzyl. In certain embodiments, $R^f$ an unsubstituted methyl, i.e., $-CH_3$. In certain embodiments, $R^f$ an unsubstituted ethyl, i.e., $-CH_2CH_3$.

In certain embodiments, $R^f$ is an amino protecting group. For example, in certain embodiments, $R^f$ is selected from $-OH$, $-OR^i$, $-N(R^k)_2$, $-C(=O)R^i$, $-C(=O)N(R^k)_2$, $-CO_2R^i$, $-SO_2R^i$, $-C(=NR^k)R^i$, $-C(=NR^k)OR^i$, $-C(=NR^k)N(R^k)_2$, $-SO_2N(R^k)_2$, $-SO_2R^i$, $-SO_2OR^i$, $-SOR^i$, $-C(=S)N(R^k)_2$, $-C(=O)SR^i$, $-C(=S)SR^i$, $C_{1-10}$ alkyl (e.g., aralkyl), $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl groups, wherein each alkyl, alkenyl, alkynyl, carbocyclyl, heterocyclyl, aralkyl, aryl, and heteroaryl is independently substituted with 0, 1, 2, 3, 4, or 5 $R^m$ groups, wherein $R^k$, $R^m$ are as defined below and herein.

However, in certain embodiments, G is —$NR^eR^f$ and $R^f$ is —H or $C_{1-3}$ alkyl, then $R^e$ is not $C_{1-6}$ alkyl or thiazolyl.

Moreover, in certain embodiments, wherein G is —OC(=O)$NR^fR^e$, then $R^e$ and $R^f$ are not both —$CH_3$.

Alternatively, in certain embodiments, $R^e$ and $R^f$ are joined to form an 3-14 membered heterocyclyl ring or an 5-14 membered heteroaryl ring; e.g., for example, when G is —$SO_2NR^fR^e$, —$PO_2NR^fR^e$, —(C=O)$NR^fR^e$, —$ONR^fR^e$, —$OPO_2NR^fR^e$, —$NR^fR^e$, —O(C=O)$NR^fR^e$, —$NR^f$(C=$NR^f$)$NR^fR^e$, —O(C=NR)$NR^fR^e$, and —[$N(R^f)_2R^e$]$^+X^-$ wherein $X^-$ is a counterion. In certain embodiments, wherein $R^e$ and $R^f$ are joined to form an 3-14 membered heterocyclyl ring or an 5-14 membered heteroaryl ring, the heterocyclyl ring or heteroaryl ring are substituted with 0, 1, 2, 3, 4 or 5 $R^h$ groups, as defined below and herein.

In certain embodiments, $R^e$ and $R^f$ are joined to form an 3-14 membered heterocyclyl ring. In certain embodiments, $R^e$ and $R^f$ are joined to form a 3-14 membered heterocyclyl ring substituted with 0, 1, 2, 3, 4 or 5 $R^h$ groups. In certain embodiments, and $R^f$ are joined to form a 5-10 membered heterocyclyl ring substituted with 0, 1, 2, 3, 4, or 5 $R^h$ groups. In certain embodiments, $R^e$ and $R^f$ are joined to form a 5-8 membered heterocyclyl ring substituted with 0, 1, 2, 3, 4, or 5 $R^h$ groups. In certain embodiments, $R^e$ and $R^f$ are joined to form a 5-6 membered heterocyclyl ring substituted with 0, 1, 2 or 3 $R^h$ groups. In certain embodiments, $R^e$ and $R^f$ are joined to form a 9-10 membered heterocyclyl ring substituted with 0, 1, 2, 3, 4, or 5 $R^h$ groups.

In certain embodiments, $R^e$ and $R^f$ are joined to form a heterocyclyl group selected from azirdinyl, azetidinyl, pyrrolidinyl, dihydropyrrolyl, pyrrolyl-2,5-dione, triazolinyl, oxadiazolinyl, thiadiazolinyl, piperidinyl, dihydropyridinyl, thianyl, piperazinyl, morpholinyl, triazinanyl, azepanyl, oxepanyl, thiepanyl, azocanyl, indolinyl, isoindolinyl, tetrahydrobenzo-thienyl, tetrahydroindolyl, tetrahydroquinolinyl, tetrahydroisoquinolinyl, decahydroquinolinyl, decahydroisoquinolinyl, indolinyl, and phthalimidyl, wherein such groups are substituted with 0, 1, 2, 3, 4 or 5 $R^h$ groups.

For example, in certain embodiments, $R^e$ and $R^f$ are joined to form a 5-membered heterocyclyl ring selected from the group:

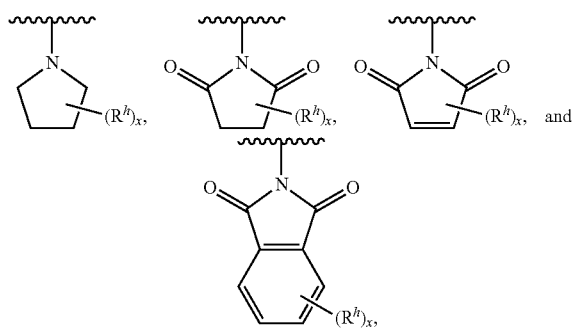

wherein x is 0, 1, 2 or 3, wherein $R^h$ and $R^k$ are as defined below and herein.

In certain embodiments, $R^e$ and $R^f$ are joined to form a 6-membered heterocyclyl ring selected from the group:

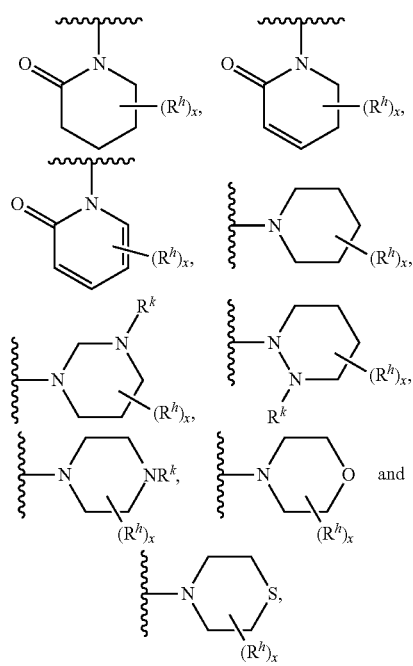

wherein x is 0, 1, 2 or 3, wherein $R^h$ and $R^k$ are as defined below and herein.

However, in certain embodiments, wherein G is —$NR^eR^f$, then $R^e$ and $R^f$ are not joined to form a pyrrolidinyl, piperidinyl or azepanyl ring.

In certain embodiments, $R^e$ and $R^f$ are joined to form a 5-14 membered heteroaryl ring. In certain embodiments, $R^e$ and $R^f$ are joined to form a 5-14 membered heteroaryl ring substituted with 0, 1, 2, 3, 4, or 5 $R^h$ groups. In certain embodiments, $R^e$ and $R^f$ are joined to form a 5-10 membered heteroaryl ring substituted with 0, 1, 2, 3, 4, or 5 $R^h$ groups. In certain embodiments, $R^e$ and $R^f$ are joined to form a 5-8 membered heteroaryl ring substituted with 0, 1, 2, 3 or 4 $R^h$ groups. In certain embodiments, $R^e$ and $R^f$ are joined to form a 5-6 membered heteroaryl ring substituted with 0, 1, 2, 3 or 4 $R^h$ groups. In certain embodiments, $R^e$ and $R^f$ are joined to form a 9-10 membered heteroaryl ring substituted with 0, 1, 2, 3, 4, or 5 $R^h$ groups.

In certain embodiments, $R^e$ and $R^f$ are joined to form a 5-membered heteroaryl ring selected from:

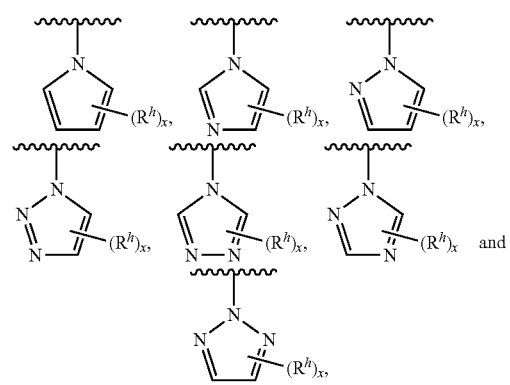

wherein x is 0, 1 or 2, and $R^h$ and $R^k$ are as defined below and herein.

However, in certain embodiments, wherein G is —NR$^f$R$^e$, R$^e$ and R$^f$ are not joined to form a 1,2,4-triazolyl ring, e.g. of the formula:

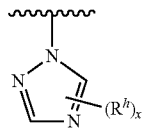

wherein x is 0 or 1, and R$^h$ is as defined below and herein.

In certain embodiments, R$^e$ and R$^f$ are joined to form a 9-membered heteroaryl ("5,6-bicyclic heteroaryl") ring selected from:

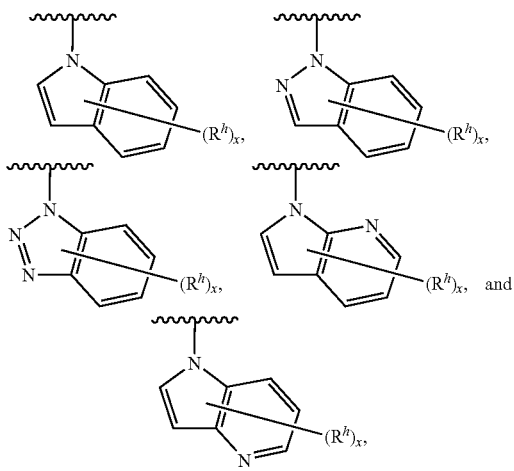

wherein x is 0, 1, 2 or 3 and R$^h$ and R$^k$ are as defined below and herein.

Group G Substituents
Embodiments of R$^h$

As used above and herein each instance of R$^h$ is, independently, selected from halogen (fluoro (—F), bromo (—Br), chloro (—Cl), and iodo (—I)), —CN, —NO$_2$, —N$_3$, —SO$_2$H, —SO$_3$H, —OH, —OR$^i$, —ON(R$^k$)$_2$, —N(R$^k$)$_2$, —N(R$^k$)$_3$—N(OR$^j$)R$^k$, —SH, —SSR$^j$, —C(=O)R$^i$, —CO$_2$H, —CHO, —CO$_2$R$^i$, —OC(=O)R$^i$, —OCO$_2$R$^i$, —C(=O)N(R$^k$)$_2$, —OC(=O)N(R$^i$)$_2$, —NR$^k$C(=O)R$^i$, —NR$^k$CO$_2$R$^i$, —NR$^k$C(=O)N(R$^k$)$_2$, —C(=NR$^k$)R$^i$, —C(=NR$^k$)OR$^i$, —OC(=NR$^k$)R$^i$, —OC(=NR$^k$)OR$^i$, —C(=NR$^k$)N(R$^k$)$_2$, —OC(=NR$^k$)N(R$^k$)$_2$, —NR$^k$C(=NR$^k$)N(R$^k$)$_2$, —C(=O)NR$^k$SO$_2$R$^i$, —NR$^i$SO$_2$Ri, —SO$_2$N(R$^k$)$_2$, —SO$_2$R$^i$, —SO$_2$OR$^i$, —OSO$_2$R$^i$, —S(=O)R$^i$, —OS(=O)R$^i$, —Si(R$^i$)$_3$, —OS$^i$(Ri)$_3$ —C(=S)N(R$^k$)$_2$, —C(=O)SR$^i$, —C(=S)SR$^i$, —SC(S)SR$^i$, —P(=O)$_2$R$^i$, —OP(=O)$_2$R$^i$, —P(=O)(R$^i$)$_2$, —OP(=O)(R$^i$)$_2$, —OP(=O)(OR$^j$)$_2$, —P(=O)$_2$N(R$^k$)$_2$, —OP(=O)$_2$N(R$^k$)$_2$, —P(=O)(NR$^k$)$_2$, —OP(=O)(NR$^k$)$_2$, —NR$^k$P(=O)(OR$^j$)$_2$, —NR$^k$P(=O)(NR$^k$)$_2$, —P(R$^j$)$_2$, —P(R$^j$)$_3$, —OP(R$^j$)$_2$, —OP(R$^j$)$_3$, —B(OR$^j$)$_2$, —BR$^i$(OR$^j$), C$_{1-10}$ alkyl, C$_{1-10}$ perhaloalkyl, C$_{2-10}$ alkenyl, C$_{2-10}$ alkynyl, C$_{3-14}$ carbocyclyl, 3-14 membered heterocyclyl, C$_{6-14}$ aryl, and 5-14 membered heteroaryl, wherein each alkyl, alkenyl, alkynyl, carbocyclyl, heterocyclyl, aryl, and heteroaryl is independently substituted with 0, 1, 2, 3, 4, or 5 R$^m$ groups;

each instance of R$^i$ is, independently, selected from C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, carbocyclyl, heterocyclyl, aryl, and heteroaryl is independently substituted with 0, 1, 2, 3, 4, or 5 R$^m$ groups;

each instance of R$^k$ is, independently, selected from hydrogen, —OH, —OR$^i$, —N(R$^j$)$_2$, —CN, —C(=O)R$^i$, —C(=O)N(R$^j$)$_2$, —CO$_2$R$^i$, —SO$_2$R$^i$, —C(=NR$^j$)OR$^i$, —C(=NR$^j$)N(R$^j$)$_2$, —SO$_2$N(R$^j$)$_2$, —SO$_2$R$^j$, —SO$_2$OR$^i$, —SOR$^i$, —C(=S)N(R$^j$)$_2$, —C(=O)SR$^j$, —C(=S)SR$^j$, —P(=O)$_2$R$^i$, —P(=O)(R$^i$)$_2$, —P(=O)$_2$N(R$^j$)$_2$, —P(=O)(NR$^i$)$_2$, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^j$ groups attached to an N atom are joined to fo R$^m$ a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^m$ groups;

each instance of is, independently, selected from hydrogen, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^j$ groups attached to an N atom are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^m$ groups;

each instance of R$^m$ is, independently, selected from fluoro (—F), bromo (—Br), chloro (—Cl), and iodo (—I), —CN, —NO$_2$, —N$_3$, —SO$_2$H, —SO$_3$H, —OH, —ORo, —ON(R'')$_2$, —N(R'')$_2$, —N(R'')$_3$$^+$X$^-$, —N(ORo)Rn, —SH, —SR$^o$, —SSR$^o$, —C(=O)R$^o$, —CO$_2$H, —CO$_2$R$^o$, —OC(=O)R$^o$, —OCO$_2$R$^o$, —C(=O)N(R'')$_2$, —OC(=O)N(R'')$_2$, —NRnC(=O)R$^o$, —NR''CO$_2$R$^o$, —NR''C(=O)N(R'')$_2$, —C(=NR'')OR$^o$, —OC(=NR'')R$^o$, —OC(=NR'')OR$^o$, —C(=NR'')N(R'')$_2$, —OC(=NR'')N(R'')$_2$, —NR''C(=NR'')N(R'')$_2$, —NR''SO$_2$R$^o$, —SO$_2$N(R'')$_2$, —SO$_2$R$^o$, —SO$_2$OR$^o$, —OSO$_2$R$^o$, —S(=O)R$^o$, —Si(R$^o$)$_3$, —OSi(R$^o$)$_3$, —C(=S)N(R'')$_2$, —C(=O)SR$^o$, —C(=S)SR$^o$, —SC(=S)SR$^o$, —P(=O)$_2$R$^o$, —P(=O)(R$^o$)$_2$, —OP(=O)(R$^o$)$_2$, —OP(=O)(OR$^o$)$_2$, C$_{1-6}$ alkyl, C$_{1-6}$ perhaloalkyl, C$_{2-6}$ alkenyl, C$_{2-6}$ alkynyl, C$_{3-10}$ carbocyclyl, 3-14 membered heterocyclyl, C$_{6-14}$ aryl, 5-14 membered heteroaryl, wherein each alkyl, alkenyl, alkynyl, carbocyclyl, heterocyclyl, aryl, and heteroaryl is independently substituted with 0, 1, 2, 3, 4, or 5 R$^p$ groups, or two geminal R$^m$ substituents can be joined to form =O or =S;

each instance of R$^o$ is, independently, selected from C$_{1-6}$ alkyl, C$_{1-6}$ perhaloalkyl, C$_{2-6}$ alkenyl, C$_2$ alkynyl, C$_{3-10}$ carbocyclyl, C$_{6-10}$ aryl, 3-10 membered heterocyclyl, and 3-10 membered heteroaryl, wherein each alkyl, alkenyl, alkynyl, carbocyclyl, heterocyclyl, aryl, and heteroaryl is independently substituted with 0, 1, 2, 3, 4, or 5 R$^p$ groups;

each instance of R'' is, independently, selected from hydrogen, C$_{1-6}$ alkyl, C$_{1-6}$ perhaloalkyl, C$_{2-6}$ alkenyl, C$_{2-6}$ alkynyl, C$_{3-10}$ carbocyclyl, 3-10 membered heterocyclyl, C$_{6-10}$ aryl and 5-10 membered heteroaryl, or two R'' groups attached to an N atom are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^p$ groups; and each instance of R$^p$ is, independently, fluoro (—F), bromo (—Br), chloro (—Cl), and iodo (—I), —CN, —NO$_2$, —SO$_2$H, —SO$_3$H, —OH, —OC$_{1-6}$ alkyl, —ON(C$_{1-6}$ alkyl)$_2$, alkyl)$_2$, alkyl)$_3$X, —NH(C$_{1-6}$ alkyl)$_2$X, —NH$_2$(C$_{1-6}$ alkyl)X, —NH$_3$X, —N(OC$_{1-6}$ alkyl)(C$_{1-6}$ alkyl), —N(OH)(C$_{1-6}$ alkyl), —NH(OH), —SH, —SC$_{is}$ alkyl, —SS(C$_{1-6}$ alkyl), —C(=O)(C$_{1-6}$ alkyl), —CO$_2$H, —CO$_2$ (C$_{1-6}$ alkyl), —OC(=O)(C$_{1-6}$ alkyl), —OCO$_2$ (C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$ —NHC(NH)N(C$_{1-6}$ alkyl)$_2$, —NHC(=NH)NH$_2$, SO$_2$ (C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$ —C(=S)N(C$_{1-6}$ alkyl)$_2$, C(=S)NH(C$_{1-6}$ alkyl), C(=S) NH$_2$, —C(=O)S(C$_{1-6}$ alkyl), —C(=S)SC$_{1-6}$ alkyl, —SC (=S)SC$_{1-6}$ alkyl, —P(=O)$_2$(C$_{1-6}$ alkyl), —P(=O)(C$_{1-6}$ alkyl)$_2$, —OP(=O)(C$_{1-6}$ alkyl)$_2$, —OP(=O)(OC$_{1-6}$ alkyl)$_2$, C$_{1-6}$ alkyl, C$_{1-6}$ perhaloalkyl, C$_{2-6}$ alkenyl, C$_2$ alkynyl, C$_{3-10}$ carbocyclyl, C$_{6-14}$ aryl, 3-14 membered heterocyclyl, 5-14 membered heteroaryl; or two geminal Rp substituents can be joined to form =O or =S;

wherein X$^-$ is a counterion.

In certain embodiments, R$^h$ is selected from fluoro (—F), bromo (—Br), chloro (—Cl), and iodo (—I), —CN, —NO$_2$, —OH, —OR$^i$, —SR$^i$, —SO$_2$H, —SO$_3$H, —N(R$^k$)$_2$, —N(R$^k$)$_3$ $^+$X$^-$, —C(=O)R$^i$, —CO$_2$H, —CHO, —CO$_2$R$^i$, —OC(=O)R$^i$, —OCO$_2$R$^i$, —C(=O)N(R$^k$)$_2$, —OC(=O)N (R)$_2$, —NR$^k$C(=O)R$^i$, —NR$^k$CO$_2$R$^i$, —NR$^k$C(=O)N(R$^k$)$_2$, —C(=NR$^k$)R$^i$, —C(=NR$^k$)OR$^i$, —OC(=NR$^k$)R$^i$, —OC (=NR$^k$)OR$^i$, —C(=NR$^k$)N(R$^k$)$_2$, —OC(=NR$^k$)N(R$^k$)$_2$, —NR$^k$C(=NR$^k$)N(R$^k$)$_2$, —C(=O)NR$^k$SO$_2$R$^i$, —NR$^k$SO$_2$R$^i$, —SO$_2$N(R$^k$)$_2$, —SO$_2$R$^i$, —SO$_2$OR$^i$, —OSO$_2$R$^i$, —S(=O)R$^i$, —OS(=O)R$^i$, —C(=S)N(R$^k$)$_2$, —C(=O)SR$^i$, —C(=S)SR$^i$, —SC(S)SR$^i$, —P(=O)$_2$R$^i$, —OP(=O)$_2$R$^i$, —P(=O)(R$^i$)$_2$, —OP(=O)(R$^i$)$_2$, —OP (=O)(OR$^j$)$_2$, —P(=O)$_2$N(R$^k$)$_2$, —OP(=O)$_2$N(R$^k$)$_2$, —P(=O)(NR$^k$)$_2$, —OP(=O)(NR$^k$)$_2$, —NR$^k$P(=O)(OR$^j$)$_2$, —NR$^k$P(=O)(NR$^k$)$_2$, —B(OR$^j$)$_2$, —BR$^i$(OR$^j$), C$_{1-10}$ alkyl, —C$_{1-10}$ perhaloalkyl, C$_{3-14}$ carbocyclyl, 3-14 membered heterocyclyl, C$_{6-14}$ aryl, and 5-14 membered heteroaryl, wherein each alkyl, carbocyclyl, heterocyclyl, aryl, and heteroaryl is independently substituted with 0, 1, 2, 3, 4, or 5 R$^m$ groups; and wherein X$^-$ is a counterion.

In certain embodiments, R$^h$ is selected from fluoro (—F), bromo (—Br), chloro (—Cl), and iodo (—I), —CN, —NO$_2$, —OH, —OR$^i$, —SR$^i$, —N(R$^k$)$_2$, —N(R$^k$)$_3$ $^+$X$^-$, —C(=O)R$^i$, —CO$_2$R$^i$, —CO$_2$H, —OC(=O)R$^i$, —OCO$_2$R$^i$, —C(=O)N (R$^k$)$_2$, —OC(=O)N(R$^k$)$_2$, —NR$^k$C(=O)R$^i$, —NR$^k$CO$_2$R$^i$, —NR$^k$C(=O)N(R$^k$)$_2$, —C(=O)NR$^k$SO$_2$R$^i$, —NR$^k$SO$_2$R$^i$, —SO$_2$N(R$^k$)$_2$, —SO$_2$R$^i$, C$_{1-10}$ alkyl, C$_6$ aryl, and 5-6 membered heteroaryl, wherein each alkyl, aryl, and heteroaryl is independently substituted with 0, 1, 2, 3 or 4 R$^m$ groups; and wherein X$^-$ is a counterion.

In certain embodiments, R$^h$ is —OR$^i$, e.g., selected from —OCH$_3$, —OCF$_3$, —OCH$_2$CH$_3$, —OCH$_2$CF$_3$, —OiPr and —OnBu.

In certain embodiments, R$^h$ is —SR$^i$, e.g., selected from —SCH$_3$.

In certain embodiments, R$^h$ is —N(R$^k$)$_2$ or —N(R$^k$)$_3$$^-$X$^-$, e.g., selected from —NH$_2$ and —NH$_3$$^+$X$^-$.

In certain embodiments, R$^h$ is —C(=O)R$^i$, e.g., selected from —C(=O)CH$_3$.

In certain embodiments, R$^h$ is —CO$_2$R$^i$, e.g., selected from —CO$_2$CH$_3$ In certain embodiments, R$^h$ is —C(=O)N(R$^k$)$_2$, e.g., selected from —C(=O)NHOH, —C(=O)NH$_2$, —C(=O) NHCH$_3$, —C(=O)N(CH$_3$)$_2$, —C(=O)NHCH$_2$CH$_3$, —C(=O)NHCH$_2$CF$_3$—C(=O)NH(CH$_2$)$_{1-6}$NH$_3$ $^+$X, —C(=O)NHCH$_2$C(=O)OCH$_3$, —C(=O)NHCH$_2$C(=O) OH and —C(=O)NHCH$_2$CH$_2$OH.

In certain embodiments, R$^h$ is —OC(=O)R$^i$, e.g., selected from —OC(=O)CH$_3$.

In certain embodiments, R$^h$ is —OCO$_2$R$^i$, e.g., selected from —OCO$_2$CH$_3$.

In certain embodiments, R$^h$ is —OC(=O)N(R$^k$)$_2$, e.g., selected from —OC(=O)NH$_2$.

In certain embodiments, R$^h$ is —NR$^k$C(=O)R$^i$, e.g., selected from —NHC(=O)CH$_3$.

In certain embodiments, R$^h$ is —NR$^k$CO$_2$R$^i$, e.g., selected from —NHC(=O)OCH$_3$ and —NHC(=O)OtBu.

In certain embodiments, R$^h$ is —NR$^k$C(=O)N(R$^k$)$_2$, e.g., selected from NHC(=O)NH$_2$.

In certain embodiments, R$^h$ is —C(=O)NR$^k$SO$_2$R$^i$, e.g., selected from —C(=O)NHSO$_2$CH$_3$, —C(=O) NHSO$_2$CH$_2$CH$_3$, —C(=O)NHSO$_2$C$_5$H$_9$ and —C(=O) NHSO$_2$iBu.

In certain embodiments, R$^h$ is —NR$^k$SO$_2$R$^i$, e.g., selected from —NHSO$_2$CH$_3$.

In certain embodiments, R$^h$ is —SO$_2$N(R$^k$)$_2$, e.g., selected from —SO$_2$NH$_2$, —SO$_2$N(CH$_3$)$_2$.

In certain embodiments, R$^h$ is —SO$_2$R$^i$, e.g., selected from —SO$_2$CH$_3$, —SO$_2$CH$_2$CH$_3$, —SO$_2$C$_5$H$_9$ and —SO$_2$iBu.

In certain embodiments, R$^h$ is C$_{1-10}$ alkyl, e.g., selected from —CH$_3$, —CH$_2$CH$_3$, -iPr, -nBu, —CF$_3$, —CH$_2$CH$_2$CO$_2$Me, —CH$_2$CH$_2$CO$_2$H and —CH$_2$CH$_2$CO$_2$NH$_2$.

In certain embodiments, R$^h$ is selected from —C(=O)R$^i$, —CO$_2$H, and —SO$_2$R$^i$. In certain embodiments, R$^h$ is —C(=O)R$^i$. In certain embodiments, R$^h$ is —SO$_2$R$^i$. In certain embodiments, R$^h$ is —CO$_2$H or —SO$_2$CH$_3$. In certain embodiments, R$^h$ is —CO$_2$H. In certain embodiments, R$^h$ is —SO$_2$CH$_3$.

In certain embodiments, each instance of R$^h$ is, independently, selected from fluoro (—F), bromo (—Br), chloro (—Cl), iodo (—I), —NH$_2$, —NH$_3$ $^+$X$^-$, —CN, —NO$_2$, —SO$_2$CH$_3$—SO$_2$CH$_2$CH$_3$, —SO$_2$C$_5$H$_9$, —SO$_2$iBu, —SO$_2$NH$_2$, —SO$_2$N(CH$_3$)$_2$, —C(=O)NHSO$_2$CH$_3$, —C(=O)NHSO$_2$CH$_2$CH$_3$, —C(=O)NHSO$_2$C$_5$H$_9$, —C(=O)NHSO$_2$iBu, —C(=O)CH$_3$, —CO$_2$H, —CO$_2$CH$_3$, —OC(=O)CH$_3$, —OCO$_2$CH$_3$, —C(=O)NHOH, —C(=O)NH$_2$, —C(=O)NHCH$_3$, —C(=O)N(CH$_3$)$_2$, —C(=O)NHCH$_2$CH$_3$, —C(=O)NHCH$_2$CF$_3$ —C(=O)NH(CH$_2$)$_{1-6}$NH$_3$ $^+$X$^-$, —OC(O)NH$_2$, —NHC(=O)CH$_3$, —NHC(=O)OCH$_3$, —NHC(=O)OtBu, —NHC(=O) NH$_2$, —NHSO$_2$CH$_3$—CH$_3$, —CH$_2$CH$_3$, -iPr, -nBu, —CF$_3$, —OH, —OCH$_3$, —SCH$_3$, —OCF$_3$, —OCH$_2$CH$_3$, —OCH$_2$CF$_3$, —OiPr, —OnBu, —CH$_2$CH$_2$CO$_2$Me, —CH$_2$CH$_2$CO$_2$H, —CH$_2$CH$_2$CO$_2$NH$_2$, —C(=O)NHCH$_2$C(=O)OCH$_3$, —C(=O)NHCH$_2$C(=O)OH, —C(=O)NHCH$_2$CH$_2$OH, C$_6$ aryl substituted with 0, 1, or 2 R$^m$ groups and 5-6 membered heteroaryl substituted with 0, 1, or 2 R$^m$ groups; and wherein X$^-$ is a counterion.

In certain embodiments, R$^h$ is a C$_6$ aryl (e.g., phenyl) substituted with 0, 1, or 2 R$^m$ groups. In certain embodiments, R$^h$ is a C$_6$ aryl (e.g., phenyl) substituted with 1 R$^m$ group, and R$^m$ is —CO$_2$H, —CO$_2$CH$_3$, —CO$_2$CH$_2$CH$_3$, and —C(=O) NH$_2$.

In certain embodiments, R$^h$ is a 5-6 membered heteroaryl substituted with 0, 1, or 2 R$^m$ groups. In certain embodiments, R$^h$ is a 5 membered heteroaryl substituted with 0, 1, or 2 R$^m$ groups. Exemplary 5 membered heteroaryl R$^h$ groups include, but are not limited to, pyrrolyl, furanyl, thiophenyl, imidazolyl, pyrazolyl, oxazolyl, isoxazolyl, thiazolyl, isothiazolyl, triazolyl, oxadiazolyl, thiadiazolyl, and tetrazolyl, wherein such groups are substituted with 0 or 1 R$^m$ groups. In certain embodiments, the $R^h$ 5 membered heteroaryl group is selected from pyrazolyl and oxadiazolyl, wherein such groups are substituted with 0 or 1 $R^m$ groups.

Embodiments of $R^i$

In certain embodiments, each instance of $R^i$ is, independently, selected from $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, wherein each alkyl, carbocyclyl, heterocyclyl, aryl, and heteroaryl is unsubstituted.

In certain embodiments, $R^i$ is unsubstituted $C_{1-10}$ alkyl. In certain embodiments, $R^i$ is $C_{1-10}$ perhaloalkyl. In certain embodiments, $R^i$ is unsubstituted $C_{2-10}$ alkenyl. In certain embodiments, $R^i$ is unsubstituted $C_{2-10}$ alkynyl. In certain embodiments, $R^i$ is unsubstituted $C_{3-10}$ carbocyclyl. In certain embodiments, $R^i$ is unsubstituted 3-14 membered heterocyclyl. In certain embodiments, $R^i$ is unsubstituted $C_{6-14}$ aryl. In certain embodiments, $R^i$ is unsubstituted 5-14 membered heteroaryl.

Embodiments of $R^m$

In certain embodiments, each instance of $R^m$ is, independently, selected from fluoro (—F), bromo (—Br), chloro (—Cl), and iodo (—I), —CN, —NO$_2$, —SO$_2$H, —SO$_3$H, —OH, —OR$^o$, —ON(R″)$_2$, —N(R″)$_2$, —N(R″)$_{3+}$X$^-$, —N(OR$^o$)R″, —SH, —SR$^o$, —SSR$^o$, —C(=O)R$^o$, —CO$_2$H, —CO$_2$R$^o$, —OC(=O)R$^o$, —OCO$_2$R$^o$, —C(=O)N(R″)$_2$, —OC(=O)N(R″)$_2$, —NR″C(=O)R$^o$, —NR″CO$_2$R$^o$, —NR″C(=O)N(R″)$_2$, —C(=NR″)OR$^o$, —OC(=NR″)R$^o$, —OC(=NR″)OR$^o$, —C(=NR″)N(R″)$_2$, —OC(=NR″)N(R″)$_2$, —NR″C(=NR″)N(R″)$_2$, —NR″SO$_2$R$^o$, —SO$_2$N(R″)$_2$, —SO$_2$R$^o$, —SO$_2$OR$^o$, —OSO$_2$R$^o$, —S(=O)R$^o$, —C(=S)N(R″)$_2$, —C(=O)SR$^o$, —C(=S)SR$^o$, —SC(=S)SR$^o$, —P(=O)$_2$R$^o$, —P(=O)(R$^o$)$_2$, —OP(=O)(R$^o$)$_2$, —OP(=O)(OR$^o$)$_2$, $C_{1-6}$ alkyl, $C_{1-6}$ perhaloalkyl, $C_{3-10}$ carbocyclyl, 3-14 membered heterocyclyl, $C_{6-14}$ aryl, 5-14 membered heteroaryl, wherein each alkyl, alkenyl, alkynyl, carbocyclyl, aryl, and heteroaryl is independently substituted with 0, 1, 2, 3, 4, or 5 $R^p$ groups.

In certain embodiments, each instance of $R^m$ is, independently, selected from fluoro (—F), bromo (—Br), chloro (—Cl), and iodo (—I), —CN, —NO$_2$, —SO$_2$H, —SO$_3$H, —OH, —OR$^o$, —ON(R″)$_2$, —N(R″)$_2$, —N(R″)$_3^+$X$^-$, —N(OR$^o$)R″, —SH, —SR$^o$, —SSR$^o$, —C(=O)R$^o$, —CO$_2$H, —CO$_2$R$^o$, —OC(=O)R$^o$, —OCO$_2$R$^o$, —C(=O)N(R″)$_2$, —OC(=O)N(R″)$_2$, —NRnC(=O)R$^o$, —NR″CO$_2$R$^o$, —NR″C(=O)N(R″)$_2$, —C(=NR″)OR$^o$, —OC(=NR″)R$^o$, —OC(=NR″)OR$^o$, —C(=NR″)N(R″)$_2$, —OC(=NR″)N(R″)$_2$, —NR″C(=NR″)N(R″)$_2$, —NR″SO$_2$R$^o$, —SO$_2$N(R″)$_2$, —SO$_2$R$^o$, —SO$_2$OR$^o$, —OSO$_2$R$^o$, —S(=O)R$^o$, —C(=S)N(R″)$_2$, —C(=O)SR$^o$, —C(=S)SR$^o$, —SC(=S)SR$^o$, —P(=O)$_2$R$^o$, —P(=O)(R$^o$)$_2$, —OP(=O)(R$^o$)$_2$, —OP(=O)(OR$^o$)$_2$, $C_{1-6}$ alkyl, $C_{1-6}$ perhaloalkyl, $C_{3-10}$ carbocyclyl, 3-14 membered heterocyclyl, $C_{6-14}$ aryl, 5-14 membered heteroaryl.

In certain embodiments, $R^m$ is selected from fluoro (—F), bromo (—Br), chloro (—Cl), and iodo (—I), —NH$_2$, —NH$_3^+$X$^-$, —CN, —NO$_2$, —SO$_2$CH$_3$, —SO$_2$CH$_2$CH$_3$, —SO$_2$C$_5$H$_9$, —SO$_2$iBu, —SO$_2$NH$_2$, —SO$_2$N(CH$_3$)$_2$, —C(=O)NHSO$_2$CH$_3$, —C(=O)NHSO$_2$CH$_2$CH$_3$, —C(=O)NHSO$_2$C$_5$H$_9$, —C(=O)NHSO$_2$iBu, —C(=O)CH$_3$, —CO$_2$H, —CO$_2$CH$_3$, —OC(=O)CH$_3$, —OCO$_2$CH$_3$, —C(=O)NHOH, —C(=O)NH$_2$, —C(=O)NHCH$_3$, —C(=O)N(CH$_3$)$_2$, —C(=O)NHCH$_2$CH$_3$, —C(=O)NHCH$_2$CF$_3$—C(=O)NH(CH$_2$)$_{1-6}$NH$_3^+$X$^-$, —OC(O)NH$_2$, —NHC(=O)CH$_3$, —NHC(=O)OCH$_3$, —NHC(=O)OtBu, —NHC(=O)NH$_2$, —NHSO$_2$CH$_3$, —CH$_3$, —CH$_2$CH$_3$, -iPr, -nBu, —CF$_3$, —OH, —OCH$_3$, —OCF$_3$, —OCH$_2$CH$_3$, —OCH$_2$CF$_3$, —OiPr, —OnBu, —CH$_2$CH$_2$CO$_2$Me, —CH$_2$CH$_2$CO$_2$H, —CH$_2$CH$_2$CO$_2$NH$_2$, —C(=O)NHCH$_2$C(=O)OCH$_3$, —C(=O)NHCH$_2$C(=O)OH, and —C(=O)NHCH$_2$CH$_2$OH.

Embodiments of $R^k$

As used above and herein each instance of $R^k$ is, independently, selected from —H, —OH, —OR$^i$, —N(R$^k$)$_2$, —C(=O)R$^i$, —C(=O)N(R$^k$)$_2$, —CO$_2$R$^i$, —SO$_2$R$^i$, —C(=NR$^k$)R$^i$, —C(=NR$^k$)OR$^i$, —C(=NR$^k$)N(R$^k$)$_2$, —SO$_2$N(R$^k$)$_2$, —SO$_2$R$^i$, —SO$_2$OR$^i$, —SOR$^i$, —C(=S)N(R$^k$)$_2$, —C(=O)SR$^i$, —C(=S)SR$^i$, $C_{1-10}$ alkyl (e.g., aralkyl), $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl groups, wherein each alkyl, alkenyl, alkynyl, carbocyclyl, heterocyclyl, aralkyl, aryl, and heteroaryl is independently substituted with 0, 1, 2, 3, 4, or 5 $R^m$ groups, wherein $R^k$, $R^m$ are as defined above and herein.

In certain embodiments, each instance of $R^k$ is, independently, selected from —H, —C(=O)R$^i$, —C(=O)OR$^i$, —SO$_2$R$^i$, or $C_{1-6}$ alkyl. In certain embodiments, each instance of $R^k$ is, independently, selected from —H or $C_{1-6}$ alkyl. In certain embodiments, each instance of $R^k$ is, independently, selected from —H and —CH$_3$. In certain embodiments, each instance of $R^k$ is, independently, selected from —H. In certain embodiments, each instance of $R^k$ is, independently, selected from —CH$_3$.

Groups $R^a$, $R^b$, and $R^c$

As generally defined above, wherein $R^d$ is the group -L-Z, each of $R^a$, $R^b$, and $R^c$ independently is selected from —H, $C_{1-10}$ alkyl and $C_{1-10}$ perhaloalkyl.

In certain embodiments, each of $R^a$, $R^b$, and $R^c$ independently is selected from —H, $C_{1-6}$ alkyl and $C_{1-6}$ perhaloalkyl. In certain embodiments, each of $R^a$, $R^b$, and $R^c$ independently is selected from —H, $C_{1-3}$ alkyl and $C_{1-3}$ perhaloalkyl. In certain embodiments, each of $R^a$, $R^b$, and $R^c$ independently is selected from —H, —CH$_3$, —CH$_2$CH$_3$ and —CF$_3$. In certain embodiments, each of $R^a$, $R^b$, and $R^c$ independently is selected from —H, —CH$_3$, and —CF$_3$.

In certain embodiments, $R^a$ and $R^b$ are H and $R^c$ is selected from $C_{1-3}$ alkyl and $C_{1-3}$ perhaloalkyl. In certain embodiments, $R^a$ and $R^b$ are H and $R^c$ is selected from —CH$_3$ and —CF$_3$. In certain embodiments, $R^a$ and $R^b$ are H and $R^c$ is —CH$_3$. In certain embodiments, $R^a$ and $R^b$ are H and $R^c$ is —CF$_3$.

In certain embodiments, $R^b$ and $R^c$ are H and $R^a$ is selected from $C_{1-3}$ alkyl and $C_{1-3}$ perhaloalkyl. In certain embodiments, $R^b$ and $R^c$ are H and $R^a$ is selected from —CH$_3$ and —CF$_3$. In certain embodiments, $R^b$ and $R^c$ are H and $R^a$ is —CH$_3$. In certain embodiments, $R^b$ and $R^c$ are H and $R^a$ is —CF$_3$.

In certain embodiments, each of $R^a$, $R^b$, and $R^c$ independently is selected from H, —CH$_3$ and —CF$_3$. In certain embodiments, each of $R^a$, $R^b$, and $R^c$ independently is selected from H or —CH$_3$. In certain embodiments, each of $R^a$, $R^b$, and $R^c$ is H.

Group $R^d$

As generally defined above, in certain embodiments, $R^d$ is the group -L-Z, wherein L is a covalent bond or a divalent $C_{1-6}$ hydrocarbon group, wherein one, two or three methylene units of L are optionally and independently replaced with one or more oxygen, sulfur or nitrogen atoms, and Z is selected from 3-14 membered heterocyclyl or 5-14 membered heteroaryl.

Group L of $R^d$

As generally defined above, L is a covalent bond or a divalent $C_1$ hydrocarbon group, wherein one, two or three methylene units of L are optionally and independently replaced with one or more oxygen, sulfur or nitrogen atoms.

In certain embodiments, L is a covalent bond.

In certain embodiments, L is a divalent $C_1$ hydrocarbon group, wherein one, two or three methylene units of L are optionally and independently replaced with one or more oxygen (—O—), sulfur (—S—) or nitrogen (e.g., —NR$^1$—) atoms.

In certain embodiments, L is a divalent $C_1$ hydrocarbon group, wherein one, two or three methylene units of L are optionally and independently replaced with one or more oxygen (—O—) atoms.

In certain embodiments, L is a divalent $C_1$ hydrocarbon group, wherein one, two or three methylene units of L are optionally and independently replaced with one or more sulfur (—S—) atoms.

In certain embodiments, L is a divalent $C_1$ hydrocarbon group, wherein one, two or three methylene units of L are optionally and independently replaced with one or more nitrogen (—NR$^1$—) atoms. However, in certain embodiments, wherein L is a divalent $C_{1-6}$ hydrocarbon group comprising one, two or three nitrogen atoms, then L is an unsubstituted divalent $C_{1-6}$ hydrocarbon group and L is not the group —CH$_2$NR$^1$— wherein R$^1$ is H, $C_{1-6}$ alkyl or an amino protecting group.

In certain embodiments, L is a divalent $C_{1-6}$ hydrocarbon group, wherein one methylene unit of L is optionally and independently replaced with an oxygen, sulfur or nitrogen atom. In certain embodiments, L is a divalent $C_{1-6}$ hydrocarbon group, wherein one methylene unit of L is optionally and independently replaced with an oxygen atom. In certain embodiments, L is a divalent $C_1$ hydrocarbon group, wherein one methylene unit of L is optionally and independently replaced with a sulfur atom. In certain embodiments, L is a divalent $C_{is}$ hydrocarbon group, wherein one methylene unit of L is optionally and independently replaced with a nitrogen atom.

In certain embodiments of L, the divalent $C_{1-6}$ hydrocarbon group is an unsubstituted divalent $C_1$ hydrocarbon group. In certain embodiments of L, the divalent $C_{1-6}$ hydrocarbon group contains one oxygen, sulfur or nitrogen atom. In certain embodiments, the divalent $C_{1-6}$ hydrocarbon group is an unsubstituted divalent $C_{1-6}$ hydrocarbon group (e.g., an unsubstituted divalent $C_{1-6}$ alkyl group).

For example, in certain embodiments, L is an unsubstituted divalent $C_{1-6}$ alkyl group, wherein one methylene unit of L is replaced with an oxygen, sulfur or nitrogen atom. In certain embodiments, L is an unsubstituted divalent $C_{1-6}$ alkyl group, wherein one methylene unit of L is replaced with an oxygen atom. In certain embodiments, L is an unsubstituted divalent $C_{1-6}$ alkyl, wherein one methylene unit of L is replaced with a sulfur atom. In certain embodiments, L is an unsubstituted divalent $C_{1-6}$ alkyl group, wherein one methylene unit of L is replaced with a nitrogen atom. However, in certain embodiments, wherein L is an unsubstituted divalent $C_{1-6}$ alkyl group, then L is not the group —CH$_2$NR$^1$— wherein R$^1$ is H, $C_{1-6}$ alkyl or an amino protecting group.

In certain embodiments, L is a divalent $C_1$ hydrocarbon group, wherein one methylene unit of L is replaced with an oxygen, sulfur or nitrogen atom, e.g., L is selected from oxygen (—O—), sulfur (—S—) or nitrogen (e.g., —NR$^1$—). In certain embodiments, L is oxygen (—O—). In certain embodiments, L is sulfur (—S—). In certain embodiments, L is nitrogen (e.g., —NR$^1$—).

In certain embodiments, L is selected from the group consisting of —(C(R$^{10}$)$_2$)$_m$—, —(C(R$^{11}$)$_2$)$_m$—O—(C(R$^{12}$)$_2$)$_n$—, —(C(R$^{11}$)$_2$)$_m$—S—(C(R$^{12}$)$_2$)$_n$—, or —(C(R$^{11}$)$_2$)$_m$—NR$^1$—(C(R$^{12}$)$_2$)$_n$—, wherein m and n are, independently, 0, 1, 2, 3, 4, 5 or 6, and each instance of R$^{10}$, R$^{11}$ and R$^{12}$ are, independently, selected from H, halogen or $C_{1-6}$ alkyl. In certain embodiments, each of R$^{10}$, R$^{11}$ and R$^{12}$ are —H.

In certain embodiments, L is —(C(R$^{10}$)$_2$)$_m$—. In certain embodiments, L is selected from —CH$_2$—, —CH$_2$CH$_2$—, —CH$_2$CH$_2$CH$_2$—, —CH$_2$CH$_2$CH$_2$CH$_2$—, —CH$_2$CH$_2$CH$_2$CH$_2$CH$_2$— and —CH$_2$CH$_2$CH$_2$CH$_2$CH$_2$CH$_2$—.

In certain embodiments, L is —(C(R″)$_2$)$_m$—O—(C(R$^{12}$)$_2$)$_n$—. In certain embodiments, L is selected from —O—, —CH$_2$O—, —OCH$_2$—, —OCH$_2$CH$_2$—, —OCH$_2$CH$_2$—, —OCH$_2$CH$_2$CH$_2$—, —CH$_2$CH$_2$CH$_2$O—, —CH$_2$OCH$_2$CH$_2$—, and —CH$_2$CH$_2$OCH$_2$—.

In certain embodiments, L is —(C(R″)$_2$)$_m$—S—(C(R$^{12}$)$_2$)$_n$—. In certain embodiments, L is selected from —S—, —CH$_2$S—, —SCH$_2$—, —SCH$_2$CH$_2$—, —CH$_2$CH$_2$S—, —SCH$_2$CH$_2$CH$_2$—, —CH$_2$CH$_2$CH$_2$S—, —CH$_2$SCH$_2$CH$_2$—, and —CH$_2$CH$_2$SCH$_2$—.

In certain embodiments, L is —(C(R$^{11}$)$_2$)$_m$—NR$^1$—(C(R$^{12}$)$_2$)$_n$—. In certain embodiments, L is selected from —NR$^1$—, —CH$_2$NR$^1$—, —NR$^1$CH$_2$—, —NR$^1$CH$_2$CH$_2$—, —CH$_2$CH$_2$NR$^1$—, —NR$^1$CH$_2$CH$_2$CH$_2$—, —CH$_2$CH$_2$CH$_2$NR$^1$—, —CH$_2$NR$^1$CH$_2$CH$_2$—, and —CH$_2$CH$_2$NR$^1$CH$_2$—, wherein R$^1$ is selected from H, an $C_{1-6}$ alkyl or an amino protecting group.

In certain embodiments, R$^1$ is selected from H or $C_{1-6}$ alkyl. In certain embodiments, R$^1$ is hydrogen. In certain embodiments, R$^1$ is —CH$_3$.

Group Z of R$^d$

As generally defined above, Z is selected from 3-14 membered heterocycyl and 5-14 membered heteroaryl.

In certain embodiments, Z is 5-14 membered heteroaryl. In certain embodiments, Z is a 5-10 membered heteroaryl substituted with 0, 1, 2, 3, 4 or 5 R$^{15}$ groups. In certain embodiments, Z is a 5-8 membered heteroaryl substituted with 0, 1, 2, 3, 4 or 5 R$^{15}$ groups. In certain embodiments, Z is a 5-6 membered heteroaryl substituted with 0, 1, 2, 3 or 4 R$^{15}$ groups. In certain embodiments, Z is a 9-10 membered heteroaryl substituted with 0, 1, 2, 3, 4 or 5 R$^{15}$ groups.

Exemplary Z heteroaryl groups include, but are not limited to, pyrrolyl, furanyl and thiophenyl, imidazolyl, pyrazolyl, oxazolyl, isoxazolyl, thiazolyl, isothiazolyl, triazolyl, oxadiazolyl, thiadiazolyl, tetrazolyl, pyridinyl (e.g., 2-pyridinyl, 3-pyridinyl, 4-pyridinyl), pyridazinyl (e.g., 3-pyridazinyl, 4-pyridazinyl), pyrimidinyl (e.g. 2-pyrimidinyl, 4-pyrimidinyl, 5-pyrimidinyl), pyrazinyl, triazinyl, tetrazinyl, azepinyl, oxepinyl, thiepinyl, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, purinyl, naphthyridinyl, pteridinyl, quinolinyl, isoquinolinyl, cinnolinyl, quinoxalinyl, phthalazinyl, quinazolinyl, phenanthridinyl, dibenzofuranyl, carbazolyl, acridinyl, phenothiazinyl, phenoxazinyl and phenazinyl, wherein such groups are substituted with 0, 1, 2, 3, 4 or 5 R$^{15}$ groups.

In certain embodiments, Z is a 5-membered heteroaryl substituted with 0, 1, 2 or 3 R$^{15}$ groups. In certain embodiments, Z is a 5-membered heteroaryl selected pyrrolyl, furanyl, thiophenyl, imidazolyl, pyrazolyl, oxazolyl, isoxazolyl, thiazolyl, isothiazolyl, triazolyl, oxadiazolyl, thiadiazolyl and tetrazolyl, wherein such groups are substituted with 0, 1, 2 or 3 R$^{15}$ groups.

For example, in certain embodiments, Z is a 5-membered heteroaryl of the formula:

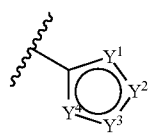

wherein $Y^1$, $Y^2$, $Y^3$ and $Y^4$ are, independently, selected from CH, $CR^{15}$, O, S, N, or $NR^{18}$, with the proviso that at least one of $Y^1$, $Y^2$, $Y^3$ and $Y^4$ are selected from O, S, N, or $NR^{18}$, and wherein $R^{15}$ and $R^{18}$ are defined below and herein.

In certain embodiments of the above formula (ii-d), $Y^1$ is O, S, or $NR^{18}$ and $Y^2$, $Y^3$ and $Y^4$ are, independently, selected from CH, $CR^{15}$ or N. In certain embodiments of the above formula (ii-d), $Y^1$ is O, S, or $NR^{18}$ and $Y^2$, $Y^3$ and $Y^4$ are, independently, selected from CH or $CR^{15}$. In certain embodiments of the above formula (ii-d), $Y^1$ is O, S, or $NR^{18}$, $Y^3$ is N and $Y^2$ and $Y^4$ are, independently, selected from CH or $CR^{15}$. In certain embodiments of the above formula (ii-d), $Y^1$ is S, $Y^3$ is N, and $Y^2$ and $Y^4$ is CH or $CR^{15}$. In certain embodiments of the above formula (ii-d), $Y^1$ is S, $Y^3$ is N, $Y^2$ is $CR^{15}$ and $Y^4$ is CH. In certain embodiments of the above formula (ii-d), $Y^1$ is S and $Y^2$, $Y^3$ and $Y^4$ is CH or $CR^{15}$.

In certain embodiments of the above formula (ii-d), $Y^2$ is O, S, or $NR^{18}$ and $Y^1$, $Y^3$ and $Y^4$ are, independently, selected from CH, $CR^{15}$ or N. In certain embodiments of the above formula (ii-d), $Y^2$ is O, S, or $NR^{18}$ and $Y^1$, $Y^3$ and $Y^4$ are, independently, selected from CH or $CR^{15}$. In certain embodiments of the above formula (ii-d), $Y^2$ is O, S, or $NR^{18}$, $Y^4$ is N and $Y^1$ and $Y^3$ are, independently, selected from CH or $CR^{15}$.

In certain embodiments, Z is a 5-membered heteroaryl of any one of the formulae:

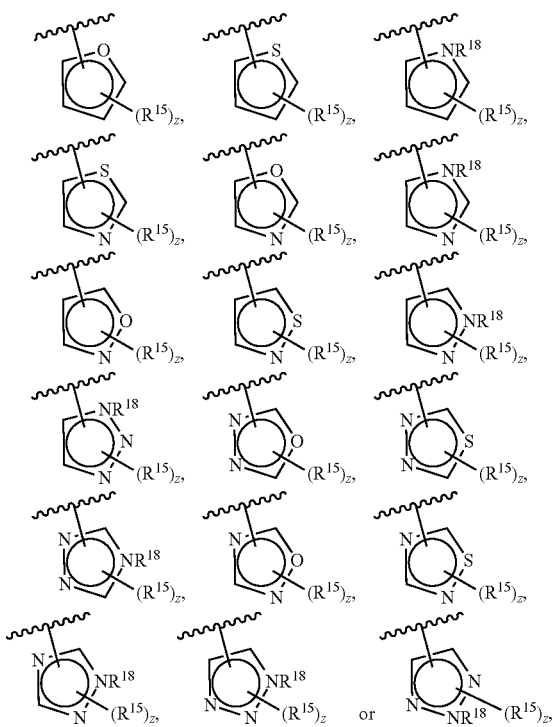

wherein $R^{15}$ and $R^{18}$ are as defined below and herein, and z is 0, 1 or 2.

wherein z is 0, 1 or 2, and $R^{15}$ and $R^{18}$ are as defined below and herein. In certain embodiments, Z is an unsubstituted 5-membered heteroaryl (i.e., wherein z is 0). In certain embodiments, Z is a substituted 5-membered heteroaryl (e.g., wherein z is 1 or 2). In certain embodiments, Z is a monosubstituted 5-membered heteroaryl (i.e., wherein z is 1). In certain embodiments, Z is a disubstituted 5-membered heteroaryl (i.e., wherein z is 2). In certain embodiments, z is 0, 1 or 2. In certain embodiments, z is 0 or 1.

In certain embodiments, Z is a 6-membered heteroaryl substituted with 0, 1, 2, 3 or 4 $R^h$ groups. In certain embodiments, Z is a 6-membered heteroaryl selected from the group consisting of pyridinyl (e.g., 2-pyridinyl, 3-pyridinyl, 4-pyridinyl), pyridazinyl (e.g., 3-pyridazinyl, 4-pyridazinyl), pyrimidinyl (e.g. 2-pyrimidinyl, 4-pyrimidinyl, 5-pyrimidinyl), pyrazinyl, triazinyl and tetrazinyl, wherein such groups are substituted with 0, 1, 2, 3 or 4 $R^{15}$ groups.

For example, in certain embodiments, $R^e$ is a 6-membered heteroaryl group of the formula:

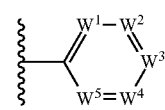

wherein $W^1$, $W^2$, $W^3$, $W^4$ and $W^5$ are, independently, selected from CH, $CR^{15}$ or N, with the proviso that at least one of $W^1$, $W^2$, $W^3$, $W^4$, and $W^5$ is N, and wherein $R^{15}$ is as defined below and herein.

In certain embodiments, Z is a pyrindinyl group. In certain embodiments, Z is a pyrindinyl group substituted with 0, 1, 2, 3 or 4 $R^{15}$ groups. For example, in certain embodiments, Z is a pyrindinyl group of the formula:

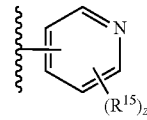

wherein z is 0, 1, 2, 3 or 4, and $R^{15}$ is as defined below and herein. In certain embodiments, Z is an unsubstituted pyrindinyl (i.e., wherein z is 0). In certain embodiments, Z is a substituted pyrindinyl (e.g., wherein z is 1, 2, 3 or 4). In certain embodiments, Z is a monosubstituted pyrindinyl (i.e., wherein z is 1). In certain embodiments, Z is a disubstituted pyrindinyl (i.e., wherein z is 2). In certain embodiments, Z is a trisubstituted pyrindinyl (i.e., wherein z is 3). In certain embodiments, z is 0, 1, 2 or 3. In certain embodiments, z is 0, 1 or 2. In certain embodiments, z is 0 or 1.

In certain embodiments, Z is a 2-pyrindinyl group, e.g., of the formula (ii-e) wherein $W^1$ is N and $W^2$, $W^3$, $W^4$ and $W^5$ are, independently, CH or $CR^{15}$. In certain embodiments Z is a 3-pyrindinyl group, e.g., of the formula (ii-e) wherein $W^2$ is N and $W^1$, $W^3$, $W^4$ and $W^5$ are, independently, CH or $CR^{15}$. In certain embodiments Z is a 4-pyrindinyl group, e.g., of the formula (ii-e) wherein $W^3$ is N and $W^1$, $W^2$, $W^4$ and $W^5$ are, independently, CH or $CR^{15}$.

In certain embodiments, $R^e$ is a substituted or unsubstituted 2-pyridinyl group of any one of the formulae:

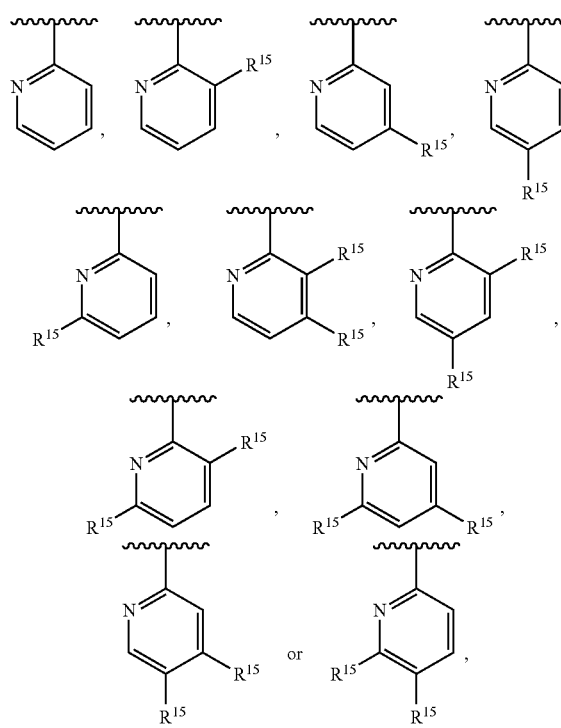

wherein $R^{15}$ is defined below and herein.

In certain embodiments, Z is a substituted or unsubstituted 3-pyridinyl group of any one of the formulae:

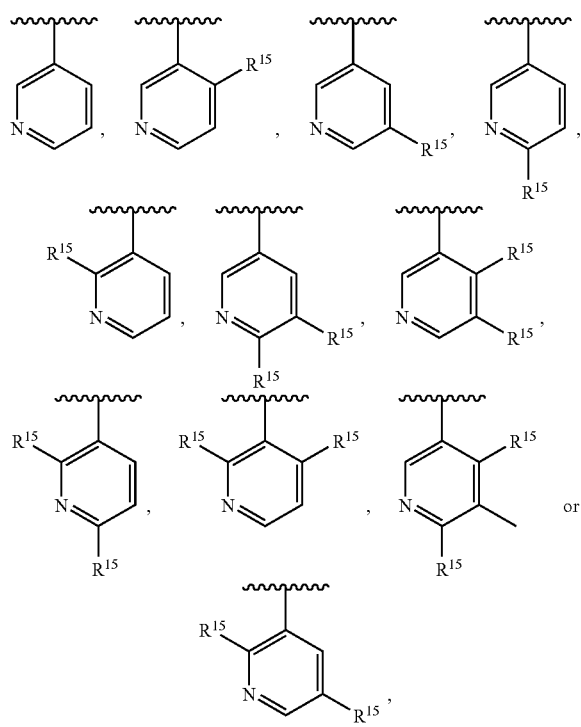

wherein $R^{15}$ is as defined below and herein.

In certain embodiments, Z is a substituted or unsubstituted 4-pyridinyl group of the formulae:

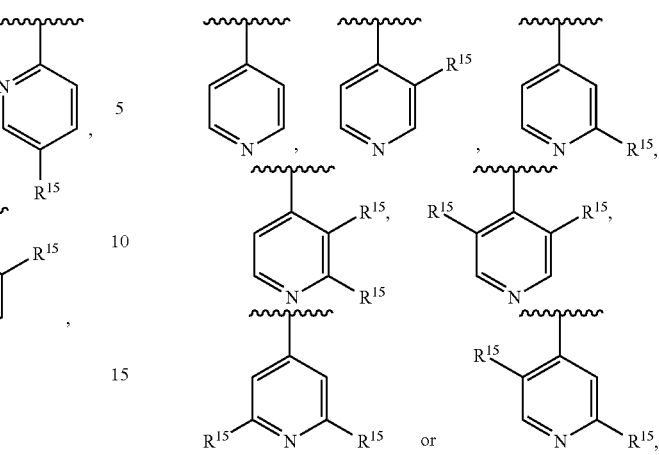

wherein $R^{15}$ is as defined below and herein.

In certain embodiments, Z is a pyridazinyl group. In certain embodiments, Z is a pyridazinyl group substituted with 0, 1, 2 or 3 $R^{15}$ groups. For example, in certain embodiments, Z is a pyridazinyl group of the formula:

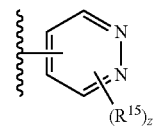

wherein z is 0, 1, 2 or 3, and $R^{15}$ is as defined below and herein. In certain embodiments, Z is an unsubstituted pyridazinyl (i.e., wherein z is 0). In certain embodiments, Z is a substituted pyridazinyl (e.g., wherein z is 1, 2 or 3). In certain embodiments, Z is a monosubstituted pyridazinyl (i.e., wherein z is 1). In certain embodiments, Z is a disubstituted pyridazinyl (i.e., wherein z is 2). In certain embodiments, Z is a trisubstituted pyridazinyl (i.e., wherein z is 3). In certain embodiments, z is 0, 1, 2 or 3. In certain embodiments, z is 0, 1 or 2. In certain embodiments, z is 0 or 1.

In certain embodiments, Z is a 3-pyridazinyl group, e.g., of the formula (ii-e) wherein $W^1$ and $W^2$ are N and $W^3$, $W^4$ and $W^5$ are, independently, CH or $CR^{15}$. In certain embodiments Z is a 4-pyridazinyl group, e.g., of the formula (ii-e) wherein $W^2$ and $W^3$ are N and $W^1$, $W^4$ and $W^5$ are, independently, CH or $CR^h$.

In certain embodiments, Z is a substituted or unsubstituted 3-pyridazinyl group of any one of the formulae:

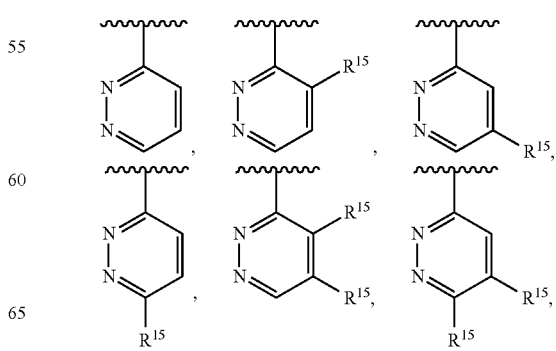

-continued

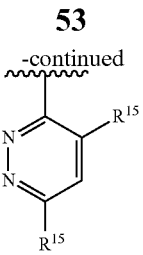

wherein R[15] is as defined below and herein.

In certain embodiments, Z is a substituted or unsubstituted 4-pyridazinyl group of any one of the formulae:

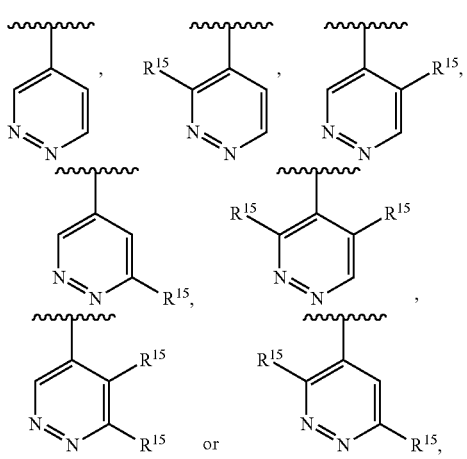

wherein R[15] is as defined below and herein.

In certain embodiments, Z is a pyrimidinyl group. In certain embodiments, Z is a pyrimidinyl group substituted with 0, 1, 2 or 3 R[15] groups. For example, in certain embodiments, Z is a pyrimidinyl group of the formula:

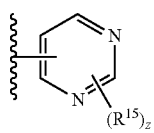

wherein z is 0, 1, 2 or 3, and R[15] is as defined below and herein. In certain embodiments, Z is an unsubstituted pyrimidinyl (i.e., wherein z is 0). In certain embodiments, Z is a substituted pyrimidinyl (e.g., wherein z is 1, 2 or 3). In certain embodiments, Z is a monosubstituted pyrimidinyl (i.e., wherein z is 1). In certain embodiments, Z is a disubstituted pyridazinyl (i.e., wherein z is 2). In certain embodiments, Z is a trisubstituted pyrimidinyl (i.e., wherein z is 3). In certain embodiments, z is 0, 1, 2 or 3. In certain embodiments, z is 0, 1 or 2. In certain embodiments, z is 0 or 1.

In certain embodiments, Z is a 2-pyrimidinyl group, e.g., of the formula (ii-e) wherein $W^1$ and $W^5$ are N and $W^2$, $W^3$ and $W^4$ are, independently, CH or CR[15]. In certain embodiments Z is a 4-pyrimidinyl group, e.g., of the formula (ii-e) wherein $W^1$ and $W^3$ are N and $W^2$, $W^4$ and $W^5$ are, independently, CH or CR[15]. In certain embodiments Z is a 5-pyrimidinyl group, e.g., of the formula (ii-e) wherein $W^2$ and $W^4$ are N and $W^1$, $W^3$ and $W^5$ are, independently, CH or CR[15].

In certain embodiments, Z is a 2-pyrimidinyl group of any one of the formulae:

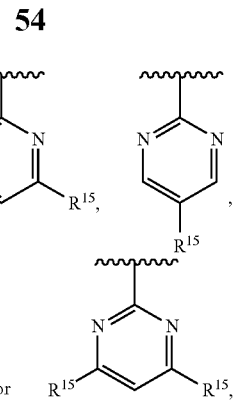

wherein R[15] is as defined below and herein.

In certain embodiments, $R^e$ is a 4-pyrimidinyl group of any one of the formulae:

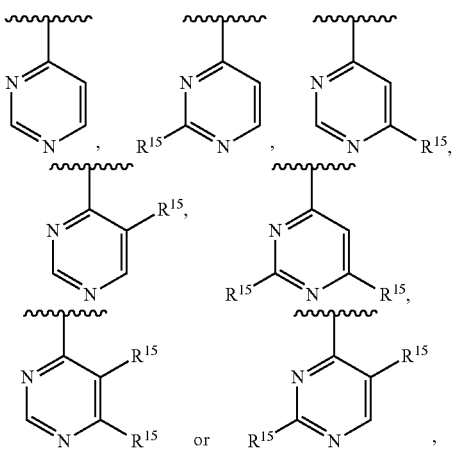

wherein R[15] is as defined below and herein.

In certain embodiments, Z is a 5-pyrimidinyl group of any one of the formulae:

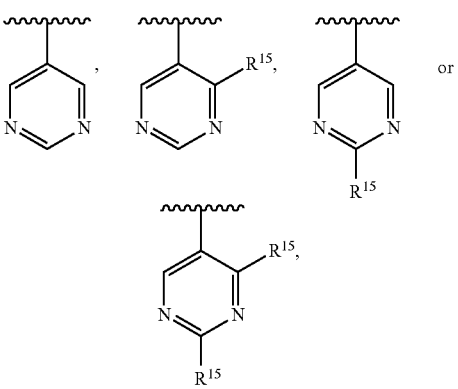

wherein R[15] is as defined below and herein.

In certain embodiments, Z is a pyrazinyl group. In certain embodiments, Z is a pyrazinyl group substituted with 0, 1, 2 or 3 R[15] groups. For example, in certain embodiments, Z is a pyrazinyl group of the formula:

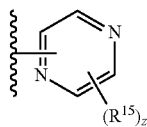

wherein z is 0, 1, 2 or 3, and $R^{15}$ is as defined below and herein. In certain embodiments, Z is an unsubstituted pyrazinyl (i.e., wherein z is 0). In certain embodiments, Z is a substituted pyrazinyl (e.g., wherein z is 1, 2 or 3). In certain embodiments, Z is a monosubstituted pyrazinyl (i.e., wherein z is 1). In certain embodiments, Z is a disubstituted pyrazinyl (i.e., wherein z is 2). In certain embodiments, Z is a trisubstituted pyrazinyl (i.e., wherein z is 3). In certain embodiments, z is 0, 1, 2 or 3. In certain embodiments, z is 0, 1 or 2. In certain embodiments, z is 0 or 1.

In certain embodiments, Z is a pyrazinyl group of any one of the formulae:

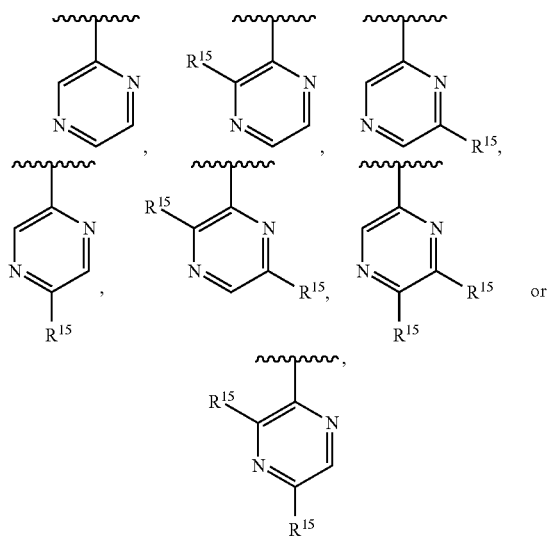

wherein $R^{15}$ is as defined below and herein.

In certain embodiments, Z is a triazinyl group. In certain embodiments, Z is a triazinyl group substituted with 0, 1 or 2 $R^{15}$ groups. For example, in certain embodiments, Z is a triazinyl group of the formula:

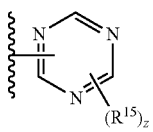

wherein z is 0, 1 or 2, and $R^{15}$ is as defined below and herein. In certain embodiments, Z is an unsubstituted pyrazinyl (i.e., wherein z is 0). In certain embodiments, Z is a substituted pyrazinyl (e.g., wherein z is 1 or 2). In certain embodiments, Z is a monosubstituted pyrazinyl (i.e., wherein z is 1). In certain embodiments, Z is a disubstituted pyrazinyl (i.e., wherein z is 2). In certain embodiments, z is 0, 1 or 2. In certain embodiments, z is 0 or 1.

In certain embodiments, Z is a substituted or unsubstituted triazinyl group of any one of the formulae:

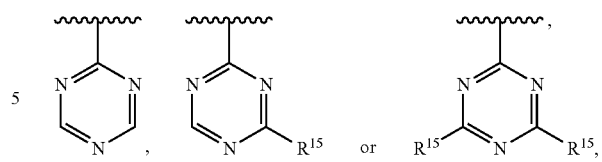

wherein $R^{15}$ is as defined below and herein.

In certain embodiments Z is a tetrazinyl group. In certain embodiments Z is a tetrazinyl group substituted with 0 or 1 $R^{15}$ groups. For example, in certain embodiments, Z is a tetrazinyl group of the formula:

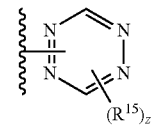

wherein z is 0 or 1, and $R^{15}$ is as defined below and herein. In certain embodiments, Z is an unsubstituted pyrazinyl (i.e., wherein z is 0). In certain embodiments, Z is a substituted pyrazinyl (e.g., wherein z is 1). In certain embodiments, z is 0 or 1.

In certain embodiments, Z is a tetrazinyl group of any one of the formulae:

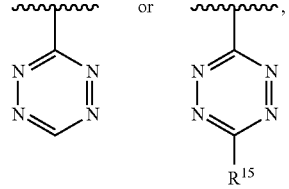

wherein $R^{15}$ is as defined below and herein.

In certain embodiments, Z is a 9-membered heteroaryl (e.g., a 5,6-bicyclic heteroaryl). In certain embodiments, Z is a 5,6-bicyclic heteroaryl substituted with 0, 1, 2, 3, 4 or 5 $R^{15}$ groups. In certain embodiments, Z is a 5,6-bicyclic heteroaryl selected from indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl, wherein such groups are substituted with 0, 1, 2, 3, 4 or 5 $R^{15}$ groups.

For example, in certain embodiments, Z is a 5,6-bicyclic heteroaryl of the formula:

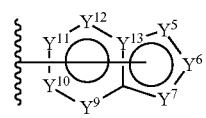

(ii-f)

wherein $Y^5, Y^6, Y^7, Y^9, Y^{10}, Y^{11}$ and $Y^{12}$ are independently, C, CH, $CR^{15}$, O, S, N, or $NR^{18}$, and $Y^{13}$ is C or N, with the proviso that at least one of $Y^5, Y^6, Y^7$ are selected from O, S, N or $NR^{18}$, and wherein $R^{15}$ and $R^{18}$ are as defined herein.

In embodiments, Z is a 5,6-bicyclic heteroaryl group of the formula wherein $Y^5$ is selected from O, S, or $NR^{18}$, $Y^{13}$ is C, and $Y^6$, $Y^7$, $Y^9$, $Y^{10}$, $Y^{11}$ and $Y^{12}$ are, independently, C, CH, or $CR^{15}$. For example, in certain embodiments, Z is a 5,6-bicyclic heteroaryl group of the formulae:

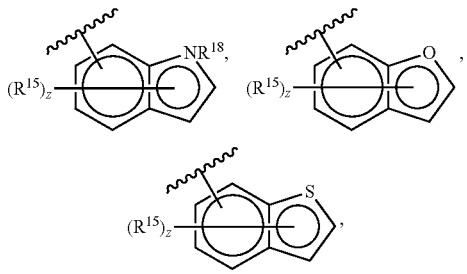

wherein z is 0, 1, 2, 3, 4 or 5 and $R^{15}$ and $R^{18}$ are defined below and herein. In certain embodiments, Z is an unsubstituted 5,6-bicyclic heteroaryl (i.e., wherein z is 0). In certain embodiments, Z is a substituted 5,6-bicyclic heteroaryl (e.g., wherein z is 1, 2, 3, 4 or 5). In certain embodiments, Z is a monosubstituted 5,6-bicyclic heteroaryl (i.e., wherein z is 1). In certain embodiments, Z is a disubstituted 5,6-bicyclic heteroaryl (i.e., wherein z is 2). In certain embodiments, Z is a trisubstituted 5,6-bicyclic heteroaryl (i.e., wherein z is 3). In certain embodiments, z is 0, 1, 2 or 3. In certain embodiments, z is 0, 1 or 2. In certain embodiments, z is 0 or 1.

In certain embodiments, Z is a 5,6-bicyclic heteroaryl wherein $Y^5$ is selected from O, S, or $NR^{18}$; $Y^7$ is N; $Y^{13}$ is C; $Y^6$ is C, CH, or $CR^{15}$ or N, and $Y^9$, $Y^{10}$, $Y^{11}$ and $Y^{12}$ are, independently, C, CH, or $CR^{15}$. For example, in certain embodiments, Z is a 5,6-bicyclic heteroaryl group of the formulae:

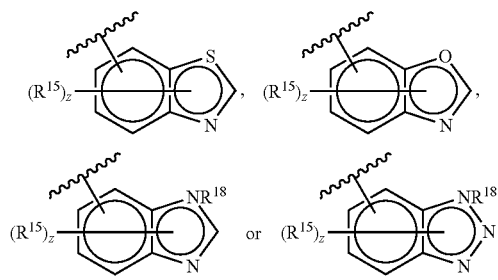

wherein z is 0, 1, 2, 3, 4 or 5 and $R^{15}$ and $R^{18}$ are defined below and herein. In certain embodiments, Z is an unsubstituted 5,6-bicyclic heteroaryl (i.e., wherein z is 0). In certain embodiments, Z is a substituted 5,6-bicyclic heteroaryl (e.g., wherein z is 1, 2, 3, 4 or 5). In certain embodiments, Z is a monosubstituted 5,6-bicyclic heteroaryl (i.e., wherein z is 1). In certain embodiments, Z is a disubstituted 5,6-bicyclic heteroaryl (i.e., wherein z is 2). In certain embodiments, Z is a trisubstituted 5,6-bicyclic heteroaryl (i.e., wherein z is 3). In certain embodiments, z is 0, 1, 2 or 3. In certain embodiments, z is 0, 1 or 2. In certain embodiments, z is 0 or 1.

In certain embodiments, Z is a 5,6-bicyclic heteroaryl wherein $Y^5$ is $NR^k$, S or O; $Y^{12}$ is N; $Y^{13}$ is C; and $Y^6$, $Y^7$, $Y^9$, $Y^{10}$, and $Y^{11}$ are independently, C, CH, or $CR^{15}$. For example, in certain embodiments, Z is a 5,6-bicyclic heteroaryl group of the formulae:

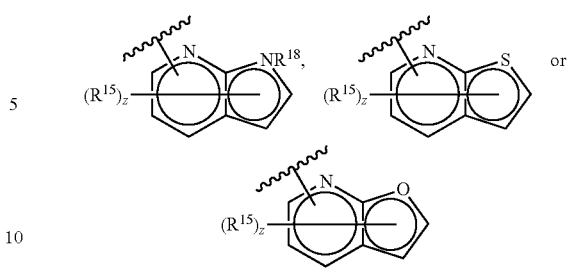

wherein z is 0, 1, 2, 3, 4 or 5 and $R^{15}$ and $R^{18}$ are defined below and herein. In certain embodiments, Z is an unsubstituted 5,6-bicyclic heteroaryl (i.e., wherein z is 0). In certain embodiments, Z is a substituted 5,6-bicyclic heteroaryl (e.g., wherein z is 1, 2, 3, 4 or 5). In certain embodiments, Z is a monosubstituted 5,6-bicyclic heteroaryl (i.e., wherein z is 1). In certain embodiments, Z is a disubstituted 5,6-bicyclic heteroaryl (i.e., wherein z is 2). In certain embodiments, Z is a trisubstituted 5,6-bicyclic heteroaryl (i.e., wherein z is 3). In certain embodiments, z is 0, 1, 2 or 3. In certain embodiments, z is 0, 1 or 2. In certain embodiments, z is 0 or 1.

In certain embodiments, Z is a 5,6-bicyclic heteroaryl wherein $Y^7$ is O, S, or $NR^k$; $Y^{12}$ is N; $Y^{13}$ is C; and $Y^5$, $Y^6$, $Y^9$; $Y^{10}$ and $Y^{11}$ are independently, C, CH, or $CR^{15}$. For example, in certain embodiments, Z is a 5,6-bicyclic heteroaryl group of the formulae:

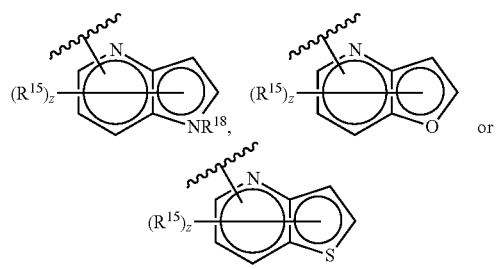

wherein z is 0, 1, 2, 3, 4 or 5 and $R^{15}$ and $R^{18}$ are defined below and herein. In certain embodiments, Z is an unsubstituted 5,6-bicyclic heteroaryl (i.e., wherein z is 0). In certain embodiments, Z is a substituted 5,6-bicyclic heteroaryl (e.g., wherein z is 1, 2, 3, 4 or 5). In certain embodiments, Z is a monosubstituted 5,6-bicyclic heteroaryl (i.e., wherein z is 1). In certain embodiments, Z is a disubstituted 5,6-bicyclic heteroaryl (i.e., wherein z is 2). In certain embodiments, Z is a trisubstituted 5,6-bicyclic heteroaryl (i.e., wherein z is 3). In certain embodiments, z is 0, 1, 2 or 3. In certain embodiments, z is 0, 1 or 2. In certain embodiments, z is 0 or 1.

In certain embodiments, Z is a 5,6-bicyclic heteroaryl wherein $Y^5$ is selected from O, S, or $NR^{18}$; $Y^{13}$ is N; and $Y^6$, $Y^7$, $Y^8$, $Y^9$ and $Y^{10}$ are independently, C, CH, or $CR^{15}$. For example, in certain embodiments, Z is a 5,6-bicyclic heteroaryl group of the formulae:

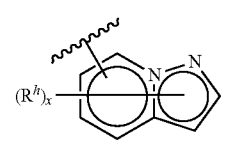

wherein z is 0, 1, 2, 3, 4 or 5 and $R^{15}$ and $R^{18}$ are defined below and herein. In certain embodiments, Z is an unsubstituted 5,6-bicyclic heteroaryl (i.e., wherein z is 0). In certain embodiments, Z is a substituted 5,6-bicyclic heteroaryl (e.g., wherein z is 1, 2, 3, 4 or 5). In certain embodiments, Z is a monosubstituted 5,6-bicyclic heteroaryl (i.e., wherein z is 1). In certain embodiments, Z is a disubstituted 5,6-bicyclic heteroaryl (i.e., wherein z is 2). In certain embodiments, Z is a trisubstituted 5,6-bicyclic heteroaryl (i.e., wherein z is 3). In certain embodiments, z is 0, 1, 2 or 3. In certain embodiments, z is 0, 1 or 2. In certain embodiments, z is 0 or 1.

In certain embodiments, Z is a 10-membered heteroaryl (e.g., a 6,6-bicyclic heteroaryl). In certain embodiments, Z is a 6,6-bicyclic heteroaryl substituted with 0, 1, 2, 3, 4 or 5 $R^{15}$ groups. In certain embodiments, Z is a 6,6-bicyclic heteroaryl selected from naphthyridinyl, pteridinyl, quinolinyl, isoquinolinyl, cinnolinyl, quinoxalinyl, phthalazinyl and quinazolinyl, wherein such groups are substituted with 0, 1, 2, 3, 4 or 5 $R^{15}$ groups.

For example, in certain embodiments, Z is a 6,6-bicyclic heteroaryl of the formula:

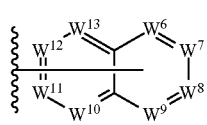

(ii-g)

wherein $W^6$, $W^7$, $W^8$, $W^9$, $W^{10}$, $W^{11}$, $W^{12}$, and $W^{13}$ are independently, selected from C, CH, $CR^{15}$ or N, with the proviso that at least one of $W^6$, $W^7$, $W^8$, $W^9$, $W^{10}$, $W^{11}$, $W^{12}$, and $W^{13}$ is N, and wherein $R^{15}$ is as defined below and herein.

In certain embodiments, Z is a quinolinyl group; e.g., of the formula (ii-g) wherein $W^9$ is N and $W^6$, $W^7$, $W^8$, $W^{10}$, $W^{11}$, $W^{12}$ and $W^{13}$ are independently, C, CH, or $CR^{15}$. For example, in certain embodiments, Z is a quinolinyl group of the formulae:

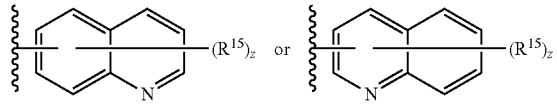

wherein z is 0, 1, 2, 3, 4 or 5, and $R^{15}$ is as defined below and herein. In certain embodiments, Z is an unsubstituted quinolinyl (i.e., wherein z is 0). In certain embodiments, Z is a substituted quinolinyl (e.g., wherein z is 1, 2, 3, 4 or 5). In certain embodiments, Z is a monosubstituted quinolinyl (i.e., wherein z is 1). In certain embodiments, Z is a disubstituted quinolinyl (i.e., wherein z is 2). In certain embodiments, Z is a trisubstituted quinolinyl (i.e., wherein z is 3). In certain embodiments, z is 0, 1, 2 or 3. In certain embodiments, z is 0, 1 or 2. In certain embodiments, z is 0 or 1.

In certain embodiments, Z is an isoquinolinyl group; e.g., of the formula (ii-g) wherein $W^8$ is N and $W^6$, $W^7$, $W^9$, $W^{10}$, $W^{11}$, $W^{12}$ and $W^{13}$ are independently, C, CH, or $CR^{15}$. For example, in certain embodiments, Z is an isoquinolinyl group of the formulae:

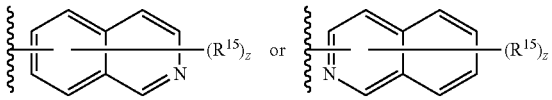

wherein z is 0, 1, 2, 3, 4 or 5, and $R^{15}$ is as defined below and herein. In certain embodiments, Z is an unsubstituted isoquinolinyl (i.e., wherein z is 0). In certain embodiments, Z is a substituted isoquinolinyl (e.g., wherein z is 1, 2, 3, 4 or 5). In certain embodiments, Z is a monosubstituted isoquinolinyl (i.e., wherein z is 1). In certain embodiments, Z is a disubstituted isoquinolinyl (i.e., wherein z is 2). In certain embodiments, Z is a trisubstituted isoquinolinyl (i.e., wherein z is 3). In certain embodiments, z is 0, 1, 2 or 3. In certain embodiments, z is 0, 1 or 2. In certain embodiments, z is 0 or 1.

In certain embodiments, Z is a quinoxalinyl group; e.g., of the formula (ii-g) wherein $W^6$ and $W^9$ are N and $W^7$, $W^8$, $W^{10}$, $W^{11}$, $W^{12}$ and $W^{13}$ are, independently, C, CH, or $CR^{15}$. For example, in certain embodiments, Z is a quinoxalinyl group of the formulae:

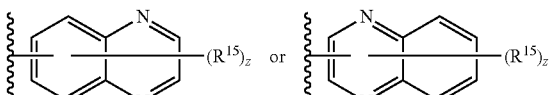

wherein z is 0, 1, 2, 3, 4 or 5, and $R^{15}$ is as defined below and herein. In certain embodiments, Z is an unsubstituted quinoxalinyl (i.e., wherein z is 0). In certain embodiments, Z is a substituted quinoxalinyl (e.g., wherein z is 1, 2, 3, 4 or 5). In certain embodiments, Z is a monosubstituted quinoxalinyl (i.e., wherein z is 1). In certain embodiments, Z is a disubstituted quinoxalinyl (i.e., wherein z is 2). In certain embodiments, Z is a trisubstituted quinoxalinyl (i.e., wherein z is 3). In certain embodiments, z is 0, 1, 2 or 3. In certain embodiments, z is 0, 1 or 2. In certain embodiments, z is 0 or 1.

In certain embodiments, Z is a 3-14 membered heterocyclyl. In certain embodiments, Z is a 3-14 membered heterocyclyl substituted with 0, 1, 2, 3, 4 or 5 $R^{15}$ groups. In certain embodiments, Z is a 5-10 membered heterocyclyl substituted with 0, 1, 2, 3, 4 or 5 $R^{15}$ groups. In certain embodiments, Z is a 5-8 membered heterocyclyl substituted with 0, 1, 2, 3, 4 or 5 $R^{15}$ groups. In certain embodiments, Z is a 5-6 membered heterocyclyl substituted with 0, 1, 2, 3, 4 or 5 $R^{15}$ groups. In certain embodiments, Z is a 9-10 membered heterocyclyl substituted with 0, 1, 2, 3, 4 or 5 $R^{15}$ groups.

Exemplary heterocyclyl Z groups include, but are not limited to, azirdinyl, oxiranyl, thiorenyl, azetidinyl, oxetanyl, thietanyl, tetrahydrofuranyl, dihydrofuranyl, tetrahydrothiophenyl, dihydrothiophenyl, pyrrolidinyl, dihydropyrrolyl, pyrrolyl-2,5-dione, dioxolanyl, oxathiolanyl, dithiolanyl, triazolinyl, oxadiazolinyl, thiadiazolinyl, piperidinyl, tetrahydropyranyl, dihydropyridinyl, thianyl, piperazinyl, morpholinyl, dithianyl, dioxanyl, triazinanyl, azepanyl, oxepanyl, thiepanyl, azocanyl, oxecanyl, thiocanyl, indolinyl, isoindolinyl, dihydrobenzofuranyl, dihydrobenzothienyl, tetrahydrobenzothienyl, tetrahydrobenzofuranyl, tetrahydroindolyl, tetrahydroquinolinyl, tetrahydroisoquinolinyl, decahydroquinolinyl, decahydroisoquinolinyl, octahydrochromenyl, octahydroisochromenyl, decahydronaphthyridinyl, decahydro-1,8-naphthyridinyl, octahydropyrrolo[3,2-b]pyrrole, indolinyl, phthalimidyl, naphthalimidyl, chromanyl, chromenyl, 1H-benzo[e][1,4]diazepinyl, 1,4,5,7-tetrahydro-pyrano[3,4- b]pyrrolyl, 5,6-dihydro-4H-furo[3,2-b]pyrrolyl, 6,7-dihydro-5H-furo[3,2-b]pyranyl, 5,7-dihydro-4H-thieno[2,3-c]pyranyl, 2,3-dihydro-1H-pyrrolo[2,3-b]pyridinyl, 2,3-dihydrofuro[2,3-b]pyridinyl, 4,5,6,7-tetrahydro-1H-pyrrolo[2,3-b]pyridinyl, 4,5,6,7-tetra-hydrofuro[3,2-c]pyridinyl, and 4,5,6,7-tetrahydrothieno[3,2-b]pyridinyl, 1,2,3,4-tetrahydro-1,6-naphthyridinyl, wherein such groups are substituted with 0, 1, 2, 3, 4 or 5 $R^{15}$ groups.

In certain embodiments, Z is a 6-membered heterocyclyl. In certain embodiments, Z is a 6-membered heterocyclyl substituted with 0, 1, 2, 3, 4 or 5 $R^{15}$ groups. In certain embodiments, Z is a 6-membered heterocyclyl selected from piperidinyl, tetrahydropyranyl, dihydropyridinyl, thianyl, piperazinyl, morpholinyl, dithianyl, dioxanyl, and triazinanyl, wherein such groups are substituted with 0, 1, 2, 3, 4 or 5 $R^{15}$ groups.

For example, in certain embodiments, Z is a 6-membered heterocyclyl of the formula:

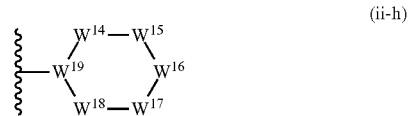

(ii-h)

wherein $W^{14}$, $W^{15}$, $W^{16}$, $W^{17}$, $W^{18}$ are, independently, $CH_2$, $CHR^{15}$, $C(R^{15})_2$, $NR^{18}$, O or S, and $W^{19}$ is N, CH or $CR^{15}$, with the proviso that at least one of $W^{14}$, $W^{15}$, $W^{16}$, $W^{17}$, $W^{18}$, and $W^{19}$ is N, $NR^{18}$, O or S, and wherein $R^{15}$ and $R^{18}$ are defined below and herein.

In certain embodiments, Z is a piperidinyl group. In certain embodiments, Z is a piperidinyl group substituted with 0, 1, 2, 3, 4 or 5 $R^{15}$ groups, e.g., of the formulae:

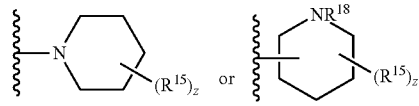

wherein z is 0, 1, 2, 3, 4 or 5, and $R^{15}$ and $R^{18}$ are as defined below and herein. In certain embodiments, Z is an unsubstituted piperidinyl (i.e., wherein z is 0). In certain embodiments, Z is a substituted piperidinyl (e.g., wherein z is 1, 2, 3, 4 or 5). In certain embodiments, Z is a monosubstituted piperidinyl (i.e., wherein z is 1). In certain embodiments, Z is a disubstituted piperidinyl (i.e., wherein z is 2). In certain embodiments, Z is a trisubstituted piperidinyl (i.e., wherein z is 3). In certain embodiments, z is 0, 1, 2 or 3. In certain embodiments, z is 0, 1 or 2. In certain embodiments, z is 0 or 1.

In certain embodiments, Z is a 1-piperidinyl group, e.g., of the formula (ii-h) wherein $W^{19}$ is N and $W^{14}$, $W^{15}$, $W^{16}$, $W^{17}$, and $W^{18}$ are, independently, selected from $CH_2$, $CHR^{15}$, $C(R^{15})_2$. In certain embodiments, Z is a 2-piperidinyl group, e.g., of the formula (ii-h) wherein $W^{14}$ is $NR^{18}$; $W^{15}$, $W^{16}$, $W^{17}$, and $W^{18}$ are, independently, $CHR^{15}$, $C(R^{15})_2$, or $CH_2$; and $W^{19}$ is CH or $CR^{15}$. In certain embodiments, Z is a 3-piperidinyl group, e.g., of the formula (ii-h) wherein $W^{15}$ is $NR^{18}$; $W^{14}$, $W^{16}$, $W^{17}$ and $W^{18}$ are, independently, $CHR^{15}$, $C(R^{15})_2$, or $CH_2$; and $W^{19}$ is CH or $CR^{15}$. In certain embodiments, Z is a 4-piperidinyl group, e.g., of the formula (ii-h) wherein $W^{16}$ is $NR^{18}$; $W^{14}$, $W^{15}$, $W^{17}$, and $W^{18}$ are, independently, $CHR^{15}$, $C(R^{15})_2$, or $CH_2$; and $W^{19}$ is CH or $CR^{15}$.

In certain embodiments, Z is a piperazinyl group. In certain embodiments, Z is a piperazinyl group substituted with 0, 1, 2, 3 or 4 $R^{15}$ groups, e.g., of the formulae:

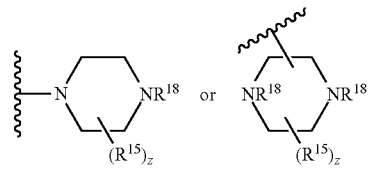

wherein x is 0, 1, 2, 3, 4 or 5, and $R^{15}$ and $R^{18}$ are as defined below and herein. In certain embodiments, Z is an unsubstituted piperazinyl (i.e., wherein z is 0). In certain embodiments, Z is a substituted piperazinyl (e.g., wherein z is 1, 2, 3, 4 or 5). In certain embodiments, Z is a monosubstituted piperazinyl (i.e., wherein z is 1). In certain embodiments, Z is a disubstituted piperazinyl (i.e., wherein z is 2). In certain embodiments, Z is a trisubstituted piperazinyl (i.e., wherein z is 3). In certain embodiments, z is 0, 1, 2 or 3. In certain embodiments, z is 0, 1 or 2. In certain embodiments, z is 0 or 1.

In certain embodiments, Z is a piperazinyl group, e.g., of the formula (ii-h) wherein $W^{19}$ is N, $W^{16}$ is $NR^{18}$, and $W^{14}$, $W^{15}$, $W^{16}$, $W^{17}$, and $W^{18}$ are independently, $CHR^{15}$, $C(R^{15})_2$, or $CH_2$. In certain embodiments, Z is a piperazinyl group wherein $W^{19}$ is CH or $CR^{15}$, $W^{14}$ and $W^{17}$ are independently $NR^{18}$, and $W^{15}$, $W^{16}$, and $W^{18}$ are, independently, $CHR^{15}$, $C(R^{15})_2$, or $CH_2$.

In certain embodiments, Z is a morpholinyl group substituted with 0, 1, 2, 3 or 4 $R^{15}$ groups, e.g., of the formulae:

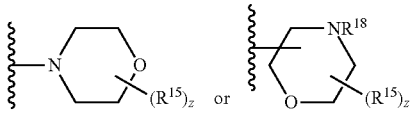

wherein z is 0, 1, 2, 3, 4 or 5, and $R^{15}$ and $R^{18}$ are as defined below and herein. In certain embodiments, Z is an unsubstituted morpholinyl (i.e., wherein z is 0). In certain embodiments, Z is a substituted morpholinyl (e.g., wherein z is 1, 2, 3, 4 or 5). In certain embodiments, Z is a monosubstituted morpholinyl (i.e., wherein z is 1). In certain embodiments, Z is a disubstituted morpholinyl (i.e., wherein z is 2). In certain embodiments, Z is a trisubstituted morpholinyl (i.e., wherein z is 3). In certain embodiments, z is 0, 1, 2 or 3. In certain embodiments, z is 0, 1 or 2. In certain embodiments, z is 0 or 1.

In certain embodiments, Z is a morpholinyl group; e.g., of the formula (ii-h) wherein $W^{19}$ is N, $W^{16}$ is O and $W^{14}$, $W^{15}$, $W^{16}$, and $W^{17}$ are, independently, selected from $CH_2$, $CHR^{15}$, $C(R^{15})_2$. In certain embodiments, Z is a morpholinyl group wherein $W^{19}$ is CH or $CR^{15}$, $W^{14}$ and $W^{17}$ are independently selected from O and $NR^{18}$, and $W^{15}$, $W^{16}$, and $W^{18}$ are, independently, $CHR^{15}$, $C(R^{15})_2$, or $CH_2$.

In certain embodiments, Z is a dioxanyl group. In certain embodiments, Z is a dioxanyl group substituted with 0, 1, 2, 3 or 4 $R^{15}$ groups, e.g., of the formulae:

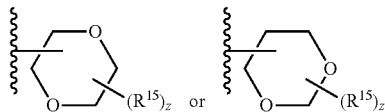

wherein z is 0, 1, 2, 3, 4 or 5, and $R^{15}$ is as defined below and herein. In certain embodiments, Z is an unsubstituted dioxanyl (i.e., wherein z is 0). In certain embodiments, Z is a substituted dioxanyl (e.g., wherein z is 1, 2, 3, 4 or 5). In certain embodiments, Z is a monosubstituted dioxanyl (i.e., wherein z is 1). In certain embodiments, Z is a disubstituted dioxanyl (i.e., wherein z is 2). In certain embodiments, Z is a trisubstituted dioxanyl (i.e., wherein z is 3). In certain embodiments, z is 0, 1, 2 or 3. In certain embodiments, z is 0, 1 or 2. In certain embodiments, z is 0 or 1.

In certain embodiments, Z is a dioxanyl group, e.g., of the formula (ii-h) wherein $W^{14}$ and $W^{17}$ are O and $W^{15}$, $W^{16}$, and $W^{18}$ are, independently, $CHR^{15}$, $C(R^{15})_2$, or $CH_2$; and $W^{19}$ is CH or $CR^{15}$. In certain embodiments, Z is a dioxanyl group wherein $W^{19}$ is CH or $CR^{15}$, $W^{14}$ and $W^{16}$ are independently selected from O, and $W^{15}$, $W^{17}$, and $W^{18}$ are, independently, $CHR^{15}$, $C(R^{15})_2$, or $CH_2$. In certain embodiments, Z is a dioxanyl group wherein $W^{19}$ is CH or $CR^{15}$, $W^{15}$ and $W^{17}$ are independently selected from O, and $W^{14}$, $W^{16}$, and $W^{18}$ are, independently, $CHR^{15}$, $C(R^{15})_2$, or $CH_2$.

In certain embodiments, Z is a $C_{3-10}$ carbocycyl. In certain embodiments, Z is a $C_{3-10}$ carbocycyl substituted with 0, 1, 2, 3, 4 or 5 $R^{15}$ groups. In certain embodiments, Z is a $C_{5-8}$ carbocycyl substituted with 0, 1, 2, 3, 4 or 5 $R^{15}$ groups. In certain embodiments, Z is a $C_{5-6}$ carbocycyl substituted with 0, 1, 2, 3, 4 or 5 $R^{15}$ groups. In certain embodiments, Z is a $C_{9-10}$ carbocycyl substituted with 0, 1, 2, 3, 4 or 5 $R^{15}$ groups.

$R^{15}$ Groups

As used herein, each instance of $R^{15}$ is, independently, selected from halogen (i.e., fluoro (—F), bromo (—Br), chloro (—Cl), and iodo (—CN, —NO$_2$, —N$_3$, —SO$_2$H, —SO$_3$H, —OH, —OR$^{16}$, —ON(R$^{18}$)$_2$, —N(R$^{18}$)$_2$, —N(R$^{18}$)$_3$$^+$X$^-$, —N(OR$^{17}$)R$^{18}$, —SH, —SR16, —SSR17, —C(=O)R$^{16}$, —CO$_2$H, —CHO, —CO$_2$R16, —OC(=O)R$^{16}$, —OCO$_2$R$^{16}$, —C(=O)N(R$^{18}$)$_2$, —OC(=O)N(R$^{18}$)$_2$, —NR$^{18}$C(=O)R$^{16}$, —NR$^{18}$CO$_2$R$^{16}$, —NR$^{18}$C(=O)N (R$^{18}$)$_2$, —C(=NR$^{18}$)R$^{16}$, —C(=NR$^{18}$)OR$^{16}$, —OC (=NR$^{18}$)R$^{16}$, —OC(=NR$^{18}$)OR$^{16}$, —C(=NR$^{18}$)N(R$^{18}$)$_2$, —OC(=NR$^{18}$)N(R$^{18}$)$_2$, —NR$^{18}$C(=NR$^{18}$)N(R$^{18}$)$_2$, —C(=O)NR$^{18}$SO$_2$R$^{16}$, —NR$^{18}$SO$_2$R$^{16}$, —SO$_2$N(R$^{18}$)$_2$, —SO$_2$R$^{16}$, —SO$_2$OR$^{16}$, —OSO$_2$R$^{16}$, —S(=O)R$^{16}$, —OS (=O)R$^{16}$, —Si(R$^{16}$)$_3$, —OSi(R$^{16}$)$_3$ —C(=S)N(R$^{18}$)$_2$, —C(=O)SR$^{16}$, —C(=S)SR$^{16}$, —SC(S)SR$^{16}$, —P(=O)$_2$ R$^{16}$, —OP(=O)$_2$R$^{16}$, —P(=O)(R$^{16}$)$_2$, —OP(=O)(R$^{16}$)$_2$, —OP(=O)(OR$^{17}$)$_2$, —P(=O)$_2$N(R$^{18}$)$_2$, —OP(=O)$_2$N (R$^{18}$)$_2$, —P(=O)(NR$^{18}$)$_2$, —OP(=O)(NR$^{18}$)$_2$, —NR18P (=O)(OR$^{17}$)$_2$, —NR$^{18}$P(=O)(NR$^{18}$)$_2$, —P(R$^{17}$)$_2$, —P (R$^{17}$)$_3$, —OP(R$^{17}$)$_2$, —OP(R$^{17}$)$_3$, —B(OR$^{17}$)$_2$, —BR$^{16}$ (OR$^{17}$), $C_{1-10}$ alkyl, $C_{1-10}$ perhaloalkyl, $C_{2-10}$ alkenyl, $C_{2-10}$ alkynyl, $C_{3-14}$ carbocyclyl, 3-14 membered heterocyclyl, $C_{6-14}$ aryl, and 5-14 membered heteroaryl, wherein each alkyl, alkenyl, alkynyl, carbocyclyl, heterocyclyl, aryl, and heteroaryl is independently substituted with 0, 1, 2, 3, 4, or 5 $R^{19}$ groups; or two vicinal $R^{15}$ groups are replaced with the group —O(C(R$^2$)$_2$)$_{1-2}$O— wherein each $R^2$ is independently H, $C_{1-6}$ alkyl or halogen;

each instance of $R^{16}$ is, independently, selected from $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, wherein each alkyl, alkenyl, alkynyl, carbocyclyl, heterocyclyl, aryl, and heteroaryl is independently substituted with 0, 1, 2, 3, 4, or 5 $R^{19}$ groups;

each instance of $R^{18}$ is, independently, selected from hydrogen, —OH, —OR$^{16}$, —N(R$^{17}$)$_2$, —CN, —C(=O)R$^{16}$, —C(=O)N(R$^{17}$)$_2$, —CO$_2$R$^{16}$, —SO$_2$R$^{16}$, —C(=NR$^{17}$) OR$^{16}$, —C(=NR$^{17}$)N(R$^{17}$)$_2$, —SO$_2$N(R$^{17}$)$_2$, —SO$_2$R$^{17}$, —SO$_2$OR$^{17}$, —SOR$^{16}$, —C(=S)N(R$^{17}$)$_2$, —C(=O)SR17, —C(=S)SR$^{17}$, —P(=O)$_2$R$^{16}$, —P(=O)(R$^{16}$)$_2$, —P (=O)$_2$N(R$^{17}$)$_2$, —P(=O)(NR$^{17}$)$_2$, $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two $R^{17}$ groups attached to an N atom are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{19}$ groups;

each instance of $R^{17}$ is, independently, selected from hydrogen, $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two $R^{17}$ groups attached to an N atom are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{19}$ groups;

each instance of $R^{19}$ is, independently, selected from halogen, —CN, —NO$_2$, —N$_3$, —SO$_2$H, —SO$_3$H, —OH, —OR$^{20}$, —ON(R$^{21}$)$_2$, —N(R$^{21}$)$_2$, —N(R$^{21}$)$_3$$^+$X$^-$, —N(OR$^{20}$)R$^{21}$, —SH, —SR$^{20}$, —SSR$^{20}$, —C(=O)R$^{20}$, —CO$_2$H, —CO$_2$R$^{20}$, —OC(=O)R$^{20}$, —OCO$_2$R$^{20}$, —C(=O)N(R$^{21}$)$_2$, —OC(=O)N(R$^{21}$)$_2$, —NR$^{21}$C(=O)R$^{20}$, —NR21CO$_2$R$^{20}$, —NR$^{21}$C(=O)N(R$^{21}$)$_2$, —C(=NR$^{21}$) OR$^{20}$, —OC(=NR$^{21}$)R$^{20}$, —OC(=NR$^{21}$)OR$^{20}$, —C(=NR$^{21}$)N(R$^{21}$)$_2$, —OC(=NR$^{21}$)N(R$^{21}$)$_2$, —NR$^{21}$C (=NR$^{21}$)N(R$^{21}$)$_2$, —NR$^{21}$SO$_2$R$^{20}$, —SO$_2$N(R$^{21}$)$_2$, —SO$_2$R$^{20}$, —SO$_2$OR$^{20}$, —OSO$_2$R$^{20}$, —S(=O)R$^{20}$, —Si (R$^{20}$)$_3$, —OSi(R$^{20}$)$_3$, —C(=S)N(R$^{21}$)$_2$, —C(=O)SR$^{20}$, —C(=S)SR$^{20}$, —SC(=S)SR$^{20}$, —P(=O)$_2$R$^{20}$, —P(=O) (R$^{20}$)$_2$, —OP(=O)(R$^{20}$)$_2$, —OP(=O)(OR$^{20}$)$_2$, $C_{1-6}$ alkyl, $C_{1-6}$ perhaloalkyl, $C_{2-6}$ alkenyl, $C_{2-6}$ alkynyl, $C_{3-10}$ carbocyclyl, 3-10 membered heterocyclyl, $C_{6-10}$ aryl, 5-10 membered heteroaryl, wherein each alkyl, alkenyl, alkynyl, carbocyclyl, heterocyclyl, aryl, and heteroaryl is independently substituted with 0, 1, 2, 3, 4, or 5 $R^{22}$ groups, or two geminal $R^{19}$ substituents can be joined to form =O or =S;

each instance of $R^{20}$ is, independently, selected from $C_{1-6}$ alkyl, $C_{1-6}$ perhaloalkyl, $C_{2-6}$ alkenyl, $C_{2-6}$ alkynyl, $C_{3-10}$ carbocyclyl, $C_{6-10}$ aryl, 3-10 membered heterocyclyl, and 3-10 membered heteroaryl, wherein each alkyl, alkenyl, alkynyl, carbocyclyl, heterocyclyl, aryl, and heteroaryl is independently substituted with 0, 1, 2, 3, 4, or 5 $R^{22}$ groups;

each instance of $R^{21}$ is, independently, selected from hydrogen, $C_{1-6}$ alkyl, $C_{1-6}$ perhaloalkyl, $C_{2-6}$ alkenyl, $C_{2-6}$ alkynyl, $C_{3-10}$ carbocyclyl, 3-10 membered heterocyclyl, $C_{6-10}$ aryl and 5-10 membered heteroaryl, or two $R^{21}$ groups attached to an N atom are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{22}$ groups; and each instance of $R^{22}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3$X, —NH(C$_{1-6}$ alkyl)$_2$X, —NH$_2$(C$_{1-6}$ alkyl)X, —NH$_3$X, —N(OC$_{1-6}$ alkyl)(C$_{1-6}$ alkyl), —N(OH)(C$_{1-6}$ alkyl), —NH (OH), —SH, —SC$_{1-6}$ alkyl, —SS(C$_{1-6}$ alkyl), —C(=O) (C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N (C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC (=NH)(C$_{1-6}$ alkyl), —OC(=NH)OC$_{1-6}$ alkyl, —C(=NH)N ($C_{1-6}$ alkyl)$_2$, —C(=NH)NH($C_{1-6}$ alkyl), —C(=NH)NH$_2$, —OC(=NH)N($C_{1-6}$ alkyl)$_2$, —OC(NH)NH($C_{1-6}$ alkyl), —OC(NH)NH$_2$, —NHC(NH)N($C_{1-6}$ alkyl)$_2$, —NHC(=NH)NH$_2$, —NHSO$_2$($C_{1-6}$ alkyl), —SO$_2$N($C_{1-6}$ alkyl)$_2$, —SO$_2$NH($C_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si($C_{1-6}$ alkyl)$_3$, —OSi($C_{1-6}$ alkyl)$_3$ —C(=S)N($C_{1-6}$ alkyl)$_2$, C(=S)NH($C_{1-6}$ alkyl), C(=S)NH$_2$, —C(=O)S($C_{1-6}$ alkyl), —C(=S)SC$_{1-6}$ alkyl, —SC(=S)SC$_{1-6}$ alkyl, —P(=O)$_2$($C_{1-6}$ alkyl), —P(=O)($C_{1-6}$ alkyl)$_2$, —OP(=O)($C_{1-6}$ alkyl)$_2$, —OP(=O)(OC$_{1-6}$ alkyl)$_2$, $C_{1-6}$ alkyl, $C_{1-6}$ perhaloalkyl, $C_{2-6}$ alkenyl, $C_2$ alkynyl, $C_{3-10}$ carbocyclyl, $C_{6-10}$ aryl, 3-10 membered heterocyclyl, 5-10 membered heteroaryl; or two geminal $R^{22}$ substituents can be joined to form =O or =S;

wherein $X^-$ is a counterion.

In certain embodiments, each instance of $R^{15}$ is, independently, selected from fluoro (—F), bromo (—Br), chloro (—Cl), and iodo (—I), —OR$^{16}$, —C(O)N($R^{18}$)$_2$, —SO$_2$N($R^{18}$)$_2$, $C_{1-10}$ alkyl, $C_{1-10}$ perhaloalkyl, $C_{2-10}$ alkenyl, $C_{2-10}$ alkynyl, $C_{6-14}$ aryl, and 5-14 membered heteroaryl, wherein each alkyl, alkenyl, alkynyl, aryl, and heteroaryl is independently substituted with 0, 1, 2, 3, 4, or 5 $R^{19}$ groups.

In certain embodiments, $R^{15}$ is, independently, selected from fluoro (—F), bromo (—Br), chloro (—Cl), and iodo (—I), —OR$^{16}$ and $C_{1-10}$ perhaloalkyl. In certain embodiments, $R^{15}$ is, independently, selected from fluoro (—F), bromo (—Br), chloro (—Cl), and iodo (—I) and —OR$^{16}$. In certain embodiments, $R^{15}$ is, independently, selected from fluoro (—F), bromo (—Br), chloro (—Cl), and iodo (—I) and $C_{1-10}$ perhaloalkyl.

In certain embodiments, $R^{15}$ is selected from —OR$^{16}$ and $C_{1-10}$ perhaloalkyl.

In certain embodiments, $R^{15}$ is —OR$^{16}$. In certain embodiments, $R^{16}$ is selected from $C_{1-10}$ alkyl, $C_{1-10}$ perhaloalkyl, $C_{2-10}$ alkenyl, $C_{2-10}$ alkynyl, $C_{6-10}$ aryl, and 5-6 membered heteroaryl, wherein each alkyl, alkenyl, alkynyl, aryl, and heteroaryl is independently substituted with 0, 1, 2, 3, 4, or 5 $R^{19}$ groups.

In certain embodiments, $R^{15}$ is —OR$^{16}$, and $R^{16}$ is selected from $C_{1-10}$ alkyl. In certain embodiments, $R^{15}$ is —OR$^{16}$, and $R^{16}$ is selected from $C_{1-6}$ alkyl. In certain embodiments, $R^{15}$ is —OR$^{16}$, and $R^{16}$ is selected from $C_{1-4}$ alkyl. In certain embodiments, $R^{15}$ is —OR$^{16}$, and $R^{16}$ is selected from $C_{1-2}$ alkyl. In certain embodiments, $R^{15}$ is —OR$^{16}$ and $R^{16}$ is —CH$_3$, -Et, -iPr, -nBu, -n-pentyl. In certain embodiments, $R^{15}$ is —OR$^{16}$ and $R^{16}$ is —CH$_3$.

In certain embodiments, $R^{15}$ is —OR$^{16}$, and $R^{16}$ is selected from $C_{1-10}$ perhaloalkyl. In certain embodiments, $R^{15}$ is —OR$^{16}$, and $R^{16}$ is selected from $C_{1-6}$ perhaloalkyl. In certain embodiments, $R^{15}$ is —OR$^{16}$, and $R^{16}$ is selected from $C_{1-4}$ perhaloalkyl. In certain embodiments, $R^{15}$ is —OR$^{16}$, and $R^{16}$ is selected from $C_{1-4}$ perhaloalkyl. In certain embodiments, $R^{15}$ is —OR$^{16}$ and $R^{16}$ is —CF$_3$, —CF$_2$CF$_3$, —CF$_2$CF$_2$CF$_3$, —CCl$_3$, —CFCl$_2$, or —CF$_2$Cl. In certain embodiments, $R^{15}$ is —OR$^{16}$ and $R^{16}$ is —CF$_3$.

In certain embodiments, $R^{15}$ is —OR$^{16}$, and $R^{16}$ is selected from $C_{2-10}$ alkenyl. In certain embodiments, $R^{15}$ is —OR$^{16}$, and $R^{16}$ is selected from $C_2$ alkenyl. In certain embodiments, $R^{15}$ is —OR$^{16}$, and $R^{16}$ is selected from $C_2$ alkenyl. In certain embodiments, $R^{15}$ is —OR$^{16}$, and $R^{16}$ is selected from —CH$_2$CHCH$_2$ (i.e., allyl).

In certain embodiments, $R^{15}$ is —OR$^{16}$, and $R^{16}$ is selected from $C_{2-10}$ alkynyl. In certain embodiments, $R^{15}$ is —OR$^{16}$, and $R^{16}$ is selected from $C_{2-6}$ alkynyl. In certain embodiments, $R^{15}$ is —OR$^{16}$, and $R^{16}$ is selected from $C_{2-4}$ alkynyl. In certain embodiments, $R^{15}$ is —OR$^{16}$, and $R^{16}$ is selected from —CH$_2$CCH (i.e., propargyl).

In certain embodiments, $R^{15}$ is —OR$^{16}$, and $R^{16}$ is selected from $C_6$ aryl (e.g., phenyl) substituted with 0, 1, 2, 3 or 4 $R^{19}$ groups. In certain embodiments, $R^{15}$ is —OR$^{16}$, and $R^{16}$ is phenyl substituted with 0, 1 or 2 $R^{19}$ groups. In certain embodiments, $R^{15}$ is —OR$^{16}$, and $R^{16}$ is phenyl substituted with 1 $R^{19}$ groups. In certain embodiments, $R^{15}$ is —OR$^{16}$, and $R^{16}$ is phenyl substituted with 0 $R^{19}$ groups (i.e., —C$_6$H$_5$).

In certain embodiments, $R^{15}$ is —OR$^{16}$, and $R^{16}$ is selected from 5-6 membered heteroaryl substituted with 0, 1, 2, 3 or 4 $R^{19}$ groups. In certain embodiments, $R^{15}$ is —OR$^{16}$, and $R^{16}$ is selected from a 6 membered heteroaryl substituted with 0, 1, 2, 3 or 4 $R^{19}$ groups. In certain embodiments, $R^{15}$ is —OR$^{16}$, and $R^{16}$ is selected from pyridinyl (e.g., 2-pyridinyl, 3-pyridinyl, 4-pyridinyl) substituted with 0, 1, 2, 3 or 4 $R^{19}$ groups. In certain embodiments, $R^{15}$ is —OR$^{16}$, and $R^{16}$ is selected from pyrimidinyl (e.g., 2-pyrimidinyl, 4-pyrimidinyl, 5-pyrimidinyl) substituted with 0, 1, 2 or 3 $R^{19}$ groups.

In certain embodiments, $R^{15}$ is —C(=O)N($R^{18}$)$_2$.

In certain embodiments, $R^{15}$ is —SO$_2$N(R-18)$_2$.

In certain embodiments, $R^{15}$ is $C_{1-10}$ perhaloalkyl. In certain embodiments, $R^{15}$ is $C_{1-6}$ perhaloalkyl. In certain embodiments, $R^{15}$ is $C_{1-4}$ perhaloalkyl. In certain embodiments, $R^{15}$ is $C_{1-2}$ perhaloalkyl. In certain embodiments, $R^{15}$ is selected from —CF$_3$, —CF$_2$CF$_3$, —CF$_2$CF$_2$CF$_3$, —CCl$_3$, —CFCl$_2$, and —CF$_2$Cl. In certain embodiments, $R^{15}$ is selected from —CF$_3$.

In certain embodiments, $R^{15}$ is $C_{1-10}$ alkyl substituted with 0, 1, 2, 3, 4, or 5 $R^{19}$ groups. In certain embodiments, $R^{15}$ is $C_{1-6}$ alkyl substituted with 0, 1, 2, 3, 4, or 5 $R^{19}$ groups. $R^{15}$ is $C_i$ alkyl substituted with 0, 1, 2, 3, 4, or 5 $R^{19}$ groups. In certain embodiments, the $R^{15}$ alkyl group is unsubstituted (0 $R^{19}$ groups). In certain embodiments, $R^{15}$ is —CH$_3$, -Et, -iPr, -nBu, -n-pentyl.

In certain embodiments, $R^{15}$ is $C_{2-10}$ alkenyl substituted with 0, 1, 2, 3, 4, or 5 $R^{19}$ groups. In certain embodiments, $R^{15}$ is $C_{2-6}$ alkenyl substituted with 0, 1, 2, 3 or 4 $R^{19}$ groups. In certain embodiments, $R^{15}$ is $C_{2-4}$ alkenyl substituted with 0, 1, 2 or 3 $R^{19}$ groups. In certain embodiments, the $R^{15}$ alkenyl group is unsubstituted (0 $R^{19}$ groups). In certain embodiments, $R^{15}$ is —CH$_2$CHCH$_2$ (i.e., allyl), In certain embodiments, $R^{15}$ is $C_{2-10}$ alkynyl substituted with 0, 1, 2, 3, 4, or 5 $R^{19}$ groups. In certain embodiments, $R^{15}$ is $C_2$ alkynyl substituted with 0, 1, 2 or 3 $R^{19}$ groups. In certain embodiments, $R^{15}$ is $C_{2-4}$ alkynyl substituted with 0, 1 or 2 $R^{19}$ groups. In certain embodiments, the $R^{15}$ alkynyl group is unsubstituted (0 $R^{19}$ groups). In certain embodiments, $R^{15}$ is —CH$_2$CCH (i.e., propargyl).

In certain embodiments, $R^{15}$ is $C_{6-14}$ aryl. In certain embodiments, $R^{15}$ is selected from $C_6$ aryl (e.g., phenyl) substituted with 0, 1, 2, 3 or 4 $R^{19}$ groups. In certain embodiments, $R^{15}$ is an unsubstituted phenyl. In certain embodiments, $R^{15}$ is a monosubstituted phenyl (i.e., substituted with 1 $R^{19}$ group).

In certain embodiments, $R^{15}$ is 5-14 membered heteroaryl substituted with 0, 1, 2, 3, 4, or 5 $R^{19}$ groups. In certain embodiments, $R^{15}$ is 5-6 membered heteroaryl substituted with 0, 1, 2, 3 or 4 $R^{19}$ groups. In certain embodiments, $R^{15}$ is a 6-membered heteroaryl substituted with 0, 1, 2, 3 or 4 $R^{19}$ groups. In certain embodiments, $R^{15}$ is pyridinyl (e.g., 2-pyridinyl, 3-pyridinyl, 4-pyridinyl) substituted with 0, 1, 2, 3 or 4 $R^{19}$ groups. In certain embodiments, $R^{15}$ is pyrimidinyl (e.g., 2-pyrimidinyl, 4-pyrimidinyl, 5-pyrimidinyl) substituted with 0, 1, 2 or 3 $R^{19}$ groups. In certain embodiments, the $R^{15}$ heteroaryl group is unsubstituted (0 $R^{19}$ groups).

$R^{18}$ Groups

In certain embodiments, each instance of $R^{18}$ is, independently, selected from —H, —OH, —OR$^{16}$, —N($R^{17}$)$_2$, —C(=O)R$^{16}$, —C(=O)N($R^{17}$)$_2$, —CO$_2$R$^{16}$, —SO$_2$R$^{16}$, —C(=NR$^{17}$)R$^{16}$, —C(=NR$^{17}$)OR$^{16}$, —C(=NR$^{17}$)N($R^{17}$)$_2$, —SO$_2$N($R^{17}$)$_2$, —SO$_2$R$^{16}$, —SO$_2$OR$^{16}$, —SOR$^{16}$, —C(=S)N($R^{17}$)$_2$, —C(=O)SR$^{16}$, —C(=S)SR$^{16}$, $C_{1-10}$ alkyl (e.g., aralkyl), $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl groups, wherein each alkyl, alkenyl, alkynyl, carbocyclyl, heterocyclyl, aralkyl, aryl, and heteroaryl is independently substituted with 0, 1, 2, 3, 4, or 5 $R^{19}$ groups, wherein $R^{16}$, $R^{17}$, $R^{19}$ are as defined above and herein.

In certain embodiments, each instance of $R^{17}$ is, independently, selected from —H, —C(=O)$R^{16}$, —C(=O)O$R^{16}$, —SO$_2R^{16}$, or $C_{1-6}$ alkyl. In certain embodiments, each instance of $R^{17}$ is, independently, selected from —H or $C_{1-6}$ alkyl. In certain embodiments, each instance of $R^{17}$ is, independently, selected from —H and —CH$_3$. In certain embodiments, each instance of $R^{17}$ is, independently, selected from —H. In certain embodiments, each instance of $R^{17}$ is, independently, selected from —CH$_3$.

Additional Embodiments of Compounds of Formula (I)

As defined generally above, the present invention provides compounds of the formula (I):

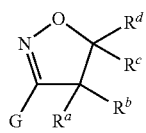

(I)

or a pharmaceutically acceptable form thereof, wherein G, $R^a$, $R^b$, $R^c$ and $R^d$ are as defined herein.

In one aspect, wherein $R^a$, $R^b$, $R^c$ are each H, and $R^d$ is the group Z, the present invention provides compounds of the formula (III):

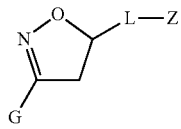

(III)

or a pharmaceutically acceptable form thereof, wherein G and Z are as defined herein. In certain embodiments, L is a covalent bond. In certain embodiments, G is —OR$^e$. In certain embodiments, G is —Br. However, in certain embodiments, G is not halogen (e.g., —Br, —Cl, —I).

In certain embodiments, wherein Z is a 5-membered heteroaryl ring, the present invention provides compounds of the formula (III-a):

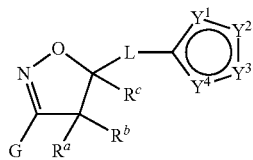

(III-a)

or a pharmaceutically acceptable form thereof, wherein $Y^1$, $Y^2$, $Y^3$, $Y^4$, G, L, $R^a$, $R^b$ and $R^c$ are as defined herein. In certain embodiments, L is a covalent bond. In certain embodiments, G is —OR$^e$. In certain embodiments, G is —Br. However, in certain embodiments, G is not halogen (e.g., —Br, —Cl, —I). In certain embodiments, $Y^1$ is S, $Y^2$ is C$R^{15}$, $Y^3$ is N, and $Y^4$ is CH or C$R^{15}$, wherein $R^{15}$ is as defined above and herein. In certain embodiments, $Y^4$ is CH. In certain embodiments, the substituent present on $Y^2$ is $C_6$ aryl (e.g., phenyl).

In certain embodiments, wherein Z is a 6-membered heteroaryl ring, the present invention provides compounds of the formula (III-b):

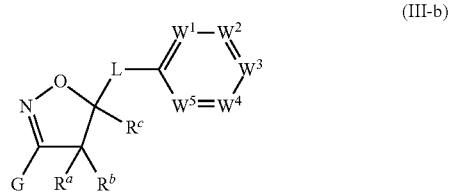

(III-b)

or a pharmaceutically acceptable form thereof, wherein $W_1$, $W_2$, $W_3$, $W_4$, G, L, $R^a$, $R^b$ and $R^c$ are as defined herein. In certain embodiments, L is a covalent bond. In certain embodiments, G is —OR$^e$. In certain embodiments, G is —Br. However, in certain embodiments, G is not halogen (e.g., —Br, —Cl, —I). In certain embodiments, the 6-membered heteroaryl ring is pyridinyl (e.g., 2-pyridinyl, 3-pyridinyl, 4-pyridinyl) or pyrimidinyl (e.g., 2-pyrimidinyl, 4-pyrimidinyl, 5-pyrimidinyl).

In certain embodiments, wherein Z is a 9-membered heteroaryl ring, the present invention provides compounds of the formula (III-c):

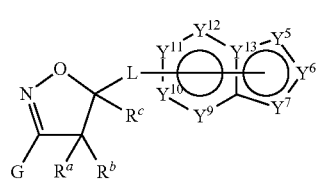

(III-c)

or a pharmaceutically acceptable form thereof, wherein $Y^5$, $Y^6$, $Y^7$, $Y^9$, $Y^{10}$, $Y^{11}$, $Y^{12}$, $Y^{13}$, G, L, $R^a$, $R^b$ and $R^c$ are as defined herein. In certain embodiments, L is a covalent bond. In certain embodiments, G is —OR$^e$. In certain embodiments, G is —Br. However, in certain embodiments, G is not halogen (e.g., —Br, —Cl, —I).

In certain embodiments, wherein Z is a 10-membered heteroaryl ring, the present invention provides compounds of the formula (III-d):

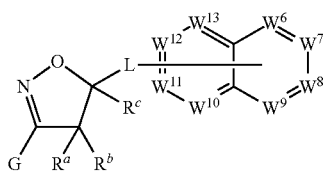

(III-d)

or a pharmaceutically acceptable form thereof, wherein $W^6$, $W^7$, $W^8$, $W^9$, $W^{10}$, $W^{11}$, $W^{12}$, $W_{13}$, G, L, $R^a$, $R^b$, $R^c$ are as defined herein. In certain embodiments, L is a covalent bond. In certain embodiments, G is —OR$^e$. In certain embodiments, G is —Br. However, in certain embodiments, G is not halogen (e.g., —Br, —Cl, —I).

In certain embodiments, wherein Z is a 6-membered heterocycyl, the present invention provides compounds of the formula (III-e):

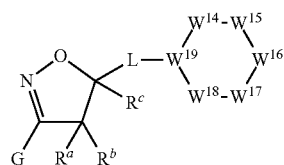

(III-e)

or a pharmaceutically acceptable form thereof, wherein $W^{14}$, $W^{15}$, $W^{16}$, $W^{17}$, $W^{18}$, $W^{19}$, G, L, $R^a$, $R^b$ and $R^c$ are as defined herein. In certain embodiments, L is a covalent bond. In certain embodiments, G is —$OR^e$. In certain embodiments, G is —Br. However, in certain embodiments, G is not halogen (e.g., —Br, —Cl, —I).

Exemplary Compounds of the Present Invention

Exemplified compounds of formulae (I), (III), and subgenera thereof, are depicted in Tables 1a to 1e, provided below, and are also described in more detail in Examples 1-31, provided herein. Compounds were assayed as inhibitors of human FAAH using the Method described in detail in Example 32.

In certain embodiments, the compound is any one of the compounds provided in Table 1a, or a pharmaceutically acceptable form thereof:

TABLE 1a

| Compound | G | $R^a$ | $R^c$ | $R^{15}$ | $R^{19}$ |
|---|---|---|---|---|---|
| II-6 | —Br | —H | —H | —H | —H |
| II-21 | (pyridin-3-yloxy) | —H | —H | —H | —H |
| II-28 | (Me-SO2-pyridin-yloxy) | —H | —H | —H | —H |
| II-18 | —Br | —H | —CH₃ | —H | —H |
| II-22 | (pyrimidin-5-yloxy) | —H | —CH₃ | —H | —H |

TABLE 1a-continued

| Compound | G | $R^a$ | $R^c$ | $R^{15}$ | $R^{19}$ |
|---|---|---|---|---|---|
| II-23 | (pyridin-3-yloxy) | —H | —CH₃ | —H | —H |
| II-29 | (Me-SO2-pyridin-yloxy) | —H | —CH₃ | —H | —H |
| II-19 (cis) | —Br | —CH₃ | —H | —H | —H |
| II-20 (trans) | —Br | —CH₃ | —H | —H | —H |
| II-17 | —Br | —H | —H | —H | —Cl |

In certain embodiments, the compound is any one of the compounds provided in Table 1b, or a pharmaceutically acceptable form thereof:

TABLE 1b

| Compound | G | $R^a$ | $R^c$ |
|---|---|---|---|
| II-25 | —Br | —H | —H |
| II-26 | (pyrimidin-5-yloxy) | —H | —H |
| II-27 | (HO₂C-pyridin-yloxy) | —H | —H |

In certain embodiments, the compound is any one of the compounds provided in Table 1c, or a pharmaceutically acceptable form thereof:

TABLE 1c

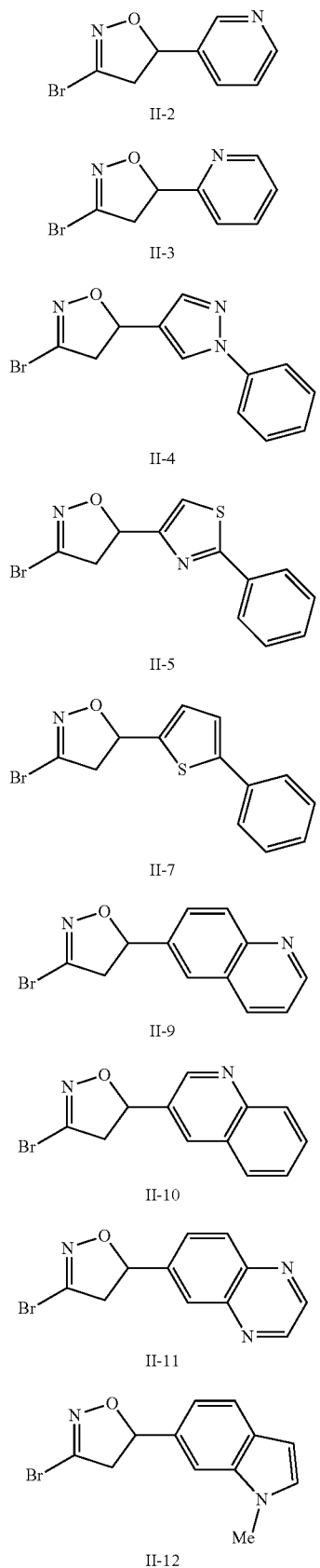

| Compound | G | $R^a$ | $R^c$ |
|---|---|---|---|
| II-8 | —Br | —H | —H |
| II-31 | (1-phenyl-2-aminoethanol, OH on left carbon) | —H | —H |
| II-30 | (1-phenyl-2-aminoethanol, OH on left carbon, opposite stereochem) | —H | —H |

In certain embodiments, the compound is any one of the compounds provided in Table 1d, or a pharmaceutically acceptable form thereof:

TABLE 1d

| Compound | G | $R^{18}$ | $R^a$ | $R^c$ |
|---|---|---|---|---|
| II-15 | —Br | —C(O)O—CH$_2$—phenyl (benzyloxycarbonyl) | —H | —H |
| II-16 | —Br | —C(O)O—C(CH$_3$)$_3$ (tert-butoxycarbonyl) | —H | —H |

In certain embodiments, the compound is any one of the compounds provided in Table 1e, or a pharmaceutically acceptable form thereof:

TABLE 1e

II-1

TABLE 1e-continued

II-2

II-3

II-4

II-5

II-7

II-9

II-10

II-11

II-12

TABLE 1e-continued

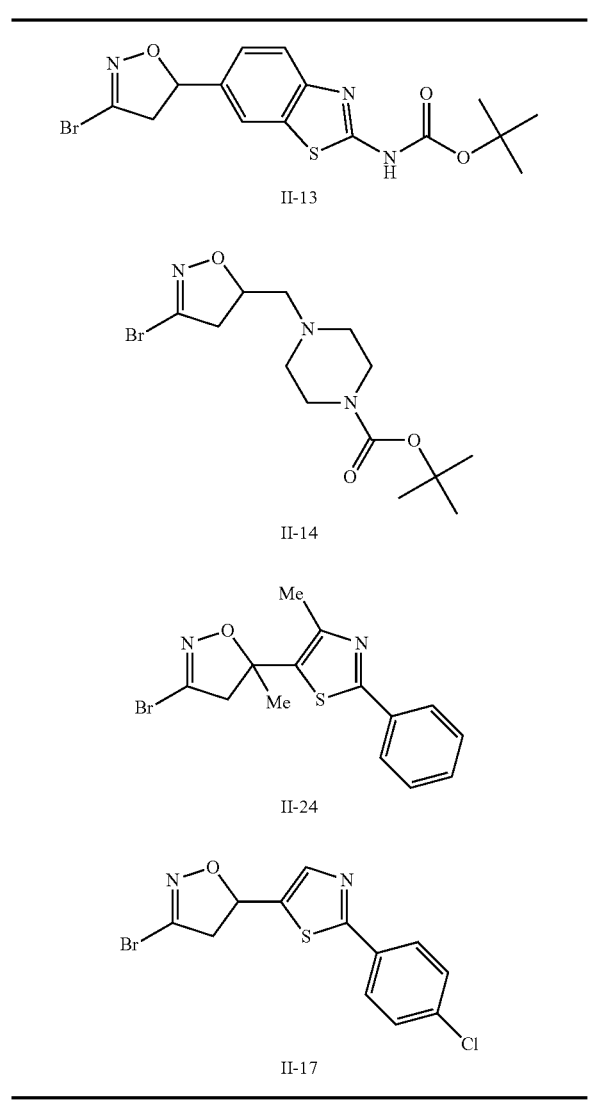

In certain embodiments of formulae (I) and (III), or subgenera thereof, any one of the following compounds, wherein $R^{18}$ is as defined herein, is specifically excluded:

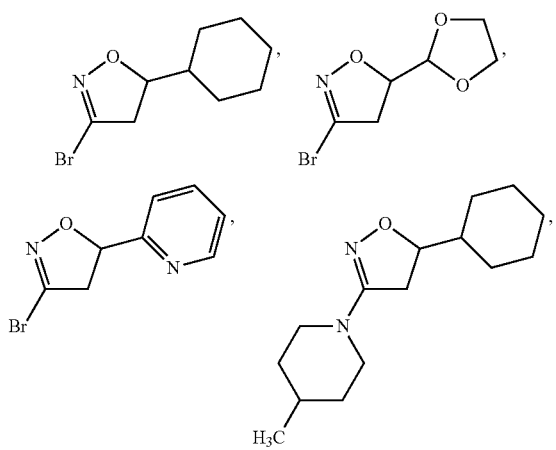

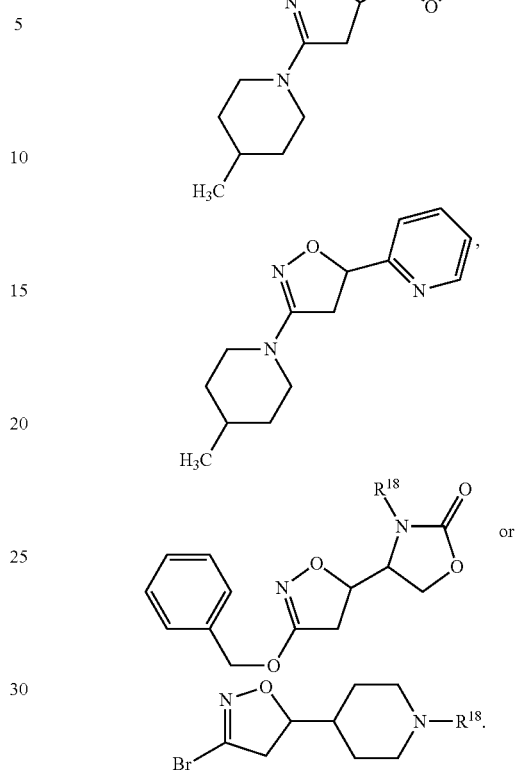

II. Pharmaceutical Compositions

In certain embodiments, the present invention provides a pharmaceutical composition comprising a compound of the formula (I) or a pharmaceutically acceptable form thereof, and a pharmaceutically acceptable excipient.

Pharmaceutically acceptable excipients include any and all solvents, diluents or other liquid vehicles, dispersion or suspension aids, surface active agents, isotonic agents, thickening or emulsifying agents, preservatives, solid binders, lubricants and the like, as suited to the particular dosage form desired. General considerations in the formulation and/or manufacture of pharmaceutical compositions agents can be found, for example, in *Remington's Pharmaceutical Sciences*, Sixteenth Edition, E. W. Martin (Mack Publishing Co., Easton, Pa., 1980), and *Remington: The Science and Practice of Pharmacy,* 21$^{st}$ Edition (Lippincott Williams & Wilkins, 2005).

Pharmaceutical compositions described herein can be prepared by any method known in the art of pharmacology. In general, such preparatory methods include the steps of bringing the active ingredient into association with a carrier and/or one or more other accessory ingredients, and then, if necessary and/or desirable, shaping and/or packaging the product into a desired single- or multi-dose unit.

Pharmaceutical compositions can be prepared, packaged, and/or sold in bulk, as a single unit dose, and/or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

Relative amounts of the active ingredient, the pharmaceutically acceptable carrier, and/or any additional ingredients in a pharmaceutical composition of the invention will vary, depending upon the identity, size, and/or condition of the subject treated and further depending upon the route by which the composition is to be administered. By way of example, the composition may comprise between 0.1% and 100% (w/w) active ingredient.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, etc., and combinations thereof.

Exemplary granulating and/or dispersing agents include potato starch, corn starch, tapioca starch, sodium starch glycolate, clays, alginic acid, guar gum, citrus pulp, agar, bentonite, cellulose and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, etc., and combinations thereof.

Exemplary surface active agents and/or emulsifiers include natural emulsifiers (e.g. acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g. bentonite [aluminum silicate] and Veegum [magnesium aluminum silicate]), long chain amino acid derivatives, high molecular weight alcohols (e.g. stearyl alcohol, cetyl alcohol, oleyl alcohol, triacetin monostearate, ethylene glycol distearate, glyceryl monostearate, and propylene glycol monostearate, polyvinyl alcohol), carbomers (e.g. carboxy polymethylene, polyacrylic acid, acrylic acid polymer, and carboxyvinyl polymer), carrageenan, cellulosic derivatives (e.g. carboxymethylcellulose sodium, powdered cellulose, hydroxymethyl cellulose, hydroxypropyl cellulose, hydroxypropyl methylcellulose, methylcellulose), sorbitan fatty acid esters (e.g. polyoxyethylene sorbitan monolaurate [Tween 20], polyoxyethylene sorbitan [Tween 60], polyoxyethylene sorbitan monooleate [Tween 80], sorbitan monopalmitate [Span 40], sorbitan monostearate [Span 60], sorbitan tristearate [Span 65], glyceryl monooleate, sorbitan monooleate [Span 80]), polyoxyethylene esters (e.g. polyoxyethylene monostearate [Myrj 45], polyoxyethylene hydrogenated castor oil, polyethoxylated castor oil, polyoxymethylene stearate, and Solutol), sucrose fatty acid esters, polyethylene glycol fatty acid esters (e.g. Cremophor), polyoxyethylene ethers, (e.g. polyoxyethylene lauryl ether [Brij 30]), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic F 68, Poloxamer 188, cetrimonium bromide, cetylpyridinium chloride, benzalkonium chloride, docusate sodium, etc. and/or combinations thereof.

Exemplary binding agents include starch (e.g. cornstarch and starch paste), gelatin, sugars (e.g. sucrose, glucose, dextrose, dextrin, molasses, lactose, lactitol, mannitol, etc.), natural and synthetic gums (e.g. acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum), and larch arabogalactan), alginates, polyethylene oxide, polyethylene glycol, inorganic calcium salts, silicic acid, polymethacrylates, waxes, water, alcohol, etc., and/or combinations thereof.

Exemplary preservatives include antioxidants, chelating agents, antimicrobial preservatives, antifungal preservatives, alcohol preservatives, acidic preservatives, and other preservatives.

Exemplary antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant Plus, Phenonip, methylparaben, Germall 115, Germaben II, Neolone, Kathon, and Euxyl. In certain embodiments, the preservative is an anti-oxidant. In other embodiments, the preservative is a chelating agent.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen—free water, isotonic saline, Ringer's solution, ethyl alcohol, etc., and combinations thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, etc., and combinations thereof.

Exemplary oils include almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macademia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and combinations thereof.

Liquid dosage forms for oral and parenteral administration include pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates of the invention are mixed with solubilizing agents such as Cremophor, alcohols, oils, modified oils, glycols, polysorbates, cyclodextrins, polymers, and combinations thereof.

Injectable preparations, for example, sterile injectable aqueous or oleaginous suspensions can be formulated according to the known art using suitable dispersing or wetting agents and suspending agents. The sterile injectable preparation can be a sterile injectable solution, suspension or emulsion in a nontoxic parenterally acceptable diluent or solvent, for example, as a solution in 1,3-butanediol. Among the acceptable vehicles and solvents that can be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Compositions for rectal or vaginal administration are typically suppositories which can be prepared by mixing the conjugates of this invention with suitable non-irritating excipients or carriers such as cocoa butter, polyethylene glycol or a suppository wax which are solid at ambient temperature but liquid at body temperature and therefore melt in the rectum or vaginal cavity and release the active ingredient.

Solid dosage forms for oral administration include capsules, tablets, pills, powders, and granules. In such solid dosage forms, the active ingredient is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may comprise buffering agents.

Solid compositions of a similar type can be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes. Solid compositions of a similar type can be employed as fillers in soft and hard-filled gelatin capsules using such excipients as lactose or milk sugar as well as high molecular weight polyethylene glycols and the like.

The active ingredients can be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active ingredient can be admixed with at least one inert diluent such as sucrose, lactose or starch. Such dosage forms may comprise, as is normal practice, additional substances other than inert diluents, e.g., tableting lubricants and other tableting aids such a magnesium stearate and microcrystalline cellulose. In the case of capsules, tablets and pills, the dosage forms may comprise buffering agents. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes.

Dosage forms for topical and/or transdermal administration of a compound of this invention may include ointments, pastes, creams, lotions, gels, powders, solutions, sprays, inhalants and/or patches. Generally, the active ingredient is admixed under sterile conditions with a pharmaceutically acceptable carrier and/or any needed preservatives and/or buffers as can be required. Additionally, the present invention contemplates the use of transdermal patches, which often have the added advantage of providing controlled delivery of an active ingredient to the body. Such dosage forms can be prepared, for example, by dissolving and/or dispensing the active ingredient in the proper medium. Alternatively or additionally, the rate can be controlled by either providing a rate controlling membrane and/or by dispersing the active ingredient in a polymer matrix and/or gel.

Suitable devices for use in delivering intradermal pharmaceutical compositions described herein include short needle devices such as those described in U.S. Pat. Nos. 4,886,499; 5,190,521; 5,328,483; 5,527,288; 4,270,537; 5,015,235; 5,141,496; and 5,417,662. Intradermal compositions can be administered by devices which limit the effective penetration length of a needle into the skin, such as those described in PCT publication WO 99/34850 and functional equivalents thereof. Jet injection devices which deliver liquid vaccines to the dermis via a liquid jet injector and/or via a needle which pierces the stratum corneum and produces a jet which reaches the dermis are suitable. Jet injection devices are described, for example, in U.S. Pat. Nos. 5,480,381; 5,599,302; 5,334,144; 5,993,412; 5,649,912; 5,569,189; 5,704,911; 5,383,851; 5,893,397; 5,466,220; 5,339,163; 5,312,335; 5,503,627; 5,064,413; 5,520,639; 4,596,556; 4,790,824; 4,941,880; 4,940,460; and PCT publications WO 97/37705 and WO 97/13537. Ballistic powder/particle delivery devices which use compressed gas to accelerate vaccine in powder form through the outer layers of the skin to the dermis are suitable. Alternatively or additionally, conventional syringes can be used in the classical mantoux method of intradermal administration.

Formulations suitable for topical administration include, but are not limited to, liquid and/or semi liquid preparations such as liniments, lotions, oil in water and/or water in oil emulsions such as creams, ointments and/or pastes, and/or solutions and/or suspensions. Topically-administrable formulations may, for example, comprise from about 1% to about 10% (w/w) active ingredient, although the concentration of the active ingredient can be as high as the solubility limit of the active ingredient in the solvent. Formulations for topical administration may further comprise one or more of the additional ingredients described herein.

A pharmaceutical composition of the invention can be prepared, packaged, and/or sold in a formulation suitable for pulmonary administration via the buccal cavity. Such a formulation may comprise dry particles which comprise the active ingredient and which have a diameter in the range from about 0.5 to about 7 nanometers or from about 1 to about 6 nanometers. Such compositions are conveniently in the form of dry powders for administration using a device comprising a dry powder reservoir to which a stream of propellant can be directed to disperse the powder and/or using a self propelling solvent/powder dispensing container such as a device comprising the active ingredient dissolved and/or suspended in a low-boiling propellant in a sealed container. Such powders comprise particles wherein at least 98% of the particles by weight have a diameter greater than 0.5 nanometers and at least 95% of the particles by number have a diameter less than 7 nanometers. Alternatively, at least 95% of the particles by weight have a diameter greater than 1 nanometer and at least 90% of the particles by number have a diameter less than 6 nanometers. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic and/or solid anionic surfactant and/or a solid diluent (which may have a particle size of the same order as particles comprising the active ingredient).

Pharmaceutical compositions of the invention formulated for pulmonary delivery may provide the active ingredient in the form of droplets of a solution and/or suspension. Such formulations can be prepared, packaged, and/or sold as aqueous and/or dilute alcoholic solutions and/or suspensions, optionally sterile, comprising the active ingredient, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxybenzoate. The droplets provided by this route of administration may have an average diameter in the range from about 0.1 to about 200 nanometers.

The formulations described herein as being useful for pulmonary delivery are useful for intranasal delivery of a pharmaceutical composition of the invention. Another formulation suitable for intranasal administration is a coarse powder comprising the active ingredient and having an average particle from about 0.2 to 500 micrometers. Such a formulation is administered. by rapid inhalation through the nasal passage from a container of the powder held close to the nares.

Formulations suitable for nasal administration may, for example, comprise from about as little as 0.1% (w/w) and as much as 100% (w/w) of the active ingredient, and may comprise one or more of the additional ingredients described herein. A pharmaceutical composition of the invention can be prepared, packaged, and/or sold in a formulation suitable for buccal administration. Such formulations may, for example, be in the form of tablets and/or lozenges made using conventional methods, and may contain, for example, 0.1 to 20% (w/w) active ingredient, the balance comprising an orally dissolvable and/or degradable composition and, optionally, one or more of the additional ingredients described herein. Alternately, formulations suitable for buccal administration may comprise a powder and/or an aerosolized and/or atomized solution and/or suspension comprising the active ingredient. Such powdered, aerosolized, and/or aerosolized formulations, when dispersed, may have an average particle and/or droplet size in the range from about 0.1 to about 200 nanometers, and may further comprise one or more of the additional ingredients described herein.

A pharmaceutical composition of the invention can be prepared, packaged, and/or sold in a formulation suitable for ophthalmic administration. Such formulations may, for example, be in the form of eye drops including, for example, a 0.1/1.0% (w/w) solution and/or suspension of the active ingredient in an aqueous or oily liquid carrier. Such drops may further comprise buffering agents, salts, and/or one or more other of the additional ingredients described herein. Other opthalmically-administrable formulations which are useful include those which comprise the active ingredient in microcrystalline form and/or in a liposomal preparation. Ear drops and/or eye drops are contemplated as being within the scope of this invention.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation. General considerations in the formulation and/or manufacture of pharmaceutical compositions can be found, for example, in *Remington: The Science and Practice of Pharmacy* $21^{st}$ ed., Lippincott Williams & Wilkins, 2005.

Still further encompassed by the invention are pharmaceutical packs and/or kits. Pharmaceutical packs and/or kits provided may comprise a provided composition and a container (e.g., a vial, ampoule, bottle, syringe, and/or dispenser package, or other suitable container). In some embodiments, provided kits may optionally further include a second container comprising a suitable aqueous carrier for dilution or suspension of the provided composition for preparation of administration to a subject. In some embodiments, contents of provided formulation container and solvent container combine to form at least one unit dosage form.

In some embodiments, a provided composition of the invention can be useful in conjunction with subject controlled analgesia (PCA) devices, wherein a subject can administer, for example, opioid analgesia as required for pain management.

Optionally, a single container may comprise one or more compartments for containing a provided composition, and/or appropriate aqueous carrier for suspension or dilution. In some embodiments, a single container can be appropriate for modification such that the container may receive a physical modification so as to allow combination of compartments and/or components of individual compartments. For example, a foil or plastic bag may comprise two or more compartments separated by a perforated seal which can be broken so as to allow combination of contents of two individual compartments once the signal to break the seal is generated. A pharmaceutical pack or kit may thus comprise such multi-compartment containers including a provided composition and appropriate solvent and/or appropriate aqueous carrier for suspension.

Optionally, instructions for use are additionally provided in such kits of the invention. Such instructions may provide, generally, for example, instructions for dosage and administration. In other embodiments, instructions may further provide additional detail relating to specialized instructions for particular containers and/or systems for administration. Still further, instructions may provide specialized instructions for use in conjunction and/or in combination with additional therapy. In one non-limiting example, the formulations of the invention can be used in conjunction with opioid analgesia administration, which may, optionally, comprise use of a subject controlled analgesia (PCA) device. Thus, instructions for use of provided formulations may comprise instructions for use in conjunction with PCA administration devices.

III. Methods of Use and Treatment

The present invention provides methods for treating a FAAH-mediated condition comprising administering to a subject in need thereof a therapeutically effective amount of a compound of formula (I) or a pharmaceutically acceptable form thereof.

The present invention also provides methods for inhibiting FAAH in a subject comprising administering to a subject in need thereof a therapeutically effective amount of a compound of formula (I) or a pharmaceutically acceptable form thereof.

The present invention also provides a method of inhibiting activation of the FAAH pathway in vitro or ex vivo, comprising contacting a FAAH protein with a compound of formula (I) in an amount sufficient to reduce the activation of the FAAH pathway.

The present invention also provides use of a compound of formula (I) for the treatment of a FAAH-mediated condition in a subject.

The present invention also provides use of a compound of formula (I) in the manufacture of a medicament. In certain embodiments, the medicament is useful for treating a FAAH-mediated condition.

A "subject" to which administration is contemplated includes, but is not limited to, humans (i.e., a male or female of any age group, e.g., a pediatric subject (e.g, infant, child, adolescent) or adult subject (e.g., young adult, middle-aged adult or senior adult)) and/or other primates (e.g., cynomolgus monkeys, rhesus monkeys); mammals, including commercially relevant mammals such as cattle, pigs, horses, sheep, goats, cats, and/or dogs; and/or birds, including commercially relevant birds such as chickens, ducks, geese, and/or turkeys.

As used herein, and unless otherwise specified, the terms "treat," "treating" and "treatment" contemplate an action that occurs while a subject is suffering from the specified disease, disorder or condition, which reduces the severity of the disease, disorder or condition, or retards or slows the progression of the disease, disorder or condition.

As used herein, unless otherwise specified, the terms "prevent," "preventing" and "prevention" contemplate an action that occurs before a subject begins to suffer from the specified disease, disorder or condition, which inhibits or reduces the severity of the disease, disorder or condition.

As used herein, and unless otherwise specified, the terms "manage," "managing" and "management" encompass preventing the recurrence of the specified disease, disorder or condition in a subject who has already suffered from the disease, disorder or condition, and/or lengthening the time that a subject who has suffered from the disease, disorder or condition remains in remission. The terms encompass modulating the threshold, development and/or duration of the disease, disorder or condition, or changing the way that a subject responds to the disease, disorder or condition.

As used herein, and unless otherwise specified, a "therapeutically effective amount" of a compound is an amount sufficient to provide a therapeutic benefit in the treatment or management of a disease, disorder or condition, or to delay or minimize one or more symptoms associated with the disease, disorder or condition. A therapeutically effective amount of a compound means an amount of therapeutic agent, alone or in combination with other therapies, which provides a therapeutic benefit in the treatment or management of the disease, disorder or condition. The term "therapeutically effective amount" can encompass an amount that improves overall therapy, reduces or avoids symptoms or causes of disease or condition, or enhances the therapeutic efficacy of another therapeutic agent.

As used herein, and unless otherwise specified, a "prophylactically effective amount" of a compound is an amount sufficient to prevent a disease, disorder or condition, or one or more symptoms associated with the disease, disorder or condition, or prevent its recurrence. A prophylactically effective amount of a compound means an amount of therapeutic agent, alone or in combination with other agents, which provides a prophylactic benefit in the prevention of the disease, disorder or condition. The term "prophylactically effective amount" can encompass an amount that improves overall prophylaxis or enhances the prophylactic efficacy of another prophylactic agent.

As used herein "inhibition", "inhibiting", "inhibit" and "inhibitor", and the like, refer to the ability of a compound to reduce, slow, halt or prevent activity of a particular biological process (e.g., FAAH activity) in a cell relative to vehicle.

"FAAH-mediated condition" as used herein, refers to a disease, disorder or condition which is treatable by inhibition of FAAH activity. "Disease", "disorder" or "condition" are terms used interchangeably herein. FAAH-mediated conditions include, but are not limited to, painful conditions, inflammatory conditions, immune disorders, disorders of the central nervous system, metabolic disorders, cardiac disorders and glaucoma.

In certain embodiments, the FAAH-mediated condition is a painful condition. As used herein, a "painful condition" includes, but is not limited to, neuropathic pain (e.g., peripheral neuropathic pain), central pain, deafferentiation pain, chronic pain (e.g., chronic nociceptive pain, and other forms of chronic pain such as post-operative pain, e.g., pain arising after hip, knee, or other replacement surgery), pre-operative pain, stimulus of nociceptive receptors (nociceptive pain), acute pain (e.g., phantom and transient acute pain), non-inflammatory pain, inflammatory pain, pain associated with cancer, wound pain, burn pain, post-operative pain, pain associated with medical procedures, pain resulting from pruritus, painful bladder syndrome, pain associated with premenstrual dysphoric disorder and/or premenstrual syndrome, pain associated with chronic fatigue syndrome, pain associated with pre-term labor, pain associated with drawl symptoms from drug addiction, joint pain, arthritic pain (e.g., pain associated with crystalline arthritis, osteoarthritis, psoriatic arthritis, gouty arthritis, reactive arthritis, rheumatoid arthritis or Reiter's arthritis), lumbosacral pain, musculo-skeletal pain, headache, migraine, muscle ache, lower back pain, neck pain, toothache, dental/maxillofacial pain, visceral pain and the like.

One or more of the painful conditions contemplated herein can comprise mixtures of various types of pain provided above and herein (e.g. nociceptive pain, inflammatory pain, neuropathic pain, etc.). In some embodiments, a particular pain can dominate. In other embodiments, the painful condition comprises two or more types of pains without one dominating. A skilled clinician can determine the dosage to achieve a therapeutically effective amount for a particular subject based on the painful condition.

In certain embodiments, the painful condition is neuropathic pain. The term "neuropathic pain" refers to pain resulting from injury to a nerve. Neuropathic pain is distinguished from nociceptive pain, which is the pain caused by acute tissue injury involving small cutaneous nerves or small nerves in muscle or connective tissue. Neuropathic pain typically is long-lasting or chronic and often develops days or months following an initial acute tissue injury. Neuropathic pain can involve persistent, spontaneous pain as well as allodynia, which is a painful response to a stimulus that normally is not painful. Neuropathic pain also can be characterized by hyperalgesia, in which there is an accentuated response to a painful stimulus that usually is trivial, such as a pin prick. Neuropathic pain conditions can develop following neuronal injury and the resulting pain may persist for months or years, even after the original injury has healed. Neuronal injury may occur in the peripheral nerves, dorsal roots, spinal cord or certain regions in the brain. Neuropathic pain conditions include, but are not limited to, diabetic neuropathy (e.g., peripheral diabetic neuropathy); sciatica; non-specific lower back pain; multiple sclerosis pain; carpal tunnel syndrome, fibromyalgia; HIV-related neuropathy; neuralgia (e.g., postherpetic neuralgia, trigeminal neuralgia); pain resulting from physical trauma (e.g., amputation; surgery, invasive medical procedures, toxins, burns, infection), pain resulting from cancer or chemotherapy (e.g., chemotherapy-induced pain such as chemotherapy-induced peripheral neuropathy), and pain resulting from an inflammatory condition (e.g., a chronic inflammatory condition). Neuropathic pain can result from a peripheral nerve disorder such as neuroma; nerve compression; nerve crush, nerve stretch or incomplete nerve transsection; mononeuropathy or polyneuropathy. Neuropathic pain can also result from a disorder such as dorsal root ganglion compression; inflammation of the spinal cord; contusion, tumor or hemisection of the spinal cord; tumors of the brainstem, thalamus or cortex; or trauma to the brainstem, thalamus or cortex.

The symptoms of neuropathic pain are heterogeneous and are often described as spontaneous shooting and lancinating pain, or ongoing, burning pain. In addition, there is pain associated with normally non-painful sensations such as "pins and needles" (paraesthesias and dysesthesias), increased sensitivity to touch (hyperesthesia), painful sensation following innocuous stimulation (dynamic, static or thermal allodynia), increased sensitivity to noxious stimuli (thermal, cold, mechanical hyperalgesia), continuing pain sensation after removal of the stimulation (hyperpathia) or an absence of or deficit in selective sensory pathways (hypoalgesia).

In certain embodiments, the painful condition is non-inflammatory pain. The types of non-inflammatory pain include, without limitation, peripheral neuropathic pain (e.g., pain caused by a lesion or dysfunction in the peripheral nervous system), central pain (e.g., pain caused by a lesion or dysfunction of the central nervous system), deafferentation pain (e.g., pain due to loss of sensory input to the central nervous system), chronic nociceptive pain (e.g., certain types of cancer pain), noxious stimulus of nociceptive receptors (e.g., pain felt in response to tissue damage or impending tissue damage), phantom pain (e.g., pain felt in a part of the body that no longer exists, such as a limb that has been amputated), pain felt by psychiatric subjects (e.g., pain where no physical cause may exist), and wandering pain (e.g., wherein the pain repeatedly changes location in the body).

In certain embodiments, the painful condition is inflammatory pain. In certain embodiments, the painful condition (e.g., inflammatory pain) is associated with an inflammatory condition and/or an immune disorder.

In certain embodiments, the FAAH-mediated condition is an inflammatory condition. The term "inflammatory condition" refers to those diseases, disorders or conditions that are characterized by signs of pain (dolor, from the generation of noxious substances and the stimulation of nerves), heat (calor, from vasodilatation), redness (rubor, from vasodilatation and increased blood flow), swelling (tumor, from excessive inflow or restricted outflow of fluid), and/or loss of function (functio laesa, which can be partial or complete, temporary or permanent. Inflammation takes on many forms and includes, but is not limited to, acute, adhesive, atrophic, catarrhal, chronic, cirrhotic, diffuse, disseminated, exudative, fibrinous, fibrosing, focal, granulomatous, hyperplastic, hypertrophic, interstitial, metastatic, necrotic, obliterative, parenchymatous, plastic, productive, proliferous, pseudomembranous, purulent, sclerosing, seroplastic, serous, simple, specific, subacute, suppurative, toxic, traumatic, and/or ulcerative inflammation.

Exemplary inflammatory conditions include, but are not limited to, inflammation associated with acne, anemia (e.g., aplastic anemia, haemolytic autoimmune anaemia), asthma, arteritis (e.g., polyarteritis, temporal arteritis, periarteritis nodosa, Takayasu's arteritis), arthritis (e.g., crystalline arthritis, osteoarthritis, psoriatic arthritis, gouty arthritis, reactive arthritis, rheumatoid arthritis and Reiter's arthritis), ankylosing spondylitis, amylosis, amyotrophic lateral sclerosis, autoimmune diseases, allergies or allergic reactions, atherosclerosis, bronchitis, bursitis, chronic prostatitis, conjunctivitis, Chagas disease, chronic obstructive pulmonary disease, cermatomyositis, diverticulitis, diabetes (e.g., type I diabetes mellitus, type 2 diabetes mellitus), a skin condition (e.g., psoriasis, eczema, burns, dermatitis, pruritus (itch)), endometriosis, Guillain-Barre syndrome, infection, ischaemic heart disease, Kawasaki disease, glomerulonephritis, gingivitis, hypersensitivity, headaches (e.g., migraine headaches, tension headaches), ileus (e.g., postoperative ileus and ileus during sepsis), idiopathic thrombocytopenic purpura, interstitial cystitis (painful bladder syndrome), gastrointestinal disorder (e.g., selected from peptic ulcers, regional enteritis, diverticulitis, gastrointestinal bleeding, eosinophilic gastrointestinal disorders (e.g., eosinophilic esophagitis, eosinophilic gastritis, eosinophilic gastroenteritis, eosinophilic colitis), gastritis, diarrhea, gastroesophageal reflux disease (GORD, or its synonym GERD), inflammatory bowel disease (IBD) (e.g., Crohn's disease, ulcerative colitis, collagenous colitis, lymphocytic colitis, ischaemic colitis, diversion colitis, Behcet's syndrome, indeterminate colitis) and inflammatory bowel syndrome (IBS)), lupus, multiple sclerosis, morphea, myeasthenia gravis, myocardial ischemia, nephrotic syndrome, pemphigus vulgaris, pernicious aneaemia, peptic ulcers, polymyositis, primary biliary cirrhosis, neuroinflammation associated with brain disorders (e.g., Parkinson's disease, Huntington's disease, and Alzheimer's disease), prostatitis, chronic inflammation associated with cranial radiation injury, pelvic inflammatory disease, reperfusion injury, regional enteritis, rheumatic fever, systemic lupus erythematosus, schleroderma, scierodoma, sarcoidosis, spondyloarthopathies, Sjogren's syndrome, thyroiditis, transplantation rejection, tendonitis, trauma or injury (e.g., frostbite, chemical irritants, toxins, scarring, burns, physical injury), vasculitis, vitiligo and Wegener's granulomatosis. In certain embodiments, the inflammatory disorder is selected from arthritis (e.g., rheumatoid arthritis), inflammatory bowel disease, inflammatory bowel syndrome, asthma, psoriasis, endometriosis, interstitial cystitis and prostatitis. In certain embodiments, the inflammatory condition is an acute inflammatory condition (e.g., for example, inflammation resulting from infection). In certain embodiments, the inflammatory condition is a chronic inflammatory condition (e.g., conditions resulting from asthma, arthritis and inflammatory bowel disease). The compounds may also be useful in treating inflammation associated with trauma and non-inflammatory myalgia. The compounds may also be useful in treating inflammation associated with cancer.

In certain embodiments, the FAAH-mediated condition is an immune disorder. Immune disorders, such as auto-immune disorders, include, but are not limited to, arthritis (including rheumatoid arthritis, spondyloarthopathies, gouty arthritis, degenerative joint diseases such as osteoarthritis, systemic lupus erythematosus, Sjogren's syndrome, ankylosing spondylitis, undifferentiated spondylitis, Behcet's disease, haemolytic autoimmune anaemias, multiple sclerosis, amyotrophic lateral sclerosis, amylosis, acute painful shoulder, psoriatic, and juvenile arthritis), asthma, atherosclerosis, osteoporosis, bronchitis, tendonitis, bursitis, skin condition (e.g., psoriasis, eczema, burns, dermatitis, pruritus (itch)), enuresis, eosinophilic disease, gastrointestinal disorder (e.g., selected from peptic ulcers, regional enteritis, diverticulitis, gastrointestinal bleeding, eosinophilic gastrointestinal disorders (e.g., eosinophilic esophagitis, eosinophilic gastritis, eosinophilic gastroenteritis, eosinophilic colitis), gastritis, diarrhea, gastroesophageal reflux disease (GORD, or its synonym GERD), inflammatory bowel disease (IBD) (e.g., Crohn's disease, ulcerative colitis, collagenous colitis, lymphocytic colitis, ischaemic colitis, diversion colitis, Behcet's syndrome, indeterminate colitis) and inflammatory bowel syndrome (IBS)), and disorders ameliorated by a gastroprokinetic agent (e.g., ileus, postoperative ileus and ileus during sepsis; gastroesophageal reflux disease (GORD, or its synonym GERD); eosinophilic esophagitis, gastroparesis such as diabetic gastroparesis; food intolerances and food allergies and other functional bowel disorders, such as non-ulcerative dyspepsia (NUD) and non-cardiac chest pain (NCCP, including costo-chondritis)).

In certain embodiments, the inflammatory disorder and/or the immune disorder is a gastrointestinal disorder. In some embodiments, the gastrointestinal disorder is selected from gastrointestinal disorder (e.g., selected from peptic ulcers, regional enteritis, diverticulitis, gastrointestinal bleeding, eosinophilic gastrointestinal disorders (e.g., eosinophilic esophagitis, eosinophilic gastritis, eosinophilic gastroenteritis, eosinophilic colitis), gastritis, diarrhea, gastroesophageal reflux disease (GORD, or its synonym GERD), inflammatory bowel disease (IBD) (e.g., Crohn's disease, ulcerative colitis, collagenous colitis, lymphocytic colitis, ischaemic colitis, diversion colitis, Behcet's syndrome, indeterminate colitis) and inflammatory bowel syndrome (IBS)). In certain embodiments, the gastrointestinal disorder is inflammatory bowel disease (IBD).

In certain embodiments, the inflammatory condition and/or immune disorder is a skin condition. In some embodiments, the skin condition is pruritus (itch), psoriasis, eczema, burns or dermatitis. In certain embodiments, the skin condition is psoriasis. In certain embodiments, the skin condition is pruritus.

In certain embodiments, the FAAH-mediated condition is a disorder of the central nervous system (CNS) ("CNS disorder"). Exemplary CNS disorders include, but are not limited to, neurotoxicity and/or neurotrauma, stroke, multiple sclerosis, spinal cord injury, epilepsy, a mental disorder, a sleep condition, a movement disorder, nausea and/or emesis, amyotrophic lateral sclerosis, Alzheimer's disease and drug addiction.

In certain embodiments, the CNS disorder is neurotoxicity and/or neurotrauma, e.g., for example, as a result of acute neuronal injury (e.g., tramatic brain injury (TBI), stroke, epilepsy) or a chronic neurodegenerative disorder (e.g., multiple sclerosis, Parkinson's disease, Huntington's disease, amyotrophic lateral sclerosis, Alzheimer's disease). In certain embodiments, the compound of the present invention provides a neuroprotective effect, e.g., against an acute neuronal injury or a chronic neurodegenerative disorder.

In certain embodiments, the CNS disorder is stroke (e.g., ischemic stroke).

In certain embodiments, the CNS disorder is multiple sclerosis.

In certain embodiments, the CNS disorder is spinal cord injury.

In certain embodiments, the CNS disorder is epilepsy.

In certain embodiments, the CNS disorder is a mental disorder, e.g., for example, depression, anxiety or anxiety-related conditions, a learning disability or schizophrenia.

In certain embodiments, the CNS disorder is depression. "Depression," as used herein, includes, but is not limited to, depressive disorders or conditions, such as, for example, major depressive disorders (e.g., unipolar depression), dysthymic disorders (e.g., chronic, mild depression), bipolar disorders (e.g., manic-depression), seasonal affective disorder, and/or depression associated with drug addiction (e.g., withdrawal). The depression can be clinical or subclinical depression. The depression can be associated with or premenstrual syndrome and/or premenstrual dysphoric disorder.

In certain embodiments, the CNS disorder is anxiety. "Anxiety," as used herein, includes, but is not limited to anxiety and anxiety-related conditions, such as, for example, clinical anxiety, panic disorder, agoraphobia, generalized anxiety disorder, specific phobia, social phobia, obsessive-compulsive disorder, acute stress disorder, post-traumatic stress disorder, adjustment disorders with anxious features, anxiety disorder associated with depression, anxiety disorder due to general medical conditions, and substance-induced anxiety disorders, anxiety associated with drug addiction (e.g., withdrawal, dependence, reinstatement) and anxiety associated with nausea and/or emesis. This treatment may also be to induce or promote sleep in a subject (e.g., for example, a subject with anxiety).

In certain embodiments, the CNS disorder is a learning disorder (e.g., attention deficit disorder (ADD)).

In certain embodiments, the CNS disorder is Schizophrenia.

In certain embodiments, the CNS disorder is a sleep condition. "Sleep conditions" include, but are not limited to, insomnia, narcolepsy, sleep apnea, restless legs syndrome (RLS), delayed sleep phase syndrome (DSPS), periodic limb movement disorder (PLMD), hypopnea syndrome, rapid eye movement behavior disorder (RBD), shift work sleep condition (SWSD), and sleep problems (e.g., parasomnias) such as nightmares, night terrors, sleep talking, head banging, snoring, and clenched jaw and/or grinding of teeth (bruxism).

In certain embodiments, the CNS disorder is a movement disorder, e.g., basal ganglia disorders, such as, for example, Parkinson's disease, levodopa-induced dyskinesia, Huntington's disease, Gilles de la Tourette's syndrome, tardive dyskinesia and dystonia.

In certain embodiments, the CNS disorder is Alzheimer's disease.

In certain embodiments, the CNS disorder is amyotrophic lateral sclerosis (ALS).

In certain embodiments, the CNS disorder is nausea and/or emesis.

In certain embodiments, the CNS disorder is drug addiction (e.g., for instance, addiction to opiates, nicotine, cocaine, psychostimulants or alcohol).

In still yet other embodiments, the FAAH-mediated condition is a cardiac disorder, e.g., for example, selected from hypertension, circulatory shock, myocardial reperfusion injury and atherosclerosis.

In certain embodiments, the FAAH-mediated condition is a metabolic disorder (e.g., a wasting condition, an obesity-related condition or complication thereof).

In certain embodiments, the metabolic disorder is a wasting condition. A "wasting condition," as used herein, includes but is not limited to, anorexia and cachexias of various natures (e.g., weight loss associated with cancer, weight loss associated with other general medical conditions, weight loss associated with failure to thrive, and the like).

In certain embodiments, the metabolic disorder is an obesity-related condition or a complication thereof. An "obesity-related condition" as used herein, includes, but is not limited to, obesity, undesired weight gain (e.g., from medication-induced weight gain, from cessation of smoking) and an over-eating disorder (e.g., binge eating, bulimia, compulsive eating, or a lack of appetite control each of which can optionally lead to undesired weight gain or obesity). "Obesity" and "obese" as used herein, refers to class I obesity, class II obesity, class III obesity and pre-obesity (e.g., being "over-weight") as defined by the World Health Organization.

Reduction of storage fat is expected to provide various primary and/or secondary benefits in a subject (e.g., in a subject diagnosed with a complication associated with obesity) such as, for example, an increased insulin responsiveness (e.g., in a subject diagnosed with Type II diabetes mellitus); a reduction in elevated blood pressure; a reduction in elevated cholesterol levels; and/or a reduction (or a reduced risk or progression) of ischemic heart disease, arterial vascular disease, angina, myocardial infarction, stroke, migraines, congestive heart failure, deep vein thrombosis, pulmonary embolism, gall stones, gastroesophagael reflux disease, obstructive sleep apnea, obesity hypoventilation syndrome, asthma, gout, poor mobility, back pain, erectile dysfunction, urinary incontinence, liver injury (e.g., fatty liver disease, liver cirrhosis, alcoholic cirrhosis, endotoxin mediated liver injury) or chronic renal failure. Thus, the method of this invention is applicable to obese subjects, diabetic subjects, and alcoholic subjects.

In some embodiments, treatment of an obesity-related condition or complication thereof involves reduction of body weight in the subject. In some embodiments, treatment of an obesity-related condition or complication thereof involves appetite control in the subject.

In other embodiments, the FAAH-mediated condition is glaucoma.

IV. Administration

Provided compounds can be administered using any amount and any route of administration effective for treatment. The exact amount required will vary from subject to subject, depending on the species, age, and general condition of the subject, the severity of the infection, the particular composition, its mode of administration, its mode of activity, and the like.

Compounds provided herein are typically formulated in dosage unit form for ease of administration and uniformity of dosage. It will be understood, however, that the total daily usage of the compositions of the present invention will be decided by the attending physician within the scope of sound medical judgment. The specific therapeutically effective dose level for any particular subject or organism will depend upon a variety of factors including the disease, disorder, or condition being treated and the severity of the disorder; the activity of the specific active ingredient employed; the specific composition employed; the age, body weight, general health, sex and diet of the subject; the time of administration, route of administration, and rate of excretion of the specific active ingredient employed; the duration of the treatment; drugs used in combination or coincidental with the specific active ingredient employed; and like factors well known in the medical arts.

The compounds and compositions provided herein can be administered by any route, including oral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, bucal, enteral, sublingual; by intratracheal instillation, bronchial instillation, and/or inhalation; and/or as an oral spray, nasal spray, and/or aerosol. Specifically contemplated routes are systemic intravenous injection, regional administration via blood and/or lymph supply, and/or direct administration to an affected site. In general the most appropriate route of administration will depend upon a variety of factors including the nature of the agent (e.g., its stability in the environment of the gastrointestinal tract), the condition of the subject (e.g., whether the subject is able to tolerate oral administration), etc.

The exact amount of a compound required to achieve a therapeutically effective amount will vary from subject to subject, depending, for example, on species, age, and general condition of a subject, severity of the side effects or disorder, identity of the particular compound(s), mode of administration, and the like. The desired dosage can be delivered three times a day, two times a day, once a day, every other day, every third day, every week, every two weeks, every three weeks, or every four weeks. In certain embodiments, the desired dosage can be delivered using multiple administrations (e.g., two, three, four, five, six, seven, eight, nine, ten, eleven, twelve, thirteen, fourteen, or more administrations).

In certain embodiments, a therapeutically effective amount of a compound for administration one or more times a day to a 70 kg adult human may comprise about 0.0001 mg to about 3000 mg, about 0.0001 mg to about 2000 mg, about 0.0001 mg to about 1000 mg, about 0.001 mg to about 1000 mg, about 0.01 mg to about 1000 mg, about 0.1 mg to about 1000 mg, about 1 mg to about 1000 mg, about 1 mg to about 100 mg, about 10 mg to about 1000 mg, or about 100 mg to about 1000 mg, of an inventive compound per unit dosage form. It will be appreciated that dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

It will be also appreciated that a compound or composition, as described herein, can be administered in combination with one or more additional therapeutically active agents. The compound or composition can be administered concurrently with, prior to, or subsequent to, one or more additional therapeutically active agents. In general, each agent will be administered at a dose and/or on a time schedule determined for that agent. In will further be appreciated that the additional therapeutically active agent utilized in this combination can be administered together in a single composition or administered separately in different compositions. The particular combination to employ in a regimen will take into account compatibility of the inventive compound with the additional therapeutically active agent and/or the desired therapeutic effect to be achieved. In general, it is expected that additional therapeutically active agents utilized in combination be utilized at levels that do not exceed the levels at which they are utilized individually. In some embodiments, the levels utilized in combination will be lower than those utilized individually.

The compounds or compositions can be administered in combination with agents that improve their bioavailability, reduce and/or modify their metabolism, inhibit their excretion, and/or modify their distribution within the body. It will also be appreciated that therapy employed may achieve a desired effect for the same disorder (for example, a compound can be administered in combination with an anti-inflammatory, anti-anxiety and/or anti-depressive agent, etc.), and/or it may achieve different effects (e.g., control of adverse side-effects).

Exemplary active agents include, but are not limited to, anti-cancer agents, antibiotics, anti-viral agents, anesthetics, anti-coagulants, inhibitors of an enzyme, steroidal agents, steroidal or non-steroidal anti-inflammatory agents, antihistamine, immunosuppressant agents, anti-neoplastic agents, antigens, vaccines, antibodies, decongestants, sedatives, opioids, pain-relieving agents, analgesics, anti-pyretics, hormones, prostaglandins, progestational agents, anti-glaucoma agents, ophthalmic agents, anti-cholinergics, anti-depressants, anti-psychotics, hypnotics, tranquilizers, anti-convulsants/anti-epileptics (e.g., Neurontin, Lyrica, valproates (e.g., Depacon), and other neurostabilizing agents), muscle relaxants, anti-spasmodics, muscle contractants, channel blockers, miotic agents, anti-secretory agents, anti-thrombotic agents, anticoagulants, anti-cholinergics, $\beta$-adrenergic blocking agents, diuretics, cardiovascular active agents, vasoactive agents, vasodilating agents, anti-hypertensive agents, angiogenic agents, modulators of cell-extracellular matrix interactions (e.g. cell growth inhibitors and anti-adhesion molecules), or inhibitors/intercalators of DNA, RNA, protein-protein interactions, protein-receptor interactions, etc. Active agents include small organic molecules such as drug compounds (e.g., compounds approved by the Food and Drugs Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins and cells.

In certain embodiments, the additional therapeutically active agent is a pain-relieving agent. Exemplary pain relieving agents include, but are not limited to, analgesics such as non-narcotic analgesics [e.g., salicylates such as aspirin, ibuprofen (MOTRIN®, ADVIL®), ketoprofen (ORUDIS®), naproxen (NAPROSYN®), acetaminophen, indomethacin] or narcotic analgesics [e.g., opioid analgesics such as tramadol, fentenyl, sufentanil, morphine, hydromorphone, codeine, oxycodone, and buprenorphine]; non-steroidal anti-inflammatory agents (NSAIDs) [e.g., aspirin, acetaminophen, COX-2 inhibitors]; steroids or anti-rheumatic agents; migraine preparations such as beta adrenergic blocking agents, ergot derivatives; tricyclic antidepressants (e.g., amitryptyline, desipramine, imipramine); anti-epileptics (e.g., clonaxepam, valproic acid, phenobarbital, phenyloin, tiagaine, gabapentin, carbamazepine, topiramate, sodium valproate); $\alpha_2$ agonists; selective serotonin reuptake inhibitors (SSRIs), selective norepinepherine uptake inhibitors; benzodiazepines; mexiletine (MEXITIL); flecamide (TAMBOCOR); NMDA receptor antagonists [e.g., ketamine, detromethorphan, methadone]; and topical agents [e.g., capsaicin (Zostrix), EMLA cream, lidocaine, prilocaine].

In other embodiments, the additional therapeutically active agent is an anti-inflammatory agent. Exemplary anti-inflammatory agents include, but are not limited to, aspirin; ibuprofen; ketoprofen; naproxen; etodolac) (LODINE®); COX-2 inhibitors such as celecoxib (CELEBREX®), rofecoxib (VIOXX®), valdecoxib (BEXTRA®, parecoxib, etoricoxib (MK663), deracoxib, 2-(4-ethoxy-phenyl)-3-(4-methanesulfonyl-phenyl)-pyrazolo[1,5-b]pyridazine, 4-(2-oxo-3-phenyl-2,3-dihydrooxazol-4-yl)benzenesulfonamide, darbufelone, flosulide, 4-(4-cyclohexyl-2-methyl-5-oxazolyl)-2-fluorobenzenesulfonamide), meloxicam, nimesulide, 1-Methylsulfonyl-4-(1,1-dimethyl-4-(4-fluorophenyl)cyclopenta-2,4-dien-3-yl)$_b$ enzene, 4-(1,5-Dihydro-6-fluoro-7-methoxy-3-(trifluoromethyl)-(2)-benzothiopyrano (4,3-c) pyrazol-1-yl)benzenesulfonamide, 4,4-dimethyl-2-phenyl-3-(4-methylsulfonyl)phenyl)cyclo-butenone, 4-Amino-N-(4-(2-fluoro-5-trifluoromethyl)-thiazol-2-yl)-benzene sulfonamide, 1-(7-tert-butyl-2,3-dihydro-3,3-dimethyl-5-benzo-furanyl)-4-cyclopropyl butan-1-one, or their physiologically acceptable salts, esters or solvates; sulindac (CLINORIL®); diclofenac (VOLTAREN®); piroxicam (FELDENE®); diflunisal (DOLOBID®), nabumetone (RELAFEN®), oxaprozin (DAYPRO®), indomethacin)(INDOCIN®); or steroids such as PEDIAPED® prednisolone sodium phosphate oral solution, SOLU-MEDROL® methylprednisolone sodium succinate for injection, PRELONE® brand prednisolone syrup.

Further examples of anti-inflammatory agents include naproxen, which is commercially available in the form of EC-NAPROSYN® delayed release tablets, NAPROSYN®, ANAPROX® and ANAPROX® DS tablets and NAPROSYN® suspension from Roche Labs, CELEBREX® brand of celecoxib tablets, VIOXX® brand of rofecoxib, CELESTONE® brand of betamethasone, CUPRAMINE® brand penicillamine capsules, DEPEN® brand titratable penicillamine tablets, DEPO-MEDROL brand of methylprednisolone acetate injectable suspension, ARAVA™ leflunomide tablets, AZULFIDIINE EN-tabs® brand of sulfasalazine delayed release tablets, FELDENE® brand piroxicam capsules, CATAFLAM® diclofenac potassium tablets, VOLTAREN® diclofenac sodium delayed release tablets, VOLTAREN®-XR diclofenac sodium extended release tablets, or ENBREL® etanerecept products.

V. Methods of Determining Biological Activity

Methods of determining the activity of the compounds provided herein for various therapeutic uses are known in the art. These include, but are not limited to, high throughput screening to identify compounds that bind to and/or modulate the activity of isolated FAAH, as well as in vitro and in vivo models of therapies.

Assays useful for screening the compounds provided herein may detect the binding of the inhibitor to FAAH or the release of a reaction product (e.g., fatty acid amide or ethanolamine) produced by the hydrolysis of a substrate such as oleoylethanolamide or ananadamide. The substrate can be labeled to facilitate detection of the released reaction products. U.S. Pat. No. 5,559,410 discloses high throughput screening methods for proteins, and U.S. Pat. Nos. 5,576,220 and 5,541,061 disclose high throughput methods of screening for ligand/antibody binding.

Methods for screening FAAH inhibitors for an antinociceptive effect are known in the art. For example, compounds can tested in the mouse hot-plate test and the mouse formalin test, and the nociceptive reactions to thermal or chemical tissue damage measured (for example, see U.S. Pat. No. 6,326,156 for a description of methods of screening for antinociceptive activity; see also Cravatt et al. Proc. Natl. Acad. Sci. U.S.A. (2001) 98:9371-9376).

Two pharmacologically validated animal models of anxiety are the elevated zero maze test, and the isolation-induced ultrasonic emission test. The zero maze consists of an elevated annular platform with two open and two closed quadrants and is based on the conflict between an animal's instinct to explore its environment and its fear of open spaces (see, for example, Bickerdike, M. J. et al., Eur. J. Pharmacol., (994) 271, 403-411; Shepherd, J. K. et al., Psychopharmacology, (1994) 116, 56-64). Clinically used anxiolytic drugs, such as the benzodiazepines, increase the proportion of time spent in, and the number of entries made into, the open compartments.

A second test for an anti-anxiety compound is the ultrasonic vocalization emission model, which measures the number of stress-induced vocalizations emitted by rat pups removed from their nest (see, for example, Insel, T. R. et al., Pharmacol. Biochem. Behav., 24, 1263-1267 (1986); Miczek, K. A. et al., Psychopharmacology, 121, 38-56 (1995); Winslow, J. T. et al., Biol. Psychiatry, 15, 745-757 (1991).

The effect of the compounds provided herein in the treatment of depression can be tested in the model of chronic mild stress induced anhedonia in rats. This model is based on the observation that chronic mild stress causes a gradual decrease in sensitivity to rewards, for example consumption of sucrose, and that this decrease is dose-dependently reversed by chronic treatment with antidepressants. See, e.g., Willner, Paul, Psychopharmacology, 1997, 134, 319-329.

Another test for antidepressant activity is the forced swimming test (Nature 266, 730-732, 1977). In this test, animals are administered an agent 30 or 60 minutes before being placed in container of water, and the time during which they remain immobile is recorded. A decrease in the immobility time of the mice is indicative of antidepressant activity.

A similar test for antidepressant activity is the mouse caudal suspension test (Psychopharmacology, 85, 367-370, 1985). In this test, animals are administered an agent 30 or 60 minutes before being suspended by the tail, and their immobility time is recorded. A decrease in the immobility time of the mice is indicative of antidepressant activity.

Animal models are available for assessing anticonvulsant activity of test compounds (see, e.g., U.S. Pat. Nos. 6,309,406 and 6,326,156).

Inhibition of FAAH has been reported to induce sleep in test animals (see, e.g., U.S. Pat. No. 6,096,784). Methods for studying sleep inducing compounds are known in the art (see, e.g., U.S. Pat. Nos. 6,096,784 and 6,271,015). Compounds can be administered to a test animal (e.g., rat or mouse) or a human and the subsequent time (e.g., onset, duration) spent sleeping (e.g., eyes closed, motor quiescence) can be monitored. See also WO 98/24396.

Methods for screening FAAH inhibitors which induce catalepsy are also well known in the art (see, e.g., Quistand et al. in Toxicology and Applied Pharmacology 173: 48-55 (2001); Cravatt et al. Proc. Natl. Acad. Sci. U.S.A. 98:9371-9376 (2001)).

Methods of assessing appetitive behavior are known in the art (see, e.g., U.S. Pat. No. 6,344,474). One method of assessing the effect on appetite behavior is to administer a FAAH inhibitor to a rat and assess its effect on the intake of a sucrose solution (see, e.g., W. C. Lynch et al., Physiol. Behav., 1993, 54, 877-880).

Two pharmacologically validated animal models of neuropathic pain are the rat spinal nerve ligation model (Chung model) and a rat model of chemotherapy-induced neuropathic pain. After establishing neuropathy in these models, as a measure of mechanical allodynia, paw withdrawal thresholds were measured by stimulation with von Frey filaments (see, for example, Kim S H and Chung J M, *Pain* (1992) 50, 355-63; Nozaki-Taguchi N, et al., *Pain* (2001) 93, 69-76). Clinically used neuropathic pain drugs, such as the Gabapentin (Neurontin), increase the paw withdrawal threshold from stimulation with von Frey filaments.

Two pharmacologically validated animal models of inflammatory and mechanical pain are a joint compression model in rats treated with adjuvant or agents that produce joint degeneration. Treatment with clinically used anti-inflammatory agents such as naproxen increases the threshold of behavioral response to joint compression (see, for example, Wilson A W, et al., *Eur. J. Pain* (2006) 10, 537-49; Ivanavicius S A, et al., *Pain* (2007) 128, 272-282).

A pharmacologically validated animal models of cancer pain is mouse model where implantation in the calcaneus bone of fibrosarcoma cells produces paw hyperalgesia. Treatment with clinically used analgesics agents such as morphine increases the threshold of behavioral response to mechanical algesia (see, for example, Khasabova, et al., *J. Neurscience* (2008) 28, 11141-52).

EXEMPLIFICATION

The invention now being generally described, it will be more readily understood by reference to the following examples, which are included merely for purposes of illustration of certain aspects and embodiments of the present invention, and are not intended to limit the invention.

General Synthetic Methods

Method 1

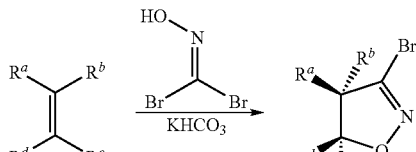

General conditions for the preparation of 3-bromo-isoxazolines: Alkene (1.2 equiv) and potassium hydrogen carbonate (2.5 equiv) are suspended in ethyl acetate (0.40 M with respect to alkene). N,N-Dibromoformaldoxime (1.0 equiv) is added and the reaction was allowed to stir at 23° C. for 14-28 h. Upon completion as judged by thin layer chromatography analysis, the reaction was split between water and tert-butyl methyl ether, and the organic layer was washed with water and brine, dried over sodium sulfate, and concentrated in vacuo. The concentrated reaction mixture was purified by flash silica gel chromatography (ethyl acetate/hexanes) to provide the desired 3-bromo-isoxazoline.

Method 2

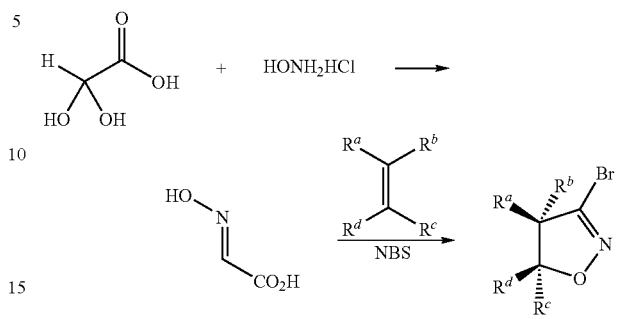

General conditions for the preparation of 3-bromo-isoxazolines: A flask is charged with glyoxylic acid monohydrate (1.0 equiv) and hydroxylamine hydrochloride (1.1 equiv). The mixture was dissolved in water (2.0 M with respect to glyoxylic acid monohydrate) and stirred at 23° C. for 24 h. The mixture was diluted with water and extracted with ethyl acetate. The organic layer was dried over sodium sulfate and concentrated to provide the desired crude oxime which was used directly in subsequent cycloaddition. The resulting oxime (1.1 equiv) from the first step is suspended in a 3:1 mixture of dimethoxyethane:water (v/v) (0.15 M with respect to oxime) and cooled to 0° C. N—Bromosuccinamide (NBS) (2.0 equiv) was added and the reaction was allowed to stir at 23° C. for 20 min. The resulting mixture is then added to a solution of alkene (1.0 equiv) and potassium bicarbonate (2.5 equiv) in dimethoxyethane (1.50 M with respect to alkene) and the reaction is allowed to stir for 20 h at 23° C. Upon completion as judged by thin layer chromatography analysis, the reaction was split between water and tert-butyl methyl ether, and the organic layer was washed with brine, dried over sodium sulfate, and concentrated in vacuo. The concentrated reaction mixture was purified by flash silica gel chromatography (ethyl acetate/hexanes) to provide the desired 3-bromo-isoxazoline.

Method 3

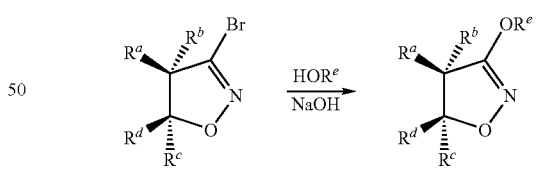

General conditions for the preparation of 3-aryloxy-isoxazolines or 3-heteroaryloxy-isoxazolines: A microwave reaction vial is charged with a given 3-bromo-isoxazoline (1.0 equiv) and an alcohol (e.g., a phenol or a hydroxypyridine) (3.0 equiv) and dissolved in N-methylpyrrolidine (0.50 M with respect to isoxazoline). Crushed sodium hydroxide (2.0 equiv) is added and the mixture was sealed and heated in a microwave reaction at 150° C. for 30 min. The reaction was then split between water and tert-butyl methyl ether, and the organic layer was washed with brine, dried over sodium sulfate, and concentrated in vacuo. The concentrated reaction mixture was purified by flash silica gel chromatography (ethyl acetate/hexanes) to provide the desired isoxazoline.

Method 4

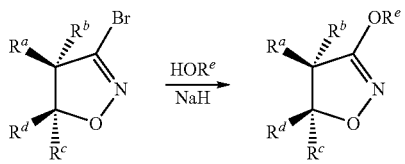

General conditions for the preparation of 3-aryloxy-isoxazolines or 3-heteroaryloxy-isoxazolines: A flask is charged with a given 3-bromo-isoxazoline (1.0 equiv) and the alcohol (e.g., a phenol or a hydroxypyridine) (2.0 equiv) and dissolved in N,N-dimethylforamide (0.4 M with respect to isoxazoline). Sodium hydride (2.0 equiv) is added and the reaction is allowed to stir for 10 min until all of the gas evolution ceases. The reaction is then heated to 150° C. for 1-5 h. After the reaction is determine to be complete by thin layer chromatography analysis, the reaction was then split between water and ethyl acetate, and the organic layer was washed with 1N NaOH and brine, and then dried over sodium sulfate, and concentrated in vacuo. The concentrated reaction mixture was purified by flash silica gel chromatography (ethyl acetate/hexanes) to provide the desired isoxazoline.

Method 5

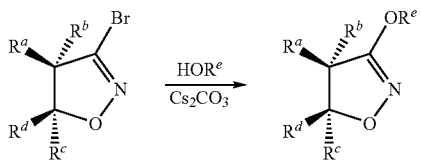

General conditions for the preparation of 3-aryloxy-isoxazolines: A flask is charged with a given 3-bromo-isoxazoline (1.0 equiv) and the alcohol (e.g., a phenol or a hydroxypyridine) (2.0 equiv) and dissolved in N,N-dimethylforamide or N-methylpyrrolidinone (0.15 M with respect to isoxazole). Cesium carbonate (1.2 to 3 equiv) is added and the reaction is heated to 120° C. in an oil bath for 1 h. The reaction was then split between water and tert-butyl methyl ether, and the organic layer was washed with brine, dried over sodium sulfate, and concentrated in vacuo. The concentrated reaction mixture was purified by flash silica gel chromatography (methanol/methylene chloride) to provide the desired isoxazoline.

Method 6

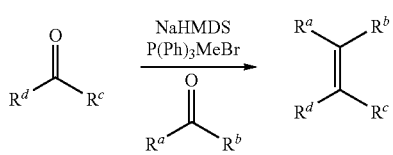

General conditions for the preparation of alkenes: under a nitrogen atmosphere, 0.25 M methyltriphenylphosphonium bromide (1.1 equiv) dissolved in tetrahydrofuran was cooled to 0° C. after which the mixture was treated drop wise with sodium hexamethyldisilazane (NaHMDS) in tetrahydrofuran (1.0 M, 1.2 equiv). After stirring an additional 30 min at 0° C., a given aldehyde or ketone is added and the reaction is allowed to warm slowly to 23° C. overnight. The mixture was quenched saturated ammonium chloride and concentrated to remove the tetrahydrofuran. The mixture was then diluted with water and extracted with ethyl acetate. The organic layer was washed with brine, dried over sodium sulfate and concentrated in vacuo. The concentrated reaction mixture was purified by flash silica gel chromatography (ethyl acetate/hexanes) to provide the desired alkene.

Method 7

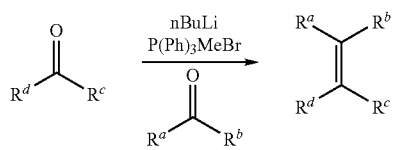

General conditions for the preparation of alkenes: under a nitrogen atmosphere, 0.15 M methyltriphenylphosphonium bromide (1.5 equiv) dissolved in tetrahydrofuran was cooled to −78° C. after which the mixture was treated drop wise with n-butyl lithium in hexanes (2.5 M, 1.5 equiv). After stirring an additional 1 h at −78° C., a given aldehyde or ketone is added and the reaction is allowed to warm slowly to 23° C. overnight. The mixture was quenched saturated ammonium chloride and concentrated to remove the tetrahydrofuran. The mixture was then diluted with water and extracted with ethyl acetate. The organic layer was washed with brine, dried over sodium sulfate and concentrated in vacuo. The concentrated reaction mixture was purified by flash silica gel chromatography (ethyl acetate/hexanes) to provide the desired alkene.

Method 8

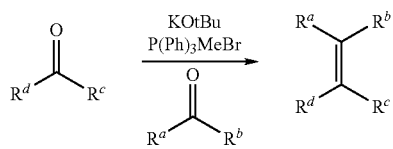

General conditions for the preparation of alkenes: under a nitrogen atmosphere, 0.12 M methyltriphenylphosphonium bromide (2.5 equiv) was dissolved in tetrahydrofuran after which potassium tert-butoxide (4.0 equiv) was added in six portions. After stirring an additional 1 h at 23° C., a given aldehyde or ketone is added and the reaction was heated to 55° C. for 2 h. The mixture was quenched saturated ammonium chloride and concentrated to remove the tetrahydrofuran. The mixture was then acidified to pH 5-6 with 1N HCl and extracted with methylene chloride. The organic layer was washed with brine and then dried over sodium sulfate and concentrated in vacuo. The concentrated reaction mixture was purified by flash silica gel chromatography (ethyl acetate/hexanes) to provide the desired alkene.

Method 9

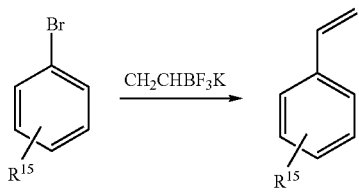

General conditions for the preparation of styrenes: a dry flask under argon atmosphere was charged with aryl bromide (1.0 equiv), potassium vinyltrifluoroborate (1.2 equiv), 1,1''-bis(diphenylphosphino)-ferrocenedichloropalladium(II) methylene chloride adduct (0.02 equiv) and triethylamine (1.0 equiv) and the mixture was suspended in isopropanol (0.25 M with respect to aryl bromide) and heated at 80° C. for 2-24 h. The mixture was then diluted with water and extracted with diethyl ether. The organic layer was washed with brine and then dried over magnesium sulfate and concentrated in vacuo. The concentrated reaction mixture was purified by flash silica gel chromatography (ethyl acetate/hexanes) to provide the desired styrene.

Method 10

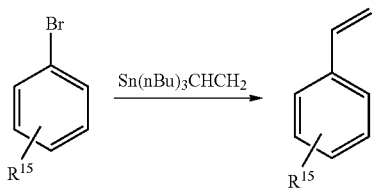

General conditions for the preparation of styrenes: a dry flask under a nitrogen atmosphere was charged with aryl bromide (1.0 equiv), tributylvinyltin (1.1 equiv) and dissolved in toluene (0.3 M with respect to bromide). The resulting mixture was further purged with nitrogen for 10 min after which tetrakis(triphenyphosphine)palladium (0.1 equiv) was added and the reaction was refluxed for 1.5 h. After the reaction was determined to be complete by TLC analysis, it was allowed to cool and loaded directly onto a silica gel column where it was purified by flash silica gel chromatography (ethyl acetate/hexanes) to provide the desired styrene.

Method 11

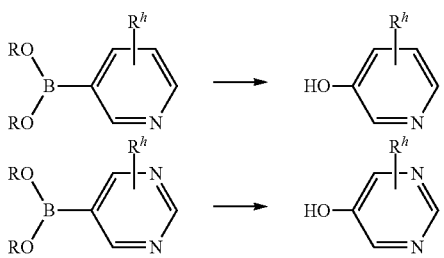

General conditions for the hydrolysis of pyridyl and pyrimidinyl boronic acids to their corresponding phenols: A flask is charged with a given boronic acid or ester thereof (1.0 equiv) and dissolved in tetrahydrofuran (1.1 M, 10 volumes). Sodium perborate (1.0 equiv) is dissolved in water (1.1 M with respect to boronic acid, 10 volumes) and sonicated for 10 min. The perborate suspension is then added to the THF solution using tetrahydrofuran (1.6 volumes) to rinse the remaining solid perborate into the reaction mixture. The reaction is allowed to stir at room temperature (reaction is mildly exothermic) after which ammonium chloride is added in three portions (10 equiv) and the reaction cooled back down to room temperature. After 40 min, the reaction was concentrated under vacuum until all of the tetrahydrofuran was removed. The resulting solid was collected by vacuum filtration, washed with excess waster and dried in a vacuum oven for 40° C. for 3d to provide the desired phenol in 80% yield.

Chiral HPLC Method

Enantiomeric or diastereomeric mixtures of compounds can be separated using known methods, including chiral high pressure liquid chromatography (HPLC) and chiral supercritical fluid chromatography (SFC). Exemplary chiral columns found useful in separating such mixtures of compounds of the present invention include, but are not limited to, ChiralPak® AD-H, ChiralPak® OD-H, ChiralPak® AY, RegisPack™, and S,S WhelkO®-1 and LUX™ Cellulose2 columns. One or more of these columns were used to separate enantiomeric mixtures of compounds of the present invention in order to obtain substantially enantiomerically pure compounds.

Synthesis of Exemplary Compounds of Formula I

Syntheses of exemplary compounds are set forth below. Compounds were assayed as inhibitors of human FAAH using the method described in detail in Example 32. Activity designated as "A" refers to compounds having a $K_i$ of less than or equal to 100 nM, "B" refers to compounds having a $K_i$ of between 100 nM and 1 microM, and "C" refers to compounds having a $K_i$ of greater than or equal to 1 microM.

EXAMPLE 1

(II-1)

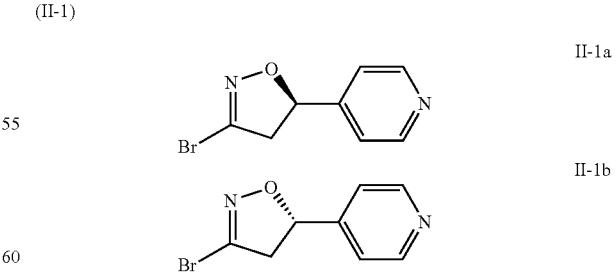

3-bromo-4,5-dihydroisoxazole II-1a and II-1b were prepared in 1 step from 4-vinylpyridine using Method 2. These compounds can be separated using chiral HPLC methods known in the art. For example, see chiral HPLC Method disclosed herein. [M−H]−=226.0 m/z. Activity: C

EXAMPLE 2

(II-2)

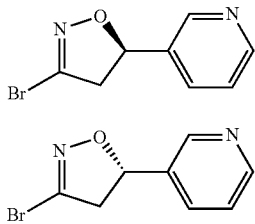

3-bromo-4,5-dihydroisoxazole II-2a and II-2b were was prepared in 1 step from 3-vinylpyridine using Method 2. These compounds can be separated using chiral HPLC methods known in the art. For example, see chiral HPLC Method disclosed herein. [M−H]−=226.0 m/z. Activity: C

EXAMPLE 3

(II-3)

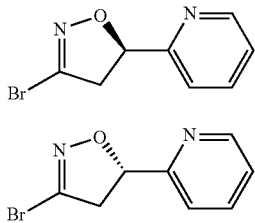

3-bromo-4,5-dihydroisoxazole II-3a and II-3b were prepared in 1 step from 2-vinylpyridine using Method 2. These compounds can be separated using chiral HPLC methods known in the art. For example, see chiral HPLC Method disclosed herein. [M−H]−=226.0 m/z. Activity: C

EXAMPLE 4

(II-4)

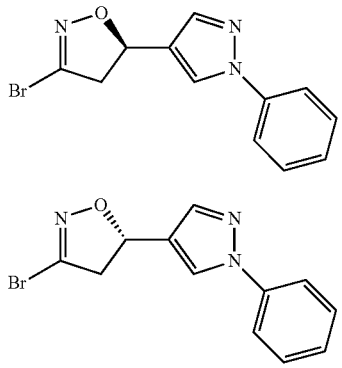

3-bromo-4,5-dihydroisoxazole II-4a and II-4-b were prepared in 2 steps starting with alkene formation from 1-phenyl-1H-pyrazole-4-carbaldehyde using Method 8 followed by cycloaddition using Method 2. These compounds can be separated using chiral HPLC methods known in the art. For example, see chiral HPLC Method disclosed herein. [M−H]−=291.0 m/z. Activity: B

EXAMPLE 5

(II-5)

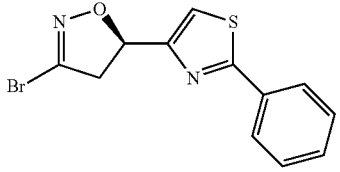

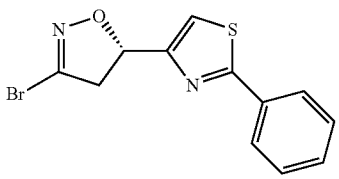

3-bromo-4,5-dihydroisoxazole II-5a and II-5b were prepared in 2 steps starting with alkene formation from 2-phenyl-1,3-thiazole-4-carbaldehyde using Method 8 followed by cycloaddition using Method 2. These compounds can be separated using chiral HPLC methods known in the art. For example, see chiral HPLC Method disclosed herein. [M−H]−=308.0 m/z. Activity: C

EXAMPLE 6

(II-6)

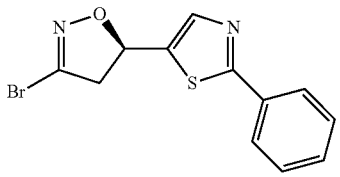

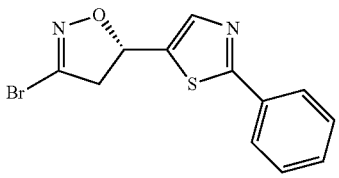

3-bromo-4,5-dihydroisoxazole II-6a and II-6b were prepared in 2 steps starting with alkene formation from 2-phenyl-1,3-thiazole-5-carbaldehyde using Method 8 followed by cycloaddition using Method 1. These compounds can be separated using chiral HPLC methods known in the art. For example, see chiral HPLC Method disclosed herein. [M−H]−=308.0 m/z. Activity: A

EXAMPLE 7

(II-7)

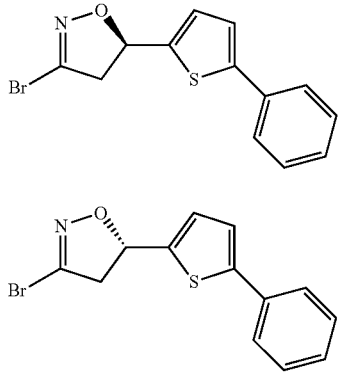

3-bromo-4,5-dihydroisoxazole II-7a and II-7b were prepared in 2 steps starting with alkene formation from 5-phenylthiophene-2-carbaldehyde using Method 8 followed by cycloaddition using Method 1. These compounds can be separated using chiral HPLC methods known in the art. For example, see chiral HPLC Method disclosed herein. [M+H]+=309.6 m/z. Activity: A

EXAMPLE 8

(II-8)

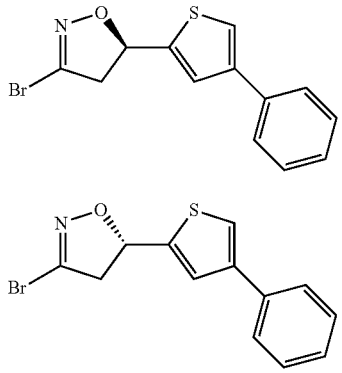

3-bromo-4,5-dihydroisoxazole II-8a and II-8b were prepared in 2 steps starting with alkene formation from 4-phenylthiophene-2-carbaldehyde using Method 8 followed by cycloaddition using Method 2. These compounds can be separated using chiral HPLC methods known in the art. For example, see chiral HPLC Method disclosed herein. [M−H]−=307.0 m/z. Activity: A

EXAMPLE 9

(II-9)

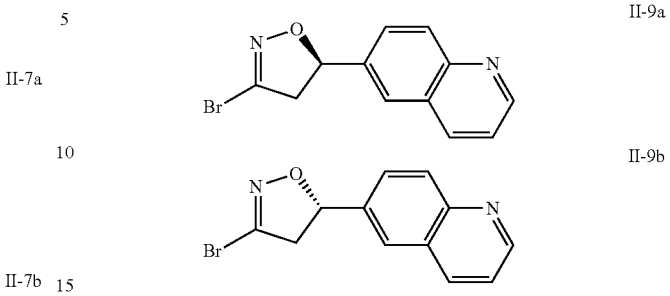

3-bromo-4,5-dihydroisoxazole II-9a and II-9b were prepared in 2 steps starting with alkene formation from 6-quinolinecarbaldehyde using Method 8 followed by cycloaddition using Method 2. These compounds can be separated using chiral HPLC methods known in the art. For example, see chiral HPLC Method disclosed herein. [M−H]−=276.0 m/z. Activity: A

EXAMPLE 10

(II-10)

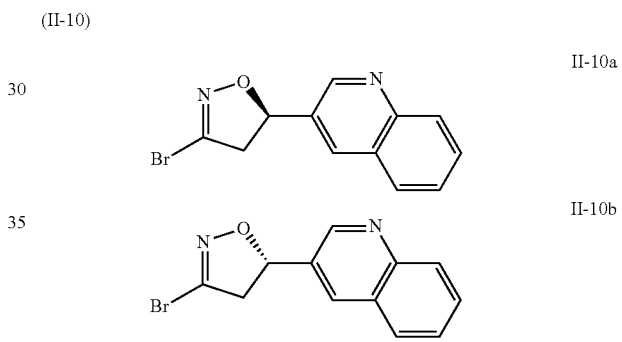

3-bromo-4,5-dihydroisoxazole II-10a and II-10b were prepared in 2 steps starting with alkene formation from 3-quinolinecarbaldehyde using Method 8 followed by cycloaddition using Method 2. These compounds can be separated using chiral HPLC methods known in the art. For example, see chiral HPLC Method disclosed herein. [M−H]−=276.0 m/z. Activity: A

EXAMPLE 11

(II-11)

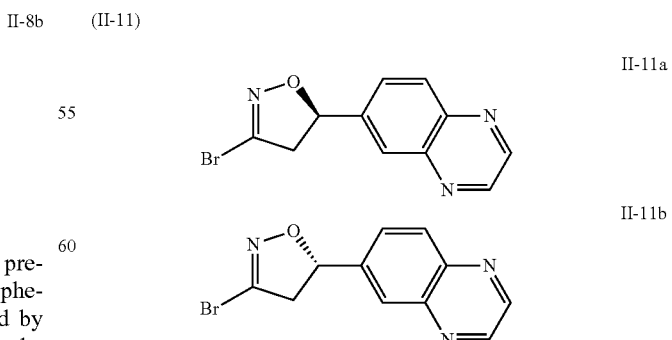

3-bromo-4,5-dihydroisoxazole II-11a and II-11b were prepared in 2 steps starting with alkene formation from 6-bro-

EXAMPLE 12

(II-12)

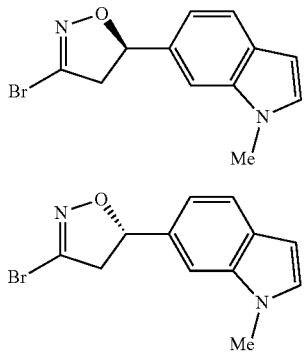

3-bromo-4,5-dihydroisoxazole II-12a and II-12b were prepared in 2 steps starting with alkene formation from 5-bromo-1-methyl-1H-indole using Method 9 followed by cycloaddition using Method 2. These compounds can be separated using chiral HPLC methods known in the art. For example, see chiral HPLC Method disclosed herein. [M−H]−=278.0 m/z. Activity: A

EXAMPLE 13

(II-13)

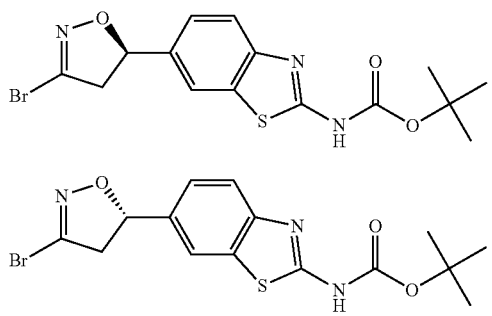

3-bromo-4,5-dihydroisoxazole II-13a and II-13b were prepared in 2 steps starting with the Boc-protection of 2-amino-6-bromobenzothiazole as follows: The benzothiazole (1.0 equiv) is dissolved in methylene chloride (0.12 M with respect to thiazole). Di-tert-butyl dicarbonate (3.0 equiv) is then added followed by the addition of DMAP (0.20 equiv) in five portions. The reaction was allowed to stir for 2 h at 23° C. after which point there was no more SM by TLC analysis. The reaction was quenched with the addition of methanol (75 equiv) and allowed to stir for 10 min after which the reaction was split between water and methylene chloride, and the organic layer was washed with 0.5 M citric acid solution (2×) and saturated sodium bicarbonate solution (1×), dried over magnesium sulfate, and concentrated in vacuo to provide a crude solid which was converted directly to the desired 3-bromo-4,5-dihydroisoxazole using Method 9 followed by Method 2. These compounds can be separated using chiral HPLC methods known in the art. For example, see chiral HPLC Method disclosed herein. [M−H]−=397.0 m/z. Activity: B

EXAMPLE 14

(II-14)

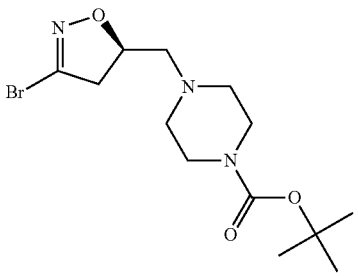

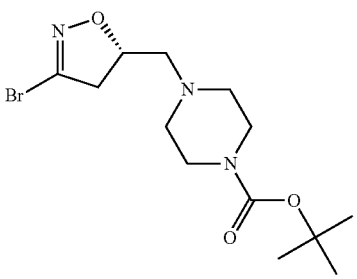

1-Allylpiperazine is dissolved in methylene chloride (1.1 M with respect to piperazine). Potassium carbonate (1.5 equiv) was added followed by di-tert-butyl dicarbonate (1.1 equiv). The reaction was allowed to stir for 16 h after which it was then split between water and tert-butyl methyl ether, and the organic layer was washed with brine, dried over sodium sulfate, and concentrated in vacuo to provide crude alkene which was directly converted to the desired 3-bromo-4,5-dihydroisoxazole II-14a and II-14b in 1 step using Method 1. These compounds can be separated using chiral HPLC methods known in the art. For example, see chiral HPLC Method disclosed herein. [M−H]−=347.1 m/z. Activity: A

EXAMPLE 15

(II-15)

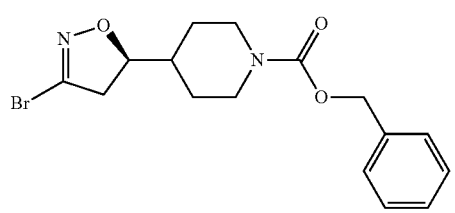

II-15b

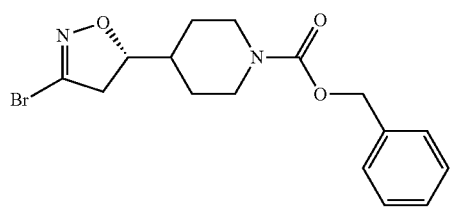

3-bromo-4,5-dihydroisoxazole II-15a and II-15b were prepared in 2 steps starting with alkene formation from benzyl 4-formylpiperidine-1-carboxylate using Method 8 followed by cycloaddition using Method 2. These compounds can be separated using chiral HPLC methods known in the art. For example, see chiral HPLC Method disclosed herein. [M−H]−=366.1 m/z. Activity: B

EXAMPLE 16

(II-16)

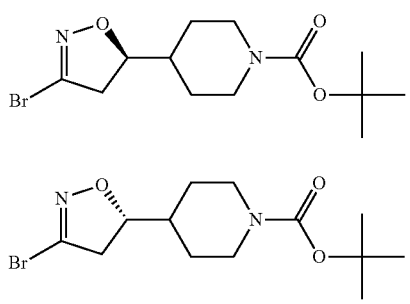

II-16a

II-16b 3-bromo-4,5-dihydroisoxazole II-16a and II-16b were prepared in 2 steps starting with alkene formation from tent-butyl 4-formylpiperidine-1-carboxylate using Method 8 followed by cycloaddition using Method 2. These compounds can be separated using chiral HPLC methods known in the art. For example, see chiral HPLC Method disclosed herein. [M−H]−=332.1 m/z. Activity: A

EXAMPLE 17

(II-17)

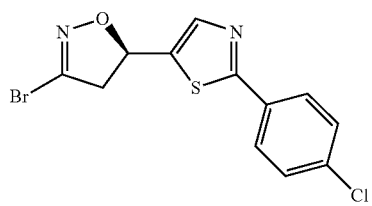

II-17a

II-17b

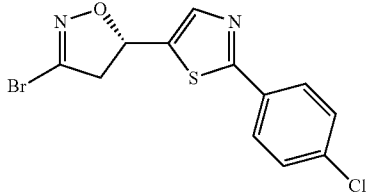

3-bromo-4,5-dihydroisoxazole II-17a and II-17b were prepared in 2 steps starting with alkene formation from 2-(4-chlorophenyl)thiazole-5-carbaldehyde using Method 8 followed by cycloaddition using Method 1. These compounds can be separated using chiral HPLC methods known in the art. For example, see chiral HPLC Method disclosed herein. [M+H]+=342.5 m/z. Activity: A

EXAMPLE 18

(II-18)

II-18a

II-18b 3-bromo-4,5-dihydroisoxazole II-18a and II-18b were prepared in 2 steps starting with alkene formation from 1-(2-phenylthiazol-5-yl)ethanone using Method 8 followed by cycloaddition using Method 1. These compounds can be separated using chiral HPLC methods known in the art. For example, see chiral HPLC Method disclosed herein. [M+H]+=322.3 m/z. Activity: A

EXAMPLE 19

(II-19)

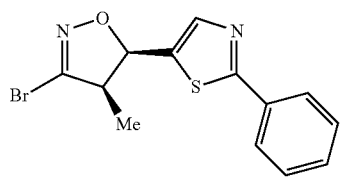

II-19a

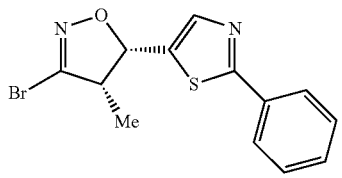
II-19b 3-bromo-4,5-dihydroisoxazole II-19a and II-19b were prepared in 2 steps starting with alkene formation from 2-phenylthiazole-5-carbaldehyde using Method 8 except that ethyltriphenylphosphoium bromide was used in place of methyltriphenylphosphoium bromide followed by cycloaddition using Method 1. [M+H]+=325.1 m/z. Activity: A

EXAMPLE 20

(II-20)

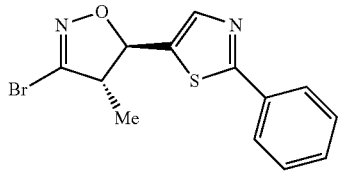
II-20a

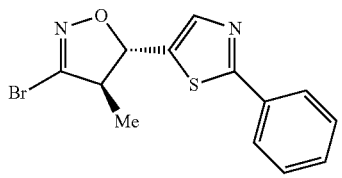
II-20b 3-bromo-4,5-dihydroisoxazole II-20a and II-20b were isolated as the trans diastereomers which also formed during the cycloaddition in Example 19. These compounds can be separated using chiral HPLC methods known in the art. For example, see chiral HPLC Method disclosed herein. [M+H]+=324.9 m/z. Activity: C

EXAMPLE 21

(II-21)

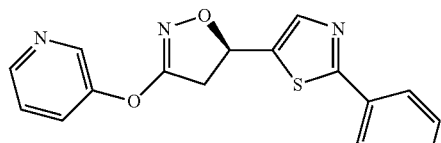
II-21a

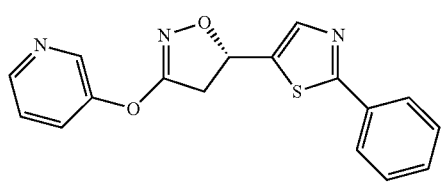
II-21b 3-(pyridin-3-yloxy)-4,5-dihydroisoxazole II-21a and II-21b were prepared in 1 step from racemic compound II-6 and 3-hydroxypyridine using Method 5. These compounds can be separated using chiral HPLC methods known in the art. For example, see chiral HPLC Method disclosed herein. [M+H]+=325.1 m/z. Activity: A

EXAMPLE 22

(II-22)

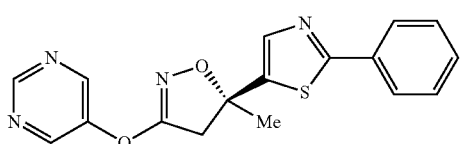
II-22a

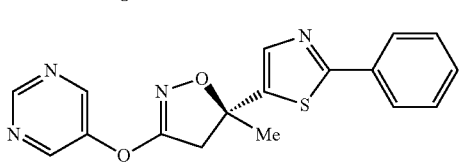
II-22b 3-(pyridin-3-yloxy)-4,5-dihydroisoxazole II-22a and II-22b were prepared in 1 step from racemic compound II-18 and 5-hydroxyprimidine using Method 5. These compounds can be separated using chiral HPLC methods known in the art. For example, see chiral HPLC Method disclosed herein. [M+H]+=340.4 m/z. Activity: A

EXAMPLE 23

(II-23)

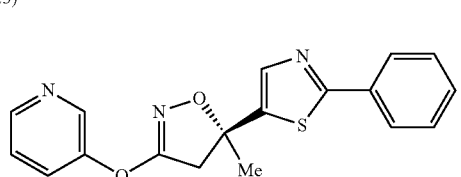
II-23a

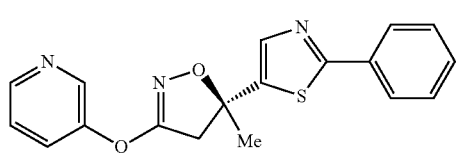
II-23b 3-(pyridin-3-yloxy)-4,5-dihydroisoxazole II-23a and II-23b were prepared in 1 step from racemic compound II-18 and 3-hydroxypyridine using Method 5. These compounds can be separated using chiral HPLC methods known in the art. For example, see chiral HPLC Method disclosed herein. [M+H]+=339.3 m/z. Activity: A

EXAMPLE 24

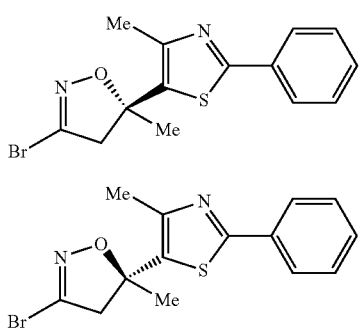

(II-24)

II-24a

II-24b 3-bromo-4,5-dihydroisoxazole II-24a and II-24b were prepared in 2 steps starting with alkene formation from 1-(4-methyl-2-phenylthiazol-5-yl)ethanone using Method 8 followed by cycloaddition using Method 1. These compounds can be separated using chiral HPLC methods known in the art. For example, see chiral HPLC Method disclosed herein. [M+H]+=339.0 m/z. Activity: B

EXAMPLE 25

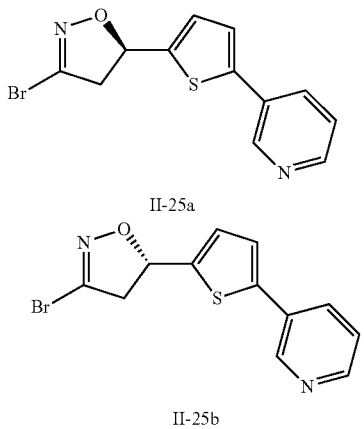

(II-25)

II-25a

II-25b 3-bromo-4,5-dihydroisoxazole II-25a and II-25b were prepared in 2 steps starting with alkene formation from 5-pyridin-3-ylthiophen-2-carbaldehyde using Method 8 followed by cycloaddition using Method 1. These compounds can be separated using chiral HPLC methods known in the art. For example, see chiral HPLC Method disclosed herein. [M+H]+=310.3 m/z. Activity: A

EXAMPLE 26

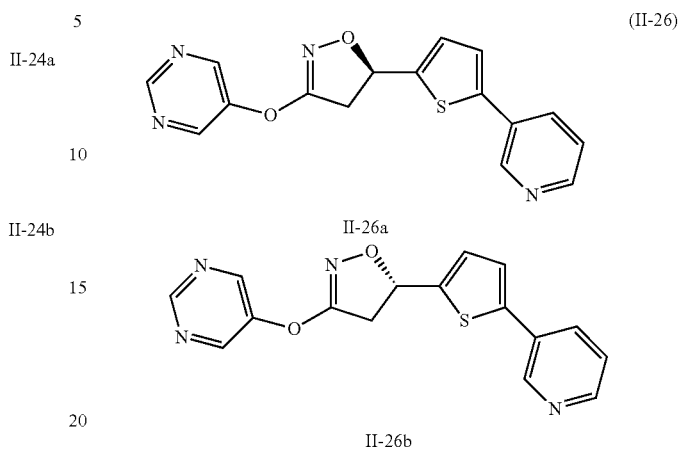

(II-26)

II-26a

II-26b 3-(pyrimidin-5-yloxy)-4,5-dihydroisoxazole II-26a and II-26b were prepared in 1 step from racemic compound II-25 and 5-hydroxypyrimidine using Method 5. These compounds can be separated using chiral HPLC methods known in the art. For example, see chiral HPLC Method disclosed herein. [M+H]+=325.1 m/z. Activity: A

EXAMPLE 27

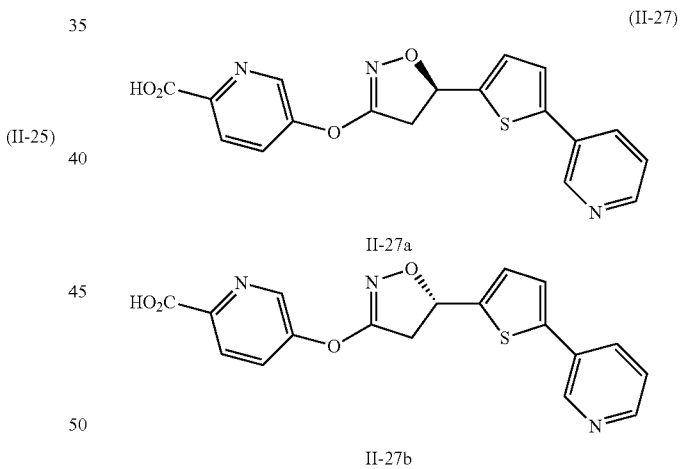

(II-27)

II-27a

II-27b 3-(pyridin-3-yloxy)-4,5-dihydroisoxazole II-27a and II-27b were prepared in 2 steps from racemic compound II-25 according to the following procedure: 5-hydroxypicolinic acid methyl ester was reacted using Method 5 followed by methyl ester hydrolysis. The methyl ester of racemic 3-(pyridin-3-yloxy)-4,5-dihydroisoxazole II-27 (1.0 equiv) was dissolved in 1:1 tetrahydrofuran/water (0.06 M) and lithium hydroxide (8.0 equiv) was added. The reaction was allowed to stir at room temperature for 1 h after which point the tetrahydrofuran was removed under a stream of nitrogen and the remaining solution was acidified to pH<2 with 1N HCl to provide desired acid II-27a and II-27b as a white solid which was isolated via vacuum filtration. These compounds can be separated using chiral HPLC methods known in the art. For example, see chiral HPLC Method disclosed herein. [M+H]+=367.5 m/z. Activity: A

EXAMPLE 28

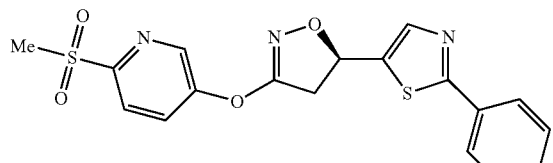

II-28a

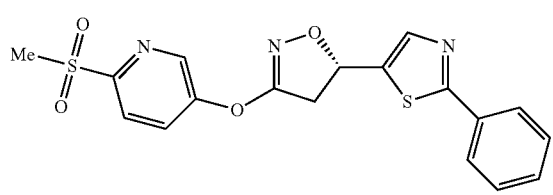

II-28b 3-(pyridin-3-yloxy)-4,5-dihydroisoxazole II-28a and II-28b were prepared in 2 steps from racemic compound II-6 by first reacting II-6 with 6-(methylthio)pyridin-3-ol (prepared from 6-(methylthio)pyridin-3-ylboronic acid using Method 11) using Method 5 followed by oxidation according to the following procedure: racemic 3-(6-(methylthio)pyridin-3-yloxy)-4,5-dihydroisoxazole was dissolved in methylene chloride (0.5 M with respect to isoxazole) after which point m-chloroperbenzoic acid (2.0 equiv) was added in 1 portion and the reaction was allowed to stir at room temperature for 1 h. After the reaction was determined to be complete by LC/MS, the solvent was evaporated. The crude mixture was then redissolved in tert-butylmethyl ether (0.5 M) after which hexane was slowly added until a solid precipitated. The solid was then collected via vacuum filtration and washed with 1:1 hexanes/MTBE to provide the desired 3-(pyridin-3-yloxy)-4,5-dihydroisoxazole II-29a and II-29b as a white solid. These compounds can be separated using chiral HPLC methods known in the art. For example, see chiral HPLC Method disclosed herein. [M+H]+=404.1 m/z. Activity: A

EXAMPLE 29

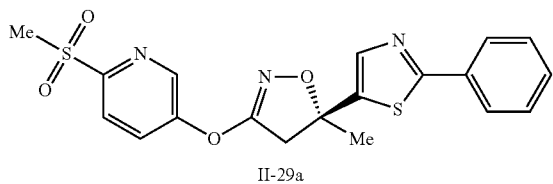

II-29a

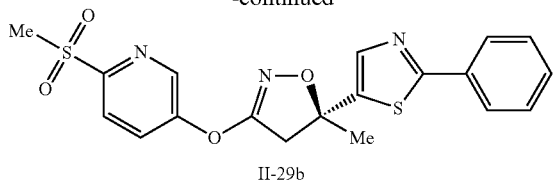

II-29b 3-(pyridin-3-yloxy)-4,5-dihydroisoxazole II-29a and II-29b were prepared in 2 steps from racemic compound II-18 by first reacting II-18 with 6-(methylthio)pyridin-3-ol (prepared from 6-(methylthio)pyridin-3-ylboronic acid using Method 11) using Method 5 followed by oxidation under analogous conditions to Example 28. These compounds can be separated using chiral HPLC methods known in the art. For example, see chiral HPLC Method disclosed herein. [M+H]+=417.9 m/z. Activity: A

EXAMPLE 30

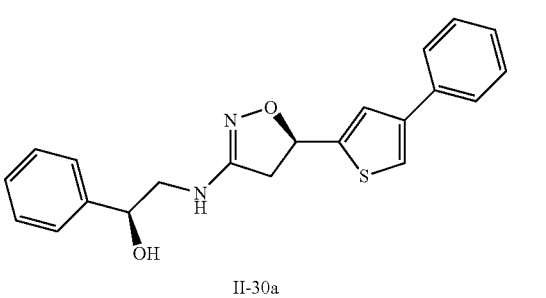

II-30a

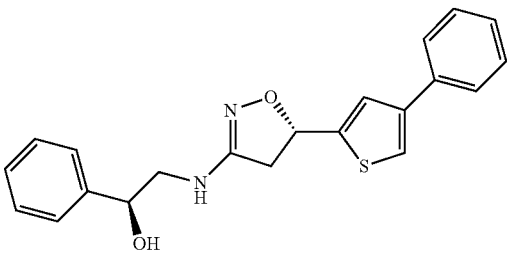

II-30b 2-(4,5-dihydroisoxazol-3-ylamino)alcohol II-30a and II-30b were prepared in 1 step according to the following procedure: racemic 3-bromo-4,5-dihydroisoxazole 1-8 (1.0 equiv) was dissolved in n-butanol (0.64 M) followed by the addition of (S)-2-amino-1-phenylethanol (1.2 equiv) and sodium carbonate (2.5 equiv). The reaction is the sealed and heated in an oil bath to 120° C. for 18 h after which it allowed to cool and then transferred to a separatory funnel with excess water and tert-butylmethyl ether. The aqueous layer was washed with tert-butylmethyl ether (2×) and the combined organic layers were washed with brine, dried over magnesium sulfate and concentrate to provide a orange solid that was purified using flash silica gel chromatography (gradient toluene/hexanes to toluene/ethyl acetate) to provide racemic II-30 as a white solid. These compounds can be separated using chiral HPLC methods known in the art. For example, see chiral HPLC Method disclosed herein. [M+H]+=374.20 m/z. Activity: C

EXAMPLE 31

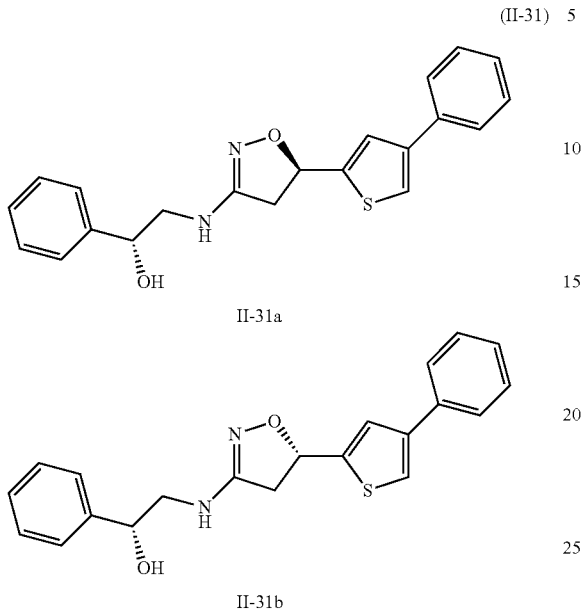

II-31a

II-31b 2-(4,5-dihydroisoxazol-3-ylamino)alcohol II-31a and II-31b were prepared using the analogous procedure as Example 30 except that (R)-2-amino-1-phenylethanol was used in place of (S)-2-amino-1-phenylethanol. These compounds can be separated using chiral HPLC methods known in the art. For example, see chiral HPLC Method disclosed herein. [M+H]+=366.4 m/z. Activity: C

EXAMPLE 32

Inhibition of Human FAAH

Human FAAH Preparation: COS-7 cells were split the day before, 1:5 into 150 mm×25 mm cell culture dishes (Corning Inc., Cat. No. 430599). Transient transfection took place at 30-40% confluency according to FuGENE 6 Transfection Reagent (Roche, Cat. No. 11814 443 001).

Transfection Procedure: The FuGENE transfection 6 reagent (45 uL) was added to 1410 µL of media (DMEM, serum free without pen/strep) in a 15 mL conical tube and incubated at room temp for 5 minutes, followed by the addition of FAAH plasmid DNA (15 µg) (OriGene Cat. No. TC119221, Genbank Accession No. NM 001441.1, 0.67 ug/uL) and a further incubation of 15 minutes at room temperature. The resulting solution was added into one dish of 30-40% confluent COS-7 cells in a drop-wise manner. The COS-7 cell dish was subsequently incubated for 48 hours. The cells are then harvested.

Harvest procedure: Media was aspirated from the dishes and the cells rinsed with 10 mL PBS. The PBS was removed and 3 mL of PBS added to the dish. The dish was scraped to resuspend the cells, and the subsequent cell suspension collected into a 15 mL conical tube. The cells were pelleted by centrifugation at 1200 rpm for 5 minutes in a bench top centrifuge. PBS was removed and the cell pellet snap frozen in liquid nitrogen and stored at −80° C.

COS-7 Cells—FAAH Purification:
(1) Fractionation: Frozen cell pellets from transient transfections were thawed on ice and resuspended in 12.5 mM Hepes pH 8.0, 100 mM NaCl, 1 mM EDTA (10 mL/0.2 g cell pellet). The pellets were dounce homogenized and then sonicated to produce cell extract. The cell extract was subsequently centrifuged at 1000 g to remove cellular debris. The pellet was discarded and the supernatant centrifuged at 13,000 g for 20 minutes. The pellet contained membrane bound FAAH. The supernatant was discarded and the pellet resolubilized.
(2) Re-solubilization: The fraction of interest, (13,000 g, membrane fraction) was re-suspended in 2.3 mL re-suspension buffer (20 mM Hepes pH 7.8, 10% v/v Glycerol, 1 mM EDTA, 1% Triton X-100) and the sample incubated on ice for 1 hour and then centrifuged to remove any particulate matter. The supernatant containing solubilized human FAAH was aliquoted and snap frozen in liquid nitrogen and stored at −80° C. until use.
(3) Characterization: Protein Concentration determined by Bradford assay.
SDS gel and Western blot to confirm presence of FAAH
FAAH activity assay
$K_m$ determination—96-well assay
Linear dependence—96-well assay
Standard compound Ki determination—384-well assay Human FAAH assay; Experimental Protocol: A 0.1 mg/mL Human FAAH solution was made up in FAAH reaction buffer, and 24 ul pipeted into a 384 well plate. To this was added 1 µL of a 3 fold serially diluted inhibitor from a DMSO stock solution. The FAAH solution and inhibitor were incubated for 30 minutes at room temperature. The FAAH reaction was initiated by the addition of 25 µL of 40 µM AMC Arachidonoyl Amide in FAAH reaction buffer, yielding a final reaction human FAAH preparation concentration of 0.05 mg/ml and AMC-Arachidonoyl substrate concentration of 20 µM, reaction volume 50 µL. The reaction was allowed to proceed for 4 hours at room temperature. The reaction was stopped by the addition of 25 µL 12 µM a-ketoheterocycle (Cayman Chemicals, catalogue # 10435). The microtiter plate was read in the envision plate reader.

The raw fluorescence was plotted on the y axis and the inhibitor concentration on the x axis to give a dose response inhibition curve. The data was fitted to a single site competitive inhibition equation, fixing the Km for the human enzyme to 12 µM and 9 µM respectively.

Other assays which can be used to determine the inhibition of FAAH by the compounds of the present invention include: (1) a fluorescence-based assay for fatty acid amide hydrolase compatible with high-throughput screening as described in Manjunath et al., *Analytical Biochemistry* (2005) 343:143-151; and (2) a high-throughput screening for the discovery of inhibitors of fatty acid amide hydrolase using a microsome-based fluorescent assay. Wang et al., *Biomolecular Screening* (2006) 1-9.

EXAMPLE 33

Evidence for Covalent Complex Formation Between Serine-241 of FAAH and Isoxazolines Treatment of rat FAAH protein with the active site-directed irreversible inhibitor methoxy arachidonyl fluorophosphonate results in a crystal structure wherein methoxy arachidonyl phosphonate is covalently bound to the side chain of Ser-241 (Bracey et al., *Science* (2002) 298:1793-1796).

Based on this data, it is hypothesized that the isoxazoline compounds of the present invention form covalent complexes with the nucleophilic side chain of Ser-241. This hypothesis is consistent with the kinetic data, with the proposed binding involving nucleophilic attack of the isoxazoline electrophile by the active site Ser-241, resulting in the elimination of the leaving group from the cytosolic port, and the subsequent formation of a covalent enzyme-isoxazoline adduct. Recovery of activity would subsequently involve a deacylation reaction, which would occur inefficiently, if at all, for the covalent enzyme-isoxazoline adduct.

Recovery of activity experiments were performed via a jump dilution method which involved rapidly diluting the enzyme-inhibitor complex 5-fold below its apparent Ki, and measuring activity as a function of time. Little or no enzyme activity was regained over a period of two hours, indicating essentially irreversible inhibition, or a very slowly hydrolysable complex, supporting the above hypothesis.

Other Embodiments

Those skilled in the art will recognize, or be able to ascertain using no more than routine experimentation, many equivalents to the specific embodiments of the invention described herein. Such equivalents are intended to be encompassed by the following claims.

---

We claim:

1. A compound of the following formula:

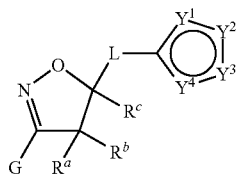

or a pharmaceutically acceptable form thereof, wherein:

each of $R^a$, $R^b$, and $R^c$ independently is selected from —H, $C_{1-10}$ alkyl and $C_{1-10}$ perhaloalkyl;

L is a covalent bond;

G is selected from —CN, —NO$_2$, —S(=O)R$^e$, —SO$_2$R$^e$, —SO$_2$NR$^f$R$^e$, —PO$_2$R$^e$, —PO$_2$OR$^e$, —PO$_2$NR$^f$R$^e$, —(C=O)R$^e$, —(C=O)OR$^e$, —(C=O)NR$^f$R$^e$, —Br, —I, —F, —Cl, —OR$^e$, —ONR$^f$R$^e$, —ONR$^f$(C=O)R$^e$, —ONR$^f$SO$_2$R$^e$, —ONR$^f$PO$_2$R$^e$, —ONR$^f$PO$_2$OR$^e$, —SR$^e$, —OSO$_2$R$^e$, —NR$^f$SO$_2$R$^e$, —OPO$_2$R$^e$, —OPO$_2$OR$^e$, —NR$^f$PO$_2$R$^e$, —NR$^f$PO$_2$OR$^e$, —OPO$_2$NR$^f$R$^e$, —O(C=O)R$^e$, —O(C=O)OR$^e$, —NR$^f$R$^e$, —NR$^f$(C=O)R$^e$, —NR$^f$(C=O)OR$^e$, —O(C=O)NR$^f$R$^e$, —NR$^f$(C=NR$^f$)NR$^f$R$^e$, —O(C=NR$^f$)NR$^f$R$^e$, —NR$^f$(C=NR$^f$)OR$^e$, —[N(R$^f$)$_2$R$^e$]$^+$X$^-$ wherein X$^-$ is a counterion; and each R$^e$ is selected from $C_{1-10}$ alkyl, $C_{2-10}$ alkenyl, $C_{2-10}$ alkynyl, $C_{3-10}$ carbocycyl, $C_{6-14}$ aryl, 3-14 membered heterocyclyl and 5-14 membered heteroaryl; each R$^f$ attached to a nitrogen atom is, independently, selected from —H, $C_{1-10}$ alkyl, or an amino protecting group; or R$^e$ and R$^f$ are joined to form an 3-14 membered heterocyclyl ring or an 5-14 membered heteroaryl ring;

wherein $Y^1$, $Y^2$, $Y^3$ and $Y^4$ are, independently, selected from CH, $CR^{15}$, S, N, or $NR^{18}$, with the proviso that at least one of $Y^1$, $Y^2$, $Y^3$ and $Y^4$ are selected from S, N, or $NR^{18}$; and each $R^{15}$ is independently selected from fluoro (—F), bromo (—Br), chloro (—Cl), and iodo (—I), —CN, —$NO_2$, —$N_3$, —$SO_2H$, —$SO_3H$, —OH, —$OR^{16}$, —$ON(R^{18})_2$, —$N(R^{18})_2$, —$N(R^{18})_3{}^+X^-$, —$N(OR^{17})R^{18}$, —SH, —$SR^{16}$, —$SSR^{17}$, —$C(=O)R^{16}$, —$CO_2H$, —CHO, —$C(OR^{17})_2$, —$CO_2R^{16}$, —$OC(=O)R^{16}$, —$OCO_2R^{16}$, —$C(=O)N(R^{18})_2$, —$OC(=O)N(R^{18})_2$, —$NR^{18}C(=O)R^{16}$, —$NR^{18}CO_2R^{16}$, —$NR^{18}C(=O)N(R^{18})_2$, —$C(=NR^{18})R^{16}$, —$C(=NR^{18})OR^{16}$, —$OC(=NR^{18})R^{16}$, —$OC(=NR^{18})OR^{16}$, —$C(=NR^{18})N(R^{18})_2$, —$OC(=NR^{18})N(R^{18})_2$, —$NR^{18}C(=NR^{18})N(R^{18})_2$, —$C(=O)NR^{18}SO_2R^{16}$, —$NR^{18}SO_2R^{16}$, —$SO_2N(R^{18})_2$, —$SO_2R^{16}$, —$SO_2OR^{16}$, —$OSO_2R^{16}$, —$S(=O)R^{16}$, —$OS(=O)R^{16}$, —$Si(R^{16})_3$, —$OSi(R^{16})_3$ —$C(=S)N(R^{18})_2$, —$C(=O)SR^{16}$, —$C(=S)SR^{16}$, —$SC(S)SR^{16}$, —$P(=O)_2R^{16}$, —$OP(=O)_2R^{16}$, —$P(=O)(R^{16})_2$, —$OP(=O)(R^{16})_2$, —$OP(=O)(OR^{17})_2$, —$P(=O)_2N(R^{18})_2$, —$OP(=O)_2N(R^{18})_2$, —$P(=O)(NR^{18})_2$, —$OP(=O)(NR^{18})_2$, —$NR^{18}P(=O)(OR^{17})_2$, —$NR^{18}P(=O)(NR^{18})_2$, —$P(R^{17})_2$, —$P(R^{17})_3$, —$OP(R^{17})_2$, —$OP(R^{17})_3$, —$B(OR^{17})_2$, —$BR^{16}(OR^{17})$, $C_{1-10}$ alkyl, $C_{1-10}$ perhaloalkyl, $C_{2-10}$ alkenyl, $C_{2-10}$ alkynyl, $C_{3-14}$ carbocyclyl, 3-14 membered heterocyclyl, $C_{6-14}$ aryl, and 5-14 membered heteroaryl, wherein each alkyl, alkenyl, alkynyl, carbocyclyl, heterocyclyl, aryl, and heteroaryl is independently substituted with 0, 1, 2, 3, 4, or 5 $R^{19}$ groups; or two vicinal $R^{15}$ groups are replaced with the group —$O(C(R^2)_2)_{1-2}O$— wherein each $R^2$ is independently —H, $C_{1-6}$ alkyl or halogen;

each instance of $R^{16}$ is, independently, selected from $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, wherein each alkyl, alkenyl, alkynyl, carbocyclyl, heterocyclyl, aryl, and heteroaryl is independently substituted with 0, 1, 2, 3, 4, or 5 $R^{19}$ groups;

each instance of $R^{18}$ is, independently, selected from hydrogen, —OH, —$OR^{16}$, —$N(R^{17})_2$, —CN, —$C(=O)R^{16}$, —$C(=O)N(R^{17})_2$, —$CO_2R^{16}$, —$SO_2R^{16}$, —$C(=NR^{17})OR^{16}$, —$C(=NR^{17})N(R^{17})_2$, —$SO_2N(R^{17})_2$, —$SO_2R^{17}$, —$SO_2OR^{17}$, —$SOR^{16}$, —$C(=S)N(R^{17})_2$, —$C(=O)SR^{17}$, —$C(=S)SR^{17}$, —$P(=O)_2R^{16}$, —$P(=O)(R^{16})_2$, —$P(=O)_2N(R^{17})_2$, —$P(=O)(NR^{17})_2$, $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two $R^{17}$ groups attached to an N atom are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{19}$ groups;

each instance of $R^{17}$ is, independently, selected from hydrogen, $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two $R^{17}$ groups attached to an N atom are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{19}$ groups;

each instance of $R^{19}$ is, independently, selected from halogen, —CN, —$NO_2$, —$N_3$, —$SO_2H$, —$SO_3H$, —OH, —$OR^{20}$, —$ON(R^{21})_2$, —$N(R^{21})_2$, —$N(R^{21})_3{}^+X^-$, —$N(OR^{20})R^{21}$, —SH, —$SR^{20}$, —$SSR^{20}$, —$C(=O)R^{20}$, —$CO_2H$, —$CO_2R^{20}$, —$OC(=O)R^{20}$, —$OCO_2R^{20}$, —$C(=O)N(R^{21})_2$, —$OC(=O)N(R^{21})_2$, —$NR^{21}C(=O)R^{20}$, —$NR^{21}CO_2R^{20}$, —$NR^{21}C(=O)N(R^{21})_2$, —$C(=NR^{21})OR^{20}$, —$OC(=NR^{21})R^{20}$, —$OC(=NR^{21})OR^{20}$, —$C(=NR^{21})N(R^{21})_2$, —$OC(=NR^{21})N(R^{21})_2$, —$NR^{21}C(=NR^{21})N(R^{21})_2$, —$NR^{21}SO_2R^{20}$, —$SO_2N(R^{21})_2$, —$SO_2R^{20}$, —$SO_2OR^{20}$, —$OSO_2R^{20}$, —$S(=O)R^{20}$, —$Si(R^{20})_3$, —$OSi(R^{20})_3$, —$C(=S)N(R^{21})_2$, —$C(=O)SR^{20}$, —$C(=S)SR^{20}$, —$SC(=S)SR^{20}$, —$P(=O)_2R^{20}$, —$P(=O)(R^{20})_2$, —$OP(=O)(R^{20})_2$, —$OP(=O)(OR^{20})_2$, $C_{1-6}$ alkyl, $C_{1-6}$ perhaloalkyl, $C_{2-6}$ alkenyl, $C_{2-6}$ alkynyl, $C_{3-10}$ carbocyclyl, 3-10 membered heterocyclyl, $C_{6-10}$ aryl, 5-10 membered heteroaryl, wherein each alkyl, alkenyl, alkynyl, carbocyclyl, heterocyclyl, aryl, and heteroaryl is independently substituted with 0, 1, 2, 3, 4, or 5 $R^{22}$ groups, or two geminal $R^{19}$ substituents can be joined to form =O or =S;

each instance of $R^{20}$ is, independently, selected from $C_{1-6}$ alkyl, $C_{1-6}$ perhaloalkyl, $C_{2-6}$ alkenyl, $C_{2-6}$ alkynyl, $C_{3-10}$ carbocyclyl, $C_{6-10}$ aryl, 3-10 membered heterocyclyl, and 3-10 membered heteroaryl, wherein each alkyl, alkenyl, alkynyl, carbocyclyl, heterocyclyl, aryl, and heteroaryl is independently substituted with 0, 1, 2, 3, 4, or 5 $R^{22}$ groups;

each instance of $R^{21}$ is, independently, selected from hydrogen, $C_{1-6}$ alkyl, $C_{1-6}$ perhaloalkyl, $C_{2-6}$ alkenyl, $C_{2-6}$ alkynyl, $C_{3-10}$ carbocyclyl, 3-10 membered heterocyclyl, $C_{6-10}$ aryl and 5-10 membered heteroaryl, or two $R^{21}$ groups attached to an N atom are joined to form a 3-14 membered heterocyclyl or 5-14 membered heteroaryl ring, wherein each alkyl, alkenyl, alkenyl, carbocyclyl, heterocyclyl, aryl, and heteroaryl is independently substituted with 0, 1, 2, 3, 4, or 5 $R^{22}$ groups; and each instance of $R^{22}$ is, independently, halogen, —CN, —$NO_2$, —$N_3$, —$SO_2H$, —$SO_3H$, —OH, —$OC_{1-6}$ alkyl, —$ON(C_{1-6}$ alkyl$)_2$, —$N(C_{1-6}$ alkyl$)_2$, —$N(C_{1-6}$ alkyl$)_3X$, —$NH(C_{1-6}$ alkyl$)_2X$, —$NH_2(C_{1-6}$ alkyl$)X$, —$NH_3X$, —$N(OC_{1-6}$ alkyl$)(C_{1-6}$ alkyl), —$N(OH)(C_{1-6}$ alkyl), —NH(OH), —SH, —$SC_{1-6}$ alkyl, —$SS(C_{1-6}$ alkyl), —$C(=O)(C_{1-6}$ alkyl), —$CO_2H$, —$CO_2(C_{1-6}$ alkyl), —$OC(=O)(C_{1-6}$ alkyl), —$OCO_2(C_{1-6}$ alkyl), —$C(=O)NH_2$, —$C(=O)N(C_{1-6}$ alkyl$)_2$, —$OC(=O)NH(C_{1-6}$ alkyl), —$NHC(=O)(C_{1-6}$ alkyl), —$N(C_{1-6}$ alkyl$)C(=O)(C_{1-6}$ alkyl), —$NHCO_2(C_{1-6}$ alkyl), —$NHC(=O)N(C_{1-6}$ alkyl$)_2$, —$NHC(=O)NH(C_{1-6}$ alkyl), —$NHC(=O)NH_2$, —$C(=NH)O(C_{1-6}$ alkyl), —$OC(=NH)(C_{1-6}$ alkyl), —$OC(=NH)OC_{1-6}$ alkyl, —$C(=NH)N(C_{1-6}$ alkyl$)_2$, —$C(=NH)NH(C_{1-6}$ alkyl), —$C(=NH)NH_2$, —$OC(=NH)N(C_{1-6}$ alkyl$)_2$, —$OC(NH)NH(C_{1-6}$ alkyl), —$OC(NH)NH_2$, —$NHC(NH)N(C_{1-6}$ alkyl$)_2$, —$NHC(=NH)NH_2$, —$NHSO_2(C_{1-6}$ alkyl), —$SO_2N(C_{1-6}$ alkyl$)_2$, —$SO_2NH(C_{1-6}$ alkyl), —$SO_2NH_2$, —$SO_2C_{1-6}$ alkyl, —$SO_2OC_{1-6}$ alkyl, —$OSO_2C_{1-6}$ alkyl, —$SOC_{1-6}$ alkyl, —$Si(C_{1-6}$ alkyl$)_3$, —$OSi(C_{1-6}$ alkyl$)_3$ —$C(=S)N(C_{1-6}$ alkyl$)_2$, $C(=S)NH(C_{1-6}$ alkyl), $C(=S)NH_2$, —$C(=O)S(C_{1-6}$ alkyl), —$C(=S)SC_{1-6}$ alkyl, —$SC(=S)SC_{1-6}$ alkyl, —$P(=O)_2(C_{1-6}$ alkyl), —$P(=O)(C_{1-6}$ alkyl$)_2$, —$OP(=O)(C_{1-6}$ alkyl$)_2$, —$OP(=O)(OC_{1-6}$ alkyl$)_2$, $C_{1-6}$ alkyl, $C_{1-6}$ perhaloalkyl, $C_{2-6}$ alkenyl, $C_{2-6}$ alkenyl, $C_{3-10}$ carbocyclyl, $C_{6-10}$ aryl, 3-10 membered heterocyclyl, 5-10 membered heteroaryl; or two geminal $R^{22}$ substituents can be joined to form =O or =S;
wherein $X^-$ is a counterion.

2. The compound according to claim 1, wherein $R^a$, $R^b$, and $R^c$ independently is selected from —H, $C_{1-3}$ alkyl and $C_{1-3}$ perhaloalkyl.

3. The compound according to claim 2, wherein each $R^a$, $R^b$, and $R^c$ is independently selected from —H, —CH$_3$ and —CF$_3$.

4. The compound according to claim 3, wherein $R^a$ and $R^b$ are —H and $R^c$ is selected from —CH$_3$ and —CF$_3$.

5. The compound according to claim 3, wherein $R^b$ and $R^c$ are —H and $R^a$ is selected from —CH$_3$ and —CF$_3$.

6. The compound according to claim 3, wherein each of $R^a$, $R^b$, and $R^c$ is —H.

7. The compound according to claim 1, wherein $R^{15}$ is selected from fluoro (—F), bromo (—Br), chloro (—Cl), and iodo (—I), —OR$^{16}$, —C(=O)N(R$^{18}$)$_2$, —SO$_2$N(R$^{18}$)$_2$, $C_{1-10}$ alkyl, $C_{1-10}$ perhaloalkyl, $C_{2-10}$ alkenyl, $C_{2-10}$ alkynyl, $C_{6-14}$ aryl, and 5-14 membered heteroaryl, wherein each alkyl, alkenyl, alkynyl, aryl, and heteroaryl is independently substituted with 0, 1, 2, 3, 4, or 5 $R^{19}$ groups.

8. The compound according to claim 1, wherein $Y^1$ is S, $Y^3$ is N, and $Y^2$ and $Y^4$ are independently CH or CR$^{15}$.

9. The compound according to claim 8, wherein the compound is of the formula:

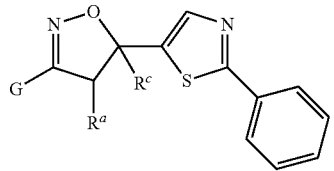

or a pharmaceutically acceptable form thereof.

10. The compound according to claim 1, wherein $Y^1$ is S and each $Y^2$, $Y^3$ and $Y^4$ is independently CH or CR$^{15}$.

11. The compound according to claim 10, wherein the compound is of the formulae:

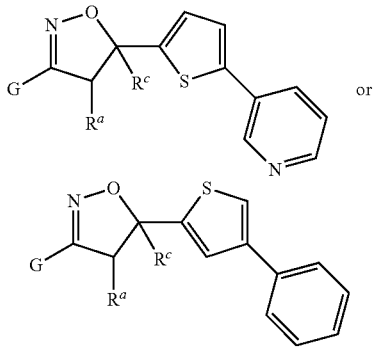

or a pharmaceutically acceptable form thereof.

12. The compound according to claim 1, wherein G is selected from —Cl, —Br, —I, —OR$^e$, —ONR$^f$R$^e$, —ONR$^f$(C=O)R$^e$, —ONR$^f$SO$_2$R$^e$, —ONR$^f$PO$_2$R$^e$, —ONR$^f$PO$_2$OR$^e$, —SR$^e$, —OSO$_2$R$^e$, —NR$^f$SO$_2$R$^e$, —OPO$_2$R$^e$, —OPO$_2$OR$^e$, —NR$^f$PO$_2$R$^e$, —NR$^f$PO$_2$OR$^e$, —OPO$_2$NR$^f$R$^e$, —O(C=O)R$^e$, —O(C=O)OR$^e$, —NR$^f$R$^e$, —NR$^f$(C=O)R$^e$, —NR$^f$(C=O)OR$^e$, —O(C=O)NR$^f$R$^e$, —NR$^f$(C=NR$^f$)NR$^f$R$^e$, —O(C=NR$^f$)NR$^f$R$^e$, —NR$^f$(C=NR$^f$)OR$^e$, and —[N(R$^f$)$_2$R$^e$]$^+$X$^-$ wherein X$^-$ is a counterion.

13. The compound according to claim 12, wherein G is —OR$^e$.

14. The compound according to claim 13, wherein $R^e$ is $C_{6-14}$ aryl.

15. The compound according to claim 14, wherein $R^e$ is phenyl.

16. The compound according to claim 15, wherein $R^e$ is a monosubstituted phenyl.

17. The compound according to claim 15, wherein $R^e$ is a phenyl group of the formula:

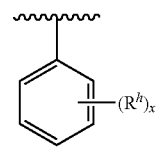

wherein:
x is 0, 1, 2, 3, 4 or 5, and
each $R^h$ is, independently, selected from fluoro (—F), bromo (—Br), chloro (—Cl), and iodo (—I), —CN, —NO$_2$, —N$_3$, —SO$_2$H, —SO$_3$H, —OH, —OR$^i$, —ON(R$^k$)$_2$, —N(R$^k$)$_2$, —N(R$^k$)$_3$$^+$X$^-$, —N(OR$^j$)R$^k$, —SH, —SR$^i$, —SSR$^j$, —C(=O)R$^i$, —CO$_2$H, —CHO, —CO$_2$R$^i$, —OC(=O)R$^i$, —OCO$_2$R$^i$, —C(=O)N(R$^k$)$_2$, —OC(=O)N(R$^k$)$_2$, —NR$^k$C(=O)R$^i$, —NR$^k$CO$_2$R$^i$, —NR$^k$C(=O)N(R$^k$)$_2$, —C(=NR$^k$)R$^i$, —C(=NR$^k$)OR$^i$, —OC(=NR$^k$)R$^i$, —OC(=NR$^k$)OR$^i$, —C(=NR$^k$)N(R$^k$)$_2$, —OC(=NR$^k$)N(R$^k$)$_2$, —NR$^k$C(=NR$^k$)N(R$^k$)$_2$, —C(=O)NR$^k$SO$_2$R$^i$, —NR$^k$SO$_2$Ri, —SO$_2$N(R$^k$)$_2$, —SO$_2$R$^i$, —SO$_2$OR$^i$, —OSO$_2$R$^i$, —S(=O)R$^i$, —OS(=O)R$^i$, —Si(R$^i$)$_3$, —OSi(R$^i$)$_3$—C(=S)N(R$^k$)$_2$, —C(=O)SR$^i$, —C(=S)SR$^i$, —SC(S)SR$^i$, —P(=O)$_2$R$^i$, —OP(=O)$_2$R$^i$, —P(=O)(R$^i$)$_2$, —OP(=O)(R$^i$)$_2$, —OP(=O)(OR$^j$)$_2$, —P(=O)$_2$N(R$^k$)$_2$, —OP(=O)$_2$N(R$^k$)$_2$, —P(=O)(NR$^k$)$_2$, —OP(=O)(NR$^k$)$_2$, —NR$^k$P(=O)(OR$^j$)$_2$, —NR$^k$P(=O)(NR$^k$)$_2$, —P(R$^j$)$_2$, —P(R$^j$)$_3$, —OP(R$^j$)$_2$, —OP(R$^j$)$_3$, —B(OR$^j$)$_2$, —BR$^i$(OR$^j$), $C_{1-10}$ alkyl, $C_{1-10}$ perhaloalkyl, $C_{2-10}$ alkenyl, $C_{2-10}$ alkynyl, $C_{3-14}$ carbocyclyl, 3-14 membered heterocyclyl, $C_{6-14}$ aryl, and 5-14 membered heteroaryl, wherein each alkyl, alkenyl, alkynyl, carbocyclyl, heterocyclyl, aryl, and heteroaryl is independently substituted with 0, 1, 2, 3, 4, or 5 $R^m$ groups;
each instance of $R^i$ is, independently, selected from $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, wherein each alkyl, alkenyl, alkynyl, carbocyclyl, heterocyclyl, aryl, and heteroaryl is independently substituted with 0, 1, 2, 3, 4, or 5 $R^m$ groups;
each instance of $R^k$ is, independently, selected from hydrogen, —OH, —OR$^i$, —N(R$^j$)$_2$, —CN, —C(=O)R$^i$, —C(=O)N(R$^j$)$_2$, —CO$_2$R$^i$, —SO$_2$R$^i$, —C(=NR$^j$)OR$^i$, —C(=NR$^j$)N(R$^j$)$_2$, —SO$_2$N(R$^j$)$_2$, —SO$_2$R$^j$, —SO$_2$OR$^j$, —SOR$^i$, —C(=S)N(R$^j$)$_2$, —C(=O)SR$^j$, —C(=S)SR$^j$, —P(=O)$_2$R$^i$, —P(=O)(R$^i$)$_2$, —P(=O)$_2$N(R$^j$)$_2$, —P(=O)(NR$^j$)$_2$, $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two Rj groups attached to an N atom are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^m$ groups;

each instance of is, independently, selected from hydrogen, $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two Rj groups attached to an N atom are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^m$ groups;

each instance of $R^m$ is, independently, selected from fluoro (—F), bromo (—Br), chloro (—Cl), and iodo (—I), —CN, —NO$_2$, —N$_3$, —SO$_2$H, —SO$_3$H, —OH, —OR$^o$, —ON(R″)$_2$, —N(R″)$_2$, —N(R″)$_3^+$X$^-$, —N(OR$^o$)R″, —SH, —SR$^o$, —SSR$^o$, —C(=O)R$^o$, —CO$_2$H, —CO$_2$R$^o$, —OC(=O)R$^o$, —OCO$_2$R$^o$, —C(=O)N(R″)$_2$, —OC(=O)N(R″)$_2$, —NR″C(=O)R$^o$, —NR″CO$_2$R$^o$, —NR″C(=O)N(R″)$_2$, —C(=NR″)OR$^o$, —OC(=NR″)R$^o$, —OC(=NR″)OR$^o$, —C(=NR″)N(R″)$_2$, —OC(=NR″)N(R″)$_2$, —NR″C(=NR″)N(R″)$_2$, —NR″SO$_2$R$^o$, —SO$_2$N(R″)$_2$, —SO$_2$R$^o$, —SO$_2$OR$^o$, —OSO$_2$R$^o$, —S(=O)R$^o$, —Si(R$^o$)$_3$, —OSi(R$^o$)$_3$, —C(=S)N(R″)$_2$, —C(=O)SR$^o$, —C(=S)SR$^o$, —SC(=S)SR$^o$, —P(=O)$_2$R$^o$, —P(=O)(R$^o$)$_2$, —OP(=O)(R$^o$)$_2$, —OP(=O)(OR$^o$)$_2$, $C_{1-6}$ alkyl, $C_{1-6}$ perhaloalkyl, $C_{2-6}$ alkenyl, $C_{2-6}$ alkynyl, $C_{3-10}$ carbocyclyl, 3-14 membered heterocyclyl, $C_{6-14}$ aryl, 5-14 membered heteroaryl, wherein each alkyl, alkenyl, alkynyl, carbocyclyl, heterocyclyl, aryl, and heteroaryl is independently substituted with 0, 1, 2, 3, 4, or 5 $R^p$ groups, or two geminal $R^m$ substituents can be joined to form =O or =S;

each instance of $R^o$ is, independently, selected from $C_{1-6}$ alkyl, $C_{1-6}$ perhaloalkyl, $C_{2-6}$ alkenyl, $C_2$ alkynyl, $C_{3-10}$ carbocyclyl, $C_{6-10}$ aryl, 3-10 membered heterocyclyl, and 3-10 membered heteroaryl, wherein each alkyl, alkenyl, alkynyl, carbocyclyl, heterocyclyl, aryl, and heteroaryl is independently substituted with 0, 1, 2, 3, 4, or 5 $R^p$ groups;

each instance of R″ is, independently, selected from hydrogen, $C_{1-6}$ alkyl, $C_{1-6}$ perhaloalkyl, $C_{2-6}$ alkenyl, $C_{2-6}$ alkynyl, $C_{3-10}$ membered heterocyclyl, $C_{6-10}$ aryl and 5-10 membered heteroaryl, or two R″ groups attached to an N atom are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^p$ groups; and each instance of $R^p$ is, independently, fluoro (—F), bromo (—Br), chloro (—Cl), and iodo (—I), —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —(C$_{1-6}$ alkyl)$_3$X, —NH(C$_{1-6}$ alkyl)$_2$X, —NH$_2$(C$_{1-6}$ alkyl)X, —NH$_3$X, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$ (C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$ (C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$alkyl)$_3$ —C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)$_2$(C$_{1-6}$ alkyl), —P(=O)(C$_{1-6}$ alkyl)$_2$, —OP(=O)(C$_{1-6}$ alkyl)$_2$, —OP(=O)(OC$_{1-6}$ alkyl)$_2$, $C_{1-6}$ alkyl, $C_{1-6}$ perhaloalkyl, $C_{2-6}$ alkenyl, $C_{2-6}$ alkynyl, $C_{3-10}$ carbocyclyl, $C_{6-14}$ aryl, 3-14 membered heterocyclyl, 5-14 membered heteroaryl; or two geminal $R^p$ substituents can be joined to form =O or =S;

wherein X$^-$ is a counterion.

18. The compound according to claim 17, wherein $R^h$ is selected from fluoro (—F), bromo (—Br), chloro (—Cl), and iodo (—I), —CN, —NO$_2$, —OH, —OR$^i$, —SR$^i$, —N(R$^k$)$_2$, —N(R$^k$)$_3^+$X$^-$, —C(=O)R$^i$, —CO$_2$R$^i$, —CO$_2$H, —OC(=O)R$^i$, —OCO$_2$R$^i$, —C(=O)N(R$^k$)$_2$, —OC(=O)N(R$^k$)$_2$, —NR$^k$C(=O)R$^i$, —NR$^k$CO$_2$R$^i$, —NR$^k$C(=O)N(R$^k$)$_2$, —C(=O)NR$^k$SO$_2$R$^i$, —NR$^k$SO$_2$R$^i$, —SO$_2$N(R$^k$)$_2$, —SO$_2$Ri, $C_{1-10}$ alkyl, $C_6$ aryl, and 5-6 membered heteroaryl, wherein each alkyl, aryl, and heteroaryl is independently substituted with 0, 1, 2, 3 or 4 $R^m$ groups; and wherein X$^-$ is a counterion.

19. The compound according to claim 18, wherein $R^h$ is selected from —C(=O)R$^i$, —CO$_2$H, —SO$_2$R$^i$, and 5-membered heteroaryl independently substituted with 0 or 1 $R^m$ groups.

20. The compound according to claim 19, wherein the 5-membered heteroaryl is selected from pyrrolyl, furanyl, thiophenyl, imidazolyl, pyrazolyl, oxazolyl, isoxazolyl, thiazolyl, isothiazolyl, triazolyl, oxadiazolyl, thiadiazolyl, and tetrazolyl.

21. The compound according to claim 15, wherein the phenyl group is a monosubstituted phenyl group of any one of the formulae:

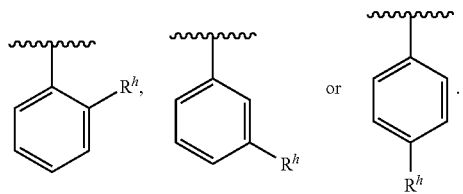

22. The compound according to claim 15, wherein the phenyl group is a disubstituted phenyl group of any one of the formulae:

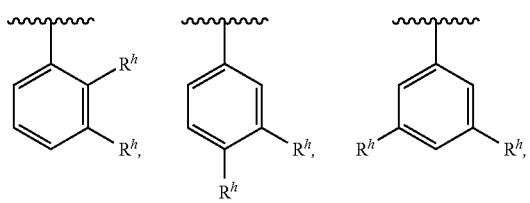

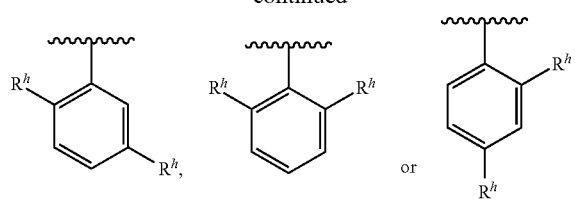
23. The compound according to claim 13, wherein G is —OR$^e$ is selected from:
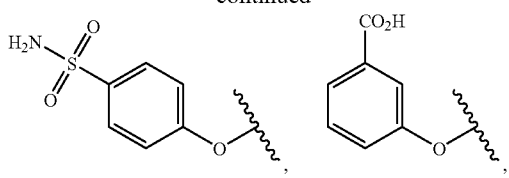
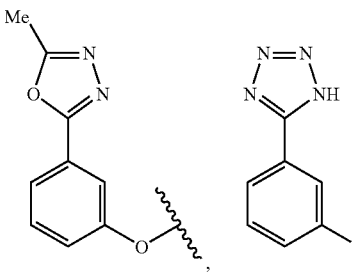
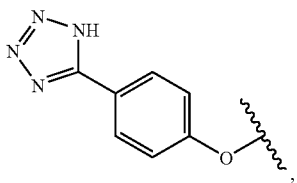
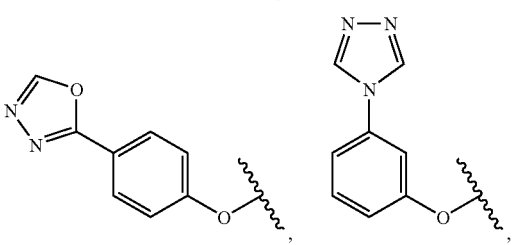
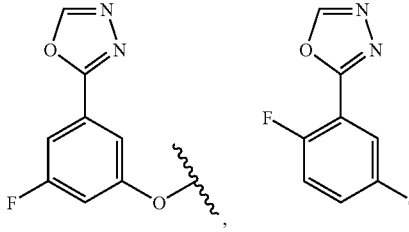

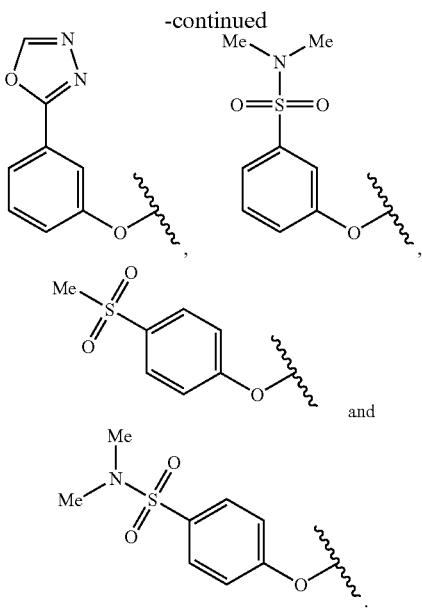

24. The compound according to claim 13, wherein $R^e$ is 5-14 membered heteroaryl.

25. The compound according to claim 24, wherein $R^e$ is a 6-membered heteroaryl.

26. The compound according to claim 25, wherein $R^e$ is a pyrindinyl group.

27. The compound according to claim 26, wherein $R^e$ is a monosubstituted pyrindinyl group.

28. The compound according to claim 26, wherein $R^e$ is a 3-pyridinyl group.

29. The compound according to claim 26, wherein $R^e$ is a pyrindinyl group of the formula:

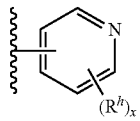

wherein x is 0, 1, 2, 3 or 4, and
each $R^h$ is, independently, selected from fluoro (—F), bromo (—Br), chloro (—Cl), and iodo (—I), —CN, —NO$_2$, —N$_3$, —SO$_2$H, —SO$_3$H, —OH, —OR$^i$, —ON(R$^k$)$_2$, —N(R$^k$)$_2$, —N(R$^k$)$_3$$^+$X$^-$, —N(OR$^j$)R$^k$, —SH, —SR$^i$, —SSR$^j$, —C(═O)R$^i$, —CO$_2$H, —CHO, —CO$_2$R$^i$, —OC(═O)R$^i$, —OCO$_2$R$^i$, —C(═O)N(R$^k$)$_2$, —OC(═O)N(R$^k$)$_2$, —NR$^k$C(═O)R$^i$, —NR$^k$CO$_2$R$^i$, —NR$^k$C(═O)N(R$^k$)$_2$, —C(═NR$^k$)R$^i$, —C(═NR$^k$)OR$^i$, —OC(═NR$^k$)R$^i$, —OC(═NR$^k$)OR$^i$, —C(═NR$^k$)N(R$^k$)$_2$, —OC(═NR$^k$)N(R$^k$)$_2$, —NR$^k$C(═NR$^k$)N(R$^k$)$_2$, —C(═O)NR$^k$SO$_2$R$^i$, —NR$^k$SO$_2$R$^i$, —SO$_2$N(R$^k$)$_2$, —SO$_2$R$^i$, —SO$_2$OR$^i$, —OSO$_2$R$^i$, —S(═O)R$^i$, —OS(═O)R$^i$, —Si(R$^i$)$_3$, —OSi(R$^i$)$_3$ —C(═S)N(R$^k$)$_2$, —C(═O)SR$^i$, —C(═S)SR$^i$, —SC(S)SR$^i$, —P(═O)$_2$R$^i$, —OP(═O)$_2$R$^i$, —P(═O)(R$^i$)$_2$, —OP(═O)(R$^i$)$_2$, —OP(═O)(OR$^j$)$_2$, —P(═O)$_2$N(R$^k$)$_2$, —OP(═O)$_2$N(R$^k$)$_2$, —P(═O)(NR$^k$)$_2$, —OP(═O)(NR$^k$)$_2$, —NR$^k$P(═O)(OR$^j$)$_2$, —NR$^k$P(═O)(NR$^k$)$_2$, —P(R$^j$)$_2$, —P(R$^j$)$_3$, —OP(R$^j$)$_2$, —OP(R$^j$)$_3$, —B(OR$^j$)$_2$, —BR$^i$(OR$^j$), $C_{1-10}$ alkyl, $C_{1-10}$ perhaloalkyl, $C_{2-10}$ alkenyl, $C_{2-10}$ alkynyl, $C_{3-14}$ carbocyclyl, 3-14 membered heterocyclyl, $C_{6-14}$ aryl, and 5-14 membered heteroaryl, wherein each alkyl, alkenyl, alkynyl, carbocyclyl, heterocyclyl, aryl, and heteroaryl is independently substituted with 0, 1, 2, 3, 4, or 5 $R^m$ groups;

each instance of $R^i$ is, independently, selected from $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, wherein each alkyl, alkenyl, alkynyl, carbocyclyl, heterocyclyl, aryl, and heteroaryl is independently substituted with 0, 1, 2, 3, 4, or 5 $R^m$ groups;

each instance of $R^k$ is, independently, selected from hydrogen, —OH, —OR$^i$, —N(R$^j$)$_2$, —CN, —C(═O)R$^i$, —C(═O)N(R$^j$)$_2$, —CO$_2$R$^i$, —SO$_2$R$^i$, —C(═NR$^j$)OR$^i$, —C(═NR$^j$)N(R$^j$)$_2$, —SO$_2$N(R$^j$)$_2$, —SO$_2$R$^j$, —SO$_2$OR$^j$, —SOR$^i$, —C(═S)N(R$^j$)$_2$, —C(═O)SR$^j$, —C(═S)SR$^j$, —P(═O)$_2$R$^i$, —P(═O)(R$^i$)$_2$, —P(═O)$_2$N(R$^j$)$_2$, —P(═O)(NR$^j$)$_2$, $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two Rj groups attached to an N atom are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^m$ groups;

each instance of $R^j$ is, independently, selected from hydrogen, $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two Rj groups attached to an N atom are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^m$ groups;

each instance of $R^m$ is, independently, selected from fluoro (—F), bromo (—Br), chloro (—Cl), and iodo (—I), —CN, —NO$_2$, —N$_3$, —SO$_2$H, —SO$_3$H, —OH, —OR$^o$, —ON(R$''$)$_2$, —N(R$''$)$_2$, —N(R$''$)$_3$$^+$X$^-$, —N(OR$^o$)R$''$, —SH, —SR$^o$, —SSR$^o$, —C(═O)R$^o$, —CO$_2$H, —CO$_2$R$^o$, —OC(═O)R$^o$, —OCO$_2$R$^o$, —C(═O)N(R$''$)$_2$, —OC(═O)N(R$''$)$_2$, —NR$''$C(═O)R$^o$, —NR$''$CO$_2$R$^o$, —NR$''$C(═O)N(R$''$)$_2$, —C(═NR$''$)OR$^o$, —OC(═NR$''$)R$^o$, —OC(═NR$''$)OR$^o$, —C(═NR$''$)N(R$''$)$_2$, —OC(═NR$''$)N(R$''$)$_2$, —NR$''$C(═NR$''$)N(R$''$)$_2$, —NR$''$SO$_2$R$^o$, —SO$_2$N(R$''$)$_2$, —SO$_2$R$^o$, —SO$_2$OR$^o$, —OSO$_2$R$^o$, —S(═O)R$^o$, —Si(R$^o$)$_3$, —OSi(R$^o$)$_3$, —C(═S)N(R$''$)$_2$, —C(═O)SR$^o$, —C(═S)SR$^o$, —SC(═S)SR$^o$, —P(═O)$_2$R$^o$, —P(═O)(R$^o$)$_2$, —OP(═O)(R$^o$)$_2$, —OP(═O)(OR$^o$)$_2$, $C_{1-6}$ alkyl, $C_{1-6}$ perhaloalkyl, $C_{2-6}$ alkenyl, $C_{2-6}$ alkynyl, $C_{3-10}$ carbocyclyl, 3-14 membered heterocyclyl, $C_{6-14}$ aryl, 5-14 membered heteroaryl, wherein each alkyl, alkenyl, alkynyl, carbocyclyl, heterocyclyl, aryl, and heteroaryl is independently substituted with 0, 1, 2, 3, 4, or 5 $R^p$ groups, or two geminal $R^m$ substituents can be joined to form ═O or ═S;

each instance of $R^o$ is, independently, selected from $C_{1-6}$ alkyl, $C_{1-6}$ perhaloalkyl, $C_{2-6}$ alkenyl, $C_2$ alkynyl, $C_{3-10}$ carbocyclyl, $C_{6-10}$ aryl, 3-10 membered heterocyclyl, and 3-10 membered heteroaryl, wherein each alkyl, alkenyl, alkynyl, carbocyclyl, heterocyclyl, aryl, and heteroaryl is independently substituted with 0, 1, 2, 3, 4, or 5 $R^p$ groups;

each instance of $R''$ is, independently, selected from hydrogen, $C_{1-6}$ alkyl, $C_{1-6}$ perhaloalkyl, $C_{2-6}$ alkenyl, $C_{2-6}$ alkynyl, $C_{3-10}$ carbocyclyl, 3-10 membered heterocyclyl, $C_{6-10}$ aryl and 5-10 membered heteroaryl, or two $R^n$ groups attached to an N atom are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^p$ groups; and each instance of $R^p$ is, independently, fluoro (—F), bromo (—Br), chloro (—Cl), and iodo (—I), —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3$X, —NH(C$_{1-6}$ alkyl)$_2$X, —NH$_2$(C$_{1-6}$ alkyl)X, —NH$_3$X, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$—C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)$_2$(C$_{1-6}$ alkyl), —P(=O)(C$_{1-6}$ alkyl)$_2$, —OP(=O)(C$_{1-6}$ alkyl)$_2$, —OP(=O)(OC$_{1-6}$ alkyl)$_2$, C$_{1-6}$ alkyl, C$_{1-6}$ perhaloalkyl, C$_{2-6}$ alkenyl, C$_2$ alkynyl, C$_{3-10}$ carbocyclyl, C$_{6-14}$ aryl, 3-14 membered heterocyclyl, 5-14 membered heteroaryl; or two geminal $R^p$ substituents can be joined to form =O or =S;

wherein $X^-$ is a counterion.

30. The compound according to claim 29, wherein $R^h$ is selected from fluoro (—F), bromo (—Br), chloro (—Cl), and iodo (—I), —CN, —NO$_2$, —OH, —OR$^i$, —SR$^i$, —N(R$^k$)$_2$, —N(R$^k$)$_3$$^+$X$^-$, —C(=O)R$^i$, —CO$_2$R$^i$, —CO$_2$H, —OC(=O)R$^i$, —OCO$_2$R$^i$, —C(=O)N(R$^k$)$_2$, —OC(=O)N(R$^k$)$_2$, —NR$^k$C(=O)R$^i$, —NR$^k$CO$_2$R$^i$, —NR$^k$C(=O)N(R$^k$)$_2$, —C(=O)NR$^k$SO$_2$R$^i$, —NR$^k$SO$_2$R$^i$, —SO$_2$N(R$^k$)$_2$, —SO$_2$Ri, C$_{1-10}$ alkyl, C$_6$ aryl, and 5-6 membered heteroaryl, wherein each alkyl, aryl, and heteroaryl is independently substituted with 0, 1, 2, 3 or 4 $R^m$ groups; and wherein $X^-$ is a counterion.

31. The compound according to claim 30, wherein $R^h$ is selected from —C(=O)R$^i$, —CO$_2$H, —SO$_2$R$^i$, and 5-membered heteroaryl independently substituted with 0 or 1 $R^m$ groups.

32. The compound according to claim 31, wherein the 5-membered heteroaryl is selected from pyrrolyl, furanyl, thiophenyl, imidazolyl, pyrazolyl, oxazolyl, isoxazolyl, thiazolyl, isothiazolyl, triazolyl, oxadiazolyl, thiadiazolyl, and tetrazolyl.

33. The compound according to claim 29, wherein the pyridinyl group is a 3-pyridinyl group of the formulae:

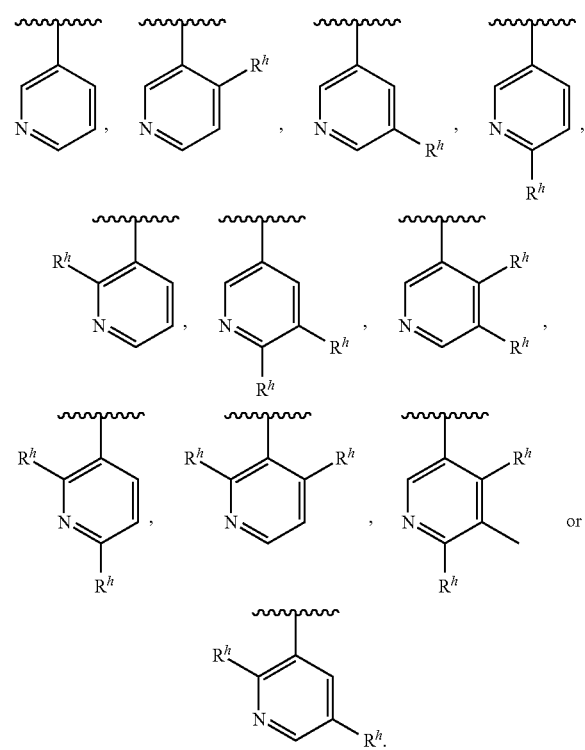

34. The compound according to claim 13, wherein G is —OR$^e$ is selected from:

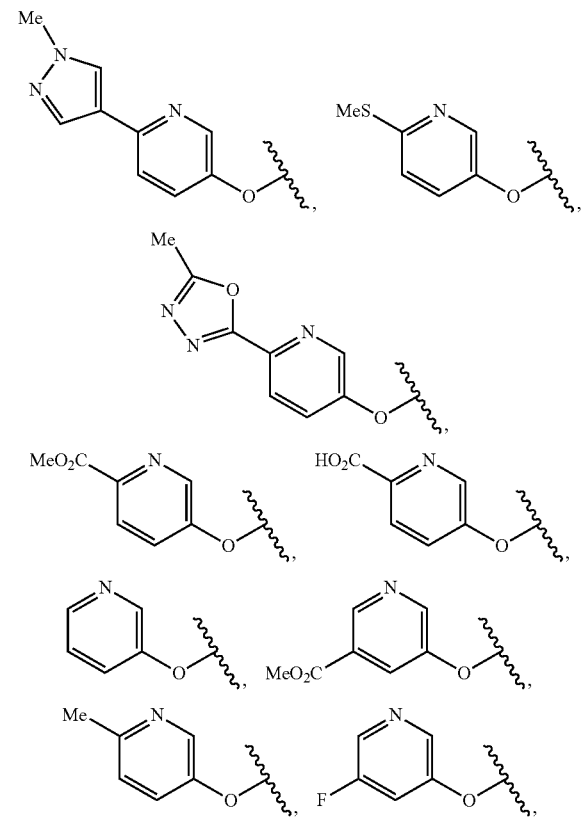

-continued
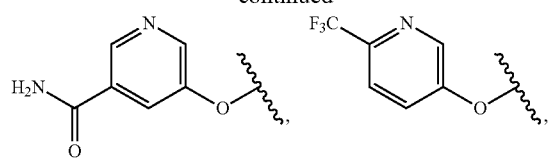
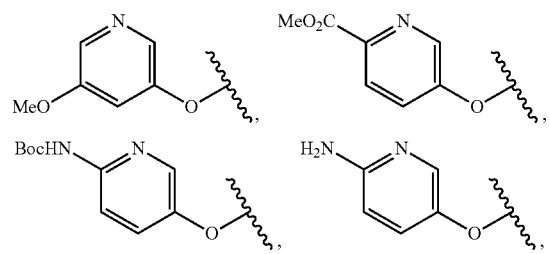
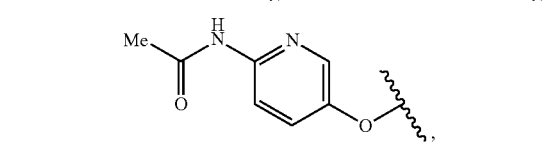
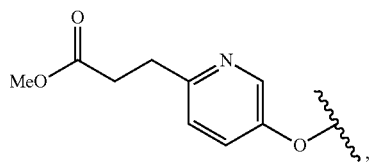
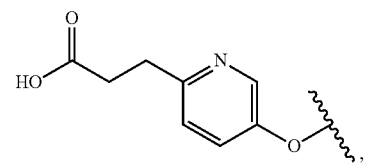
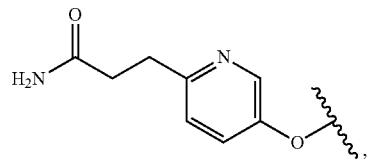
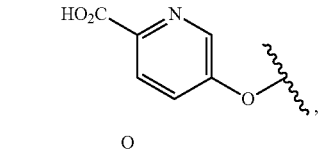
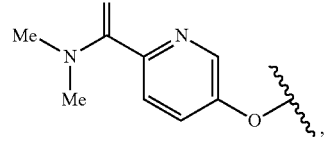
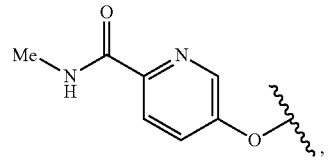
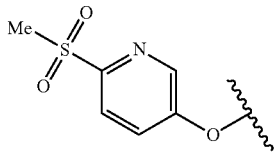
-continued
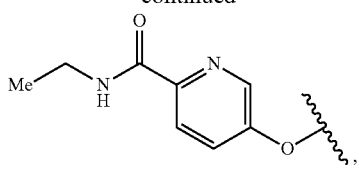
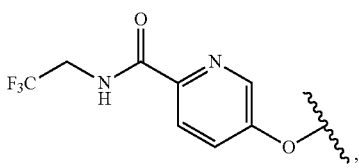
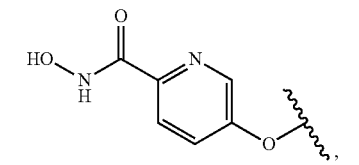
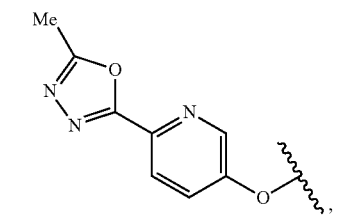
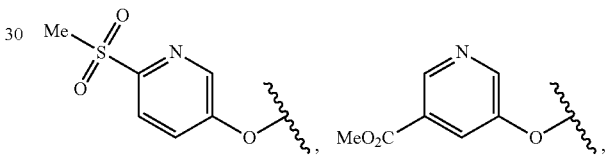
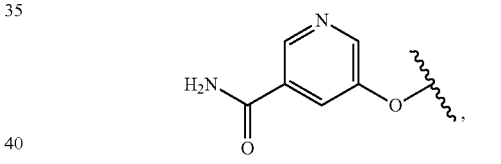
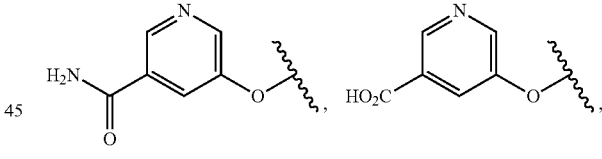
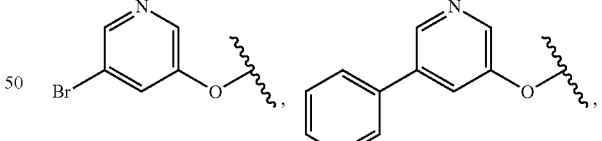
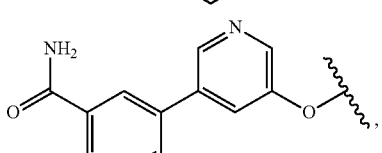
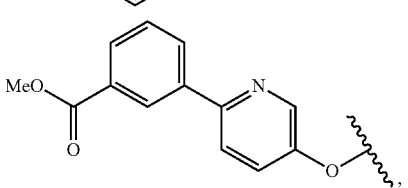

133
-continued
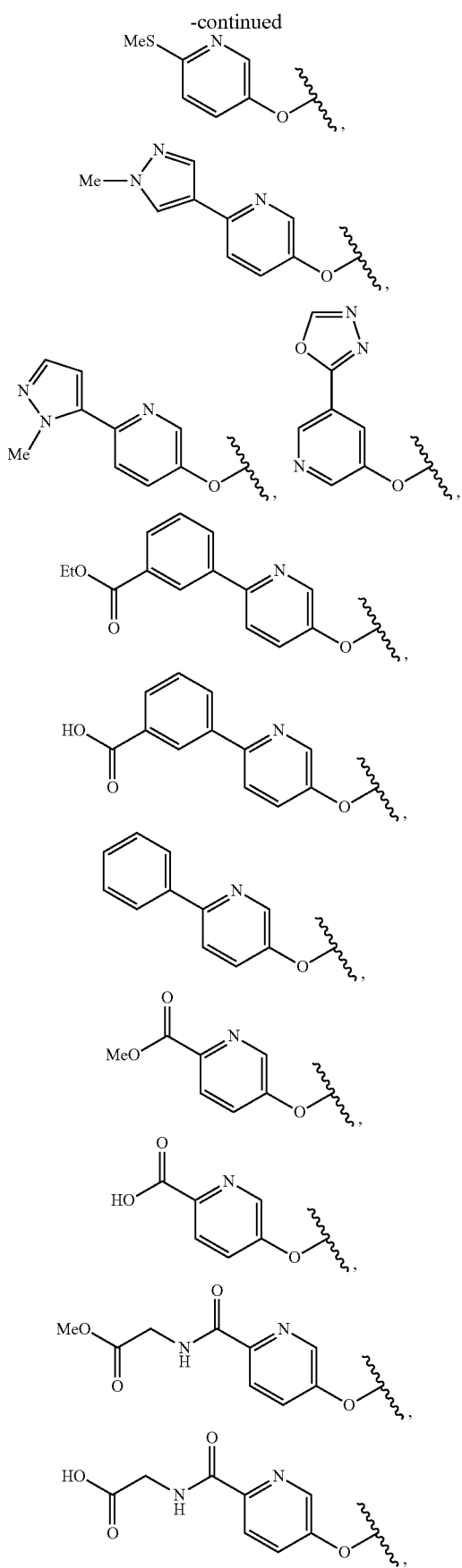
134
-continued
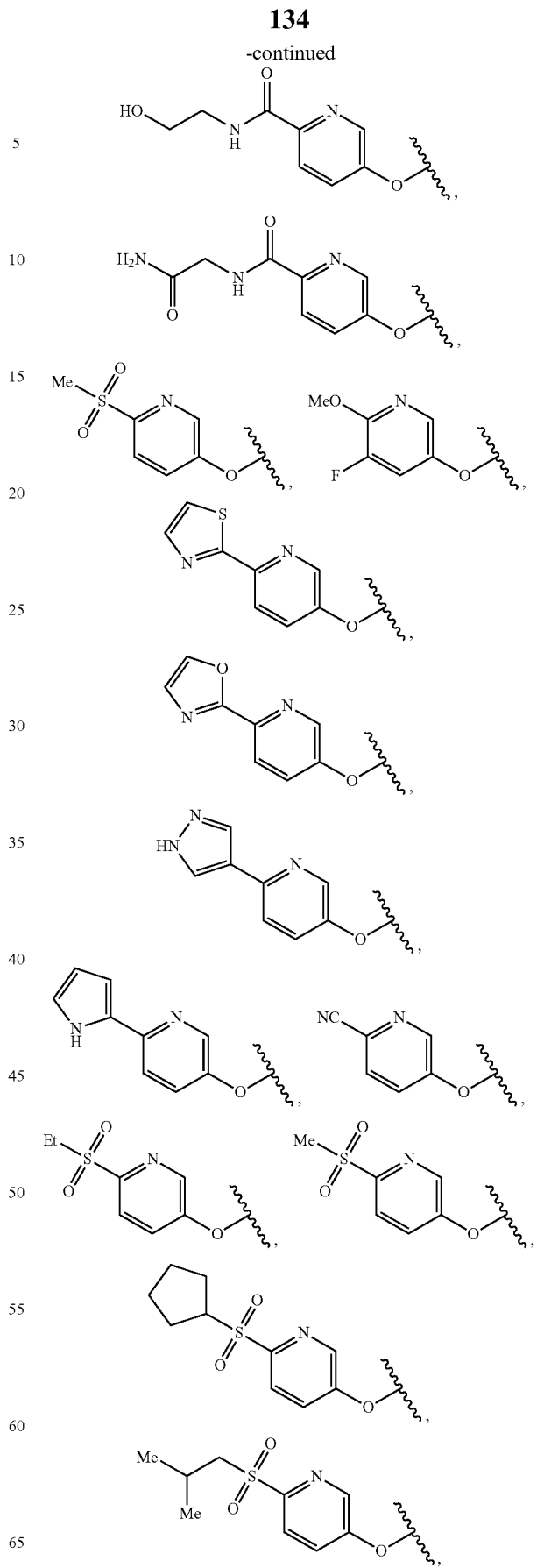

135
-continued
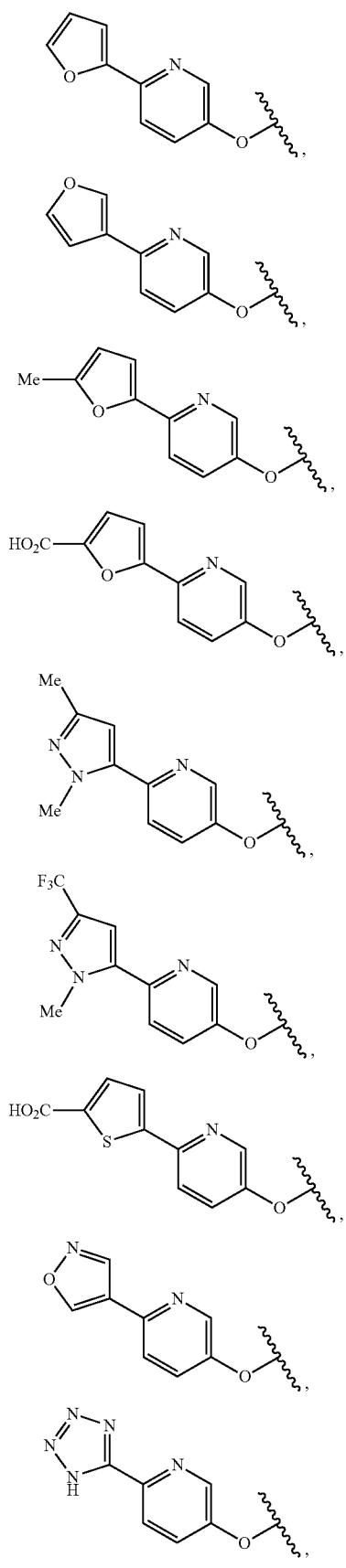
136
-continued
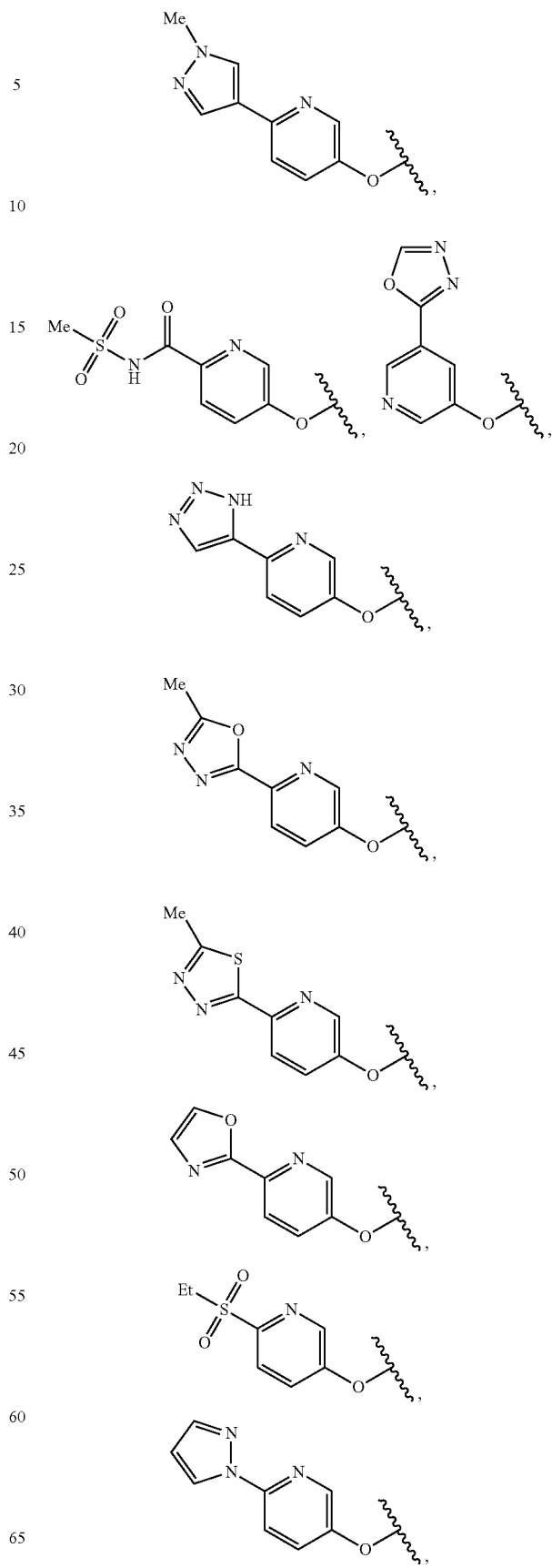

137
-continued

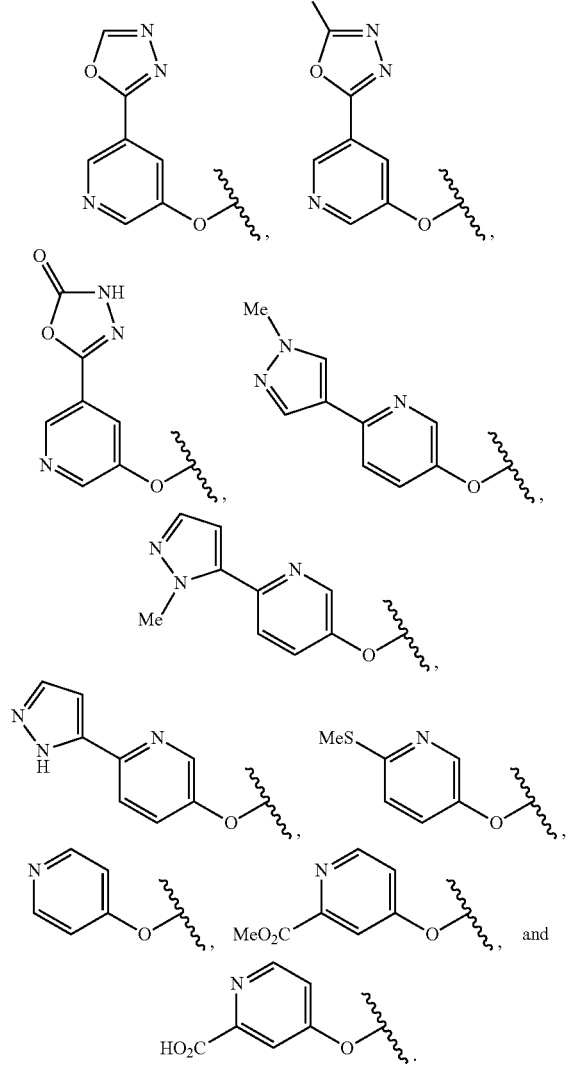

35. The compound according to claim 1, wherein the compound is substantially enantiomerically pure.

36. A pharmaceutical composition comprising a compound of claim 1, or a pharmaceutically acceptable form thereof, and a pharmaceutically acceptable excipient.

37. The compound according to claim 34, wherein G is —OR$^e$ selected from the group consisting of:

138
-continued

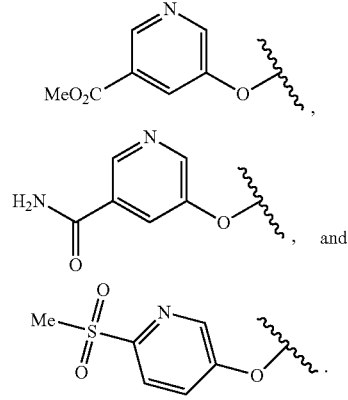

38. The compound according to claim 1, wherein the compound is:

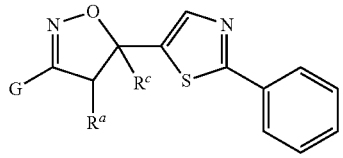

| Compound | G | R$^a$ | R$^c$ |
|---|---|---|---|
| II-6 | —Br | —H | —H |
| II-21 | 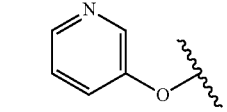 [SMILES: *Oc1cccnc1] | —H | —H |
| II-28 | 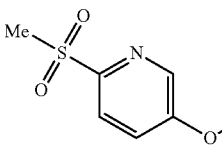 | —H | —H |
| II-18 | —Br | —H | —CH$_3$ |
| II-22 | 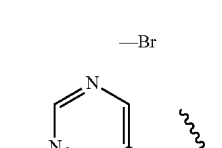 | —H | —CH$_3$ |
| II-23 | 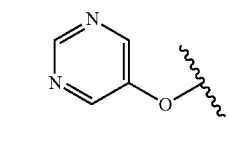 [SMILES: *Oc1cncnc1] | —H | —CH$_3$ |
| II-29 | 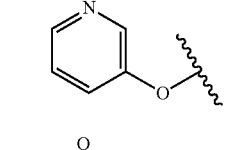 | —H | —CH$_3$ |
| II-19 (cis) | —Br | —CH$_3$ | —H |
| II-20 (trans) | —Br | —CH$_3$ | —H |

-continued

| Compound | G | $R^a$ | $R^c$ |
|---|---|---|---|
| II-25 | —Br | —H | —H |
| II-26 | (pyrimidin-5-yloxy) | —H | —H |
| II-27 | (6-carboxypyridin-3-yloxy, HO₂C) | —H | —H |

| Compound | G | $R^a$ | $R^c$ |
|---|---|---|---|
| II-8 | —Br | —H | —H |
| II-31 | (R)-2-hydroxy-2-phenylethylamino | —H | —H |
| II-30 | (S)-2-hydroxy-2-phenylethylamino | —H | —H |

II-4

II-5 or a pharmaceutically acceptable form thereof.

39. The compound according to claim 1, wherein the compound is:

II-7

II-24

II-17

II-4a,

II-4b,

II-5a,

II-5b,

II-6a,

II-6b,

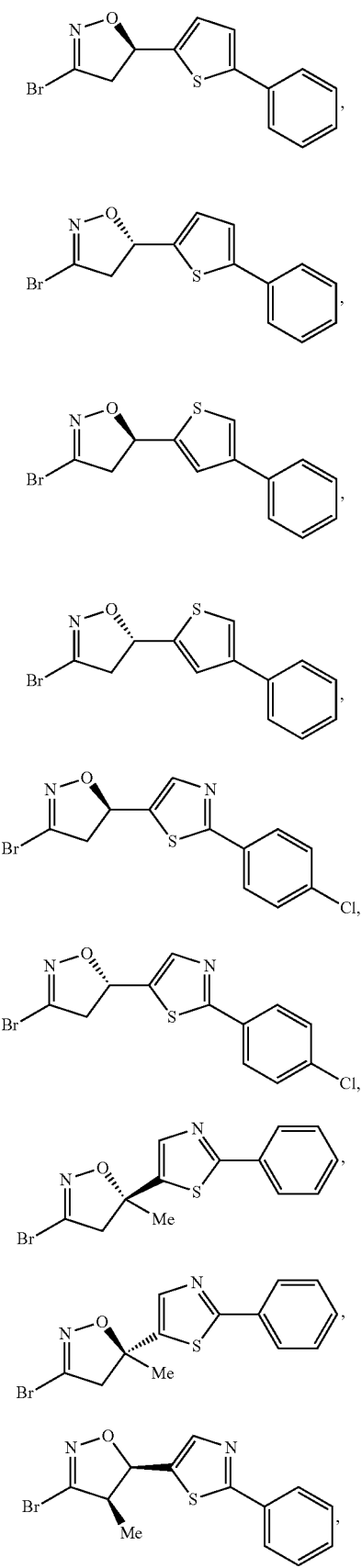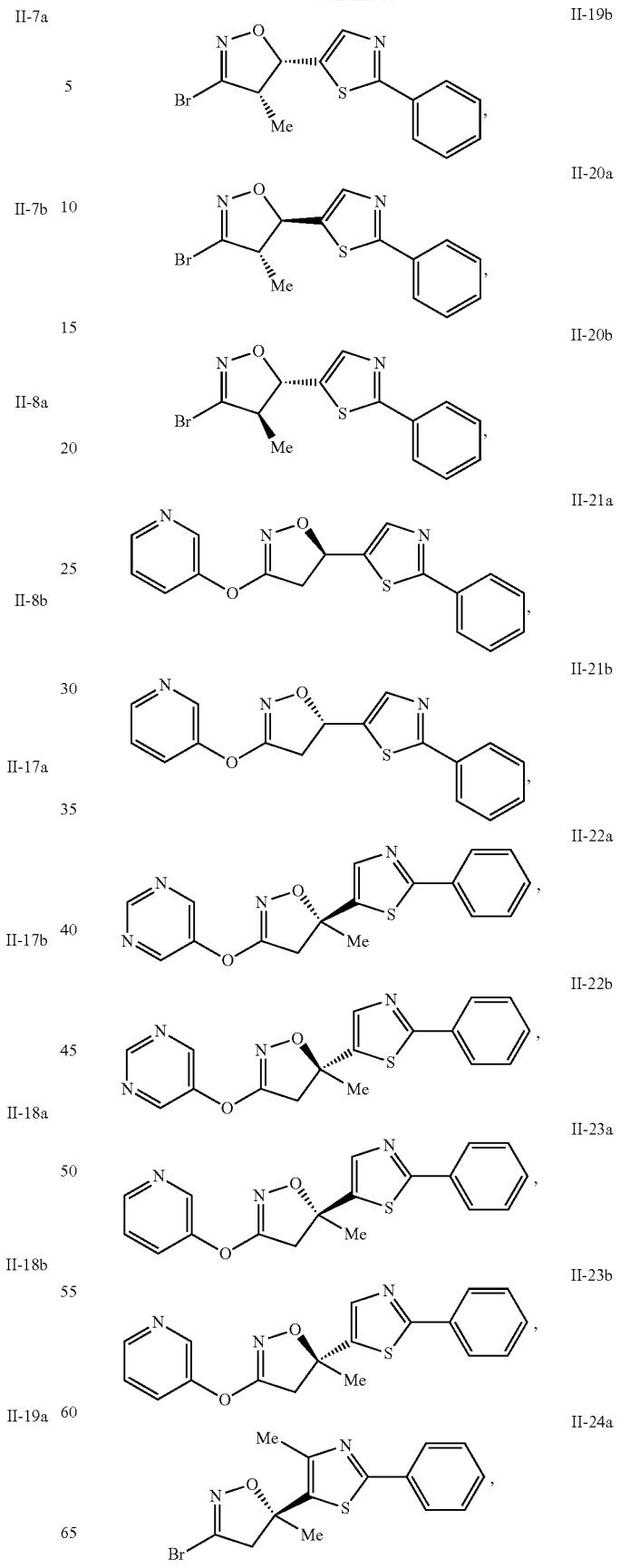

II-24b
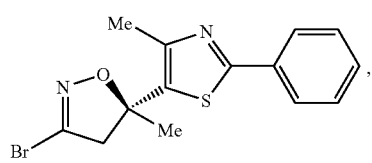
II-25a
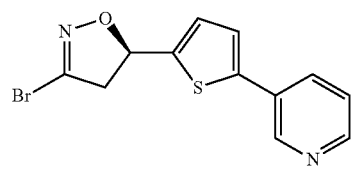
II-25b
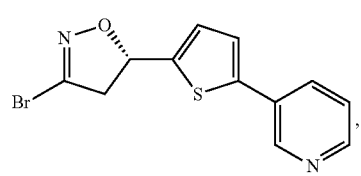
II-26a
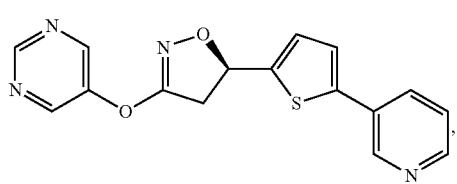
II-26b
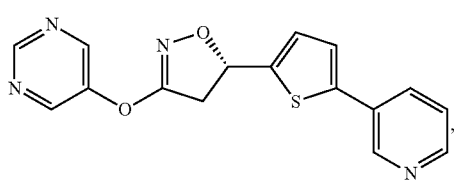
II-27a
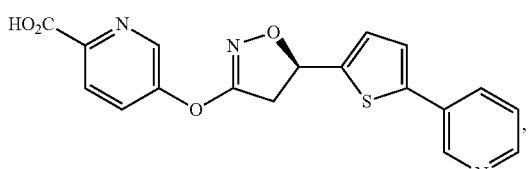
II-27b
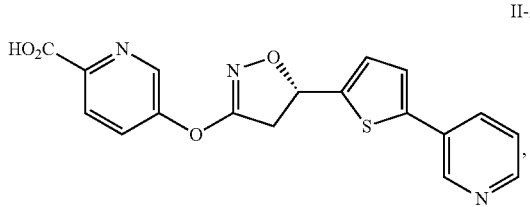
II-28a
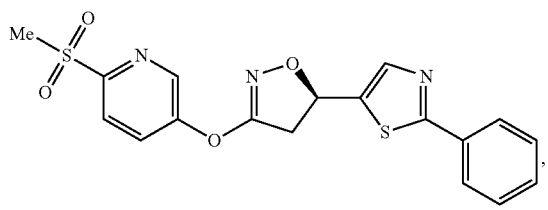
II-28b
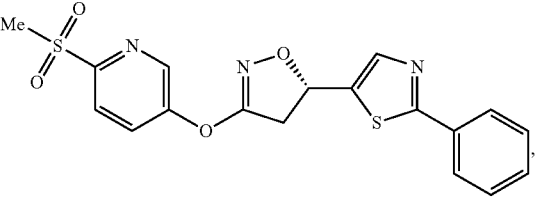
II-29a
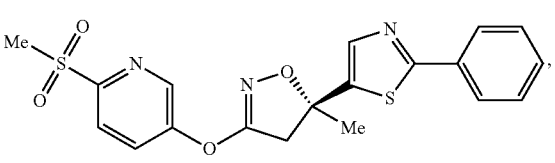
II-29b
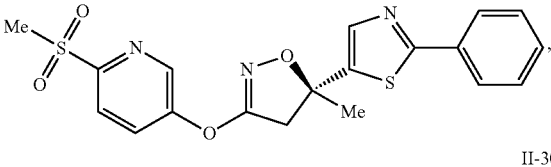
II-30a
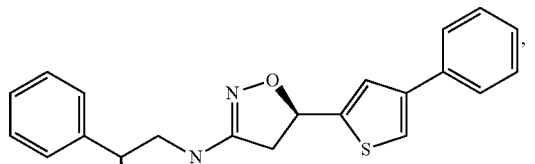
II-30b
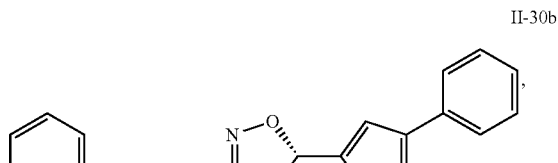
II-31a
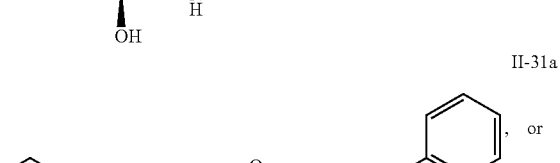
or
II-31b
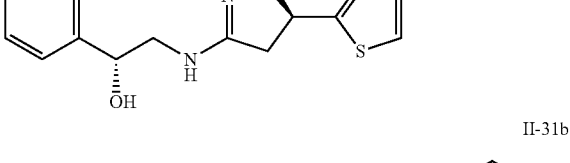
or a pharmaceutically acceptable form thereof.
40. The compound according to claim 1, wherein the compound is:
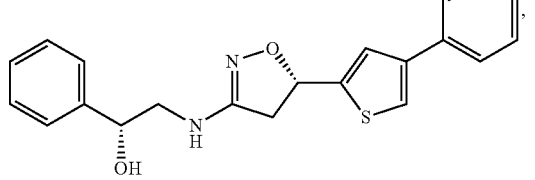

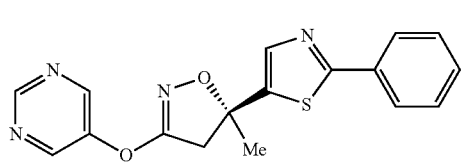

II-22a or a pharmaceutically acceptable form thereof.
41. The compound according to claim 1, wherein the compound is:

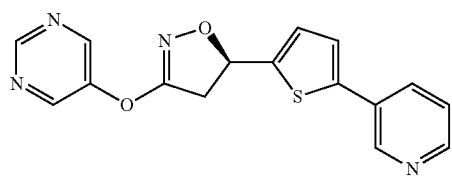

II-26a or a pharmaceutically acceptable form thereof.
42. The compound according to claim 1, wherein the compound is:

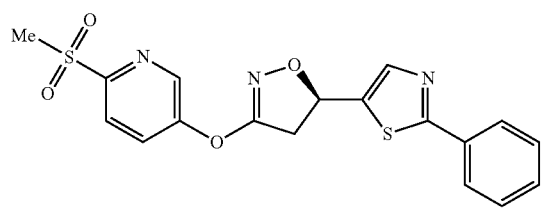

II-28a or a pharmaceutically acceptable form thereof.
43. The pharmaceutical composition according to claim 36, wherein the compound is:

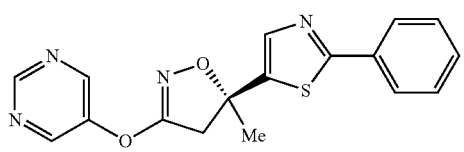

II-22a or a pharmaceutically acceptable form thereof.
44. The pharmaceutical composition according to claim 36, wherein the compound is:

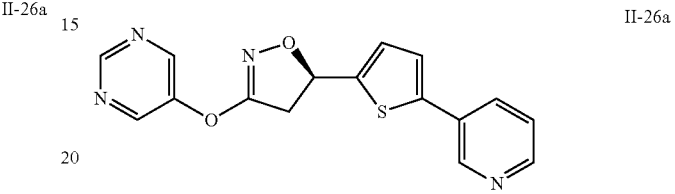

II-26a or a pharmaceutically acceptable form thereof.
45. The pharmaceutical composition according to claim 36, wherein the compound is:

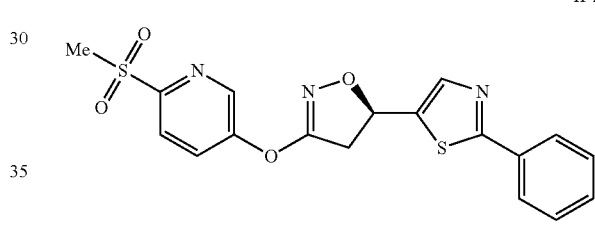

II-28a or a pharmaceutically acceptable form thereof.

* * * * *